US011939370B2

(12) United States Patent
Crowe, Jr. et al.

(10) Patent No.: US 11,939,370 B2
(45) Date of Patent: Mar. 26, 2024

(54) PAN-EBOLA VIRUS NEUTRALIZING HUMAN ANTIBODIES AND METHODS OF USE THEREFOR

(71) Applicants: VANDERBILT UNIVERSITY, Nashville, TN (US); BOARD OF REGENTS, THE UNIVERSITY OF TEXAS SYSTEM, Austin, TX (US)

(72) Inventors: James E. Crowe, Jr., Nashville, TN (US); Pavlo Gilchuk, Nashville, TN (US); Alexander Bukreyev, Galveston, TX (US)

(73) Assignees: VANDERBILT UNIVERSITY, Nashville, TN (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 415 days.

(21) Appl. No.: 17/259,263

(22) PCT Filed: Jul. 11, 2019

(86) PCT No.: PCT/US2019/041349
§ 371 (c)(1),
(2) Date: Jan. 11, 2021

(87) PCT Pub. No.: WO2020/014443
PCT Pub. Date: Jan. 16, 2020

(65) Prior Publication Data
US 2021/0403538 A1     Dec. 30, 2021

Related U.S. Application Data

(60) Provisional application No. 62/697,027, filed on Jul. 12, 2018.

(51) Int. Cl.
| | | |
|---|---|---|
| C07K 16/10 | (2006.01) | |
| A61K 39/00 | (2006.01) | |
| A61P 31/14 | (2006.01) | |
| G01N 33/569 | (2006.01) | |

(52) U.S. Cl.
CPC ............ *C07K 16/10* (2013.01); *A61P 31/14* (2018.01); *G01N 33/56983* (2013.01); *A61K 2039/505* (2013.01); *A61K 2039/507* (2013.01); *A61K 2039/545* (2013.01); *A61K 2039/55* (2013.01); *C07K 2317/24* (2013.01); *C07K 2317/31* (2013.01); *C07K 2317/34* (2013.01); *C07K 2317/52* (2013.01); *C07K 2317/565* (2013.01); *C07K 2317/732* (2013.01); *C07K 2317/76* (2013.01); *C07K 2317/92* (2013.01); *G01N 2469/10* (2013.01)

(58) Field of Classification Search
CPC ............... C07K 16/10; C07K 2317/24; C07K 2317/31; C07K 2317/34; C07K 2317/52; C07K 2317/565; C07K 2317/732; C07K 2317/76; C07K 2317/92; A61P 31/14; G01N 33/56983; G01N 2469/10; A61K 2039/505; A61K 2039/507; A61K 2039/545; A61K 2039/55
See application file for complete search history.

(56) References Cited

U.S. PATENT DOCUMENTS

| 9,771,414 B2 * | 9/2017 | Kyratsous ............ C07K 16/10 |
| 2016/0215040 A1 | 7/2016 | Kyratsous et al. |

FOREIGN PATENT DOCUMENTS

| WO | WO-2007027713 A2 * | 3/2007 | ....... A61K 39/39558 |
| WO | WO 2016/022916 | 2/2016 | |
| WO | WO 2016/196343 | 12/2016 | |

OTHER PUBLICATIONS

Bornholdt et al., "Host-Primed Ebola Virus GP Exposes a Hydrophobic NPC1 Receptor-Binding Pocket, Revealing a Target for Broadly Neutralizing Antibodies." mBio. Feb. 23, 2016;7(1):e02154-15, 2016.
Bornholdt et al., "Isolation of potent neutralizing antibodies from a survivor of the 2014 Ebola Virus outbreak" *Science* 351, 1078-1083, 2016.
Borholdt et al., "A Two-Antibody Pan-Ebolavirus Cocktail Confers Broad Therapeutic Protection in Ferrets and Nonhuman Primates" *Cell Host Microbe.* 25(1):49-58.e5, 2019.
Corti et al., "Protective monotherapy against lethal Ebola virus infection by a potently neutralizing antibody" *Science* 351 ,1339-1342, 2016.

(Continued)

*Primary Examiner* — Adam Weidner
*Assistant Examiner* — Laura Ann Essex
(74) *Attorney, Agent, or Firm* — Parker Highlander PLLC

(57) ABSTRACT

The present disclosure is directed to human antibodies binding to and neutralizing ebolavirus and methods for use thereof. A further embodiment involves a monoclonal antibody, wherein the antibody or antibody fragment is characterized by clone-paired heavy and light chain CDR sequences. In yet another embodiment, there is provided a hybridoma or engineered cell encoding an antibody or antibody fragment. An additional embodiment comprises a vaccine formulation comprising one or more antibodies or antibody fragments characterized by clone-paired heavy and light chain CDR sequences. In still a further embodiment, there is provided a method of protecting the health of a placenta and/or fetus of a pregnant a subject infected with or at risk of infection with ebolavirus comprising delivering to said subject the antibody or antibody fragment.

15 Claims, 48 Drawing Sheets

Specification includes a Sequence Listing.

(56) References Cited

OTHER PUBLICATIONS

Duehr et al. "Novel Cross-Reactive Monoclonal Antibodies against Ebolavirus Glycoproteins Show Protection in a Murine Challenge Model." *Journal of Virology*, 91(16), 2017.
Flyak et al., "Mechanism of human antibody-mediated neutralization of Marburg virus." *Cell* 160, 893-903, 2015.
Flyak al., "Cross-Reactive and Potent Neutralizing Antibody Responses in Human Survivors of Natural Ebolavirus Infection" *Cell* 164, 392-405, 2016.
Furuyama et al., "Discovery of an antibody for pan-ebolavirus therapy" *Sci. Rep.* 6, 20514, 2016.
Gilchuk et al., "Multifunctional Pan-ebolavirus Antibody Recognizes a Site of Broad Vulnerability on the Ebolavirus Glycoprotein." *Immunity.* 49(2):363-374, 2018.
Gunn et al., "A Role for Fc Function in Therapeutic Monoclonal Antibody-Mediated Protection against Ebola Virus." *Cell Host Microbe* 24, 221-233 e225, 2018.
Hashiguchi et al., "Structural basis for Marburg virus neutralization by a cross-reactive human antibody" *Cell* 160, 904-912, 2015.
Howell et al., "Antibody Treatment of Ebola and Sudan Virus Infection via a Uniquely Exposed Epitope within the Glycoprotein Receptor-Binding Site" *Cell Rep* 15, 1514-1526, 2016.
Howell et al., "Cooperativity Enables Non-neutralizing Antibodies to Neutralize Ebolavirus" *Cell Rep* 19, 413-424, 2017.
International Preliminary Report on Patentability issued in corresponding PCT Application No. PCT/US2019/041349, dated Jan. 21, 2021.
International Search Report and Written Opinion issued in corresponding PCT Application No. PCT/US2019/041349, dated Nov. 25, 2019.
Janus et al., Structural basis for broad neutralization of ebolaviruses by an antibody targeting the glycoprotein fusion loop » *Nat. Commun.* 9, 3934, 2018.
Keck et al. Macaque Monoclonal Antibodies Targeting Novel Conserved Epitopes within Filovirus Glycoprotein » *J. Virol.* 90, 279-291, 2015.
King et al. "The Marburgvirus-Neutralizing Human Monoclonal Antibody MR191 Targets a Conserved Site to Block Virus Receptor Binding" *Cell Host Microbe* 23, 101-109 e104, 2018.
King et al., "Achieving cross-reactivity with pan-ebolavirus antibodies" *Curr. Opin. Virol.* 34, 140-148, 2019.
Kuzmina et al., "Antibody-Dependent Enhancement of Ebola Virus Infection by Human Antibodies Isolated from Survivors" *Cell. Rep.* 24, 1802-1815, 2018.
Mire and Geisbert, "Neutralizing the Threat: Pan-Ebolavirus Antibodies Close the Loop," *Trends Mol Med* 23, 669 671, 2017.
Misasi et al. "Structural and molecular basis for Ebola virus neutralization by protective human antibodies," *Science* 351, 1343-1346, 2016.
Murin et al., "Structures of protective antibodies reveal sites of vulnerability on Ebola virus" *Proc. Natl. Acad. Sci. U.S.A.* 111, 17182-17187, 2014.
Murin et al., "Structural basis of pan-ebolavirus neutralization by an antibody targeting the glycoprotein fusion loop" *Cell. Rep.* 24, 2723-2732 e2724, 2018.
Oswald et al., "Neutralizing Antibody Fails to Impact the Course of Ebola Virus Infection in Monkeys" *PLoS Pathog.* 3, e9, 2007.
Overdijk et al., Crosstalk between human IgG isotypes and murine effector cells » *Journal Immunol.* 189, 3430-3438, 2012.
Pallesen et al. "Structures of Ebola virus GP and sGP in complex with therapeutic antibodies" *Nat. Microbiol.* 1, 16128, 2016.
The Prevail II Writing Group (R Davey et al.), for the Multi-National Prevail II Study Team. A Randomized, Controlled Trial of ZMapp for Ebola Virus Infection. The New England Journal of Medicine DOI: 10.1056/NEJMoa1604330 (2016).
Qiu et al., "Reversion of advanced Ebola virus disease in nonhuman primates with ZMapp" *Nature* 514, 47-53, 2014.
Saphire and Aman "Feverish Quest for Ebola Immunotherapy: Straight or Cocktail," *Trends Microbiol.* 24, 684-686.
Shedlock et al., "Antibody-mediated neutralization of Ebola virus can occur by two distinct mechanisms" *Virology* 401, 228-235, 2010.
Wec et al., "Antibodies from a Human Survivor Define Sites of Vulnerability for Broad Protection against Ebolaviruses" *Cell* 169, 878-890 e815, 2017.
West et al., "Structural Basis of Pan-Ebolavirus Neutralization by a Human Antibody against a Conserved, yet Cryptic Epitope," *mBio* 9, 2018.
West et al., "Structural Basis of Broad Ebolavirus Neutralization by a Human Survivor Antibody" *Nat. Struct. Mol. Biol.* 26, 204-212, 2019.
Yamayoshi and Kawaoka, "Ebolavirus's Foibles" *Cell* 169, 773-775, 2017.
Zhao et al., Immunization-Elicited Broadly Protective Antibody Reveals Ebolavirus Fusion Loop as a Site of Vulnerability » *Cell* 169, 891-904 e815, 2017.

\* cited by examiner

FIG. 1C

ELISA binding of plasma

FIG. 1A

ELISA binding of B cell line supernatants

| Reactivity | # reactive B cell lines | % reactive cultures of total |
|---|---|---|
| EBOV GP only | 335 | 44 |
| EBOV and BDBV GP | 178 | 23 |
| EBOV and SUDV GP | 22 | 3 |
| EBOV, BDDV, and SUDV GP | 77 | 10 |
| None | 156 | 20 |

Neutralization of plasma (EBOV)

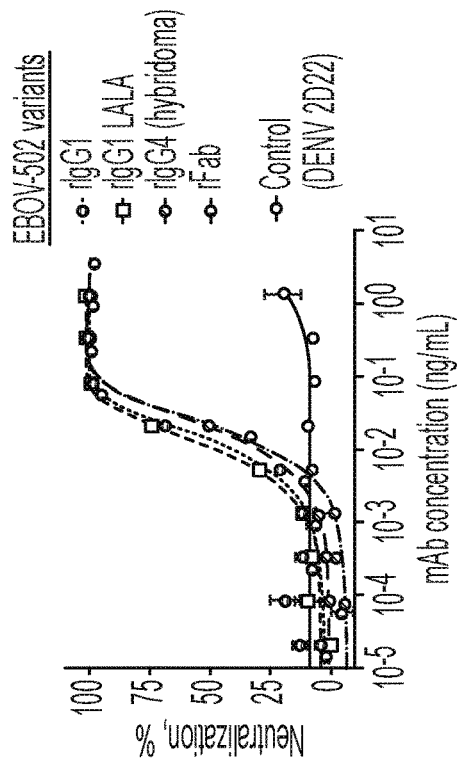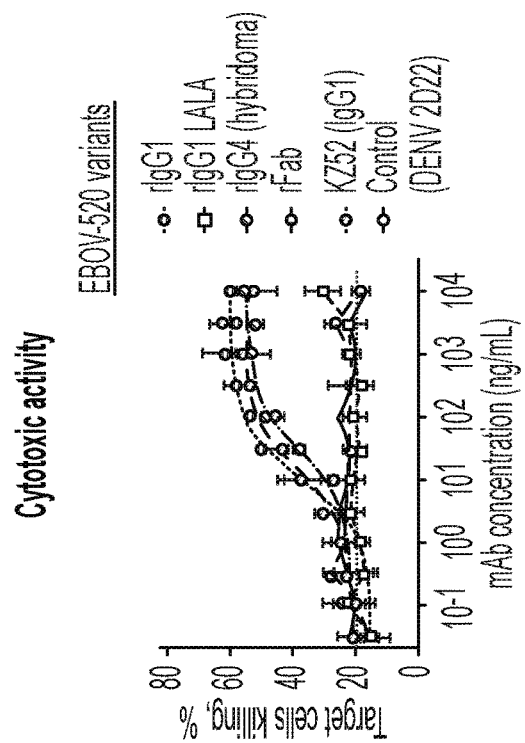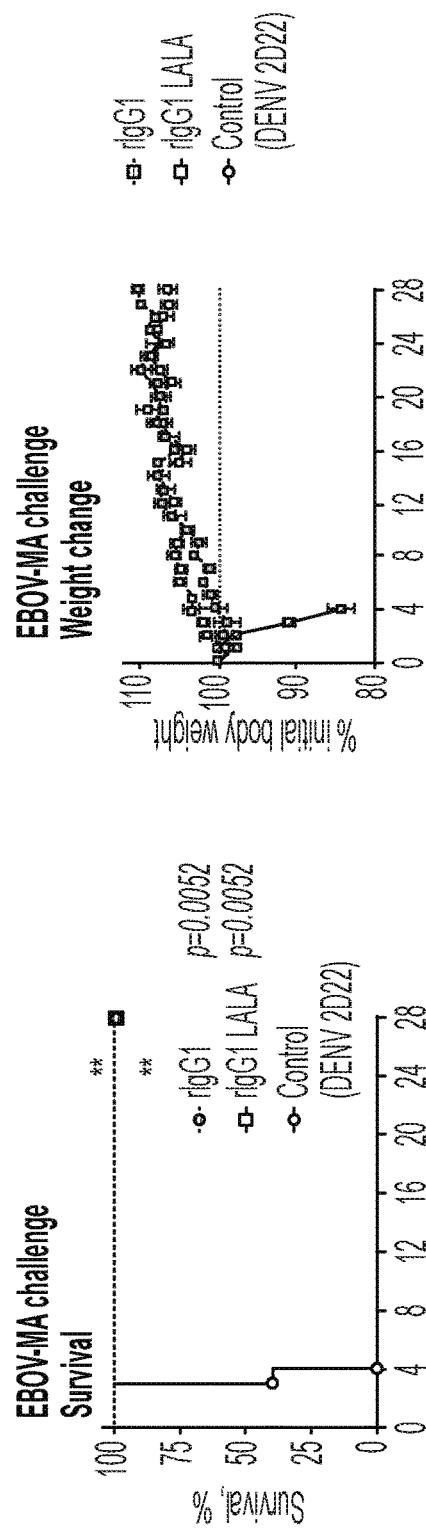
FIG. 3A  FIG. 3B  FIG. 3C  FIG. 3D

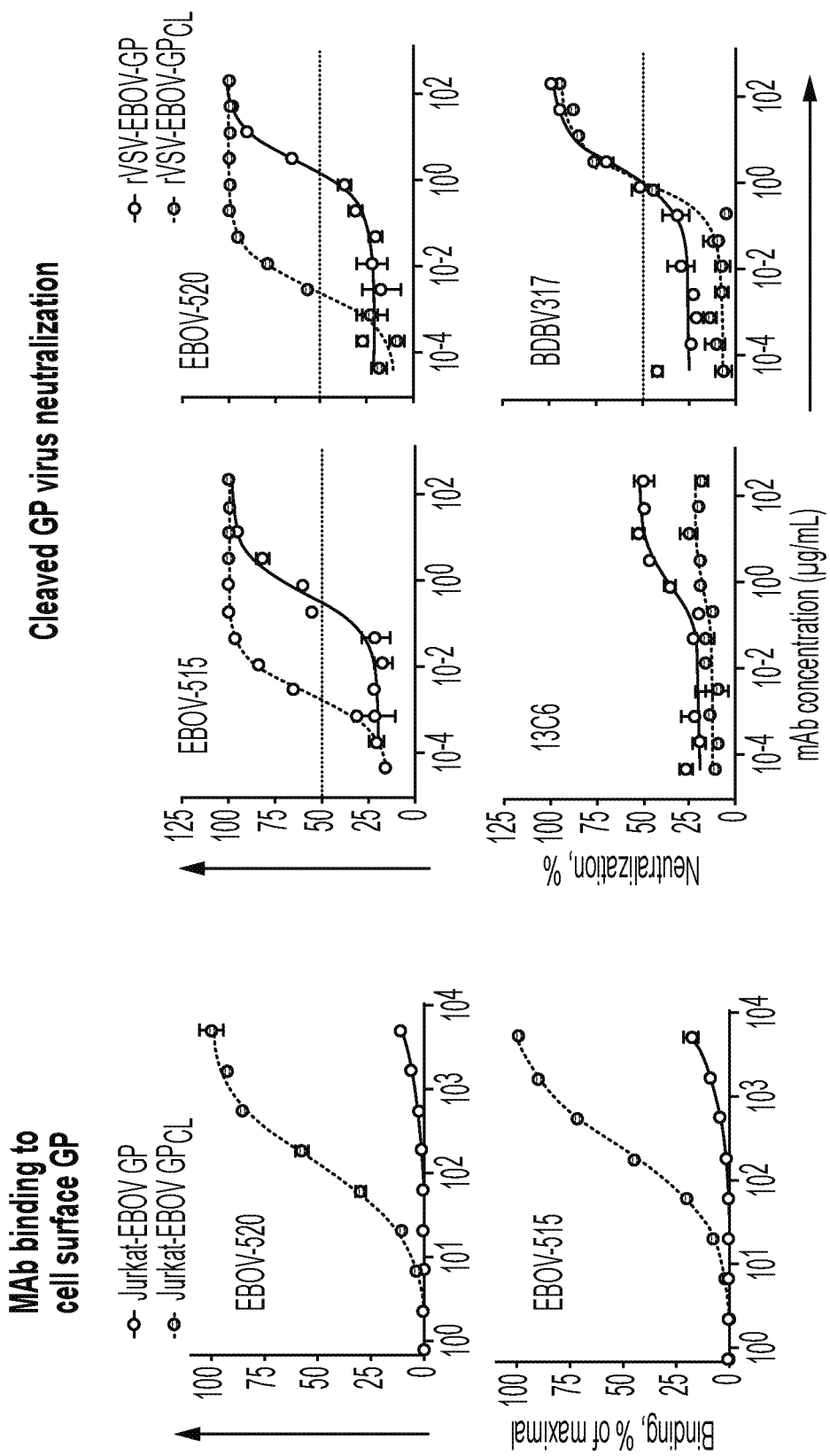

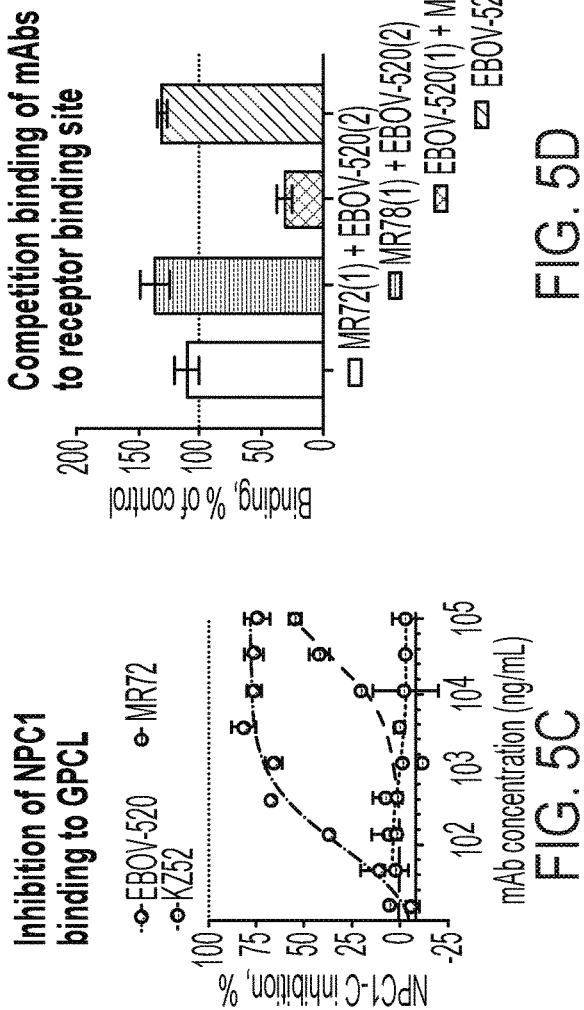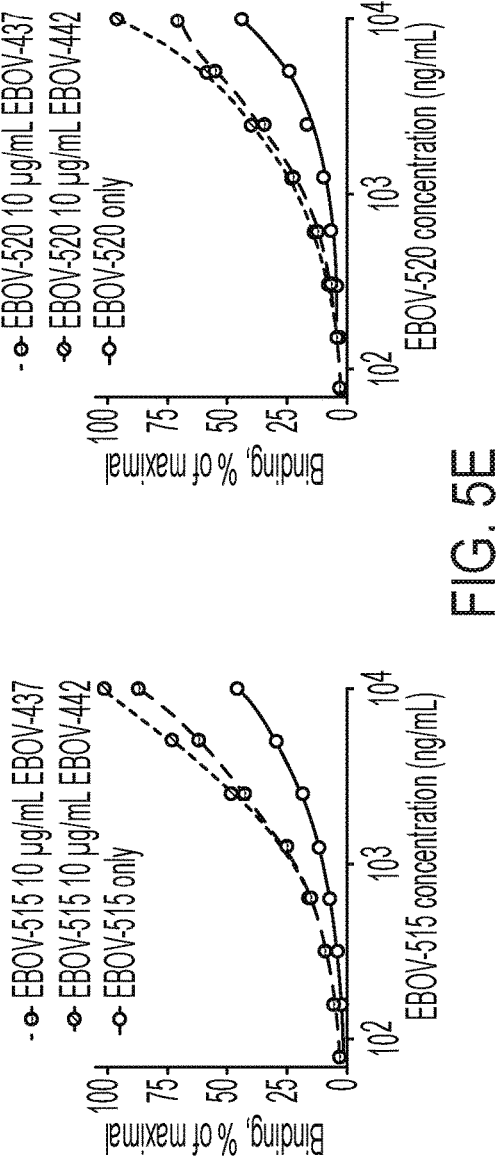
FIG. 5C
FIG. 5D
FIG. 5E

Electron microscopy of EBOV GP/Fab

Side view

Top view

Red: IFL

Blue: EBOV-515
Orange: EBOV-520
Purple: CA45
Green: ADI-15878

FIG. 6A

Escape mutations

EBOV-520         EBOV-515
    Side view

E106K

N512A

N514D

P513L

GP1
GP2
100% conserved
Escape mutation

|  |  | 106 | 512 | 513 514 |
|---|---|---|---|---|
| EBOV, | Makona | YEAGEWAENCYNL | ......... KCNPNLHYWT | KCNPNLHYWT |
| EBOV, | Mayinga | YEAGEWAENCYNL | ......... KCNPNLHYWT | KCNPNLHYWT |
| EBOV, | Kikwit | YEAGEWAENCYNL | ......... KCNPNLHYWT | KCNPNLHYWT |
| BDBV, | Uganda | YEAGEWAENCYNL | ......... KCNPNLHYWT | KCNPNLHYWT |
| SUDV, | Gulu | YEAGEWAENCYNL | ......... KCNPNLHYWT | KCNPNLHYWT |
| SUDV, | Boniface | YEAGEWAENCYNL | ......... KCNPNLHYWT | KCNPNLHYWT |
| TAFV |  | YEAGEWAENCYNL | ......... KCNPNLHYWT | KCNPNLHYWT |

Jurkat-EBOV GP → Jurkat-EBOV GP$_{CL}$

Glycan cap    Base    HR2/MPER

Blue: EBOV-515
Orange: EBOV-520
Purple: CA45
Green: ADI-15878

Viremia

FIG. 13A

Cinical score

FIG. 13B

Weight change

Days after challenge

EBOV-520 IgG4 treated ferrets
-o- 200051F  -□- 199111F
-▽- 197681F  -△- 19275M

Control ferrets (DENV 2D22)
-o- 192921M  -□- 192931M
-△- 197671F  -▽- 198021F

FIG. 13C

Complex of rEBOV-520 and rEBOV-548 Fab with EBOV GP ΔTM by negative stain EM

FIG. 19A rEBOV-520 CDRH3 bound into the 3₁₀ pocket of GPCL

FIG. 19B

Mutations in the β17-β18 loop that enhance binding of rEBOV-520

Complex of rEBOV-548 and rEBOV-520 Fab with GP ΔMucΔTM by cryo-EM

FIG. 20G — Poorly exposed rEBOV-520 epitope

FIG. 20H — rEBOV-548 unmasks rEBOV-520 epitope

GP residues contacting with rEBOV-548 CDRH3

FIG. 21A

GP residues contacting with rEBOV-520 CDRH3

FIG. 21B

FIG. 22A — NHP survival

FIG. 22B — NHP clinical score

FIG. 22C — NHP viremia

FIG. 22D — NHP blood chemistry (ALT, GGT, CRE)

----- Treated (n=5)  —— Untreated (n=1)  —— Historical (n=10)

| Epitope specificity | mAb | IgG subclass | Kinetic binding constant ($K_c$499) to GP TΔM, pM | ELISA binding to GP ΔTM, $EC_{50}$ (ng/mL) | | | Virus neutralization, $IC_{50}$ (ng/mL) | | | Capacity to mediate Fc region effector function[b] | | | Protection against EBOV in mice (% survival)[c] |
|---|---|---|---|---|---|---|---|---|---|---|---|---|---|
| | | | | EBOV | BDBV | SUDV | EBOV | BDBV | SUDV | Neutrophils [Hu], phagocytic score | Monocytes [Hu], phagocytic score | Activated NK cells (Hu), % IFNγ+ | |
| Glycan cap | EBOV-337 | G1 | ND | 3 | 11 | 4 | (62%)[d] | ND[e] | (21%) | 57 | 244 | 5 | ND |
| | EBOV-442 | G1 | ND | 1 | 3 | 6 | 467 | 1,489 | (75%) | 115 | 267 | 10 | 80 |
| | rEBOV-548 | G1 | 41 | 6 | 7 | 132 | 1,601 | 2,262 | (12%) | 73 | 163 | 10 | 40 |
| | c13C6 | G1 | 1,200 | 20 | >[f] | > | > | > | > | 128 | 176 | 10 | 100 |
| GP base (IFL) | EBOV-515 | G1 | 530 | 9 | 15 | 14 | 1,224 | 1,485 | 891 | 26 | 227 | 16 | 100 |
| | rEBOV-520 LALA | G1 | 2,120 | 18 | 45 | 377 | 1,801 | 200 | 1,672 | 19 | 99 | 2 | 100 |
| | rEBOV-542 | G3 | 260 | 11 | 8 | ND | 7,791 | 2,606 | 987 | 79 | 84 | 32 | 100 |
| Negative control | DENV-2D22 | G1 | > | > | > | > | > | > | > | 6 | 63 | 2 | 0 |

Images of Fab-antigen complexes obtained by negative stain EM rEBOV-548 Fab with EBOV GP ΔTM

FIG. 24A rEBOV-520 and rEBOV-548 Fab with EBOV GP ΔTM

FIG. 24B

Enhanced binding to cell surface GP rEBOV-548 potentiates rEBOV-520
[rEBOV-520 AF647] 10 µg/mL

Binding fold-increase normalized to mAb alone:
- 0: 1.0
- 1: 1.5
- 10: 3.2
- 20: 3.9
- 50: 4.4
- 100: 4.6

+ unlabeled rEBOV-548 (µg/mL)

rEBOV-520 potentiates rEBOV-548
[rEBOV-548 AF647] 10 µg/mL

- 0: 1.0
- 1: 1.0
- 10: 1.2
- 20: 1.3
- 50: 1.4
- 100: 1.5

+ unlabeled rEBOV-548 (µg/mL)

Saturated binding
Labeled mAb alone

FIG. 25

FIG. 26A rEBOV-520 bound to intact GP

FIG. 28A rEBOV-520 + rEBOV-548 bound to intact GP

FIG. 28B rEBOV-520 bound to cleaved GP

FIG. 28C

GP binding and virus neutralization

+
++
+++

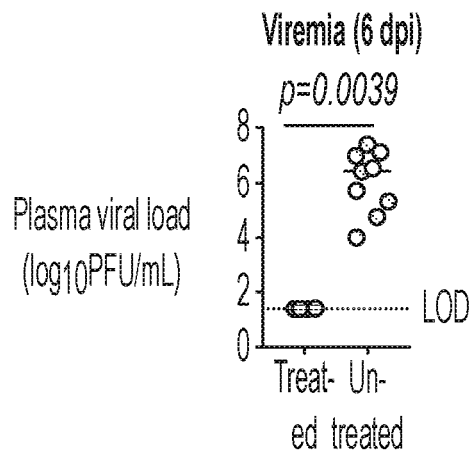
FIG. 29A
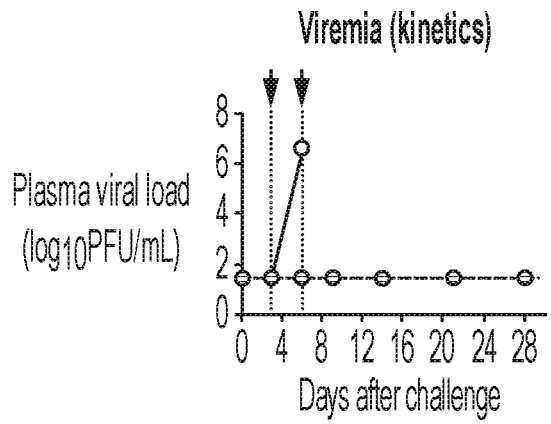
FIG. 29B
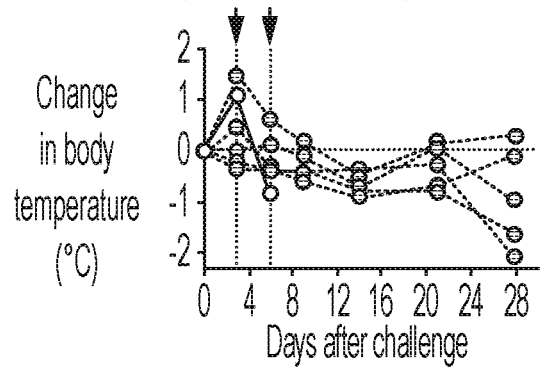
FIG. 29C
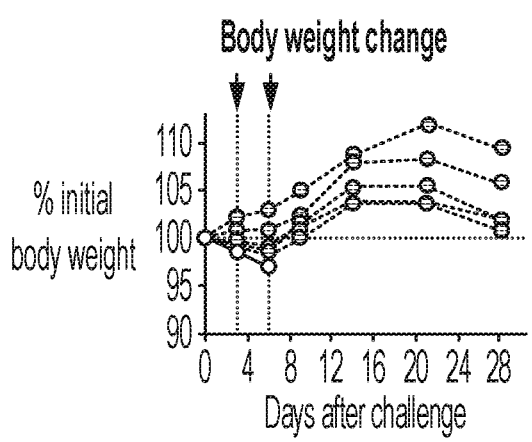
FIG. 29D
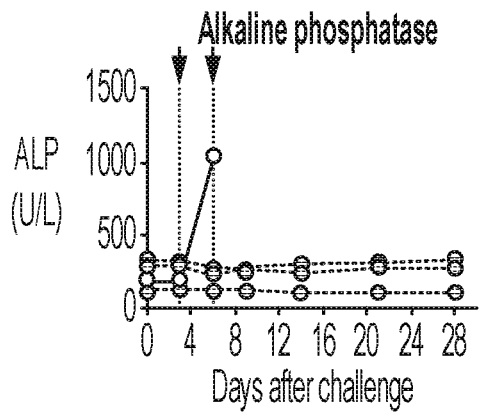
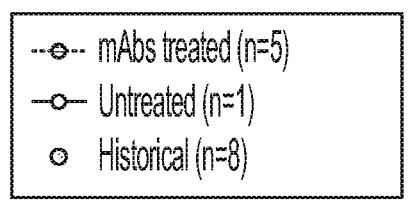
FIG. 29E

PAN-EBOLA VIRUS NEUTRALIZING HUMAN ANTIBODIES AND METHODS OF USE THEREFOR

PRIORITY CLAIM

This application is a national phase application under 35 U.S.C. § 371 of International Application No. PCT/US2019/041349, filed Jul. 11, 2019, which claims benefit of priority to U.S. Provisional Application Ser. No. 62/697,027, filed Jul. 12, 2019, the entire contents of each of which are hereby incorporated by reference.

STATEMENT OF FEDERALLY FUNDED RESEARCH

This invention was made with government support under grant no. U19 AI109711 from the National Institutes of Health and grant no. HDRTA1-13-1-0034 from the Defense Threat Reduction Agency. The government has certain rights in the invention.

BACKGROUND

1. Field of the Disclosure

The present disclosure relates generally to the fields of medicine, infectious disease, and immunology. More particular, the disclosure relates to human antibodies binding to ebolaviruses and methods of use therefor.

2. Background

Ebolaviruses are members of the Filoviridae family which cause a severe disease in humans with 25% to 90% mortality rates and significant epidemic potential. There are no licensed ebolavirus vaccines or treatments. There are five known ebolavirus species: Zaire ebolavirus (EBOV), Bundibugyo ebolavirus (BDBV), Sudan ebolavirus (SUDV), Tai Forest ebolavirus (TAFV), and Reston (RESTV) viruses. EBOV, BDBV, and SUDV are clinically relevant viruses that are known to cause lethal disease in humans (WHO, 2017). The 2013-2016 EBOV epidemic in West Africa was the largest of the known 29 outbreaks of Ebola virus disease (EVD) reported since EBOV was first identified (CDC, 2017), with a total of 28,646 cases and 11,323 deaths identified (Coltart et al., 2017). The Makona variant of the EBOV caused the most recent epidemic. Infections with RESTV are usually asymptomatic in humans, and only one case of non-lethal human infection has been reported for TAFV (CDC, 2017).

The ebolavirus envelope contains a single surface protein, the type I integral membrane glycoprotein (GP), which forms a trimer. The GP is solely responsible for viral attachment to the host cell, endosomal entry, and membrane fusion (Lee and Saphire, 2009), and thus it is also the major target for neutralizing antibodies and vaccine design (Zeitlin et al., 2016). The GP protomer consists of two disulfide-linked subunits, GP1 and GP2. The GP1 subunit has a heavily glycosylated mucin-like domain and a glycan cap, which shields the host receptor binding site (RBS) that binds to domain C of the human endosomal protein Niemann-Pick C1 (NPC1-C). The GP2 subunit contains the internal fusion loop (IFL) and stalk and is anchored into the viral membrane by a transmembrane domain (Lee et al., 2008).

The human monoclonal antibody (mAb) KZ52, which was isolated from a phage display library, recognizes residues of GP1 and GP2 within the "base" region of EBOV GP. This antibody neutralizes virus in vitro but failed to protect non-human primates (NHPs) against EBOV at the doses tested (Oswald et al., 2007). An experimental therapeutic mAb mixture ZMapp comprising three murine-human chimeric EBOV GP-specific mAbs, 2G4 and 4G7 recognizing the base region, and c13C6 recognizing the glycan cap, fully protected NHPs from lethal EBOV challenge (Qiu et al., 2014). This cocktail also exhibited activity when used as treatment of EVD in humans in incomplete clinical trial testing during the recent epidemic (PREVAIL II Writing Group et al., 2016). ZMapp mAbs bind only to the EBOV, however, and do not recognize BDBV or SUDV. The inventors and others have isolated hundreds of new ebolavirus GP-specific mAbs from EBOV or BDBV survivors since the last EVD outbreak. New Abs have been described that recognize diverse antigenic sites on GP, including epitopes on the glycan cap, the IFL, the GP1 head, the GP1/GP2 interface, the RBS, and the stalk (Bornholdt et al., 2016a; Bornholdt et al., 2016b; Corti et al., 2016; Flyak et al., 2016; Furuyama et al., 2016; Howell et al., 2016; Keck et al., 2016; Misasi et al., 2016; Pallesen et al., 2016; Wec et al., 2017; Zhao et al., 2017). It is desirable to isolate pan-ebolavirus mAbs from EBOV survivors, but such clones are rare because of the low level of amino acid sequence homology between the GPs of diverse ebolaviruses (<60%), and also the low accessibility of sites of vulnerability to neutralization on ebolavirus GP (Flyak et al., 2015; Hashiguchi et al., 2015; Murin et al., 2014). Most of the human mAbs isolated to date neutralize only one or two ebolavirus species. There is a medical need for mAb therapeutics that exhibit a pan-ebolavirus pattern of breadth, because the nature of future EVD outbreaks cannot be predicted. Recently, investigators identified the IFL as a site of vulnerability on GP, and they reported the isolation of three broadly neutralizing mAbs that also possessed protective capacity against EBOV, BDBV, and SUDV. One antibody was derived from the B cells of immunized NHPs (Zhao et al., 2017), and two others were isolated from the B cells of a human survivor (Wec et al., 2017). These studies demonstrated that it is possible to isolate broadly neutralizing mAbs against ebolaviruses.

Filoviruses readily acquire mutations in their genomic RNA through error-prone replication (Holmes et al., 2016). It is notable that during the 2013-2016 EVD epidemic, the highest level of amino acid coding changes occurred in the GP (Park et al., 2015; Tong et al., 2015). Such variability raises the possibility the antibody-escape mutants could be selected during the use of therapeutic neutralizing antibodies. Potent pan-ebolavirus human antibodies are needed for use in therapeutic cocktails to resist the emergence of viral escape mutants (Mire and Geisbert, 2017). Furthermore, identifying and defining unique molecular and immunological features of potent human mAbs that mediate protection is important for rational selection of the most effective therapeutic mAb candidates.

SUMMARY

Thus, in accordance with the present disclosure, a method of detecting an ebolavirus infection in a subject comprising (a) contacting a sample from said subject with an antibody or antibody fragment having clone-paired heavy and light chain CDR sequences from Tables 3 and 4, respectively; and (b) detecting ebolavirus in said sample by binding of said antibody or antibody fragment to an ebolavirus antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in ebolavirus antigen levels as compared to the first assay. The antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another embodiment, there is provided a method of treating a subject infected with ebolavirus, or reducing the likelihood of infection of a subject at risk of contracting ebolavirus, comprising delivering to said subject an antibody or antibody fragment having clone-paired heavy and light chain CDR sequences from Tables 3 and 4, respectively. The antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may be administered prior to infection or after infection. The subject may be a pregnant female, a sexually active female, or a female undergoing fertility treatments. Delivering comprises antibody or antibody fragment administration, or genetic delivery with an RNA or DNA sequence or vector encoding the antibody or antibody fragment. The antibody or antibody fragment may further comprise a cell penetrating peptide and/or is an intrabody.

A further embodiment involves a monoclonal antibody, wherein the antibody or antibody fragment is characterized by clone-paired heavy and light chain CDR sequences from Tables 3 and 4, respectively. The antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody, or is bispecific antibody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may further comprise a cell penetrating peptide and/or is an intrabody.

In yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be a chimeric antibody or a bispecific antibody. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may further comprise a cell penetrating peptide and/or is an intrabody.

An additional embodiment comprises a vaccine formulation comprising one or more antibodies or antibody fragments characterized by clone-paired heavy and light chain CDR sequences from Tables 3 and 4, respectively. The at least one antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The at least one antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The at least one antibody fragment may be a recombinant scFv (single chain fragment variable) antibody, Fab fragment, F(ab')$_2$ fragment, or Fv fragment. The at least one of said antibodies is a chimeric antibody, or is bispecific antibody. The at least one antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The at least one antibody or antibody fragment may further comprise a cell penetrating peptide and/or is an intrabody.

In still an additional embodiment, there is provide a vaccine formulation comprising one or more expression vectors encoding a first antibody or antibody fragment as defined above. The expression vector(s) may be Sindbis virus or VEE vector(s). The vaccine formulation may be formulated for delivery by needle injection, jet injection, or electroporation. The vaccine formulation may further comprise one or more expression vectors encoding for a second antibody or antibody fragment, such as a distinct antibody or antibody fragment as described above.

In still a further embodiment, there is provided a method of protecting the health of a placenta and/or fetus of a pregnant a subject infected with or at risk of infection with ebolavirus comprising delivering to said subject an antibody or antibody fragment having clone-paired heavy and light chain CDR sequences from Tables 3 and 4, respectively. The antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may be administered prior to infection or after infection. The subject may a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control, and/or reduce viral load and/or pathology of the fetus as compared to an untreated control.

In a further embodiment, there is provided a method of determining the antigenic integrity, correct conformation and/or correct sequence of an ebolavirus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen. The sample may comprise a vaccine formulation or vaccine production batch. Detection may comprise ELISA, RIA, western blot, a biosensor using surface plasmon resonance or biolayer interferometry, or flow cytometric staining. The first antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired variable sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

Also provided are:

a human monoclonal antibody or antibody fragment, or hybridoma or engineered cell producing the same, wherein said antibody or antibody fragment confers broad and potent activity against EBOV, BDBV and SUDV, such as by engagement of a quaternary epitope spanning glycoprotein (GP) 1 and GP2 subunits;

a human monoclonal antibody or antibody fragment, or hybridoma or engineered cell producing the same, wherein said antibody or antibody fragment mediates protection as monotherapy in vivo solely by neutralizing activity, such as wherein said antibody is a naturally-occurring IgG4 antibody or an IgG of another isotype with an altered Fc region sequence eliminating Fc mediated function or FcR binding;

a human monoclonal antibody or antibody fragment, or hybridoma or engineered cell producing the same, wherein said antibody or antibody fragment binds to the glycoprotein (GP) base region and reduces GP binding to the soluble NPC1-C;

a human monoclonal antibody or antibody fragment, or hybridoma or engineered cell producing the same, wherein said antibody or antibody fragment is a pan-ebolavirus glycan cap-specific antibody or antibody fragment, such as one that "primes" the GP to enhance accessibility of the deep base region site of vulnerability; and a composition comprising at least two distinct human monoclonal antibodies or antibody fragments that bind to ebolavirus glycoprotein (GP), wherein said composition comprises (i) a first antibody or antibody fragment that is a pan-ebolavirus glycan cap-specific antibody or antibody fragment, and (ii) a second antibody or antibody fragment that is a pan-ebolavirus base-specific antibody or antibody fragment, wherein said first and second antibodies or antibody fragments synergize in one or more of enhanced GP binding, enhanced ebolavirus neutralization, and/or enhanced protection from infection as compared to each antibody or antibody fragment used alone.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. A small subset of potent mAbs isolated from B cells of survivors of EVD recognize EBOV, BDBV, and SUDV GP. (FIG. 1A) Binding of Abs in donor plasma samples to EBOV, BDBV, and SUDV GP ΔTM was assessed by ELISA. (FIG. 1 B) Neutralization activity of donor plasma was determined using EBOV. (FIG. 1C) Binding of Abs in the supernatants of in vitro expanded B cell cultures to EBOV, BDBV, or SUDV GPs was assessed by ELISA. Each dot indicates results for an individual LCL. Dashed circle indicates the most cross-reactive LCLs. FIGS. 1A-C represented data for a survivor of the DRC EVD epidemic. Mean±SD of triplicates are shown, and data are representative of two independent experiments in FIGS. 1A and 1B. See also Table 51.

FIGS. 2A-F. MAbs EBOV-515 and -520 potently neutralize EBOV, BDBV and SUDV and confer protection against EBOV. (FIG. 2A) Heat map chart summarizing binding, neutralizing, and protective capacity of newly isolated, or previously described (shaded box) mAbs. The red arrow indicates potent broadly neutralizing mAbs. MFI—mean fluorescence intensity. * - incomplete (<100%) virus neutralization at highest tested Ab concentration (200 μg/mL); N/A—not assessed. Protection data by mAbs are from previous reports and included here for comparative purposes. Representative ELISA binding (FIG. 2B) or neutralization (FIG. 2C) by selected broadly reactive mAbs from FIG. 2A. C+ or C− indicates the assay was performed with or without complement, respectively. Means±SD of triplicates are shown. In vivo protective efficacy of broadly neutralizing mAbs against EBOV that assessed by survival (FIG. 2D), weight change (FIG. 2E), and clinical score (FIG. 2F). Groups of C57BL/6 mice were challenged with 1,000 pfu of mouse-adapted EBOV (EBOV-MA), treated with 100 μg of EBOV or irrelevant mAb at 1 dpi, and monitored for 28 days. Mean±SD of triplicates are shown, and data are representative of 2-3 independent experiments in FIGS. 2B and 2C. Mean±SEM are shown, and data represent one experiment with five mice per group in FIGS. 2D-F. **$p<0.01$ (two-sided log rank test). See also FIG. 8 and FIG. 9, and Tables S2 and S3.

FIGS. 3A-D. EBOV-520 possesses Fc region effector function activity but mediates protection principally through virus neutralization. (FIG. 3A) In vitro killing capacity curves for engineered variants of mAb EBOV-520 that determined using SNAP-tagged EBOV GP-expressing 293F cell line as a target and human PBMCs as source of effector cells. Dotted line indicates assay background. (FIG. 3B) Neutralization of EBOV by engineered IgG heavy chain variants of mAb EBOV-520. (FIG. 3C-D) In vivo protective efficacy of EBOV-520 rIgG1 or rIgG1-LALA against EBOV. C57BL/6 mice were challenged with EBOV-MA, treated with indicated mAb in 1 dpi, and monitored for 28 days. Mean±SD of triplicates are shown, and data are representative of two independent experiments in FIGS. 3A and 3B. Mean±SEM are shown, and data represent one experiment with five mice per group in FIGS. 3C and 3D. **$p<0.01$ (two-sided log rank test). See also FIGS. 10A-B and Table S4.

FIGS. 4A-D. EBOV-515 and -520 are specific to the base region of GP and possess a capacity to inhibit GP cleavage. (FIGS. 4A-B) Identification of major antigenic sites for three broadly neutralizing mAbs using a competition binding assay with intact Jurkat-EBOV GP (FIG. 4A), or thermolysin-cleaved Jurkat-EBOV $GP_{CL}$ (FIG. 4B). Numbers indicate the percent binding of the second fluorescently-labeled mAb in the presence of the first unlabeled mAb, compared to binding of the second labeled mAb alone. MAb binding measured by flow cytometry; data shown is representative of three independent experiments. (FIG. 4C) Capacity of bound mAbs to inhibit the exposure of the RBS after EBOV GP→EBOV $GP_{CL}$. Varying concentrations of mAbs (1, 10, 20, or 40 µg/mL) were incubated with Jurkat-EBOV GP, followed by cleavage and measurement of the exposure of the RBS with fluorescently labeled RBS-specific mAb MR78. Dotted line indicates % RBS exposure in the presence of irrelevant dengue virus specific mAb DENY 2D22. (FIG. 4D) Cells displaying GP or $GP_{CL}$ on the surface were fixed, pre-incubated with fluorescently-labeled mAb at neutral pH, and then exposed to neutral or low pH for 60 min. MAb binding was assessed by flow cytometry. Stability of binding was expressed as the percent of the control (maximal binding) when cells were analyzed immediately after staining and without exposure to the neutral or low pH. Mean±SD of triplicates are shown, and data are representative of 2-3 independent experiments. See also FIGS. 11A-D.

FIGS. 5A-E. EBOV-515 and -520 target both, intact GP and cleaved $GP_{CL}$ intermediate to neutralize the virus. (FIG. 5A) Binding curves for EBOV-515 or EBOV-520 using Jurkat-EBOV GP or Jurkat-EBOV $GP_{CL}$. (FIG. 5B) Neutralization curves for EBOV-515 or EBOV-520 or control mAbs 13C6 or BDBV317 using rVSV/EBOV-GP or rVSV/EBOV-$GP_{CL}$. Means±SD of triplicates are shown. FIG. 5C) Capacity of mAbs to inhibit NPC1-C binding to EBOV $GP_{CL}$. Varying concentrations of mAbs were incubated with cells displaying EBOV $GP_{CL}$, then with purified NPC1-C tagged with FLAG-epitope. Complexes were detected with anti-FLAG antibodies by flow cytometry. (FIG. 5D) Competition binding of EBOV-515 or EBOV-520 mAbs with RBS-specific mAbs MR72 or MR78 using Jurkat-EBOV $GP_{CL}$. Numbers indicate the percent binding of the second fluorescently-labeled mAb in the presence of the first unlabeled mAb, compared to binding of second labeled mAb alone (left panel). Change in binding (right panel) when compared to that of second mAb alone (dotted line). (FIG. 5E) Binding curves of EBOV-515 and -520 mAbs Jurkat-EBOV GP in the presence of a fixed concentration (10 µg/mL) of glycan cap-specific mAbs EBOV-437 or EBOV-442. Mean±SD of triplicates are shown, and data in FIGS. 5A and 5C-E are representative of two independent experiments. Data in FIG. 5B represent one experiment. See also FIGS. 11A-D.

FIGS. 6A-B. EBOV-515 and -520 recognize distinct vulnerable epitopes in the ebolavirus GP base region. (FIG. 6A) 3D reconstructions of Fab/EBOV GP ΔTM complexes from single particle electron microscopy (EM) experiments. EM density for Fab of EBOV-515, or EBOV-520, or previously described CA45, or ADI-15878 are superimposed to compare the angle of approach for these four GP base-reactive mAbs. A model of the EBOV GP ΔTM trimer was fitted into the EM density. (FIG. 6B) Escape mutations for EBOV-515 or EBOV-520 mAbs identified by alanine-scanning mutagenesis of cell surface-displayed EBOV GP library or by sequence analysis of escape mutant viruses (top panel). Conservation of ebolavirus GP sequences within putative antigenic sites (bottom panel). [YEAGEWAENCYNL=SEQ ID NO:211; KCNPNLHYWT=SEQ ID NO:212; KCNPNLHYWT=SEQ ID NO:213] See also FIGS. 12A-D.

FIGS. 7A-D. EBOV-515 and -520 mediate protection against heterologous SUDV or BDBV challenge. (FIG. 7A) Groups of STAT1 KO mice (n=5 per group) were inoculated with 1,000 pfu of wt SUDV strain Gulu), treated at 1 dpi with 10 mg/kg of indicated mAb, and monitored for 28 days. (FIG. 7B) Groups of guinea pigs (n=4-5 per group) were inoculated with 1,000 pfu of SUDV-GA (guinea-pig adapted strain Boniface), treated on dpi 1 and 3 with mg of indicated mAb and monitored for 28 days. Historical controls shown included untreated animals from a separate study for comparative purposes. (FIG. 7C) Ferrets (n=4 per group) were inoculated with BDBV, treated on 3 and 6 dpi with indicated mAb by i.p. injection, and monitored for 28 days. (FIG. 7D) A comparison of viral load in blood that was determined at 6 dpi for treated or control animals, as in FIG. 7C. Median of titer for each group is shown. Data in FIGS. 7A-D represent one experiment. Survival curves were estimated using the Kaplan Meier method and curves compared using the two-sided log rank test. Viral titers were compared using a Mann-Whitney U test. *$p<0.05$, and **$p<0.01$. See also FIGS. 13A-C and FIG. 14.

(FIG. 10A) Heat map of Fc-mediated functional activity for a selected panel of broadly reactive mAbs. Purified mAbs were assessed at 5 µg/mL by the indicated in vitro assays, and the results were compared to the controls. The HIV-specific mAb 2G12, and glycan cap-specific mAb c 13C6 served as a negative (−) or positive (+) controls, respectively. The red arrow indicates newly identified bNAbs. * Indicates Z-score: $z=(x−\mu)/\sigma$, where x is raw score (a phagocytic score, or MFI, or percent activated cells that determined as described in the Methods Details section), $\mu$ is the mean of the population, and 6 is the standard deviation of the population. (FIG. 10B) Functional capacity curves for IgG heavy chain engineered variants of bNAb EBOV-520. Mean±SD of duplicates are shown for ADCP and ADNP assays. NK activation data are representative for one of two biological replicates.

FIGS. 11A-D. EBOV-515 and -520 use several mechanisms to facilitate virus neutralization, related to FIGS. 4A-D and FIGS. 5A-E. (FIG. 11A) Capacity of mAbs to inhibit RBS exposure after GP to $GP_{CL}$ cleavage using Jurkat-EBOV GP. Cells were pre-incubated with 40 µg/mL of indicated mAb before cleavage with thermolysin. RBS exposure was determined by binding of fluorescently labeled RBS-specific mAb MR78. Binding of MR78 mAb alone to EBOV GP (crosshatch) or to EBOV $GP_{CL}$ (white) served as negative or positive controls, respectively. (FIG. 11B) Fold change in mAb binding after EBOV GP to EBOV $GP_{CL}$ cleavage using cell surface display. Each mAb was tested at 5 µg/mL. Positive values indicate increase in binding, and negative values indicate decrease, respectively. (FIG. 11C) Capacity to inhibit receptor binding. Binding of soluble NPC1-C to $GP_{CL}$ was assessed after incubation of Jurkat-EBOV $GP_{CL}$ with individual mAbs. EBOV-520 and MR72, but not EBOV-515, KZ52, or BDBV317 mAbs inhibit NPC1-C binding. Binding of NPC1-C to Jurkat-EBOV $GP_{CL}$ or Jurkat-EBOV cells served as controls. MAbs were assessed at 50 µg/mL. (FIG. 11D) Identification of mAbs that cooperated in binding with EBOV-515 or -520 mAbs. A mixture of individual unlabeled non-competing mAb and fluorescently-labeled EBOV-515 or -520 mAb was incubated with Jurkat-EBOV GP, followed by flow cytometric analysis. Binding of fluorescently-labeled EBOV-515 or -520 alone served as a control to define 100% binding activity (dotted line). Binding to untransduced Jurkat cells served as a negative control for the assay background. Red arrows indicate two mAbs that cooperated in binding with EBOV-515 or -520. Mean±SD of triplicates are shown. Data shown are representative of 2-3 experiments.

FIGS. 12A-D. EBOV-515 and -520 recognize distinct vulnerable epitopes in the ebolavirus GP base region, related to FIGS. 6A-B. (FIG. 12A) 2D class average of EBOV-520 Fab bound to EBOV GP ΔTM determined by single particle EM. (FIG. 12B) 3D reconstructions of Fab/EBOV GP ΔTM complexes from single particle EM studies. Fab of EBOV-515, EBOV-520, CA45, or ADI-15878 were superimposed to compare the angle of approach for newly identified (EBOV-515 and -520) and previously reported (CA45 and ADI-15878) broadly neutralizing base mAbs. A model of EBOV GP ΔTM trimer was fitted into the density. (FIG. 12C-D) Shotgun mutagenesis epitope mapping of EBOV-520. (FIG. 12C) Identified two critical clones E106A and N512A (shown in red) that showed specifically reduced binding for EBOV-520 Fab (<30% of binding to wt EBOV GP), but a high level of binding to the control mAb. (FIG. 12D) Mutation to of either E106 and N512 to alanine reduced EBOV-520 binding (striped bars) but did not affect binding of control mAbs EBOV237 (crosshatch bars) or BDBV425 (white bars). Error bars represent the mean and range (half of the maximum minus minimum values) of at least two replicates.

FIGS. 13A-C. EBOV-520 mediates protection against BDBV in ferret challenge model, related to FIGS. 7A-D. Groups of male and female ferrets (denoted with M or F suffix to animal number) were inoculated with 1,000 PFU of BDBV, treated on 3 and 6 dpi with 18 mg of the EBOV-520 IgG4 or control DENY 2D22 mAb by i.p. injection, and monitored for 28 days. (FIG. 13A) Viral burden measured in blood using plaque assay is shown. Mean of technical duplicates is shown. (FIG. 13B) Clinical score is shown. +, diseased animal that was euthanized as mandated by IACUC. ++, animal found dead (8 dpi) between observations prior to reaching the pre-determined clinical score and despite the increased observation schedule. (FIG. 13C) Body weight change is shown. Data represent one experiment.

(FIG. 16A) In vitro killing capacity curves for IgG1-engineered variants of mAbs determined using SNAP-tagged EBOV GP-expressing 293F cell line as a target and human PBMCs as source of effector cells. Dotted line indicates assay background. (FIG. 16B) EBOV, BDBV, or SUDV neutralization. Viruses encoding eGFP were incubated with increasing concentrations of purified mAbs and infection was determined at 3 days post-inoculation by measuring eGFP fluorescence in cells. (FIG. 16C) Binding of candidate mAbs to intact cell surface displayed EBOV GP (solid shapes) or cleaved EBOV $GP_{CL}$ (open shapes). Fluorescently-labeled mAbs were incubated with a suspension of cells from a Jurkat cell line that was stably transduced with EBOV GP (Jurkat-EBOV GP), or the same cells treated with thermolysin to cleave GP (Jurkat-EBOV $GP_{CL}$); binding was assessed by flow cytometry. Dotted lines (black) indicate a dynamic range of mAb binding to the GP. Dashed lines show estimated curve slopes based on a constraint for saturating binding values. Mean±SD (n=3 replicates) from a representative experiment are shown in FIGS. 16A-C. See also Table S5.

FIGS. 17A-D. Complementary mechanisms of action by mAbs comprising the cocktail. (FIG. 17A) 2D class averages of Fab/EBOV GP ΔTM complexes by negative stain EM of Fab/EBOV GP ΔTM complexes demonstrate simultaneous binding of rEBOV-520 and rEBOV-548 to GP. (FIG. 17B) Enhanced binding to cell surface displayed GP in the cocktail of rEBOV-520/rEBOV-548. Binding to Jurkat-EBOV, -BDBV, or -SUDV GP was assessed using Alexa Fluor 647 (AF647) labeled mAb rEBOV-520 or rEBOV-548 alone (patterned shape), or AF647-labeled mAb titrated into a fixed concentration (20 µg/mL) of unlabeled partner mAb (open shape), as indicated. The effect of antibody composition on the GP binding level was assessed by overall test using two-way ANOVA. Saturated binding was estimated as in FIG. 16C. Arrows show comparisons for -fold change in binding to the GP by the mixture of two mAbs or the labeled mAb alone. (FIG. 17C) Enhanced neutralization of SUDV by rEBOV-520 in the presence of non-neutralizing mAb rEBOV-548. Virus was incubated with increasing concentrations of rEBOV-520 alone (patterned shape), or rEBOV-520 titrated into a fixed concentration (20 µg/mL) of rEBOV-548 (open shape). Percent SUDV neutralization by rEBOV-548 alone (20 µg/mL) is shown with dotted line. (FIG. 17D) Cooperative enhancement of protection against SUDV infection in mice by non-neutralizing and non-protective mAb rEBOV-548 in the cocktail of rEBOV-520/ rEBOV-548. STAT1 KO mice were inoculated with wt SUDV and treated at 1 dpi with 10 mg/kg rEBOV-520 alone, 10 mg/kg of rEBOV-548 alone, 20 mg/kg rEBOV-520/ rEBOV-548 cocktail (1:1 mixture of each mAb), or DENV 2D22 antibody (control). Survival of the mice group treated with the cocktail was compared to that of the group treated with rEBOV-520 alone using the log-rank (Mantel-Cox) test. Mean±SD (n=3 replicates) from a representative experiment are shown in (FIGS. 17B-C).

FIGS. 18A-D. Molecular determinants for broad ebolavirus activity by the cocktail. (FIG. 18A) Negative stain EM reconstruction of rEBOV-548 Fab was overlaid onto a reconstruction of rEBOV-520 (EMDB-7955) to show these mAbs bind distinct sites on GP. A single protomer of EBOV GP is shown fit into GP density (PDB 5JQ3). (FIG. 18B) Mutations to alanine in indicated residues that reduced EBOV-548 binding (<25% of binding to WT EBOV GP, striped bars) but did not affect binding of control mAbs BDBV425 (crosshatch bars) or rEBOV-520 (white bars) were identified (top panel). The exception is the W275A mutation that reduced binding of BDBV425, because W275 is part of the BDBV425 epitope on the GP. Error bars represent the mean and range (half of the maximum minus minimum values) of at least two replicates. Identified epitope residues are shown on EBOV GP trimer (PDB 5JQ3) in red (bottom panel). (FIG. 18C) Crystal structure of EBOV GP$_{CL}$ in complex with rEBOV-520 Fab. EBOV GP$_{CL}$ is shown in surface representation with GP1 (dark gray) and GP2 (light gray). rEBOV-520 Fab is shown in cartoon representation with the heavy chain in dark gray and the light chain in light gray. The approach angle of ADI-15946 is indicated with a dashed arrow. (FIG. 18D) The footprints of rEBOV-520 or ADI-15946 Fab on EBOV GP$_{CL}$ (represented as in FIG. 18C). The location of the non-conserved EBOV GP residue N506 is indicated within a dashed circle. See also Table S6.

FIGS. 19A-B. Binding site of principal neutralizing mAb rEBOV-520 includes the $3_{10}$ pocket that is fully exposed in GP$_{CL}$ but masked by the 1117-1118 loop in intact GP. (FIG. 19A) An enlarged view showing occupation of the $3_{10}$ pocket of the GP by rEBOV-520 CDRH3 residues. Ten residues of the CDRH3 tip are shown in cartoon/sticks. EBOV GP$_{CL}$ is shown in surface representation with GP1 (dark gray) and GP2 (light gray). The $3_{10}$ pocket residues involved in the interface with rEBOV-520 CDRH3 and that showed a decrease in hydrogen-deuterium binding to uncleaved GP as determined by HDX-MS, are mapped onto the surface of GP1 (upper dashed outline) and GP2 (lower dashed outline). (FIG. 19B) Individual alanine mutation of six residues in the β17-β18 loop increased binding by mAb EBOV-520 (striped bars) but did not affect binding of a recombinant form of the GP base mAb KZ52 (white bars) were identified (top panel). Mean and range (half of the maximum minus minimum values) of at least two replicate data points are shown. Positions of identified residues in the β17-β18 loop are shown on EBOV GP (PDB 5JQ3) with grey spheres (bottom panel).

FIGS. 20A-H. Structural basis of rEBOV-520 and rEBOV-548 cooperativity illuminated by cryo-EM. (FIG. 20A) Cryo-EM structure of EBOV GP ΔMucΔTM bound to rEBOV-548 Fab and rEBOV-520 Fab. Shown is a side view (left) and top view (right) in relation to the viral membrane. Fab constant domains were excluded by masking. (FIG. 20B) The crystal structure of apo-EBOV GP ΔMucΔTM (PDB XXXX) with the (318-(318' region and the β17-β18 loop. On the right is the EBOV ΔMucΔTM:rEBOV-520/rEBOV-548 structure, with the rEBOV-548 CDRH3 loop, displacing the β18-β18' region as well as the β17-β18 loop, which has been replaced by the rEBOV-520 CDRH3 loop. (FIG. 20C) The rEBOV-548 LC makes a single interaction with GP1 at residue D117 through Q27$_{L1}$. (FIG. Enlarged view of the rEBOV-520 epitope overlaid with the unliganded structure of EBOV GP ΔMucΔTM. (FIG. 20E) The β17-β18 loop and the base of the al helix in the glycan cap presenting in the unliganded GP structure interfere with rEBOV-520 binding. (FIG. 20F) In the rEBOV-520/rEBOV-548 bound GP structure, the al helix has been pulled back and the β17-β18 loop displaced, allowing rEBOV-520 to bind more efficiently. (FIGS. 20G-H) A cartoon of proposed cooperativity mechanism by the cocktail of rEBOV-520 and rEBOV-548 showing that rEBOV-520 must overcome interference of the β17-β18 loop and al helix in apo-GP (FIG. 20G); when rEBOV-548 binds, the (318-(318' region is displaced and the glycan cap moved, along with the β17-β18 loop, to allow greater binding of rEBOV-520 (FIG. 20HG). See also Table S7.

FIGS. 21A-B. Principles of molecular mimicry of rEBOV-520 and rEBOV-548 interaction with the GP. (FIG. 21A) The rEBOV-548 CDRH3 loop makes contacts along the 1317 sheet in GP1 (from K272-K276), forming several hydrogen bonds within an extended beta sheet in the glycan cap (black dotted lines) and mimic this interaction by the 13184318' region in the unliganded structure. Another key contact is with W275, which is cradled within a hydrophobic pocket formed by the tip of the CDRH3 at W108 and H112. (FIG. 21B) The rEBOV-520 CDRH3 loop interacts with the $3_{10}$ pocket residues and an additional portion of GP when the glycan cap is intact. These interactions include W100 with N512 in GP1 that mimics interaction by the 017-018 loop residue in the unliganded structure, Y108 with K510 in GP2, Y106 with T77 and a hydrophobic patch in GP1 and T104 with the base of the α1 loop at P250 in GP1. See also Table S7.

FIGS. 22A-D. Therapeutic potency of the cocktail in nonhuman primates. Animals received a lethal dose of the EBOV Kikwit isolate intramuscularly (i.m.) on day 0 and were treated with total 30 mg/kg of the cocktail (1:1 mixture of each mAb) intravenously on 3 and 6 dpi (n=5). The contemporaneous control was an untreated NHP challenged with the virus (n=1). (FIG. 22A) Kaplan-Meier survival plot. (FIG. 22B) Clinical score. (FIG. 22C) Kinetics of blood viral load as determined by qRT-PCR. (FIG. 22D) Selected blood chemistry measurements: ALT, alanine aminotransferase; GGT, gamma-glutamyl transpeptidase; CRE, creatinine. MAb treatment times are indicated with vertical dotted lines and arrows. Dashed line curves indicate treated, and solid lines indicate untreated animals in FIGS. 22A-D. Ten historical controls (grey) are shown for comparative purposes in FIG. 22A. The horizontal dotted line in FIG. 22B indicates the clinical score threshold for euthanasia. The horizontal dotted line in FIG. 22C indicates the limit of detection (LOD) for genome equivalents (GEq), which was 3.7 log$_{10}$ (GEq/mL); each measurement represents the mean of technical duplicates. See also Tables S8-11.

FIGS. 23A-E. Binding and functional activities of two identified class representatives of human mAbs that bind cooperatively to the GP. Related to FIGS. 16A-C. (FIG. 23A) Heat map chart of binding and functional activities of mAbs described in this study. MAbs c13C6 and DENY 2D22 are positive and negative controls, respectively, that are shown for comparative purposes. (FIG. 23B) Binding of mAbs rEBOV-520 LALA and rEBOV-548 IgG1 to EBOV, BDBV, or SUDV GP ΔTM was assessed by ELISA. Mean±SD (n=3 replicates) are shown. (FIG. 23C) Fc-mediated effector function activities mediated by rEBOV-520 LALA and rEBOV-548 IgG1 that were measured as in (FIG. 23A). Data shown as mean±SD of triplicate measurements using NK cells from three donors, and as mean±SD of technical triplicates for neutrophils or THP-1 cell line. MAbs c13C6, DENY 2D22, and rEBOV-520 LALA served as controls. (FIG. 23D) In vivo efficacy of rEBOV-548 IgG1 against EBOV was assessed by survival. C57BL/6 mice were challenged with mouse-adapted EBOV-MA, treated with mAb (~5 mg/kg) at 1 dpi, and monitored for 28 days. Kaplan-Meier survival plots are shown, and Mantel-Cox test was used to compare treatments. (FIG. 23E) Sensorgrams for rEBOV-520 LALA and rEBOV-548 IgG1 interactions with EBOV GP. Dashed lines show curve fits to a 1:1 binding model. [a]Measurements for mAbs from a previous report (Gilchuk et al., 2018) and for new mAbs that were identified in this study are included. Measurements for c13C6 are from previous reports and are included here for comparative purposes. [b]Measured with EBOV GP-coupled beads or plate-immobilized GP at single mAb concentration as detailed in the STAR METHODS. [c]Therapeutic protection in mice after ~5 mg/kg mAb treatment as detailed in the Experimental Procedures. [d]Incomplete (<100%) virus neutralization at highest tested Ab concentration (200 µg/mL), % symbol indicates percent virus neutralization. [e]Not determined (ND) [f]Symbol > indicates that neutralizing activity was <10% at the highest mAb concentration tested (200 µg/mL).

FIGS. 24A-B. Negative stain EM of the cocktail candidate mAbs that bound to the GP. Related to FIGS. 17A-D. (FIG. 24A) 2D class average (left) or 2D reconstructions (right) of rEBOV-548 Fab bound to EBOV GP ΔTM, as determined by single particle EM. rEBOV-548 Fab is shaded gray. (FIG. 24B) 2D class average (left) or 2D reconstructions (right) of rEBOV-548 and rEBOV-520 Fab that bound simultaneously to EBOV GP ΔTM, as determined by single particle EM. rEBOV-548 Fab and rEBOV-520 Fab are shaded gray.

FIG. 25. Enhanced binding of rEBOV-520 or rEBOV-548 to cell surface displayed GP mediated by binding of partner mAb in the cocktail. Related to FIGS. 17A-D. Binding to Jurkat-EBOV GP cells was assessed by flow cytometry from a single concentration (10 µg/mL) of AF647-labeled mAb alone, or the same labeled mAb that was mixed with indicated increasing concentrations (0 to 100 µg/mL) of unlabeled partner mAb of the cocktail. Binding of labeled rEBOV-520 increased steadily, up to 4.6-fold, with the increase of unlabeled rEBOV-548 concentration, as shown in the left panel. Binding of labeled rEBOV-548 increased steadily, up to 1.5-fold, with the increase of unlabeled rEBOV-520 concentration, as shown in the right panel. Numbers above each bar indicate fold change in relative fluorescence values when binding to the GP by the mixture of two mAbs compared to that of labeled mAb alone. Saturated binding values were estimated from binding of rEBOV-520 (10 µg/mL) to $GP_{CL}$ as detailed in the Experimental Procedures. Mean±SD of technical triplicates from a representative experiment are shown.

FIGS. 26A-B. Molecular surface of $GP_{CL}$ with rEBOV-520 footprint and HDX-MS analysis of deuterium binding to the $3_{10}$ pocket residues. Related to FIGS. 19A-B. (FIG. 26A) The surface of EBOV $GP_{CL}$ is shown in surface representation, and rEBOV-520 Fab is shown in ribbon representation from a crystal structure of the complex. GP1 is dark gray, GP2 is light gray, rEBOV-520 heavy chain is shown in orange, and rEBOV-520 light chain is shown in light orange. The footprint of EBOV-520 is shown with CDRH1, CDRH2, CDR3, CDRL1, CDRL2, and CDRL3 labeled arrows. The borders of the $3_{10}$ pocket are indicated with a dashed white line. (FIG. 26B) Difference map (GP ΔTM (SEQ ID NO:214) minus $GP_{CL}$ (SEQ ID NO:215)) of deuterium binding to the $3_{10}$ pocket residues involved in the interface with rEBOV-520 CDR H3 as in FIG. S4A. Horizontal rows indicate the respective time point tested. Residues that were removed after thermolysin cleavage of GP ΔTM and not present in $GP_{CL}$ are shown with dashes. The percentage of deuterium level change is represented as a gradient decrease or increase of deuteration level in GP ΔTM when compared to $GP_{CL}$. The first box (GP1) and the second box (GP2) show the $3_{10}$ pocket epitope residues determined from FIG. 26A.

FIGS. 28A-C. Structural basis of rEBOV-520 and rEBOV-548 cooperativity illuminated by cryo-EM. Related to FIGS. 20A-H. (FIG. 28A) In the full-length glycoprotein, rEBOV-520 must displace the β17-β18 loop, likely accounting for the lower GP binding and virus neutralization by rEBOV-520 alone. (FIG. 28B) Upon rEBOV-548 binding to the glycan cap, the β17-β18 loop is displaced and the glycan cap domain is pulled back, facilitating rEBOV-520 binding and enhancing neutralization. However, the CDRH3 loop of rEBOV-520 still interacts with parts of the glycan cap. (FIG. 28C) Without the glycan cap, rEBOV-520 can bind freely, accounting for the greatest level of binding and neutralization to this form of GP.

FIGS. 29A-E. Therapeutic potency of the cocktail in nonhuman primates. Related to FIGS. 22A-D. Animals were treated with mAbs and challenged with virus, as indicated in FIGS. 20A-H. Plasma viral load was assessed by plaque assay on 6 dpi (FIG. 29A) or kinetically (FIG. 29B) at indicated time points after challenge. Each measurement represents the mean of technical duplicates. The horizontal dotted line indicates the limit of detection (LOD) for plaque assay, which was 1.4 $\log_{10}$ PFU/mL. If virus was not detected at lowest tested plasma dilution, titer values were denoted to the assay's LOD. Viral titers in FIG. 29A were compared using a Wilcoxon signed-rank test. Body temperature change FIG. 29C, body weight change FIG. 29D, and alkaline phosphatase measurements that are indicators of EVD and treatment efficacy are shown. Dots indicate individual NHPs in FIG. 29A, and treatment groups in FIGS. 29B-E: solid-stripe shape—treated (n=5), open shape—untreated (this study, n=1), and dashed-stripe shape—untreated historical controls that were assessed at the same time point (n=8). MAb treatment times are indicated with vertical dotted lines and arrows.

DESCRIPTION OF ILLUSTRATIVE EMBODIMENTS

Figures 4A, 4B:
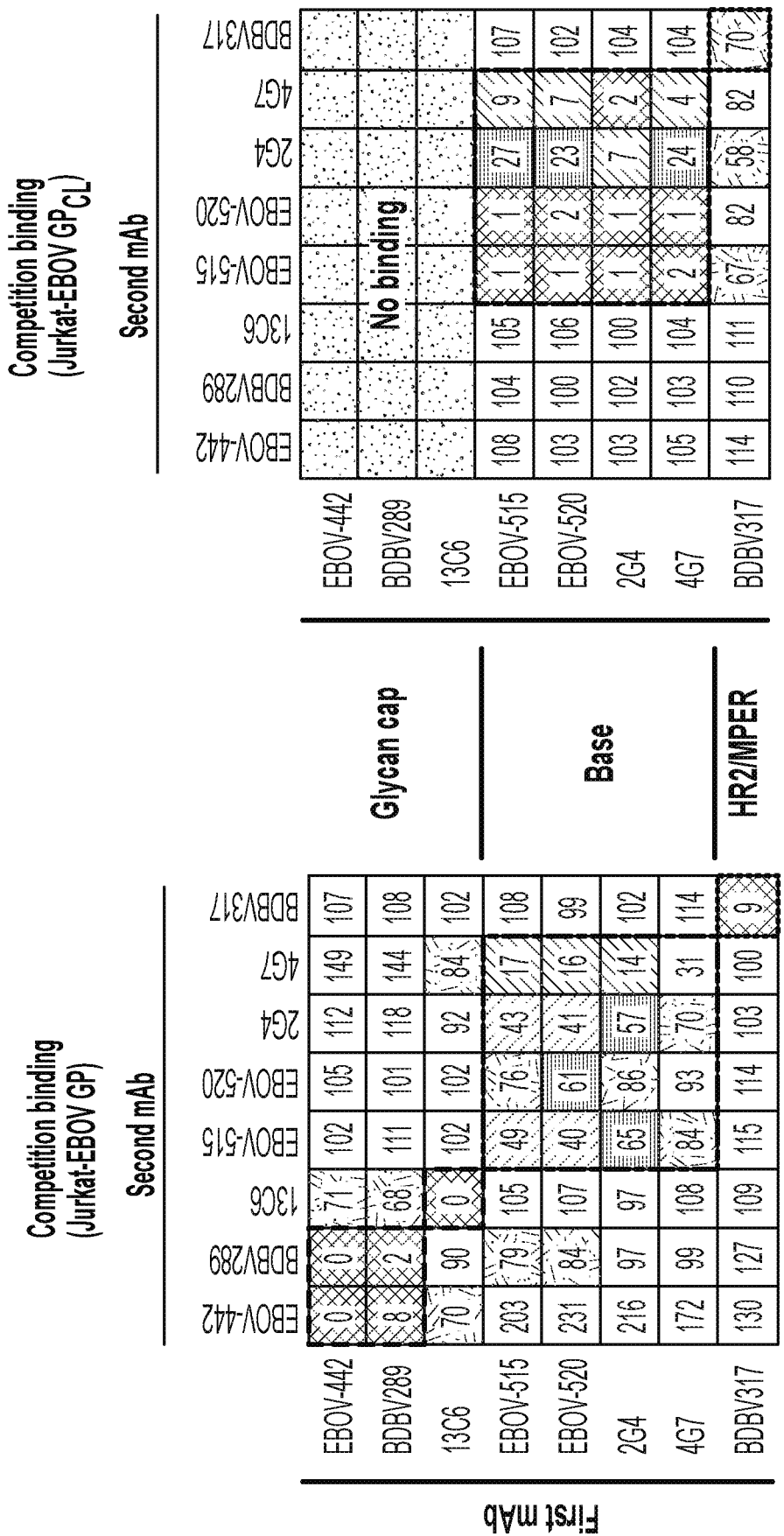

As discussed above, ebolaviruses remain a significant health risk in under-developed countries, as well as presenting a pandemic threat to the world in general. Here, the inventors isolated a large panel of naturally occurring broadly reactive human IgG mAbs by surveying about 600 EBOV GP-reactive B cell lines from human survivors of the most recent 2014 outbreak the Democratic Republic of the Congo (DRC) or the 2013-2016 EVD epidemic in West Africa. Two mAbs, designated EBOV-515 and EBOV-520, potently neutralized all three clinically-relevant live ebolaviruses (EBOV, BDBV, and SUDV), and also mediated protection against EBOV, BDBV, or SUDV after monotherapy against lethal disease in mouse, guinea pig, or ferret live virus challenge models. EBOV-515 recognized a novel epitope in the IFL of GP2, a region that was recently defined as the only site of broad vulnerability for human mAbs. EBOV-520 bound near the base of IFL but in an unusual site that with an epitope spanning both GP subunits. Remarkably, EBOV-520 inhibited soluble NPC1-C binding even though its epitope does not reside in the RBS. In-depth analysis of the mechanism of action EBOV-520 and EBOV-515 revealed key features that contributed to the broad reactivity, neutralization, and protection mediated by these mAbs.

The inventors also designed a cooperative two-antibody cocktail against the primary ebolaviruses that are responsible for outbreaks in humans—Ebola (EBOV), Bundibugyo (BDBV), and Sudan (SUDV) viruses (Kuhn, 2017). A comprehensive analysis of >1,800 human mAbs against GP (Gilchuk et al., 2018; unpublished data) was conducted and identified two rare classes of broadly-reactive mAbs that cooperate for binding to GP and neutralization of virus. Crystal structures illuminated a mechanism of cooperative binding of identified mAbs to the GP. These findings suggested a clear rational strategy for a broadly active two-antibody cocktail design based on molecular and structural features of mAbs interaction with ebolavirus GPs. The cocktail offered protection in mice against the most antigenically divergent virus SUDV and demonstrated a high level of therapeutic efficacy against live EBOV challenge in nonhuman primates. Thus, the inventors show that comprehensive study of the epitopes and mechanism-of-action of human mAbs to a virus can facilitate the rational development of a highly protective and broad mAb cocktail using cooperativity based on structural changes in the target protein induced by antibody binding.

Together, the findings suggest high promise for these newly identified human mAbs as components of mAb cocktails that could improve the performance of candidate pan-ebolavirus therapeutics. These and other aspects of the disclosure are described in detail below.

I. EBOLAVIRUSES

The genus Ebolavirus is a virological taxon included in the family Filoviridae, order Mononegavirales. The members of this genus are called ebolaviruses. As discussed above, the five known virus species are named for the region where each was originally identified: Bundibugyo ebolavirus, Reston ebolavirus, Sudan ebolavirus, Taï Forest ebolavirus (originally Cote d'Ivoire ebolavirus), and Zaire ebolavirus.

The EBOV protein VP24 inhibits type I and II interferon (IFN) signaling by binding to NPI-1 subfamily karyopherin α (KPNA) nuclear import proteins, preventing their interaction with tyrosine-phosphorylated STAT1 (phospho-STAT1). This inhibits phospho-STAT1 nuclear import. A biochemical screen now identifies heterogeneous nuclear ribonuclear protein complex C1/C2 (hnRNP C1/C2) nuclear import as an additional target of VP24. Co-immunoprecipitation studies demonstrate that hnRNP C1/C2 interacts with multiple KPNA family members, including KPNA1. Interaction with hnRNP C1/C2 occurs through the same KPNA1 C-terminal region (amino acids 424-457) that binds VP24 and phospho-STAT1. The ability of hnRNP C1/C2 to bind KPNA1 is diminished in the presence of VP24, and cells transiently expressing VP24 redistribute hnRNP C1/C2 from the nucleus to the cytoplasm. These data further define the mechanism of hnRNP C1/C2 nuclear import and demonstrate that the impact of EBOV VP24 on nuclear import extends beyond STAT1.

Ebolaviruses were first described after outbreaks of EVD in southern Sudan in June 1976 and in Zaire in August 1976. The name Ebolavirus is derived from the Ebola River in Zaire (now the Democratic Republic of the Congo), the location of the 1976 outbreak, and the taxonomic suffix -virus (denoting a viral genus). This genus was introduced in 1998 as the "Ebola-like viruses." In 2002 the name was changed to Ebolavirus and in 2010, the genus was emended. Ebolaviruses are closely related to Marburg viruses, which are included in family Filoviridae as a separate genus.

Researchers have now found evidence of EBOV infection in three species of fruit bats. The bats show no symptoms of the disease, indicating that they might be spreading it. Researchers found that bats of three species—*Hypsignathus monstrosus*, *Epomops franqueti*, and *Myonycteris torquata*—had either genetic material from the EBOV, known as RNA sequences, or evidence of an immune response to the disease. The bats showed no symptoms themselves. Other hosts are possible as well.

A. Taxonomy

A virus of the family Filoviridae is a member of the genus Ebolavirus if its genome has several gene overlaps, its fourth gene (GP) encodes four proteins (sGP, ssGP, Δ-peptide, and $GP_{1,2}$) using co-transcriptional editing to express $GP_{1,2}$ and ssGP and proteolytic cleavage to express sGP and Δ-peptide, peak infectivity of its virions is associated with particles ≈805 nm in length, its genome differs from that of Marburg virus by ≥50% and from that of ebolaviruses by <50% at the nucleotide level, its virions show almost no antigenic cross reactivity with Marburg virions.

The genera Ebolavirus and Marburgvirus were originally classified as the species of the now-obsolete Filovirus genus. In March 1998, the Vertebrate Virus Subcommittee proposed in the International Committee on Taxonomy of Viruses (ICTV) to change the Filovirus genus to the Filoviridae family with two specific genera: Ebola-like viruses and Marburg-like viruses. This proposal was implemented in Washington, D.C., as of April 2001 and in Paris as of July 2002. In 2000, another proposal was made in Washington, D.C., to change the "-like viruses" to "-virus" resulting in today's Ebolavirus and Marburgvirus.

Each species of the genus Ebolavirus has one member virus, and four of these cause Ebola virus disease (EVD) in humans, characterized by having a very high case fatality rate; the fifth, Reston virus, has caused EVD in other primates. EBOV is the type species (reference or example species) for Ebolavirus, and has the highest mortality rate of the ebolaviruses, and is also responsible for the largest number of outbreaks of the five known members of the genus, including the 1976 EBOV outbreak and the 2013-2017 epidemic with the most deaths. The five characterized species of the Ebolavirus genus are:

Zaire ebolavirus (EBOV). Also known simply as the Zaire virus, EBOV has the highest case-fatality rate, up to 90% in some epidemics, with an average case fatality rate of approximately 83% over 27 years. There have been more outbreaks of EBOV than of any other species. The first outbreak took place on 26 Aug. 1976 in Yambuku. Mabalo Lokela, a 44-year-old schoolteacher, became the first recorded case. The symptoms resembled malaria, and subsequent patients received quinine. Transmission has been attributed to reuse of unsterilized needles and close personal contact. The virus is responsible for the 2014 West Africa EBOV outbreak, with the largest number of deaths to date.

Sudan ebolavirus (SUDV). Like EBOV, SUDV emerged in 1976; it was at first assumed to be identical with EBOV. SUDV is believed to have broken out first amongst cotton factory workers in Nzara, Sudan (now in South Sudan), in June 1976, with the first case reported as a worker exposed to a potential natural reservoir. Scientists tested local animals and insects in response to this; however, none tested positive for the virus. The carrier is still unknown. The lack of barrier nursing (or "bedside isolation") facilitated the spread of the disease. The average fatality rates for SUDV were 54% in 1976, 68% in 1979, and 53% in 2000 and 2001.

Reston ebolavirus (RESTV). This virus was discovered during an outbreak of simian hemorrhagic fever virus (SHFV) in crab-eating macaques from Hazleton Laboratories (now Covance) in 1989. Since the initial outbreak in Reston, Virginia, it has since been found in nonhuman primates in Pennsylvania, Texas, and Siena, Italy. In each case, the affected animals had been imported from a facility in the Philippines, where the virus has also infected pigs. Despite its status as a Level-4 organism and its apparent pathogenicity in monkeys, RESTV did not cause disease in exposed human laboratory workers.

Tai Forest ebolavirus (TAFV). Formerly known as "Côte d'Ivoire ebolavirus," it was first discovered among chimpanzees from the Tai Forest in Côte d'Ivoire, Africa, in 1994. Necropsies showed blood within the heart to be brown; no obvious marks were seen on the organs; and one necropsy displayed lungs filled with blood. Studies of tissues taken from the chimpanzees showed results similar to human cases during the 1976 EBOV outbreaks in Zaire and Sudan. As more dead chimpanzees were discovered, many tested positive for EBOV using molecular techniques. The source of the virus was believed to be the meat of infected western red colobus monkeys (Procolubus badius) upon which the chimpanzees preyed. One of the scientists performing the necropsies on the infected chimpanzees contracted the virus. She developed symptoms similar to those of dengue fever approximately a week after the necropsy, and was transported to Switzerland for treatment. She was discharged from hospital after two weeks and had fully recovered six weeks after the infection.

Bundibugyo ebolavirus (BDBV). On Nov. 24, 2007, the Uganda Ministry of Health confirmed an outbreak of ebolavirus in the Bundibugyo District. After confirmation of samples tested by the United States National Reference Laboratories and the CDC, the World Health Organization confirmed the presence of the new species. On 20 Feb. 2008, the Uganda Ministry officially announced the end of the epidemic in Bundibugyo, with the last infected person discharged on 8 Jan. 2008. An epidemiological study conducted by WHO and Uganda Ministry of Health scientists determined there were 116 confirmed and probable cases the new Ebola species, and that the outbreak had a mortality rate of 34% (39 deaths).

B. Ebola Virus Disease

Symptoms of Ebola virus disease. The incubation period from infection with the virus to onset of symptoms is 2 to 21 days. Humans are not infectious until they develop symptoms. First symptoms are the sudden onset of fever fatigue, muscle pain, headache and sore throat. This is followed by vomiting, diarrhea, rash, symptoms of impaired kidney and liver function, and in some cases, both internal and external bleeding (e.g., oozing from the gums, blood in the stools). Laboratory findings include low white blood cell and platelet counts and elevated liver enzymes.

Diagnosis. It can be difficult to distinguish ebolavirus infections from other infectious diseases such as malaria, typhoid fever and meningitis. Confirmation that symptoms are caused by ebolaviruses infection are made using antibody-capture ELISA, antigen-capture detection tests, serum neutralization test, RT-PCR assay, electron microscopy, and virus isolation by cell culture. Samples from patients are an extreme biohazard risk; laboratory testing on non-inactivated samples should be conducted under maximum biological containment conditions.

Treatment and vaccines. Supportive care-rehydration with oral or intravenous fluids- and treatment of specific symptoms, improves survival. There is as yet no proven treatment available for ebolavirus. However, a range of potential treatments including blood products, immune therapies and drug therapies are currently being evaluated. No licensed vaccines are available yet, but 2 potential vaccines are undergoing human safety testing.

Prevention and control. Good outbreak control relies on applying a package of interventions, namely case management, surveillance and contact tracing, a good laboratory service, safe burials and social mobilization. Community engagement is key to successfully controlling outbreaks. Raising awareness of risk factors for ebolavirus infection and protective measures that individuals can take is an effective way to reduce human transmission. Risk reduction messaging should focus on several factors:

reducing the risk of wildlife-to-human transmission from contact with infected fruit bats or monkeys/apes and the consumption of their raw meat;

reducing the risk of human-to-human transmission from direct or close contact with people with Ebola symptoms, particularly with their bodily fluids;

outbreak containment measures including prompt and safe burial of the dead;

identifying people who may have been in contact with someone infected with Ebola and monitoring the health of contacts for 21 days;

the importance of separating the healthy from the sick to prevent further spread; and the importance of good hygiene and maintaining a clean environment In terms of controlling infection in health-care settings, health-care workers should always take standard precautions when caring for patients, regardless of their presumed diagnosis. These include basic hand hygiene, respiratory hygiene, use of personal protective equipment (to block splashes or other contact with infected materials), safe injection practices and safe burial practices. Health-care workers caring for patients with suspected or confirmed Ebola virus should apply extra infection control measures to prevent contact with the patient's blood and body fluids and contaminated surfaces or materials such as clothing and bedding. When in close contact (within 1 meter) of patients with EBV, health-care workers should wear face protection (a face shield or a medical mask and goggles), a clean, non-sterile long-sleeved gown, and gloves (sterile gloves for some procedures). Laboratory workers are also at risk. Samples taken from humans and animals for investigation of Ebola infection should be handled by trained staff and processed in suitably equipped laboratories.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to ebolavirus will have several applications. These include the production of diagnostic kits for use in detecting and diagnosing ebolavirus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce ebolavirus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke, *Methods Mol. Biol.* 248: 443-63, 2004), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer, *Prot. Sci.* 9: 487-496, 2000). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring, *Analytical Biochemistry* 267: 252-259, 1999: Engen and Smith, *Anal. Chem.* 73: 256A-265A. 2001. When the antibody neutralizes ebolavirus, antibody escape mutant variant organisms can be isolated by propagating ebolavirus in vitro or in animal models in the presence of high concentrations of the antibody. Sequence analysis of the ebolavirus gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see U.S. Patent Publication No. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand. if the test antibody is not able to bind to the target molecule following saturation binding with the reference antibody, then the test antibody may bind to the same epitope as the epitope bound by the reference antibody.

To determine if an antibody competes for binding with a reference anti-ebolavirus antibody, the above-described binding methodology is performed in two orientations: In a first orientation, the reference antibody is allowed to bind to the ebolavirus antigen under saturating conditions followed by assessment of binding of the test antibody to the ebolavirus antigen molecule. In a second orientation, the test antibody is allowed to bind to the ebolavirus antigen molecule under saturating conditions followed by assessment of binding of the reference antibody to the ebolavirus antigen molecule. If, in both orientations, only the first (saturating) antibody is capable of binding to the ebolavirus antigen, then it is concluded that the test antibody and the reference antibody compete for binding to the ebolavirus antigen. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 50:1495-1502, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework"

regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenies pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) *Proc. Natl. Acad. Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One particular example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1-6) *Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody*," Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity*," J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as $E. coli$, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAbs but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells, but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. 0-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline.

Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications. such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21(2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., *J Mol Biol* 427, 478-490). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., *J. Exp. Med.,* 175: 217-225 (1992) describe the production of a humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16. 677-681 (1998). doi:10.1038/nbt0798-677pmid: 9661204). For example, bispecific antibodies have been produced using leucine zippers (Kostelny et al., *J. Immunol.,* 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., *J. Immunol.* 147: 60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multi-specific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
  (a) a first Fab molecule which specifically binds to a first antigen
  (b) a second Fab molecule which specifically binds to a second antigen, and wherein the variable domains VL and VH of the Fab light chain and the Fab heavy chain are replaced by each other,
  wherein the first antigen is an activating T cell antigen and the second antigen is a target cell antigen, or the first antigen is a target cell antigen and the second antigen is an activating T cell antigen; and wherein
  i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
  ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a noncleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF EBOLAVIRUS INFECTION

A. Formulation and Administration

The present disclosure provides pharmaceutical compositions comprising anti-ebolavirus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of ebolavirus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{86}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{11}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting ebolavirus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of ebolavirus in a subject. A wide variety of assay formats are contemplated, but specifically those that would be used to detect ebolavirus in a fluid obtained from a subject, such as saliva, blood, plasma, sputum, semen or urine. In particular, semen has been demonstrated as a viable sample for detecting ebolavirus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of ebolavirus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing ebolavirus, and contacting the sample with a first antibody in accordance with the present disclosure, as the case may be, under conditions effective to allow the formation of immunocomplexes.

These methods include methods for purifying ebolavirus or related antigens from a sample. The antibody will preferably be linked to a solid support, such as in the form of a column matrix, and the sample suspected of containing the ebolavirus or antigenic component will be applied to the immobilized antibody. The unwanted components will be washed from the column, leaving the ebolavirus antigen immunocomplexed to the immobilized antibody, which is then collected by removing the organism or antigen from the column.

The immunobinding methods also include methods for detecting and quantifying the amount of ebolavirus or related components in a sample and the detection and quantification of any immune complexes formed during the binding process. Here, one would obtain a sample suspected of containing ebolavirus or its antigens, and contact the sample with an antibody that binds ebolavirus or components thereof, followed by detecting and quantifying the amount of immune complexes formed under the specific conditions. In terms of antigen detection, the biological sample analyzed may be any sample that is suspected of containing ebolavirus or ebolavirus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to ebolavirus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the ebolavirus or ebolavirus antigen is added to the wells. After binding and washing to remove non-specifically bound immune complexes, the bound antigen may be detected. Detection may be achieved by the addition of another anti-ebolavirus antibody that is linked to a detectable label. This type of ELISA is a simple "sandwich ELISA." Detection may also be achieved by the addition of a second anti-ebolavirus antibody, followed by the addition of a third antibody that has binding affinity for the second antibody, with the third antibody being linked to a detectable label.

In another exemplary ELISA, the samples suspected of containing the ebolavirus or ebolavirus antigen are immobilized onto the well surface and then contacted with the anti-ebolavirus antibodies of the disclosure. After binding and washing to remove non-specifically bound immune complexes, the bound anti-ebolavirus antibodies are detected. Where the initial anti-ebolavirus antibodies are linked to a detectable label, the immune complexes may be detected directly. Again, the immune complexes may be detected using a second antibody that has binding affinity for the first anti-ebolavirus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection.

Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of ebolavirus antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled ebolavirus monoclonal antibodies to determine the amount of ebolavirus antibodies in a sample. The basic format would include contacting a known amount of ebolavirus monoclonal antibody (linked to a detectable label) with ebolavirus antigen or particle. The ebolavirus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material —the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect ebolavirus or ebolavirus antigens, the antibodies may be included in the kit. The immunodetection kits will thus comprise, in suitable container means, a first antibody that binds to ebolavirus or ebolavirus antigen, and optionally an immunodetection reagent.

In certain embodiments, the ebolavirus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the ebolavirus or ebolavirus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones —malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective ebolavirus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Ethics Statement. Human PBMCs were obtained from survivors of the 2013-2016 EVD epidemic in Nigeria or of the 2014 Boende outbreak in the Democratic Republic of the Congo (DRC) (unpublished). PBMCs were collected after the illness or hospital discharge following informed consent. At time of blood collection, plasma samples were tested by RT-PCR and found to be negative for the presence of viral RNA. The studies were approved by the Institutional Review Boards of Vanderbilt University Medical Center, the UCLA Fielding School of Public Health and the Kinshasa School of Public Health (DRC).

The animal protocols for testing of mAbs in mice, guinea pigs and ferrets were approved by the Institutional Animal Care and Use Committee of the University of Texas Medical Branch (UTMB) in compliance with the Animal Welfare Act and other applicable federal statutes and regulations relating to animals and experiments involving animals. Challenge studies were conducted under maximum containment in an animal biosafety level 4 (ABSL-4) facility of the Galveston National Laboratory, UTMB.

Cell lines. Vero-E6, THP-1, and Jurkat cell lines were obtained from the American Type Culture Collection. Vero-E6 cells were cultured in Minimal Essential Medium (MEM) (ThermoFisher Scientific) supplemented with 10% fetal bovine serum (HyClone) and 1% penicillin-streptomycin at 5% $CO_2$, 37° C. THP-1 and Jurkat cells were cultured in RPMI 1640 (Gibco) medium supplemented with 10% heat-inactivated fetal bovine serum (Gibco), 1% GlutaMax (Gibco), and 1% penicillin-streptomycin (Gibco) at 37° C. in 5% $CO_2$. The HMAA 2.5 non-secreting mouse-human heteromyeloma cell line was a kind gift from L. Cavacini and was cultured as described previously (Yu et al., 2008). A 293F cell line stably-transfected to express SNAP-tagged EBOV GP was described recently (Domi et al., 2018). ExpiCHO and FreeStyle 293F cell lines were purchased from ThermoFisher Scientific and cultured according to the manufacturer's protocol. The Jurkat-EBOV GP cell line stably expressing EBOV GP Makona on the surface (Davis and Ahmed, 2018) was a kind gift from Carl Davis of Emory. An NIH3T3 engineered fibroblast line constitutively expressing cell-surface human CD154 (CD40 ligand), secreted human B-cell activating factor (BAFF) and human IL-21 was kindly provided by Dr. Deepta Bhattacharya (Washington University in St. Louis). All cell lines were tested on a monthly basis for *Mycoplasma* and found to be negative in all cases.

Viruses. The authentic recombinant EBOV expressing enhanced green fluorescent protein (GFP) EBOV-eGFP, mouse-adapted EBOV Mayinga (EBOV-MA, GenBank: AF49101), guinea pig-adapted SUDV (SUDV-GA, GenBank: KT878488), SUDV strain Gulu, and BDBV strain 200706291 Uganda viruses were described previously (Bray et al., 1998; Sanchez and Rollin, 2005; Towner et al., 2005; Towner et al., 2008; Wong et al., 2015). The chimeric infectious EBOV/BDBV-GP and EBOV/SUDV-GP viruses expressing eGFP were obtained by replacing the gene encoding EBOV GP with that of BDBV (GenBank: KU174137) or SUDV (GenBank: KU174142), respectively (Ilinykh et al., 2016), and passaged two times in Vero-E6 cell culture monolayers. Recombinant chimeric vesicular stomatitis virus in which the G protein was replaced with EBOV GP (rVSV/EBOV-GP) were provided by Heinz Feldmann (Rocky Mountain Laboratories, NIH, Hamilton, MT) (Garbutt et al., 2004).

Mouse challenge with EBOV and SUDV. Mice were housed in microisolator cages and provided food and water ad libitum. Groups of 7-8-week-old BALB/c mice (Charles River Laboratories) were inoculated with 1,000 PFU of the EBOV-MA by the intraperitoneal (i.p.) route. Mice were treated i.p. with 100 µg (~5 mg/kg) of individual mAb per mouse on day 1 post-challenge. Human mAb DENV 2D22 (specific to an unrelated target, dengue virus) served as negative control. Mice were monitored twice daily from day 0 to day 14 post-challenge for illness, survival, and weight loss, followed by once daily monitoring from day 15 to the end of the study at day 28. The extent of disease was scored using the following parameters: dyspnea (possible scores 0-5), recumbence (0-5), unresponsiveness (0-5), and bleeding/hemorrhage (0-5). Moribund mice were euthanized as per the IACUC-approved protocol. All mice were euthanized on day 28 after EBOV challenge.

Groups of 7-8-week-old STAT1 KO (Taconic) mice were challenged i.p. with 1,000 pfu WT SUDV (Gulu). Animals were treated i.p. with 200 µg (~10 mg/kg) of EBOV-specific or control DENV-specific mAb 2D22 per mouse on day 1 post-challenge and were monitored as above.

Guinea pig challenge with SUDV. Groups of 5- to 6-week-old Hartley guinea pigs (n=5/group) were injected i.p. with 1,000 pfu of SUDV-GA (guinea pig adapted strain Boniface) (Wong et al., 2015). MAb EBOV-520 was delivered by i.p. route at indicated time points and doses. Control groups were treated with mAb DENV 2D22 or left untreated. Animals were monitored for the illness, survival, and weight loss. Blood was collected from surviving animals on day 3, 6, 9, 12, and 28 for determination of virus titers. All animals were euthanized at day 28 after challenge.

Ferret challenge with BDBV. Groups of 6-month-old male and female animals (*Mustela putorius* furo, Marshall BioResources) were challenged intramuscularly with 1,000 pfu of BDBV, as described previously (Kozak et al., 2016). Animals were treated by i.p. route with 18 mg of mAb EBOV-520 or the control mAb DENV 2D22 on day 3, and the same dose of the mAb on day 6 after challenge. The disease scores were assessed as follows: healthy, 1; developing clinical disease, 2; advanced disease, 3; moribund, 4. Ferrets were monitored for 28 days after infection and then euthanized.

Generation of human B cell hybridomas producing monoclonal antibodies (mAbs). PBMCs from heparinized blood were isolated with Ficoll-Histopaque by density gradient centrifugation. The cells were cryopreserved in the vapor phase of liquid nitrogen until use. Human B cell hybridomas were generated as described previously (Huang et al., 2013; Yu et al., 2008) with some modifications. Briefly, previously cryopreserved samples were thawed and expanded on irradiated NIH3T3 cells that had been engineered to express human IL-21, CD40L, and BAFF in medium A (STEMCELL Technologies) supplemented with CpG, a Chk2 inhibitor (Sigma), and cyclosporine A (Sigma). After 7 days, supernatants from each well of the 384-well culture plates were assessed by ELISA for reactivity against various ebolavirus proteins using enzyme-linked immunosorbent assays (ELISAs), as described below. The next day, cells from wells with supernatants reacting with antigen in an ELISA were fused with HMMA2.5 myeloma cells using an established electrofusion technique (Yu et al., 2008). After the fusion reaction, hybridoma lines were cultured in ClonaCell-HY Medium E (STEMCELL Technologies) supplemented with HAT Media Supplement (Sigma) in 384-well plates for 18 days before screening of supernatants for antibody production. Hybridoma cell lines producing ebolavirus GP-reactive antibodies were cloned biologically by single-cell fluorescence-activated cell sorting. Hybridomas were expanded in Medium E until 50% confluent in 75-cm$^2$ flasks (Corning).

MAb isotype and gene sequence analysis. The isotype and subclass of secreted antibodies were determined using murine anti-human IgG1, IgG2, IgG3 or IgG4 mouse antibodies conjugated with alkaline phosphatase (Southern Biotech). Antibody heavy- and light-chain variable region genes were sequenced from hybridoma lines that had been cloned biologically from flow cytometry. Briefly, total RNA was extracted using the RNeasy Mini kit (QIAGEN) and reverse-transcriptase PCR (RT-PCR) amplification of the antibody gene cDNAs was performed using the PrimeScript One Step RT-PCR kit (CLONTECH) according to the manufacturer's protocols with gene-specific primers (Thornburg et al., 2016). The thermal cycling conditions were as follows: 50° C. for 30 min, 94° C. for 2 min, 40 cycles of (94° C. for 30 s, 58° C. for 30 s and 72° C. for 1 min). PCR products were purified using Agencourt AMPure XP magnetic beads (Beckman Coulter) and sequenced directly using an ABI3700 automated DNA sequencer. The identities of gene segments and mutations from germlines were determined by alignment using the ImMunoGeneTics database (Brochet et al., 2008; Giudicelli and Lefranc, 2011).

MAb production and purification. Hybridoma cells secreting GP-reactive mAbs were grown in serum-free medium (Hybridoma-SFM, Life Technologies). MAbs were purified from filtered culture supernatants by fast protein liquid chromatography (FPLC) on an ÄKTA instrument using HiTrap MabSelect Sure or HiTrap Protein G columns (GE Healthcare). Purified mAbs were buffer exchanged into PBS, filtered using sterile 0.45-µm pore size filter devices (Millipore), concentrated, and stored in aliquots at −80° C. until use.

For recombinant mAb production, cDNA encoding the genes of heavy and light chains were cloned into DNA plasmid expression vectors encoding IgG (IgG1, IgG3, Ig4, or IgG1-LALA)—or Fab-heavy chain (McLean et al., 2000) and transformed into *E. coli* cells. MAb proteins were produced following transiently transfection of FreeStyle 293F or ExpiCHO cells following the manufacturer's protocol and were purified as described above.

GP expression and purification. The ectodomains of EBOV GP ATM (residues 1-636; strain Makona; GenBank: KM233070), BDBV GP ATM (residues 1-643; strain 200706291 Uganda; GenBank: NC_014373), SUDV GP ATM (residues 1-637, strain Gulu; GenBank: NC_006432), and MARV GP ATM aa 1-648 (strain Angola2005; GenBank: DQ447653) were expressed transiently in Expi293F cells with a C-terminal strep II tag using the pcDNA3 plasmid vector. Secreted proteins were purified using 5 mL StrepTrap HP column (GE Healthcare) following the manufacturer's protocol, and then purified further and buffer exchanged into PBS using Supedex200 (GE Healthcare) size exclusion chromatography. Formation of EBOV GP ATM trimer was confirmed by negative stain EM. For some experiments, the inventors used EBOV GP that was produced in *Drosophila* Schneider 2 (S2) cells. Briefly, recombinant ectodomain of EBOV GP ATM in modified pMTpuro vector was transfected into S2 cells followed by stable selection of transfected cells with 6 µg/mL puromycin. GP ectodomain expression was induced with 0.5 mM CuSO$_4$ for 4 days. Protein was purified using Strep-Tactin resin (Qiagen) via an engineered strep II tag and purified further by Superdex 200 (S200) column chromatography. Purity of recombinant GP was confirmed by SDS-PAGE.

ELISA binding assays. Wells of microtiter plates were coated with purified, recombinant EBOV, BDBV, SUDV, or MARV GP ATM and incubated at 4° C. overnight. Plates were blocked with 2% non-fat dry milk and 2% normal goat serum in DPBS containing 0.05% Tween-20 (DPBS-T) for 1 hr. For mAb screening assays, hybridoma culture supernatants were diluted in blocking buffer 1:5, added to the wells, and incubated for 1 hr at ambient temperature. The bound antibodies were detected using goat anti-human IgG conjugated with HRP (Southern Biotech) and TMB substrate (ThermoFisher). Color development was monitored, iN hydrochloric acid was added to stop the reaction, and the absorbance was measured at 450 nm using a spectrophotometer (Biotek).

For dose-response and cross-reactivity assays, serial dilutions of plasma or purified mAbs were applied to the wells in triplicate or quadruplicate, as detailed above. EC$_{50}$ values for mAb binding were determined using Prism 7.0 software (GraphPad) after log transformation of antibody concentration using sigmoidal dose-response nonlinear regression analysis, as described previously (Thornburg et al., 2013). Similarly, a non-linear regression analysis was performed on the resulting curves to calculate plasma dilution that yielded a half-maximum O.D. 450 nm value. Antibody titer in plasma was expressed as the inverse of plasma dilution.

Cell surface displayed GP mAb binding assays. Jurkat-GP cells were washed with the incubation buffer containing DPBS, 2% of heat-inactivated FBS and 2 mM EDTA (pH 8.0) by centrifugation at 400×g for 5 min at room temperature. For antibody staining, ~5×10$^4$ cells were added per each well of V-bottom 96-well plate (Corning) in 5 µL of the incubation buffer. Serial dilutions of antibody were added to the cells in triplicate or quadruplicate for total volume of 50 µL per well, followed by 1 hr incubation at room temperature, or 4° C. in some experiments. Unbound antibody was removed by washing with 200 µL of the incubation buffer as described above, and cells were incubated with phycoerythrin (PE)-labeled secondary goat anti-human antibodies (Southern Biotech) for 30 min at 4° C. In some experiments, cells were fixed with 4% PFA in DPBS before staining with secondary antibodies. Staining of cells was measured by flow cytometric analysis using an Intellicyt iQue high throughput cytometer (Intellicyt), or an LSRII flow cytometer (BD Biosciences). Data for up to 20,000 events were acquired, and data were analyzed with ForeCyt (Intellicyt) or FlowJo (Tree Star) software. Dead cells were excluded from the analysis on the basis of forward and side scatter gate for viable cell population. Binding to untransfected Jurkat cells, or binding of dengue antigen-specific mAb DENV 2D22 served as negative controls for most experiments.

In some experiments, binding to cell surface displayed GP was assessed with mAbs that were directly fluorescently-labeled. Briefly, mAbs were labeled with Alexa Fluor 667 NHS ester (ThermoFisher) by following the manufacturer's protocol. Labeled mAbs were purified further and buffer exchanged into the PBS using desalting Zeba columns (ThermoFisher) and stored at 4° C. with 0.1% bovine serum albumin (Sigma) and 0.01% sodium azide.

To assess binding of mAbs to Jurkat-EBOV GP$_{CL}$, Jurkat-GP cells were counted and cleaved by thermolysin (Promega) as described elsewhere (Davis and Ahmed, 2018). Cell staining and flow cytometric analysis was performed as described above. Binding to untransfected Jurkat or uncleaved Jurkat-EBOV GP served as controls.

Cell surface displayed GP mAb competition-binding assays. Jurkat-EBOV GP or Jurkat-EBOV$_{CL}$ cells were pre-incubated with a saturating concentration (typically 20 µg/mL) of the first unlabeled mAb at room temperature for 30 min, followed by addition of the second fluorescently-labeled mAb (typically 5 µg/mL) and incubated for an additional 30 min. The second mAb was added after the first mAb and without washing of cells to minimize a dissociation of the first mAb from cell surface GP during a prolonged incubation. Cells were washed, fixed with PFA, and cell staining was analyzed using an Intellicyt iQue flow cytometer as detailed above. Background values were determined from binding of the second labeled mAbs to untransfected Jurkat. Results are expressed as the percent of binding in the presence of competitor mAb relative to primary mAb-only control (maximal binding) minus background. The antibodies were considered competing if the presence of first antibody reduced the signal of the second antibody to less than 30% of its maximal binding or non-competing if the signal was greater than 70%. A level of 30-70% was considered intermediate competition. Of note, mAbs from the GP base region competitor epitope group revealed much stronger binding to Jurkat-EBOV GP$_{CL}$ than to Jurkat-EBOV GP cells. This finding was revealed by nearly complete cross-blocking capacity of these mAbs on Jurkat-EBOV GP$_{CL}$ when compared to those determined for Jurkat-EBOV GP cells (FIGS. 4A-B).

Cell surface displayed GP cleavage inhibition assay. Jurkat-EBOV GP cells were pre-incubated with serial dilutions of mAbs in PBS for 20 min at room temperature, then incubated with thermolysin for 20 min at 37° C. The reaction was stopped by addition of the incubation buffer as described above. Washed cells were incubated with 5 µg/mL of fluorescently-labeled RBS-specific mAb MR78 at 4° C. for 60 min. Stained cells were washed, fixed, and analyzed by flow cytometry using Intellicyt iQue. Background staining was determined from binding of the labeled mAb MR78 to Jurkat-EBOV GP (uncleaved) cells. Results are expressed as the percent of RBS exposure in the presence of tested mAb relative to labeled MR78 mAb-only control (maximal binding to Jurkat-EBOV GP$_{CL}$) minus background.

Cell surface displayed GP$_{CL}$ soluble NPC1-C binding inhibition assay. Jurkat-EBOV GP$_{CL}$ cells were prepared as detailed above and resuspended in the incubation buffer. Approximately 5×10$^4$ cells per well in V-bottom 96-well plate were incubated with serial 3-fold dilutions of mAbs in a total volume of 50 µL at ambient temperature for 30 min, followed by washing and incubation with pre-titrated concentration (typically 50 µg/mL) of soluble, FLAG epitope-tagged, recombinant NPC1—C protein (Creative BioMart). Cells were washed, incubated with PE-labeled secondary mouse anti-FLAG tag antibody (BioLegend) for 2 hrs at 4° C., fixed with PFA, and then analyzed by flow cytometry using LSRII cytometer equipped with 535 nm green laser. Results are expressed as the percent of NPC1-C binding inhibition in the presence of tested mAb relative to NPC1-only control (maximal binding to Jurkat-EBOV GP$_{CL}$) minus background.

Cooperative binding to cell surface displayed GP. The cell surface display assay was based on principles from previously described enhanced binding ELISA assay (Howell et al., 2017). Briefly, Jurkat-EBOV GP cells were incubated with individual unlabeled glycan cap-specific mAbs at a saturating concentration (10 µg/ml), and then were mixed with serial dilutions of fluorescently-labeled mAbs EBOV-515 or EBOV-520. Cells were washed, and antibody binding was analyzed by flow cytometry using Intellicyt iQue.

Epitope mapping using an EBOV GP alanine-scan mutation library. Epitope mapping was carried out as described previously (Davidson et al., 2015). Comprehensive high-throughput alanine scanning ('shotgun mutagenesis') was carried out on an expression construct for EBOV GP lacking the mucin-like domain (residues 311-461) (based on the Yambuku-Mayinga variant GP sequence), mutagenizing GP residues 33-310 and 462-676 to create a library of clones, each representing an individual point mutant. Residues were changed to alanine (with alanine residues changed to serine). The resulting library, covering 492 of 493 (99.9%) of target residues, was arrayed into 384-well plates, one mutant per well, then transfected into HEK-293T cells and allowed to express for 22 hours. Cells, unfixed or fixed in 4% paraformaldehyde, were incubated with primary antibody and then with an Alexa Fluor 488-conjugated secondary antibody (Jackson ImmunoResearch Laboratories, Westgrove, PA). After washing, cellular fluorescence was detected using the Intellicyt high throughput flow cytometer (Intellicyt). MAb reactivity against each mutant EBOV GP clone was calculated relative to wild-type EBOV GP reactivity by subtracting the signal from mock-transfected controls and normalizing to the signal from wild-type GP-transfected controls. Mutated residues within clones were identified as critical to the mAb epitope if they did not support reactivity of the test mAb but did support reactivity of other control EBOV mAbs. This counter-screen strategy facilitated the exclusion of GP mutants that were misfolded locally or that exhibited an expression defect. The detailed algorithms used to interpret shotgun mutagenesis data were described previously (Davidson and Doranz, 2014).

Generation of virus neutralization escape mutants. To generate escape mutants for EBOV-520 and EBOV-442 mAbs, 100 pfu of EBOV-eGFP were combined with 2-fold dilutions of the respective mAb starting at 200 µg/mL in U-bottom 96-well plates and incubated for 1 hr at 37° C. Mixtures were placed on Vero-E6 cell monolayer cultures in 96-well plates and incubated for 1 hr. Supernatants were removed, freshly-diluted mAb was added at the same concentrations in 200 µL of MEM supplemented with 2% FBS, and plates were incubated for 7 days at 37° C. Viruses that replicated in the presence of the highest concentrations of mAb, as determined by monitoring eGFP fluorescence by microscopy, were collected. 20 µL aliquots were incubated with 2-fold dilutions of mAbs starting at 200 µg/mL, and viruses were propagated in the presence of mAbs as described above. The procedure was repeated once more with mAb dilutions starting at 400 µg/mL. Viruses that replicated at the highest mAb concentrations were amplified in Vero-E6 cell culture monolayers in 24-well plates in the presence of mAbs at 200 µg/mL for 7 days. Cells were used for isolation of RNA using TRIzol reagent, and cDNA copies of viral RNA encoding GP were amplified by RT-PCR and sequenced. To determine susceptibility of the isolated escape mutants to mAbs, 100 pfu of the viruses in MEM supplemented with 2% FBS in triplicate were combined in U-bottom 96-well plates with 8 to 12 two-fold dilutions of mAb, starting at 200 µg/mL, in total volumes of 50 µL, and incubated for 1 hr at 37° C. The virus/antibody mixtures then were added in triplicate to Vero-E6 cell culture monolayers in 96-well plates, incubated for 1 hr at 37° C., washed with MEM, overlaid with 200 µL of MEM containing 2% FBS and 0.8% methylcellulose, and incubated for 48 hrs at 37° C. Plates were fixed with 10% phosphate-buffered formalin (Fisher). Plaques were counted using a fluorescence microscopy.

To generate EBOV-515 escape mutants, aliquots containing 100 pfu of rVSV/EBOV-GP virus were pre-incubated with serial 2-fold dilutions starting from 200 µg/mL of mAb for 1 hr at 37° C. and inoculated into 96-well plate Vero-E6 cell monolayers. After 48 hrs, virus samples were harvested and titrated. Virus-positive samples from the highest mAb concentration were selected for the next passage. After seven passages, a 200 pfu virus aliquot was pre-incubated with mAb EBOV-515 and inoculated into a 24-well plate Vero-E6 cell monolayer culture. After 72 hours, the infected cell monolayer was solubilized in TRIzol (Ambion, Life Technologies) and subjected to total RNA isolation, RT-PCR and sequencing of EBOV GP.

Neutralization assays. Antibody neutralization assays were performed in a high-throughput or plaque reduction format using the recombinant EBOV-eGFP (Towner et al., 2005), rVSV/EBOV-GP, or chimeric EBOV viruses in which GP was replaced with its counterpart from BDBV or SUDV as described previously (Ilinykh et al., 2016). For the assays with thermolysin-cleaved virus, rVSV/EBOV-GP virus was propagated in Vero-E6 cells. At 48 hrs after infection, virus suspension was harvested and clarified from cell debris by centrifugation for 10 min at 10,000×g. Next, the supernatant was ultracentrifuged through a 25% sucrose cushion for 2 hours at 175,000×g at 4° C. Pelleted virus was resuspended in thermolysin digestion buffer (50 mM Tris, 0.5 mM $CaCl_2$, pH 8.0) and divided into 2 aliquots: one aliquot was treated with 0.5 mg/mL of thermolysin (Promega), another one—with equal volume of thermolysin digestion buffer (mock-treated virus) for 40 min at 37° C. The reactions were stopped by addition of EDTA up to the final concentration 10 mM. Virus samples were re-pelleted through a 25% sucrose cushion and were washed by ultracentrifugation in buffer containing 10 mM Tris (pH 8.0) and 0.1 M NaCl for 1 hour at 175,000×g at 4° C. Virus pellets were resuspended in the same buffer, incubated with 100 µg/mL mAb for 1 hour at 37° C., or mock-incubated, and titrated by applying to Vero-E6 cell culture monolayers in triplicate.

Antibody-mediated cellular phagocytosis by human monocytes (ADCP). Recombinant EBOV GP ATM (IBT Biosciences) was biotinylated and coupled to AlexaFluor488 Neutravidin beads (Life Technologies). Antibodies were diluted to 5 µg/ml in cell culture medium and incubated with beads for 2 hrs at 37° C. THP-1 monocytes (ATCC) were added at $2.5 \times 10^4$ cells per well and incubated for ~18 hrs at 37° C. Cells were fixed with 4% paraformaldehyde and analyzed on a BD LSRII flow cytometer, and a phagocytic score was determined using the percentage of $FITC^+$ cells and the MFI of the $FITC^+$ cells. The glycan cap-specific mAb c13C6 (IBT Bioservices) was used as a positive control, and the HIV-specific mAb 2G12 (Polymun Scientifics) was used as a negative control.

Antibody-mediated neutrophil phagocytosis (ADNP). Recombinant EBOV GP ATM (IBT Bioservices) was biotinylated and coupled to AlexaFluor488 Neutravidin beads (Life Technologies). Antibodies were diluted to 5 µg/mL in cell culture medium and incubated with beads for 2 hrs at 37° C. White blood cells were isolated from donor peripheral blood by lysis of red blood cells, followed by three washes with PBS. Cells were added at a concentration of $5.0 \times 10^4$ cells/well and incubated for 1 hr at 37° C. Cells were stained with CD66b (Pacific Blue, Clone G10F5; Biolegend), CD3 (Alexa 700, Clone UCHT1; BD Biosciences), and CD14 (APC-Cy7, Clone MφpP9; BD Biosciences), and fixed with 4% paraformaldehyde, and analyzed by flow cytometry on a BD LSR II flow cytometer. Neutrophils were defined as SSC-$A^{high}$ $CD66b^+$, $CD3^-$, $CD14^-$. A phagocytic score was determined using the percentage of $FITC^+$ cells and the median fluorescent intensity (MFI) of the $FITC^+$ cells. The glycan cap-specific mAb c13C6 (IBT Bioservices) was used as a positive control, and the HIV-specific mAb 2G12 (Polymun Scientifics) was used as a negative control.

Antibody-dependent NK cell degranulation. Recombinant EBOV GP ATM (IBT Bioservices) was coated onto a MaxiSorp 96 well plates (Nunc) at 300 ng/well at 4° C. for 18 hrs. Wells were washed three times with PBS and blocked with 5% bovine serum albumin in PBS. Antibodies were diluted to 5 µg/mL in PBS, and added to the plates, and were incubated for an additional 2 hrs at 37° C. Unbound antibodies were removed by washing three times with PBS, and human NK cells freshly isolated from peripheral blood of human donors by negative selection (Stem Cell Technologies, Canada) were added at $5 \times 10^4$ cells/well in the presence of 4 µg/mL brefeldin A (Sigma Aldrich) and 5 µg/mL GolgiStop (Life Technologies) and anti-CD107a antibody (PE-Cy5, Clone H4A3, BD Biosciences). Plates were incubated for 5 hrs at 37° C. Cells were stained for NK cell markers (CD56 PE-Cy7, clone B159, BD Biosciences; CD16 APC-Cy7, clone 3G8, BD Biosciences; CD3 AlexaFluor700, clone UCHT1, BD Biosciences), followed by fixation and permeabilization with Fix and Perm (Life Technologies) according to the manufacturer's instructions to stain for intracellular IFNγ (APC, Clone B27, BD Biosciences) and MIP-10 (PE, Clone D21-1351, BD Biosciences). Cells were analyzed on a BD LSRII flow cytometer. The glycan cap-specific mAb c13C6 (IBT Bioservices) was used as a positive control, and the HIV-specific mAb 2G12 (Polymun Scientifics, Austria) was used as a negative control.

Antibody-mediated complement deposition (ADCD). Recombinant EBOV GP (IBT Bioservices, MD) was biotinylated and coupled to red fluorescent Neutravidin beads (Life Technologies). Antibodies were diluted to 5 µg/ml in RPMI-1640, and incubated with GP-coated beads for 2 hrs at 37° C. Freshly reconstituted guinea pig complement (Cedarlane Labs) was diluted in veronal buffer with 0.1% fish gelatin (Boston Bioproducts), added to the antibody-bead complexes, and incubated for 20 min at 37° C. Beads were washed twice with phosphate buffered saline containing 15 mM EDTA, and stained with an anti-guinea pig C3 antibody conjugated to FITC (MP Biomedicals) for 15 minutes at ambient temperature. Beads were washed twice more with PBS, and C3 deposition onto beads was analyzed on a BD LSRII flow cytometer and the MFI FITC of all beads was measured.

Rapid fluorimetric antibody-mediated cytotoxicity assay (RFADCC). Antibody-dependent cell-mediated cytotoxicity (ADCC) activity of EBOV GP-reactive IgG or Fab was quantified with an EBOV-adapted modification of the RFADCC assay assess (Domi et al., 2018; Orlandi et al., 2016). Briefly, a target cell line was made by transfecting 293F cells with a full-length DNA expressing GP from the EBOV-Kikwit isolate followed by transfecting with two separate DNA constructs expressing EGFP and the chimeric CCR5-SNAP tag protein. The new cell line, designated EBOV GPkik-293FS EGFP CCR5-SNAP, expresses EBOV-Kikwit GP on the plasma membrane, EGFP in the cytoplasm and the SNAP-Tag CCR5, which can be specifically labeled with SNAP-Surface Alexa Fluor-647 (NEB), on the cell surface (unpublished). A human anti-EBOV GP mAb KZ52 (a neutralizing antibody) (IBT) were used as positive control and the unrelated human mAb DENV 2D22 as a negative control. The ADCC activity was quantified by incubating three-fold serial dilutions of mAbs with EBOV GPkik-293FS EGFP CCR5-SNAP target cells for 15 min at ambient temperature and then adding human PBMC as effector cells for 2 hrs at 37° C., after which cells were washed once with PBS, fixed with 2% PFA, stained and analyzed with an LSRII Fortessa flow cytometer (BD Biosciences). Data analysis was performed with FlowJo software (Tree Star Inc.). The percentage cytotoxicity of the mAb was determined as the number of target cells losing EGFP (by virtue of ADCC) but retaining the surface expression of CCR5 SNAP.

Analysis of viremia by plaque assay. Virus titration was performed in Vero-E6 cells by plaque assay on serum samples collected from guinea pigs, as previously described (Ilinykh et al., 2016) with some modifications. Briefly, duplicate 10-fold serial dilutions of sera were applied to Vero-E6 cell monolayers in 96 well plates for 1 hr, covered with 100 µL of 0.9% methylcellulose (Sigma) overlay and incubated at 37° C. for 6 days. The overlay was removed, cell monolayers were fixed with formalin, washed three times with PBS, and blocked for 1 hr with 5% non-fat dry milk in PBS-T. Plaques were immunostained with rabbit anti-GP primary antibodies (IBT Bioservices) at a 1:5,000 followed by goat-anti rabbit secondary HRP-labeled antibodies (Southern Biotech) at a 1:1,000 dilution in PBS-T. Virus plaques were visualized by staining with a 4CN two component peroxidase substrate system (Seracare).

Single particle electron microscopy. Antibody Fab proteins were obtained by recombinant expression as described above or were generated by digestion of the corresponding IgG with papain (ThermoFisher). Fabs of EBOV-515 or EBOV-520 were added in 5 M excess to EBOV GP ATM and allowed to bind overnight at 4° C. Complexes were purified subsequently by size exclusion chromatography on an S200 Increase column (GE HealthCare), then deposited on copper mesh grids coated with carbon and stained 2% uranyl formate. Micrographs were collected using a 120KeV Tecnai Spirit with TVIPS TemCam F416 (4 k×4 k) at a defocus of about 1.5e-06 defocus and a dose of $25e-/Å^2$. Micrographs were collected using Leginon (Potter et al., 1999) and processed on Appion (Lander et al., 2009). Particles were picked using DoGpicker (Voss et al., 2009) and aligned with MSA/MRA (Ogura et al., 2003) where excess Fab or blurry particles were removed. An unbinned, clean dataset was deposited into Relion (Scheres, 2012) where 3D classification and refinement was performed. Figures were created in Chimera to compare EBOV complexes and show epitope location.

Homology models of mAb EBOV-520 were generated using ROSETTAANTIBODY (Finn et al., 2016; Sivasubramanian et al., 2009) and an ensemble of Fab models was docked into the crystal structure of Ebola GP protein from PDB ID 5jg3 (Zhao et al., 2016) using the EM density map as a restraint (Bender et al., 2016).

Quantification and Statistical Analysis. The descriptive statistics mean±SEM or mean±SD were determined for continuous variables as noted. Survival curves were estimated using the Kaplan Meier method and curves compared using the log rank test with subjects right censored, if they survived until the end of the study. *–$p<0.05$; **– was used to reject a "null hypothesis." *=$p<0.05$; =$p<0.01$; *–= $p<0.001$; ns—non-significant. Statistical analyses were performed using Prism v7.0 (GraphPad).

Data and Software Availability. All relevant data are included with the manuscript; source data for each of the display items is provided in Supplemental Information.

Example 2—Results

A small subset of mAbs mediate broadly-reactive responses in human survivors of EVD. Plasma samples from 16 human survivors of the EBOV outbreak in the DRC and one survivor of the 2013-2016 EBOV epidemic in West Africa were assessed by ELISA for cross-reactivity against EBOV (Makona variant), BDBV (Uganda 2007 strain), and SUDV (Gulu strain) GP ectodomains (GP ATM) to identify survivors that most likely have circulating memory B cells encoding broadly reactive mAbs. Several donor plasma samples showed broad reactivity profiles to diverse ebolaviruses (unpublished data). Plasma from one DRC survivor showed the highest activity to all three GPs, and also neutralized live EBOV (FIGS. 1A-B). Peripheral blood mononuclear cells (PBMCs) from the two donors with the highest levels of seroreactivity were used to generate >600 EBOV GP-reactive lymphoblastoid B cell lines (LCLs) using an optimized in vitro human B cell expansion technique (Huang et al., 2013). Over half of these EBOV-reactive LCLs produced Abs that bound to recombinant GP of at least two ebolavirus species, and >10% bound in ELISA to EBOV, BDBV, and SUDV GP (FIG. 1C). LCLs producing broadly reactive Abs were rescued by fusion with myeloma cells to generate human B cell hybridomas using an established method (Yu et al., 2008). To identify cell lines secreting broadly neutralizing mAbs, the supernatants of hybridomas that secreted cross-reactive mAbs were assayed for neutralizing activity against EBOV, BDBV, and SUDV. The activity also was confirmed for those mAb clones using purified IgGs. Similarly, the inventors generated hybridomas producing broadly reactive Abs from PBMCs of 2013-2016 EBOV epidemic survivor. The inventors isolated 19 broadly-reactive mAbs with unique sequences (Table S1), three of which (designated EBOV-442, -515, and -520) neutralized all three viruses (Tables S2 and S3). These data suggest that EBOV infection elicits a large and diverse B cell response including many clones secreting mAbs that bind to heterologous ebolavirus GPs, although only a small subset of those mAbs mediate cross-neutralizing responses.

Figure 2A:
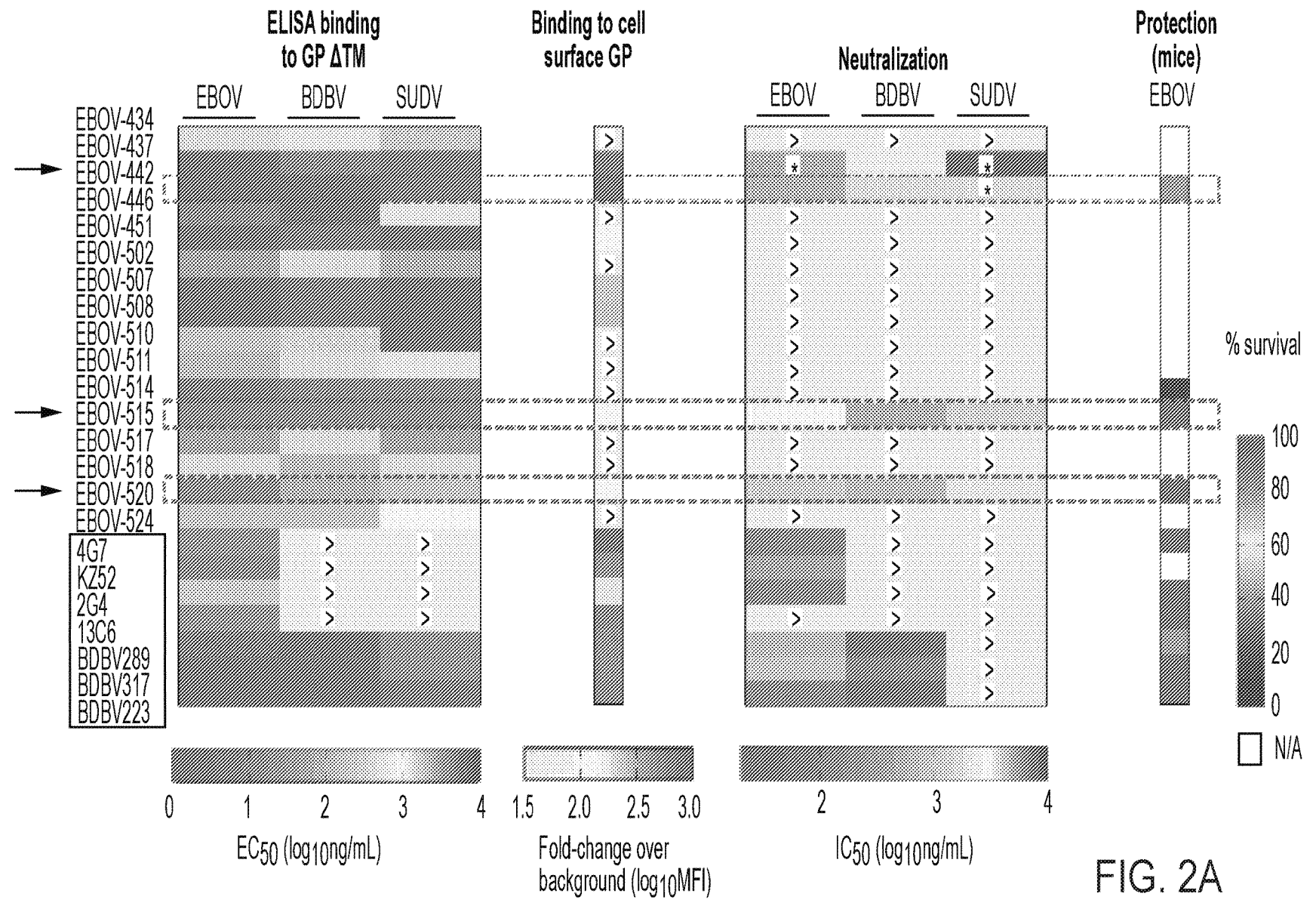
Figures 2B, 2C:
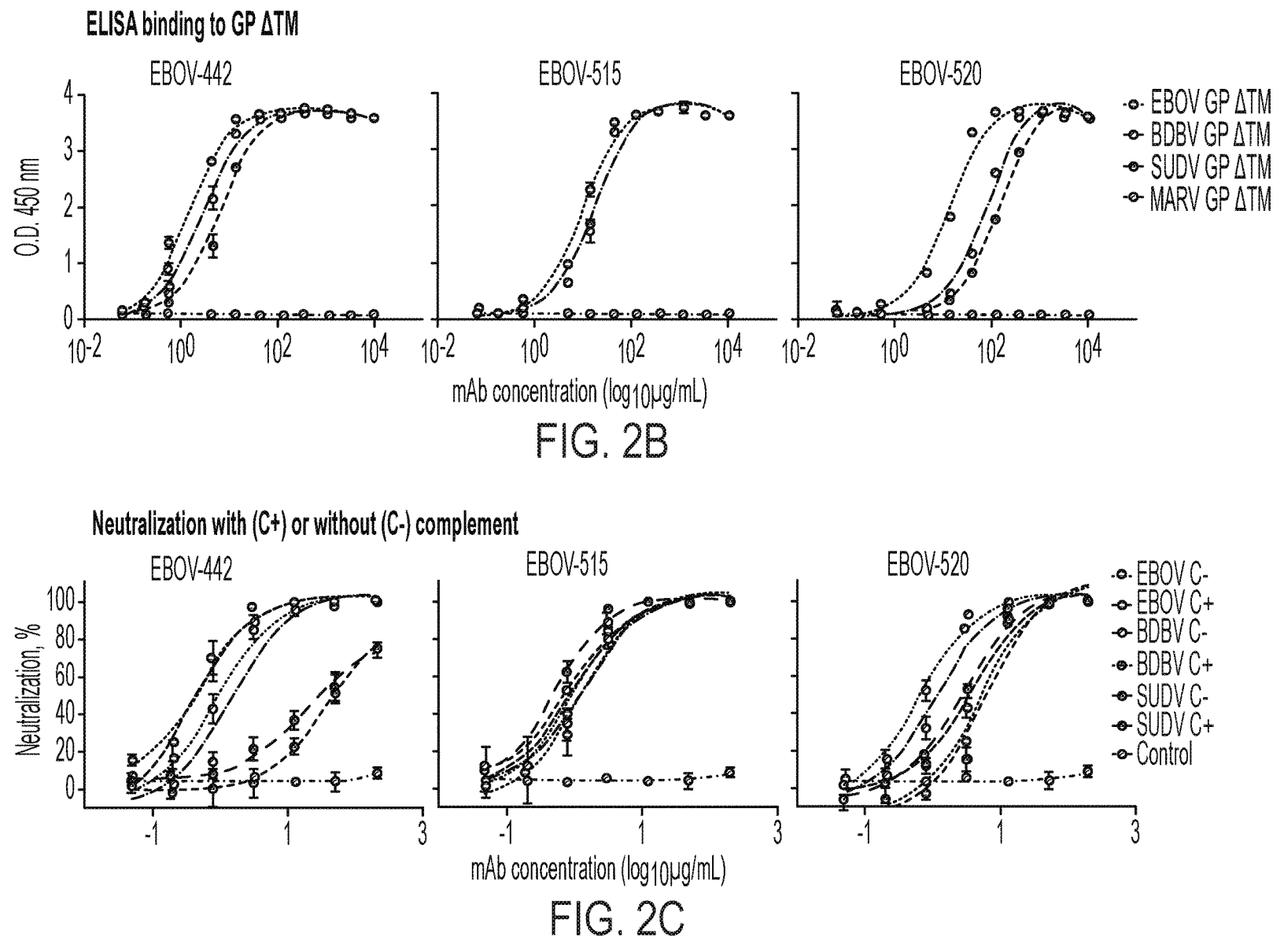
Figure 8:
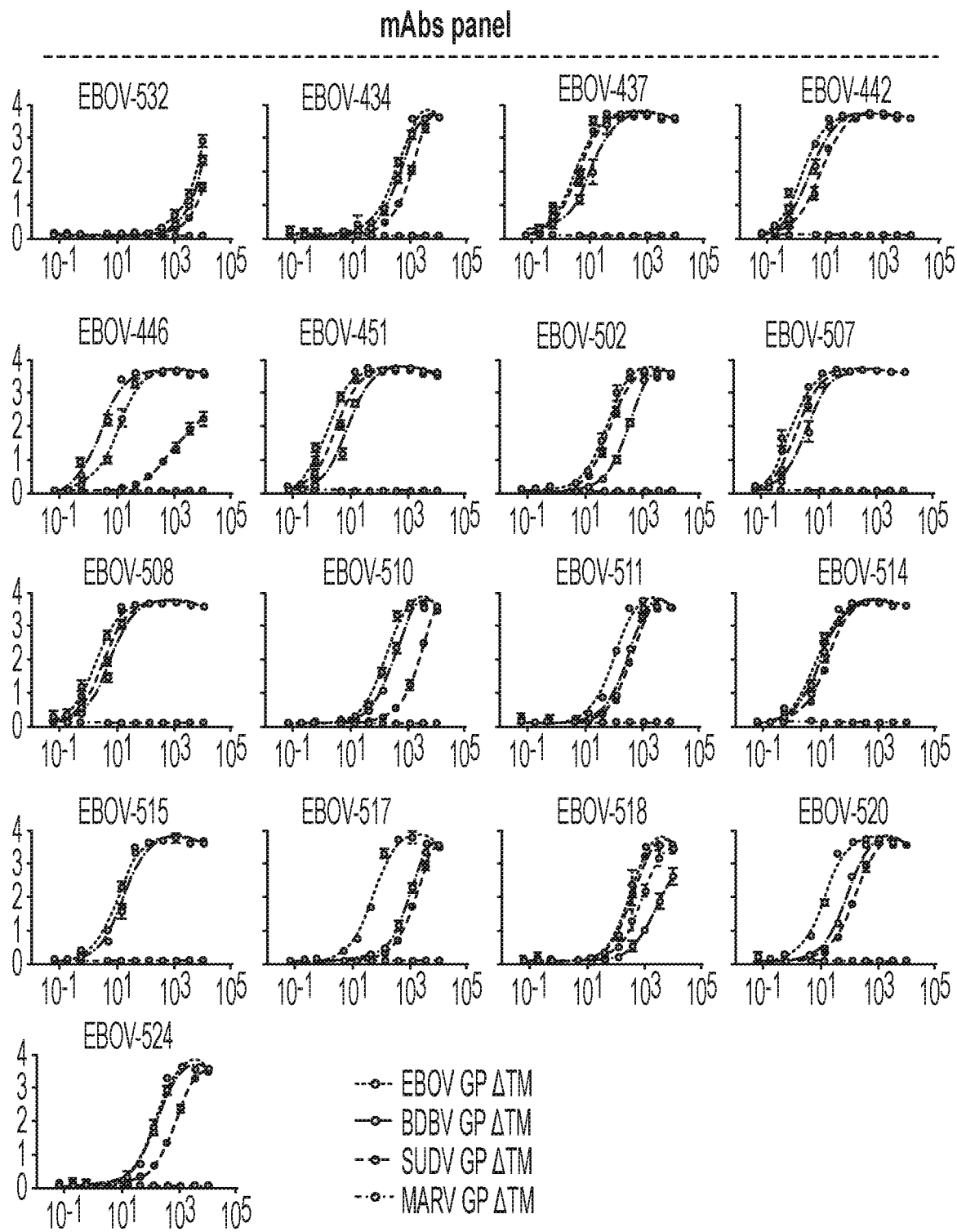
FIG. 8. B High level of binding of isolated broadly reactive mAbs to EBOV, BDBV, and SUDV GP ΔTM in ELISA, related to FIGS. 2A-F Binding curves for newly isolated, or previously isolated mAbs to recombinant filovirus GP ΔTM in ELISA. Mean±SD of four replicates are shown, and data represent one of three independent experiments.
Figure 9:
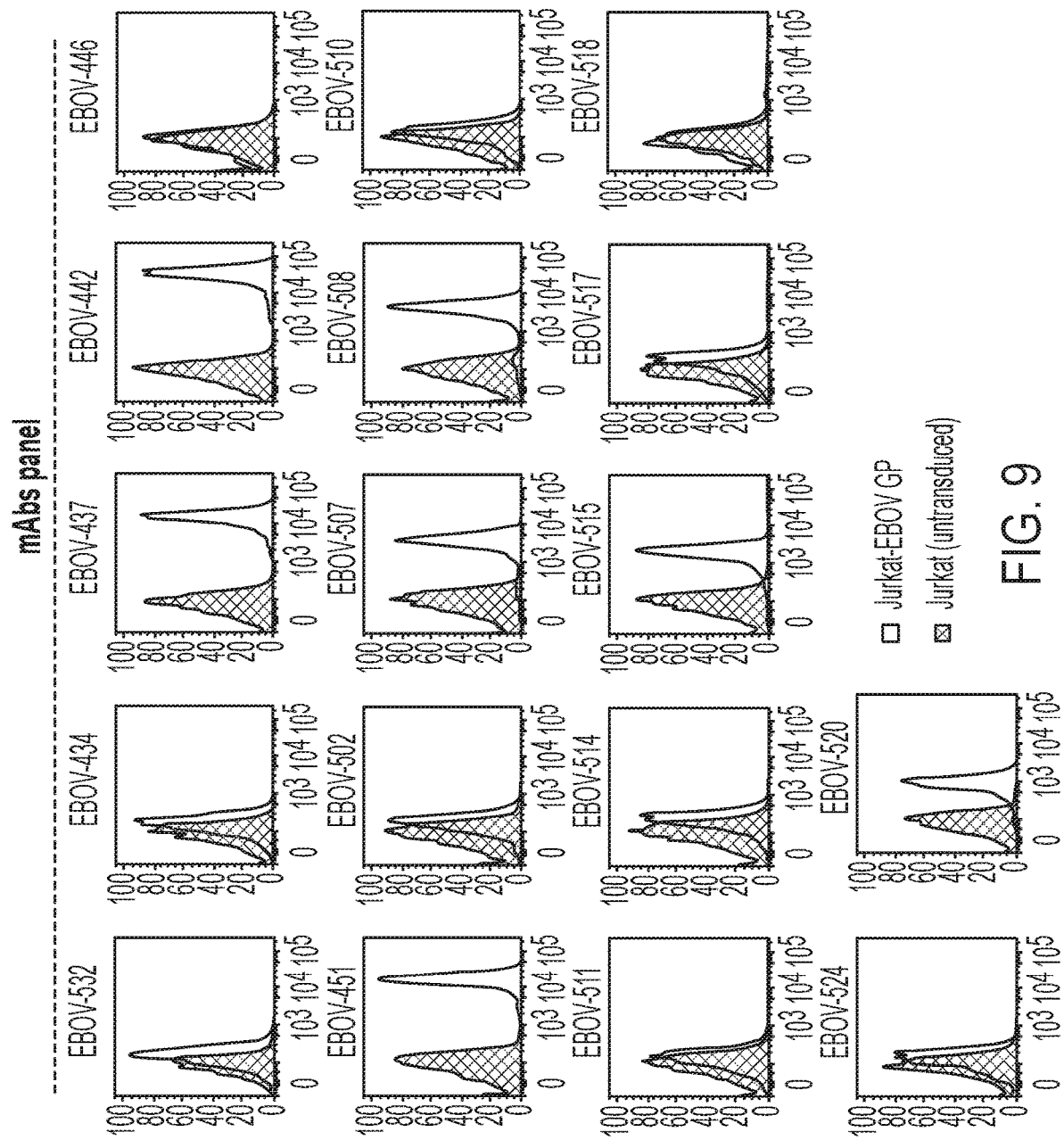
FIG. 9. A fraction of broadly reactive mAbs of the panel bind to a cell surface displayed EBOV GP, related to FIGS. 2A-F. Overlay histograms showing mAbs binding to Jurkat-EBOV GP by flow cytometric analysis. Fluorescently labeled mAbs were assessed at 5 µg/mL. Cells were gated for the viable cell population. Data represent one of three independent experiments.
Figure 9:
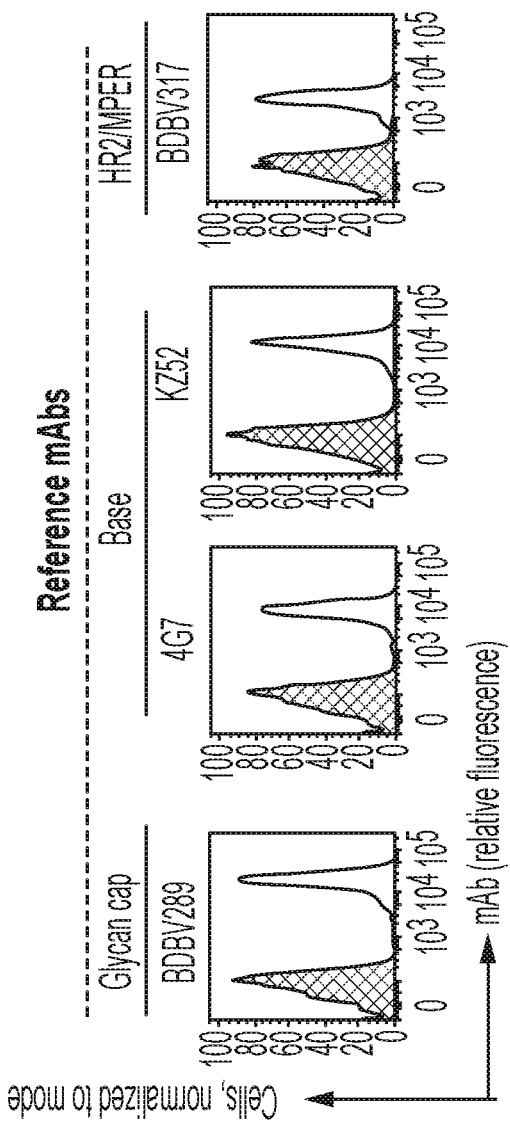

MAbs EBOV-515 and -520 potently neutralize EBOV, BDBV and SUDV and confer protection against EBOV. To assess the potency of EBOV-442, -515, and -520, the inventors compared their inhibitory activity to that of the other broadly reactive mAbs from the panel, or to previously described GP-specific mAbs recognizing the base, glycan cap, or HR2/MPER region (FIG. 2A) (Flyak et al., 2016; Murin et al., 2014; Shedlock et al., 2010). Dose-response binding curves for the newly identified neutralizing mAbs showed high levels of binding to EBOV, BDBV, and SUDV GPs ATM in ELISA, with half-maximal effective concentration ($EC_{50}$) values ranging from 10 to 200 ng/mL (FIGS. 2A-B; FIG. 8; Table S2). One mAb also bound to MARV GP ATM but did not neutralize MARV (FIG. 8; Table S2). The inventors next assessed dose-dependent neutralization by mAb EBOV-442, -515, or -520. Antibodies EBOV-515 and EBOV-520 potently neutralized EBOV, BDBV and SUDV with half-maximal inhibitory concentration ($IC_{50}$) values ranging from ~400 to 5,000 ng/mL. EBOV-442 mAb neutralized EBOV, BDBV, and to a lesser extent SUDV. Complement was not required for neutralizing activity in vitro (FIG. 2C, Table S3). The inventors next used a recently described flow cytometric assay to further characterize binding of individual mAbs to EBOV GP expressed on the surface of Jurkat cells (Jurkat-EBOV GP), which have been shown to express a form of trimeric GP likely very similar to the native form on virion particles or naturally-infected cells (David and Ahmed, unpublished). Cell surface-expressed GP may more closely mimic the presentation of native GP antigen on viruses than does recombinant GP ATM, since some mAbs may only recognize a fully glycosylated GP trimer that is anchored in a membrane (Beniac and Booth, 2017; Davis and Ahmed, 2018). Only a fraction of mAbs in the panel that bound to the GP ATM also bound to Jurkat-EBOV GP, but this group included all neutralizing mAbs (FIG. 2A; FIG. 9). These data suggest the high utility of using cell surface GP display for identifying potently neutralizing mAbs. The results also showed that the lead therapeutic candidate broadly neutralizing mAbs EBOV-442, -515, and -520 all efficiently recognized a form of trimeric GP on transduced cells likely very similar to the native form on virion particles or naturally-infected cells.

Figures 2D, 2E, 2F:
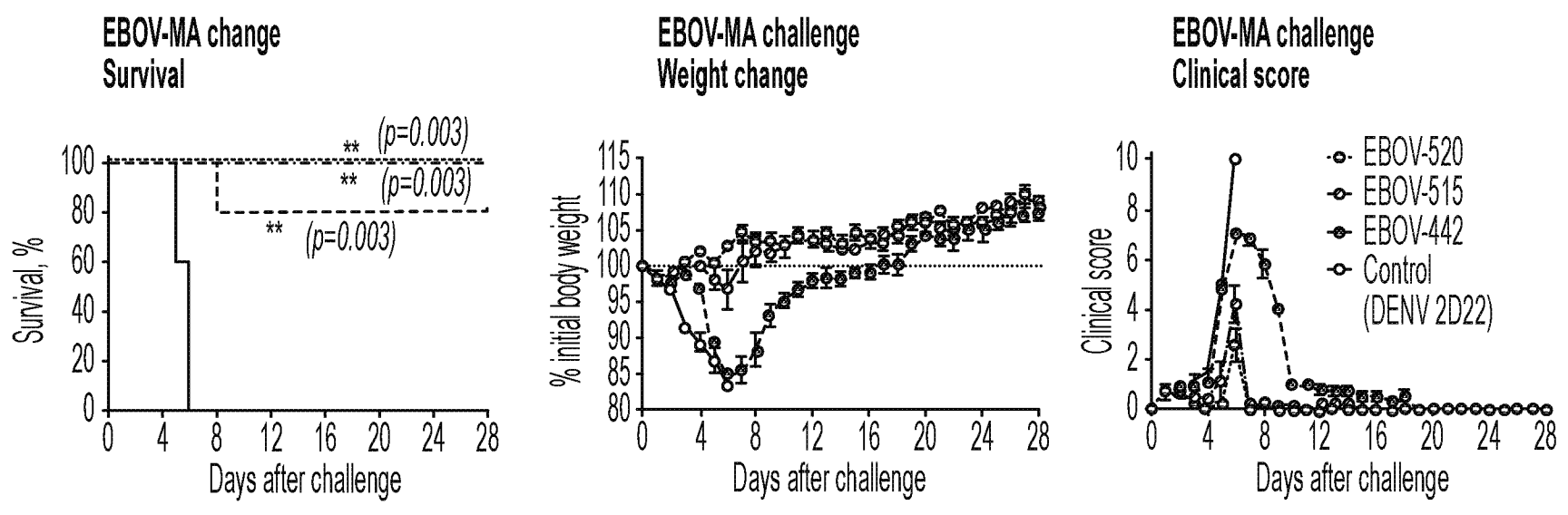

To determine the protective capacity of the mAbs in vivo, the inventors first tested mAbs EBOV-442, -515, and -520 in mice, against the mouse-adapted EBOV, strain Mayinga (EBOV-MA). MAbs EBOV-515 and -520 each conferred complete protection from death, weight loss, and disease when delivered at a 5 mg/kg dose one day post-inoculation (1 dpi) with EBOV-MA (FIG. 2D-F). Even though mAb EBOV-442 exhibited the highest neutralizing capacity against EBOV ($IC_{50}$=0.47 µg/mL), it protected poorly in mice.

EBOV-520 mediates protection principally through virus neutralization. In addition to neutralizing activity, antibodies may possess Fc-mediated functional activities that contribute to protection in vivo. To assess these additional functions in these broadly reactive human mAbs, the inventors used antibody-dependent cellular phagocytosis (ADCP), antibody-dependent neutrophil phagocytosis (ADNP), NK cell activation, and antibody-dependent complement deposition (ADCD) assays. These assays used immobilized EBOV GP ATM to determine the capacity of bound mAb to activate human effector cells in vitro. Functional profiling of 16 broadly reactive mAbs from the panel revealed a diverse activation pattern (FIG. 10A; Table S4). The broadly neutralizing and protective hybridoma-derived EBOV-515 (IgG1) and EBOV-520 (IgG4) mAbs triggered ADCP and NK-activation, suggesting that they also could function through their Fc in vivo.

Figures 10A, 10B:
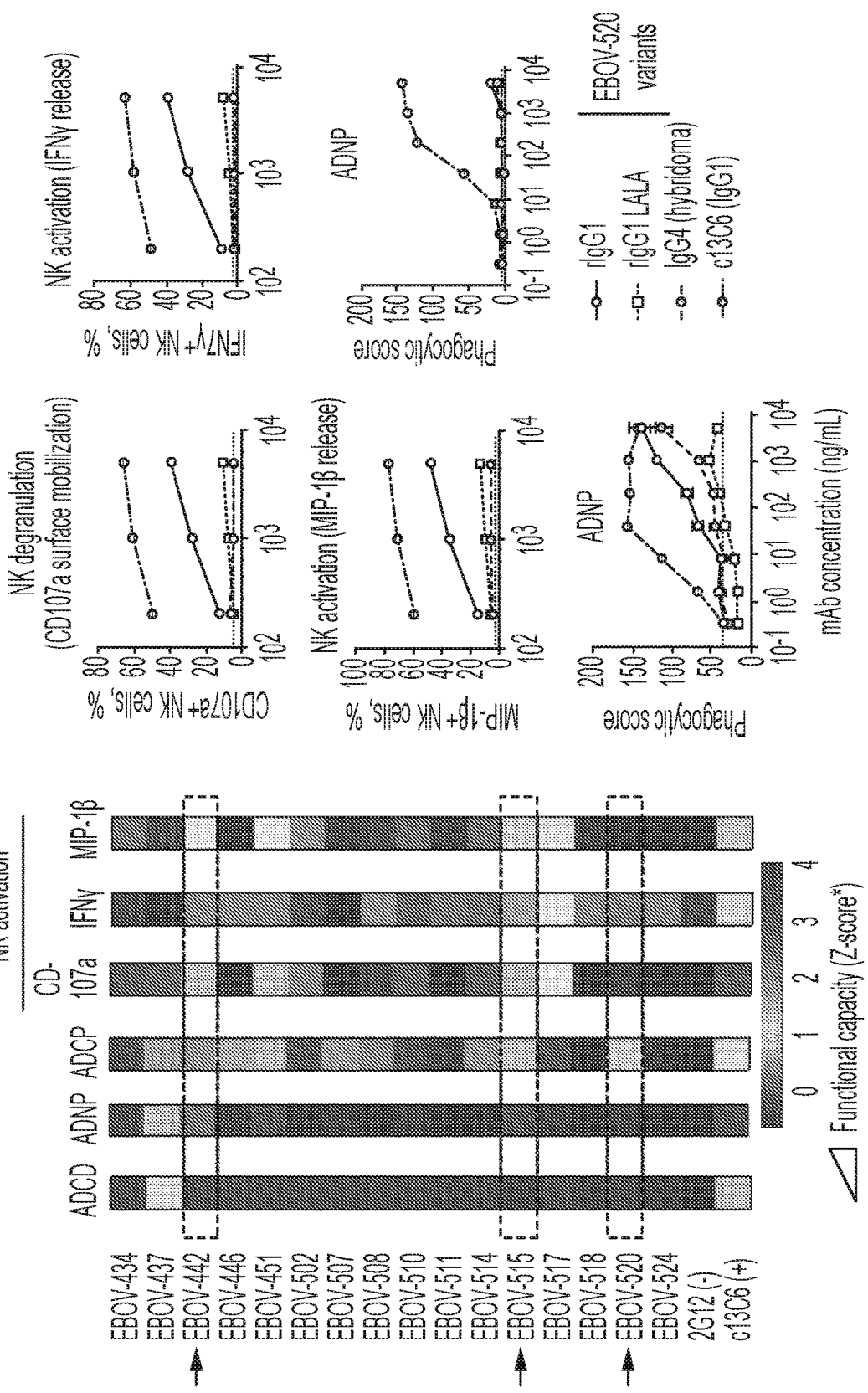
FIGS. 10A-B. Broadly neutralizing mAbs possess Fc region effector function activity, related to FIGS. 3A-D.

Because many IgG4 antibodies possess anti-inflammatory activity (van der Neut Kolfschoten et al., 2007), the inventors determined the functional capacity for Fc-engineered variants of the EBOV-520 mAb. They expressed the EBOV-520 variable region in recombinant form with the human IgG1 isotype (rIgG1) and also as a LALA Fc mutant (rIgG1-LALA) that binds only weakly to human Fcγ-receptors (FcγR) and has diminished function (Hessell et al., 2007). The inventors compared the activity of the variant IgGs using dose response curves in ADCP, ADNP, NK-activation, and ADCD assays (FIG. 10B). The rIgG1 antibody showed higher functional capacity, and rIgG1-LALA had a lower capacity, when compared to the wt hybridoma IgG4 antibody.

The Fc-mediated activity assays above used solid-phase display of GP ATM. The inventors next determined if mAb EBOV-520 has a capacity to engage human effector cells in a system with properly oriented full-length antigen displayed on a cell surface. They used a stably-transfected EBOV GP-expressing SNAP-tagged 293F cell line as a target, with heterologous human PBMCs as source of effector cells, and a rapid fluorimetric antibody-mediated cytotoxicity assay to assess dose-killing response (Domi et al., 2018; Orlandi et al., 2016). The EBOV-520 rIgG1 and wt IgG4 showed dose-responsive cell killing, with activities comparable to that of the base region mAb KZ52 (IgG1), while the low level of cell killing activity of rIgG1-LALA and rFab was similar to that of the control mAb of irrelevant antigen specificity (FIG. 3A). These findings demonstrated the high functional potency of the broadly neutralizing EBOV-520 mAb when expressed as rIgG1.

In tests of neutralization of EBOV, however, the inventors detected a similar level of activity for all tested EBOV-520 variants, including the wt hybridoma IgG4 mAb. Interestingly, even monovalent binding with rFab was sufficient for mediating a level of neutralizing activity comparable to that of the full-length IgG (FIG. 3B).

To evaluate if Fc-mediated function was required for protection in vivo by EBOV-520 mAb, the inventors tested rIgG1 and rIgG1-LALA variants in mice against EBOV-MA. The rIgG1 and rIgG1-LALA antibodies conferred complete protection when delivered at 5 mg/kg dose one day post-challenge (1 dpi) with EBOV-MA (FIGS. 3C-D). Together, these results suggest that direct virus neutralization alone could be sufficient to confer protection in vivo by broadly neutralizing mAbs, although this unique type of mAb also may function through Fc-mediated activities that can be tuned by class switch of the isotype.

EBOV-515 and -520 use several mechanisms to facilitate virus neutralization. The inventors next sought to elucidate the molecular basis of neutralization by the three broadly neutralizing mAbs identified above. Filovirus entry is a complex process that involves cathepsin-mediated cleavage of GP into cleaved GP intermediate ($GP_{CL}$) in the acidified endosomal compartment (Brecher et al., 2012; Chandran et al., 2005; Schornberg et al., 2006). Cleavage removes the glycan cap and mucin-like domain of GP ectodomain, thereby exposing a receptor binding site (RBS) for endosomal receptor NPC1-C(Carette et al., 2011; Cote et al., 2011; Wang et al., 2016). Binding to NPC1 triggers structural rearrangements in GP2 that lead to membrane fusion (Miller et al., 2012; Spence et al., 2016).

The inventors first defined groups of neutralizing mAbs that bind to common major antigenic sites using a competition-binding assay with cell surface expressed intact EBOV GP (Jurkat-EBOV GP), or the same cells that had been treated with thermolysin to mimic cathepsin cleavage to yield membrane-displayed $GP_{CL}$ (Jurkat-EBOV $GP_{CL}$). MAb EBOV-442 targeted the glycan cap (as shown by competition with glycan cap mAbs BDBV289 or 13C6), and it only recognized intact EBOV GP. The most potent broadly neutralizing mAbs in the panel, EBOV-515 and -520, bound moderately to intact GP but strongly to $GP_{CL}$, and they targeted the GP base (as shown by competition for binding with mAb 2G4 or 4G7) (FIGS. 4A-B). This finding suggests that EBOV-442 most likely acts prior to GP cleavage, while EBOV-515 and -520 may act either prior to or after cleavage.

Figure 11A:
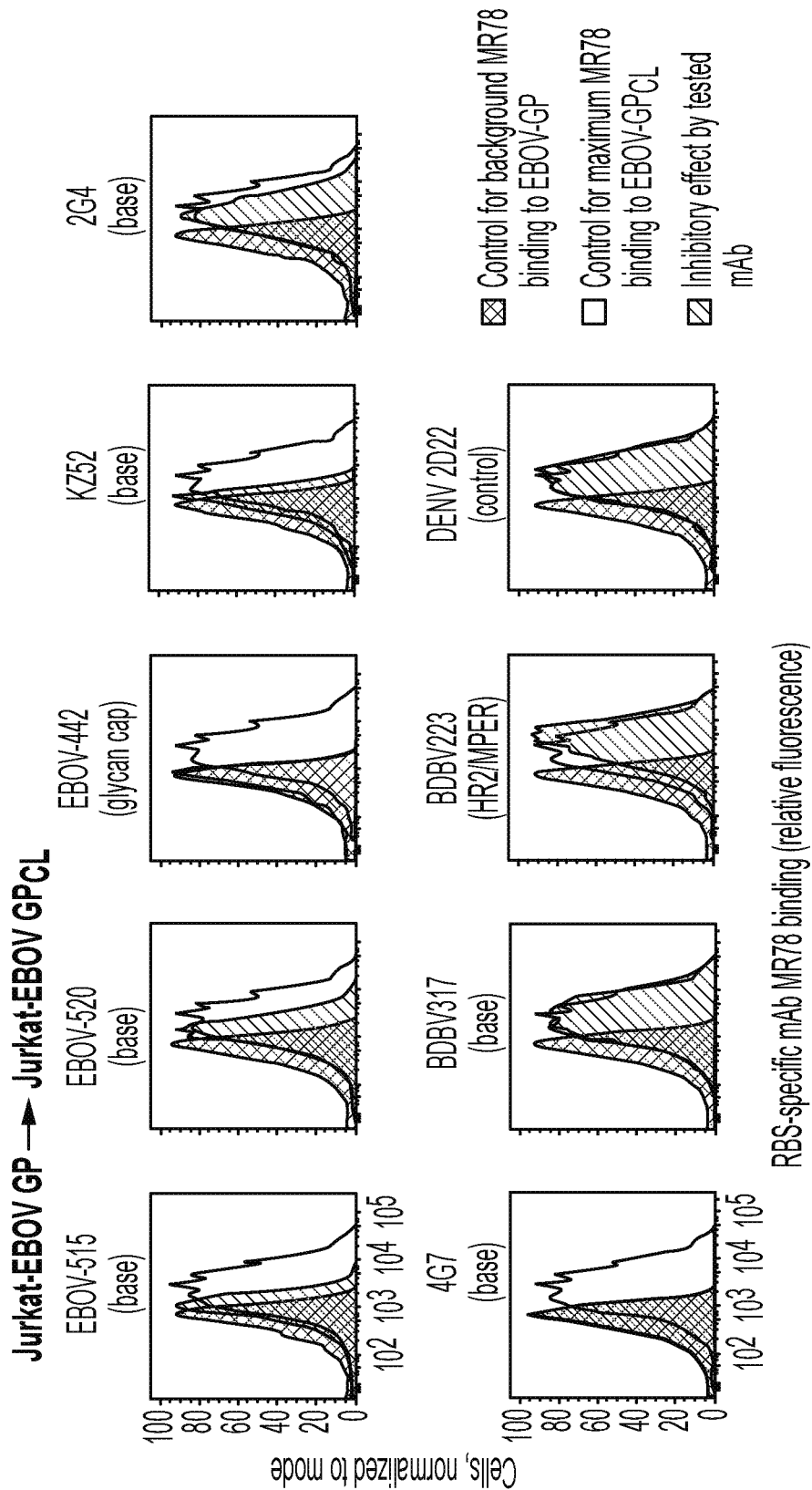

The inventors next assessed the capacity of the three broadly neutralizing mAbs to inhibit GP cleavage. Jurkat-EBOV GP cells were pre-incubated with mAb EBOV-442, EBOV-515, or EBOV-520. For comparison, the inventors tested in parallel the GP base region specific mAb KZ52 with known inhibitory activity (positive control) (Misasi et al., 2016), or an irrelevant mAb to dengue virus DENV 2D22 or the HR2/MPER specific non-inhibitory mAb BDBV223 (negative controls, unpublished). After cleavage, exposure of the RBS on $GP_{CL}$ was measured by the level of binding of fluorescently-labeled RBS-specific mAb MR78 that does not bind uncleaved EBOV GP (Flyak et al., 2015). MAbs EBOV-442, -515, and -520, inhibited cleavage in a dose-dependent manner, similarly to KZ52 (FIG. 4C; FIG. 11A). The glycan cap specific mAb EBOV-442 was the most efficient mAb and completely inhibited GP cleavage at 0.3 µM, while the base targeted mAbs EBOV-515 or -520 revealed only partial inhibition at the same concentration. This finding suggests that the most potently neutralizing base region specific mAbs also may act after GP cleavage. Interestingly, the non-blocking mAb BDBV223 modestly enhanced binding of MR72 to the RBS after cleavage.

Figures 4C, 4D:
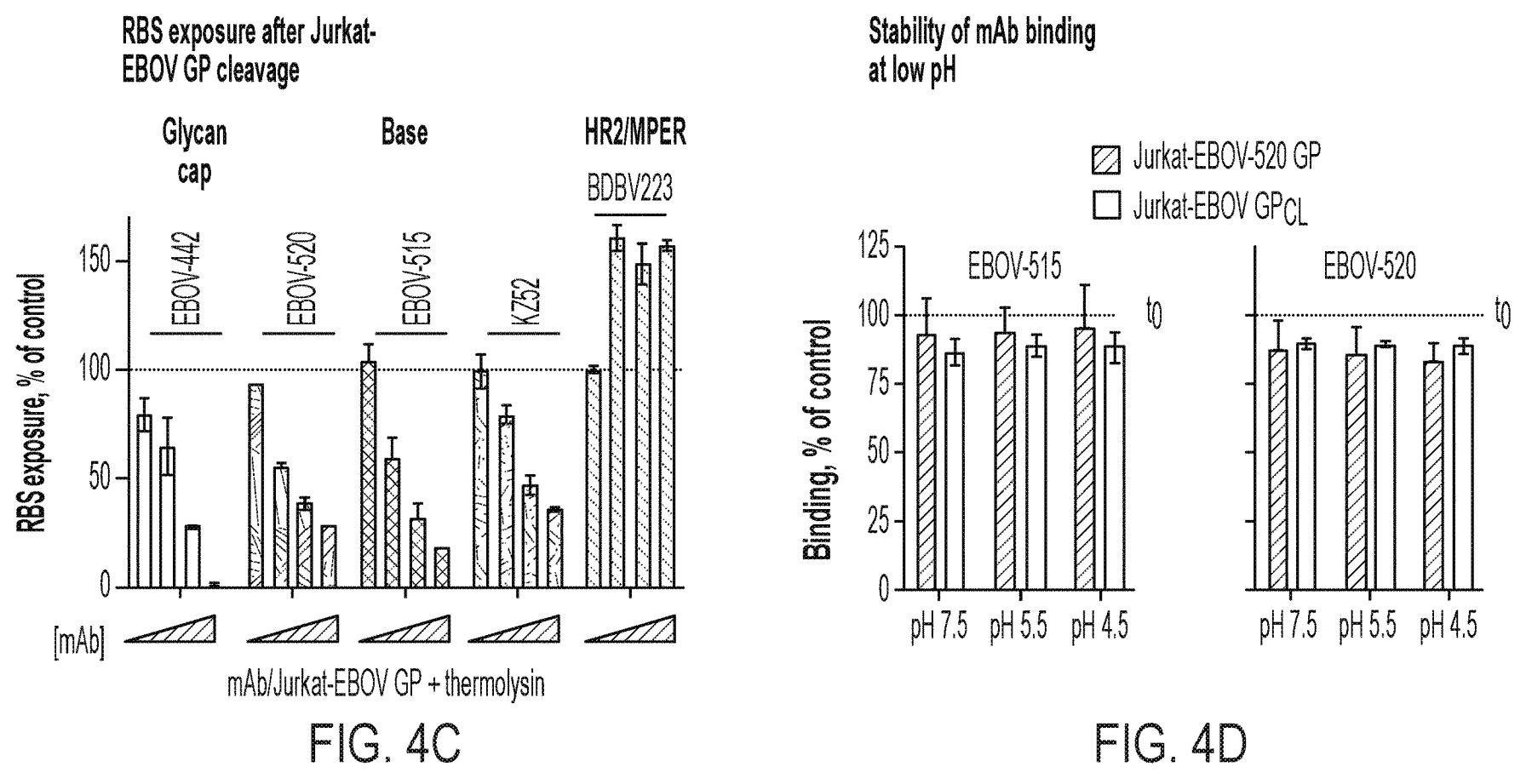

During infection, GP cleavage occurs in the acidified endosome with a pH estimated to be about 5.5. To test mAb binding under these conditions, the inventors first determined binding of EBOV-515 or -520 to EBOV, BDBV, or SUDV GP ATM at neutral or low or neutral pH. Since antibody binding initially occurs at neutral pH during infection, the inventors investigated the pH stability of mAb that was pre-bound to cell surface displayed EBOV GP or $GP_{CL}$. Cells displaying GP or $GP_{CL}$ on the surface were fixed, pre-incubated with fluorescently-labeled mAb at neutral pH, and then exposed to neutral or low pH for 2 hours. Stability of association was measured as percent of maximal mAb binding by flow cytometry. Both EBOV-515 and -520 demonstrated stable association with GP or $GP_{CL}$ at low pH, ranging from −84 to 96% of the total mAb bound at neutral pH and assessed before the exposure to low pH (FIG. 4D). This finding suggests that both mAbs bind tightly to GP or $GP_{CL}$ in low pH compartments, which may allow them to act prior to or after the proteolytic priming step.

The inventors next examined in more detail the interaction of mAbs with cell surface displayed $GP_{CL}$. Binding of base region specific mAbs to Jurkat-EBOV $GP_{CL}$ was enhanced relative to binding of with uncleaved Jurkat-EBOV GP, while binding of the HR2/MPER-specific mAb BDBV317 to Jurkat-EBOV $GP_{CL}$ was similar to that for uncleaved Jurkat-EBOV GP (FIG. 11B). Dose-response testing showed a dramatic increase (~80- to 250-fold) in binding efficiency of EBOV-515 or -520 to $GP_{CL}$ compared to intact GP (FIG. 5A). This finding was concordant with the large (~200 to 800-fold) increase in neutralizing potency for these mAbs against a replication-competent recombinant vesicular stomatitis virus (rVSV) displaying EBOV $GP_{CL}$ (FIG. 5B). Therefore, the inventors conclude that the antigenic site for these broadly neutralizing mAbs is partially occluded on intact GP and more accessible after proteolytic priming to produce $GP_{CL}$.

Figure 11C:
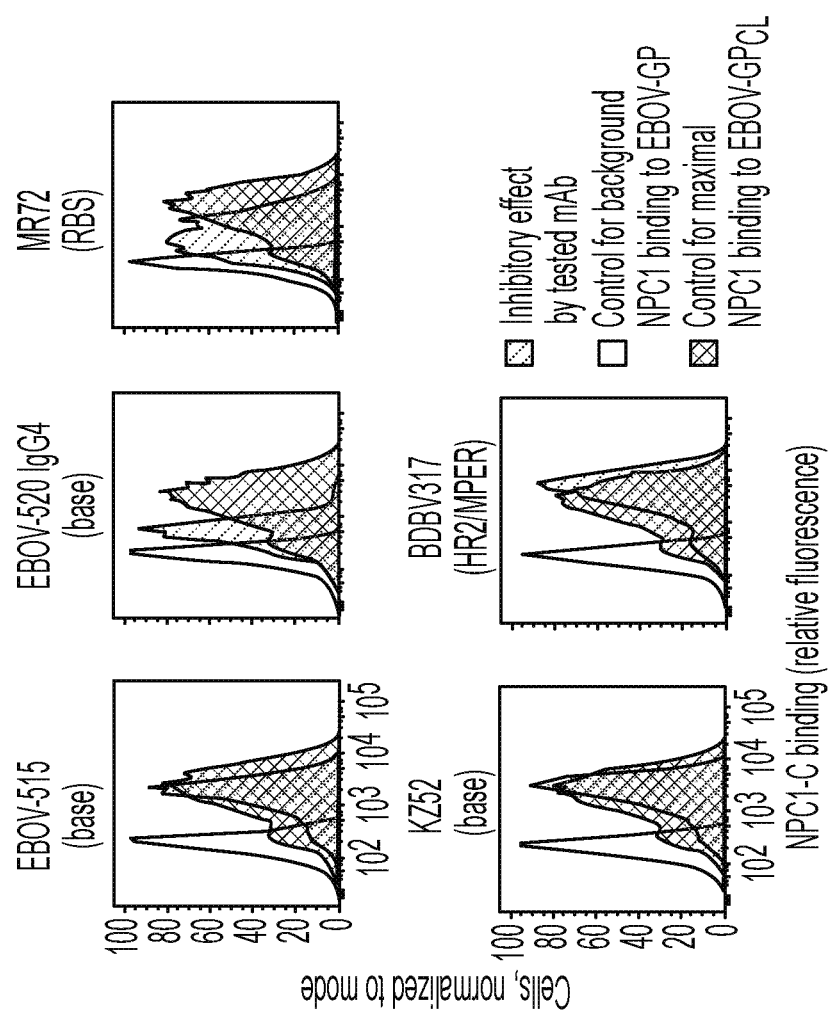

Given that these broadly neutralizing mAbs were more potent against particles displaying $GP_{CL}$, the inventors next assessed their ability to inhibit binding of GP to the receptor NPC1. Binding of soluble FLAG-tagged NPC1-C to Jurkat-EBOV $GP_{CL}$ was assessed in the presence of increasing concentrations of mAbs EBOV-515 or -520 (base), negative control KZ52 (base), BDBV317 (HR2/MPER), or positive control mAb MR72 (RBS-specific, with NPC1-C-blocking activity) (Bornholdt et al., 2016a; Flyak et al., 2015). EBOV-520, similarly to MR72, exhibited dose-dependent inhibition of NPC1 binding to $GP_{CL}$ (FIG. 5C, FIG. 11C), suggesting that EBOV-520 may act by inhibiting receptor engagement in the endosomal compartment.

MR72 and MR78 target a hydrophobic pocket of the RBS that is exposed only on $GP_{CL}$ of ebolaviruses or GP of the most divergent filovirus Marburg (MARV) (Bornholdt et al., 2016a). Hence, the inventors next tested if EBOV-520 competes for binding with the RBS-specific MR72 or MR78. Jurkat-EBOV $GP_{CL}$ cells were pre-incubated with an unlabeled mAb, and next incubated with a second, fluorescently labeled mAb for flow cytometric analysis. Pre-bound MR72 or MR78 did not block binding of EBOV-520 to $GP_{CL}$ (FIG. 5D), indicating that MR72 and EBOV-520 recognize distinct, non-overlapping epitopes. In contrast, EBOV-520 partially inhibited binding of MR72 (~2.8-fold decrease) when $GP_{CL}$ was pre-incubated with EBOV-520, suggesting that EBOV-520 could inhibit receptor binding indirectly by changing the conformation of the RBS.

Figure 11D:
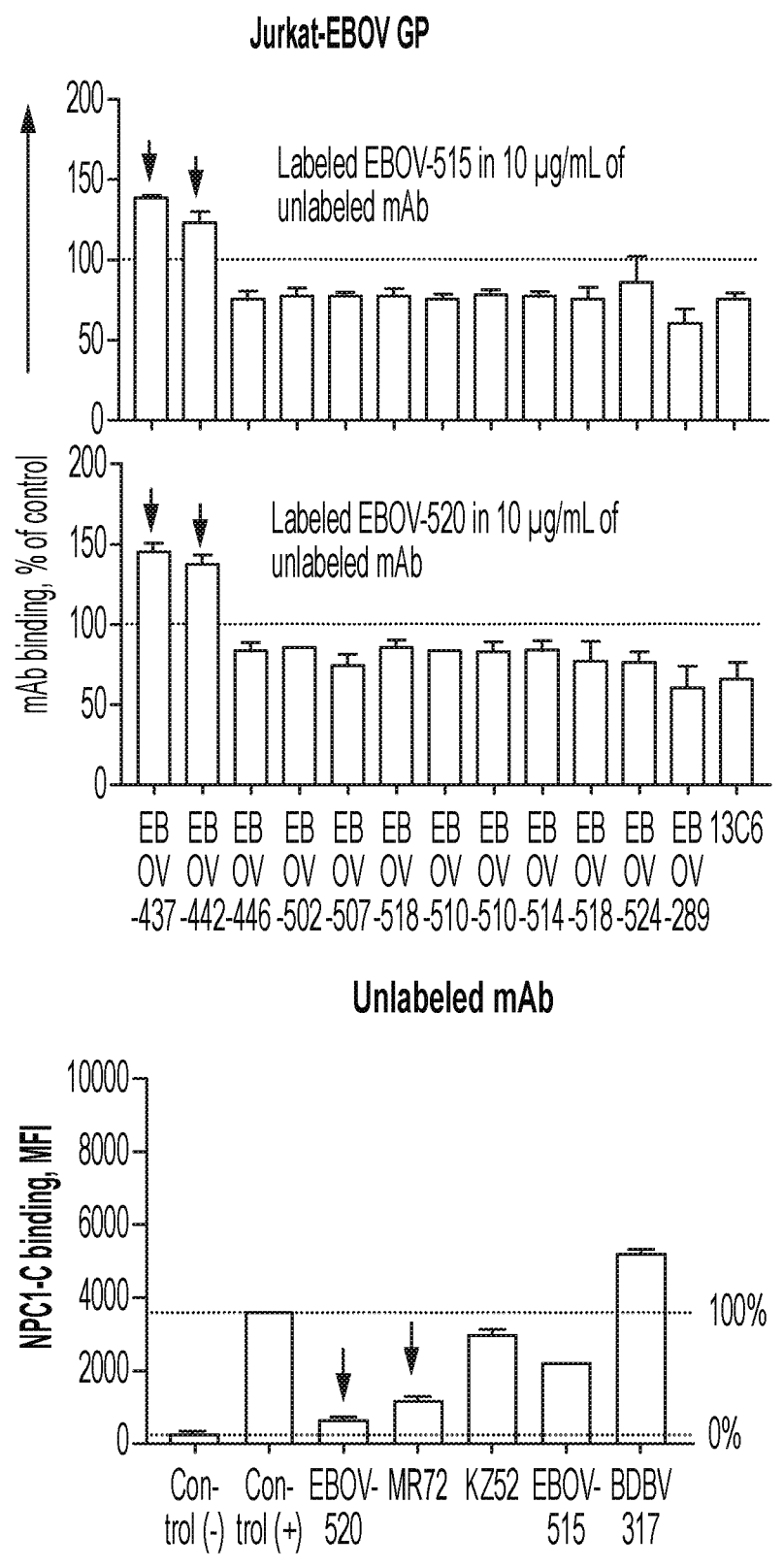

The inventors considered whether any of these antibodies of differing epitope specificity could cooperate in binding to ebolavirus GP, since cooperativity has been reported previously (Howell et al., 2017). They tested whether some non-competing mAbs in the inventors panel could enhance binding of the new broadly neutralizing mAbs by unmasking their epitopes, and thereby, increasing the recognition of intact GP. Fifteen non-competing mAbs from the panel (Table S1) were combined individually with mAbs EBOV-515 or -520, and then assessed for cooperative binding to Jurkat-EBOV GP (FIG. 11D). Two neutralizing mAbs, EBOV-437 and-442 (from the glycan cap specific group identified by competition binding), enhanced the binding of both EBOV-515 and -520 to intact GP ~3- to 5-fold (FIG. 5E). Such a cooperative binding effect could facilitate recognition of intact GP by broadly neutralizing mAbs in polyclonal plasma or therapeutic antibody mixtures.

Together, these findings suggest that broadly neutralizing mAbs act on different stages of ebolavirus entry by inhibiting GP cleavage and by affecting receptor binding.

EBOV-515 and -520 recognize distinct vulnerable epitopes in the ebolavirus GP base region. To define the structural basis of broad neutralization by the isolated mAbs, the inventors performed negative-stain single-particle electron microscopy (EM) studies using complexes of EBOV-515 or EBOV-520 Fab with recombinant trimeric EBOV GP ATM. The EM class averages obtained showed the binding of three Fab molecules on each GP trimer, and confirmed recognition of the base region of GP by both mAbs (FIG. 6A; FIGS. 12A-B). The inventors overlaid the class averages of EBOV-515 and EBOV-520 Fab bound to GP over a class average of Fab/EBOV GP ATM complexes for two previously identified broadly neutralizing mAbs (CA45 and ADI-15878) (Wec et al., 2017; Zhao et al., 2017). The structures showed that the epitopes of EBOV-515 and EBOV-520 are similar to that of CA45 antibody, which recognizes the IFL) region on GP2, and also GP1 below the IFL (Zhao et al., 2017). However, EBOV-515 and EBOV-520 approach GP with different angles than does CA45. In addition, EBOV-520 bound to a region closer to the head region of GP1, above the IFL region epitope of antibody CA45. The binding sites and approach angles of EBOV-515 and EBOV-520 differ from that of mAb ADI-15878, which binds to a non-overlapping adjacent epitope on the IFL and with a relative rotation of about 900 about the long axis (FIG. 6A; FIG. 12B).

To define the epitope for the broadly neutralizing mAbs, the inventors used alanine scanning mutagenesis of GP and tested the binding of mAb EBOV-515 or -520 to individual GP members of a shotgun mutagenesis alanine mutation library of EBOV GP. The inventors also generated antibody escape mutant viruses by passing recombinant infectious EBOV expressing eGFP (EBOV-eGFP) or rVSV/EBOV-GP in the presence of mAb and determined the GP sequence of escape variants. Consistent with the EM data, the virus escaped EBOV-515 neutralization by independent mutations at IFL residues P513L or N514D. None of the single alanine mutants affected binding of mAb EBOV-515, likely due to its high-affinity binding mode. For mAb EBOV-520, the N512A (GP2, IFL base) and E106A (GP1 head region) mutations reduced binding to GP, and escape mutation E106K in the head region of GP1 reduced neutralizing potency (FIG. 6B, top; FIGS. 12C-D). The EBOV-520 epitope is a quaternary structure located within a large, continuous, and highly conserved region that spans the GP1 and GP2 subunits (FIG. 6B, top). The residues critical for EBOV-515 or -520 binding are 100% identical among multiple ebolaviruses, including EBOV, BDBV, SUDV, and TAFV (FIG. 6B, bottom), which explains the high level of neutralization breadth of these mAbs.

The EBOV-520 epitope and EM analysis also suggest that, in addition to any allosteric alteration of the NPC1-C binding site, this mAb would further impede binding by full-length NPC1, since a co-crystal of $GP_{CL}$ and NPC1 (PDB ID: 5JNX) (Gong et al., 2016) shows that the lumenal N-terminal domain of NPC1 is in close proximity to N512 and E106, and that EBOV-520 would sterically hinder access by NPC1.

Together with the observed NPC1-C inhibitory capacity by EBOV-520 shown above, these data suggested that binding to this unique GP1/2 spanning epitope adjacent to the RBS may interfere with binding of GP to receptor in the endosome. In summary, mAb EBOV-520 appears to bind a unique highly conserved, quaternary epitope near the RBS, and therefore, it represents a distinct new class of potent, broadly neutralizing antibody.

Figures 7A, 7B, 7C, 7D:
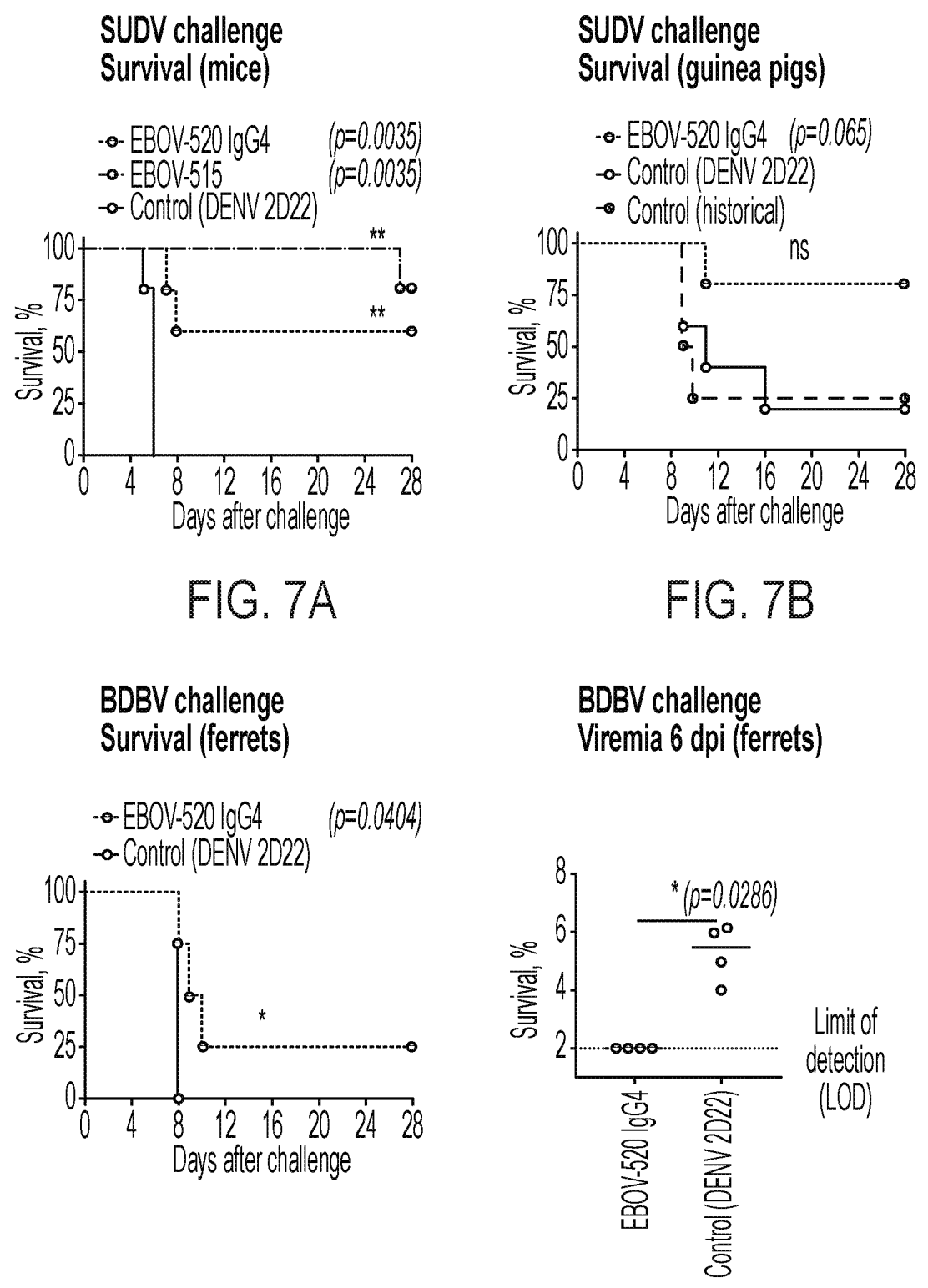
Figure 14:
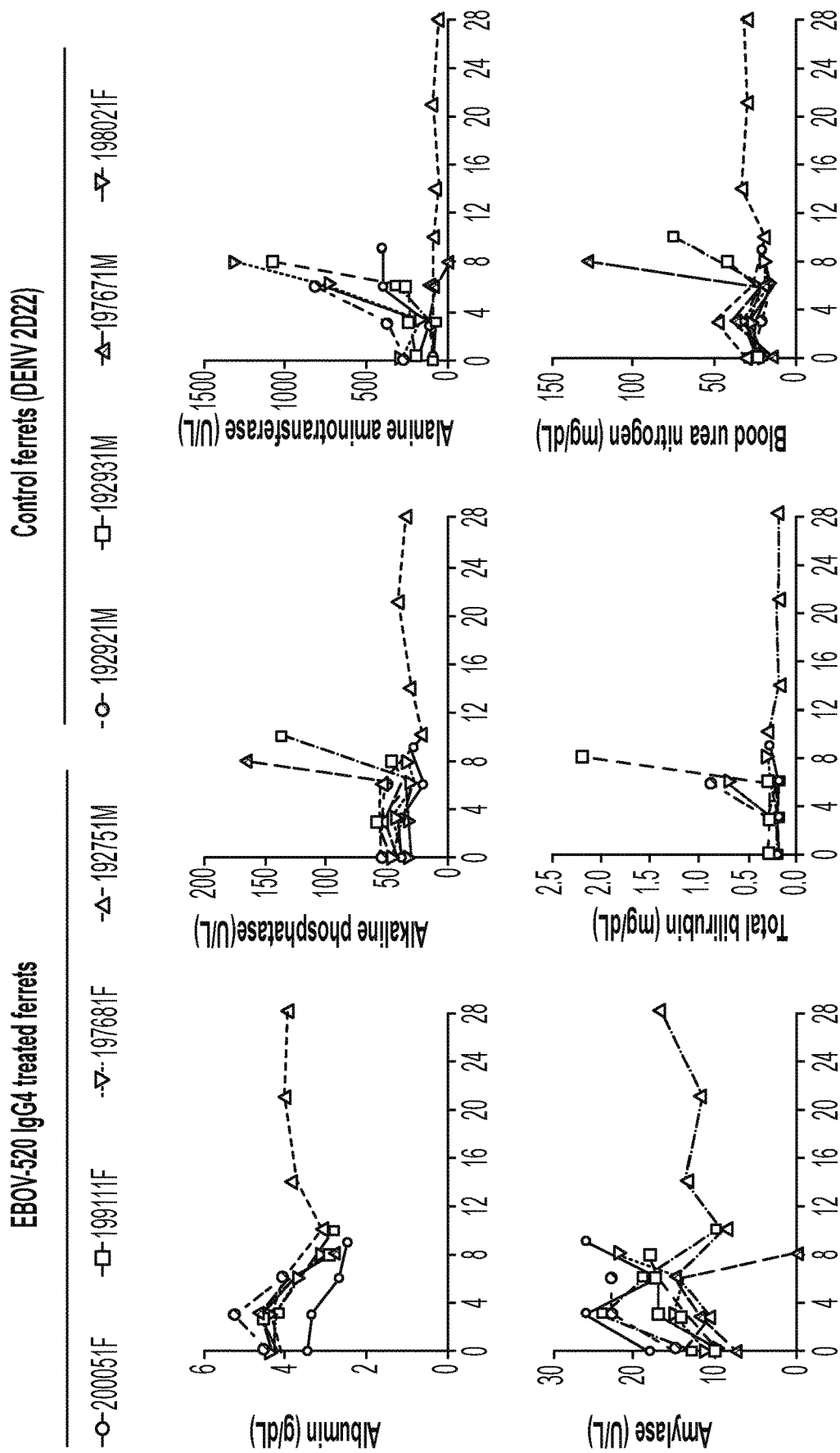
FIG. 14. Analysis of blood chemistry markers in BDBV-challenged ferrets, related to FIGS. 7A-D. Blood chemistry changes in ferrets treated with EBOV-520 IgG4 or DENY 2D22 as a control. Data represent one experiment.
Figure 14:
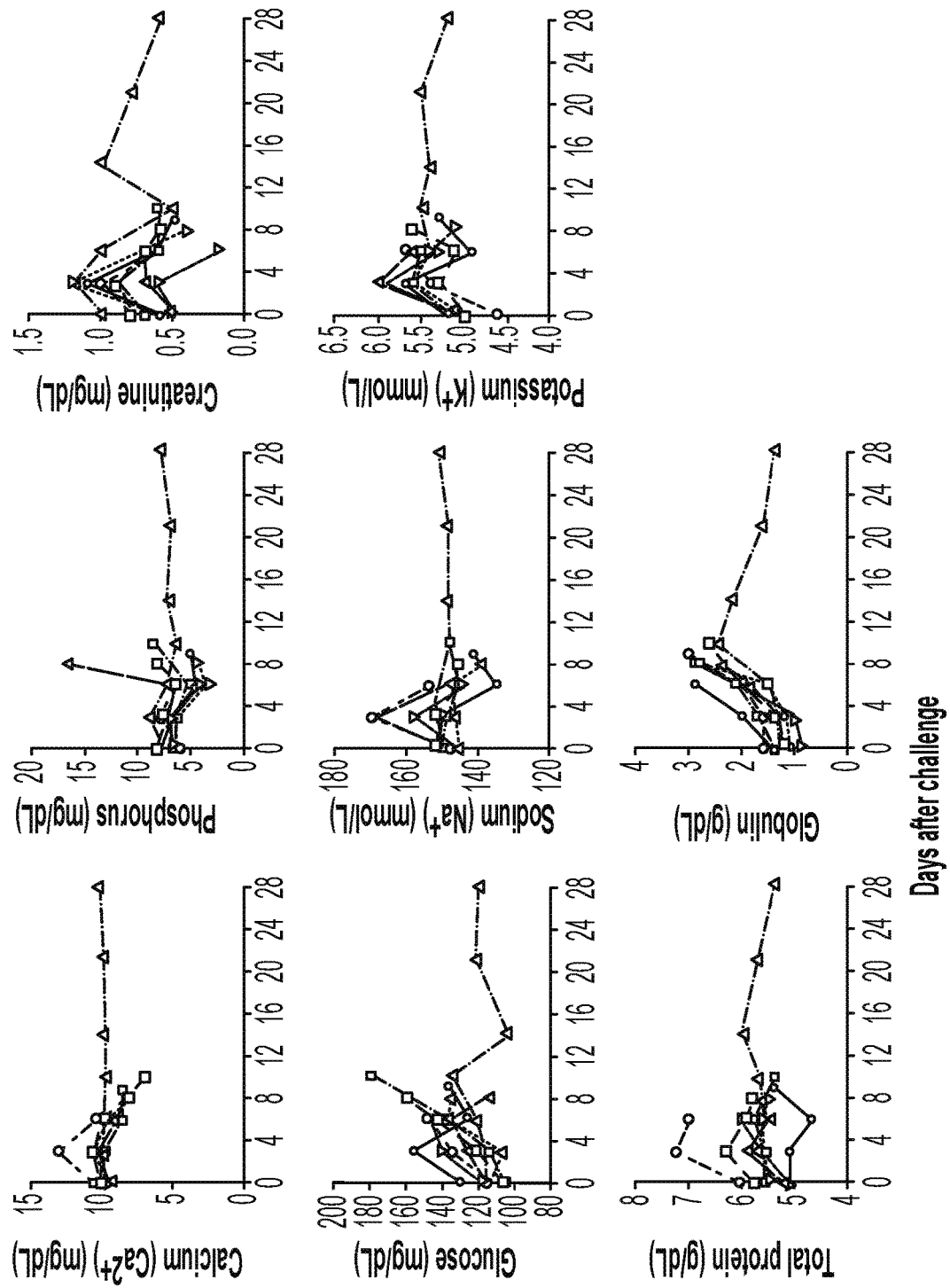

EBOV-515 and -520 mediate protection against heterologous SUDV or BDBV challenge. The inventors next determined the capacity of these mAbs to reduce infection in vivo. They tested the post-exposure efficiency of hybridoma-derived wt EBOV-515 IgG1 or EBOV-520 IgG4 antibodies against SUDV, the virus that diverges antigenically the most from EBOV. Previous studies used a type I interferon $\alpha/\beta$ receptor deficient mouse model for SUDV, in which 20-40% challenged animals survived in the untreated control group (Howell et al., 2016; Wec et al., 2017; Wec et al., 2016). The inventors adopted a more stringent STAT1-deficient (STAT KO) mouse challenge model for SUDV (Raymond et al., 2011), in which 100% of animals in the mock-treated group succumbed to the disease, with a mean time to death (MTD) of six days. A single treatment with EBOV-515 or EBOV-520 (10 mg/kg) conferred significant protection against mortality (p=0.035) and disease, with 80% or 60% of animals in the respective mAb treatment group surviving by 28 dpi (FIG. 7A). Monotherapy with EBOV-520 IgG4 afforded partial protection against infection with guinea pig-adapted SUDV (SUDV-GA) challenge in a guinea pig model (Wong et al., 2015), when mAb (~15 mg/kg) was delivered on dpi 1 and 3. Four of five animals (80%) survived by 28 dpi in the EBOV-520-treated group, as compared to two of nine (~22%) that survived in the combined mock-treated groups (FIG. 7B). The inventors next determined if mAb EBOV-520 could protect against BDBV infection using a recently developed ferret model (Kozak et al., 2016). Ferrets were challenged with a lethal dose of BDBV and treated at 3 and 6 dpi with 18 mg of EBOV-520 or DENV 2D22 as a control by i.p. injection. All control animals became ill by 7 dpi. Two of them succumbed to the infection between observations, and two were euthanized 8 dpi as mandated by IACUC. In the EBOV-520 mAb-treated group, the male animal survived and showed no disease, while female animals became ill and were euthanized on 8-10 dpi (FIG. 7C; FIGS. 13A-C). At time of the second i.p. treatment with mAb (6 dpi), all control animals developed high viremia with an infectious BDBV load that ranged from $10^4$ to $10^6$ PFU per mL of blood, and >107 at 7 dpi as measured by plaque assay. In contrast, all EBOV-520 treated animals had undetectable infectious virus levels in blood on 6 dpi, and only one of three animals that succumbed, showed detectable viremia on 10 dpi (FIG. 7D; FIG. 13A). The plaque assay, which detects infectious virus not neutralized by mAb, suggested that treatment with EBOV-520 reduced viremia. No obvious difference was observed for weight change or blood chemistry markers between the two groups (FIG. 14). Given the incomplete protection observed, the physiological relevance and the efficacy of monotherapy with EBOV-520 IgG4 isotype against BDBV is uncertain, and an IgG1 form of the mAb would be preferred for future development as a therapeutic antibody. However, a significant difference in survival and infectious viral load in blood mediated by the IgG4 suggested that EBOV-520 has capacity to protect against BDBV. Together, these findings revealed that newly identified bNAbs can mediate protection against the heterologous ebolavirus infection.

Figure 15:
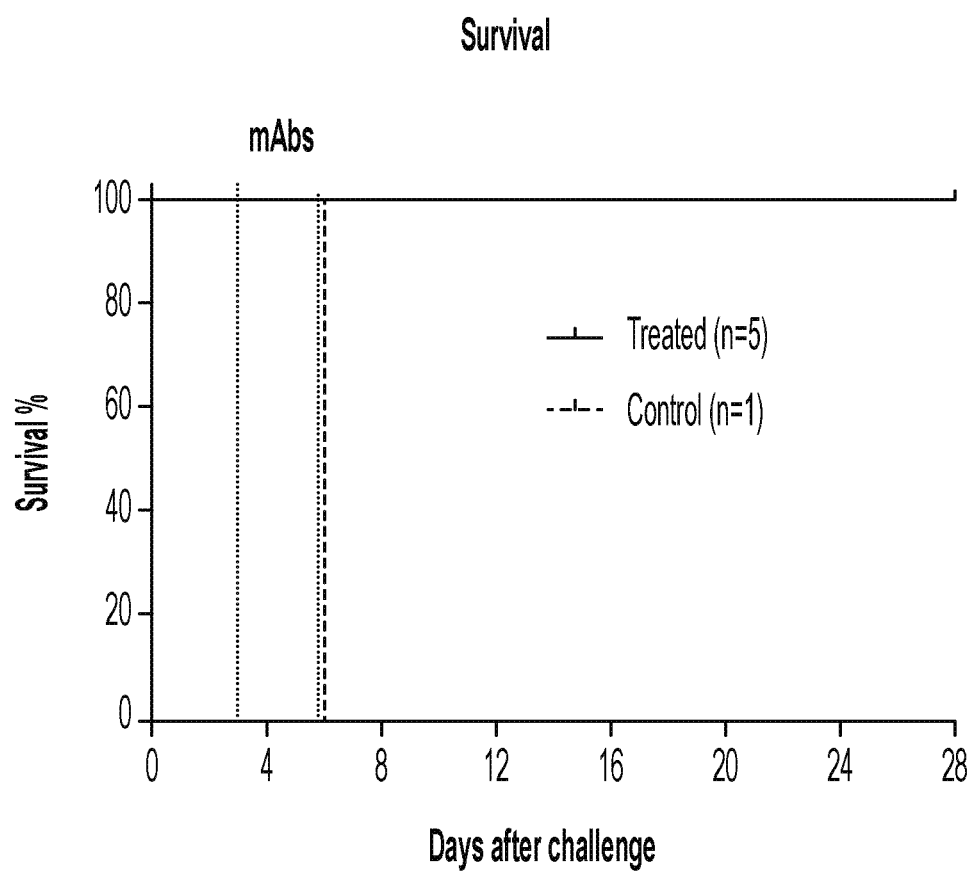
FIG. 15. Therapeutic potency of EBOV-520 IgG1-LALA and EBOV-548 IgG1 antibodies mixture to prevent death of NHPs that lethally challenged with EBOV. NHPs received 1,000 PFU of EBOV intramuscularly and a dose of mAb mixture (15 mg/kg of each mAb, 30 mg/kg of the mixture) intravenously at 3 and 6 dpi (n=6 treated animals, n=1 untreated control this study). Kaplan-Meier survival plot is shown. Dotted lines indicate the day of mAbs dosing.

A rhesus macaque EBOV challenge model was used to determine efficacy of treatment with the mixture of recombinant EBOV-520 IgG1-LALA and EBOV-548 IgG1 antibodies produced in CHO cells. In this experiment, rhesus macaques were assigned to one treatment group of five animals, and all treated NHPs received two doses of 1:1 mAb mixture (30 mg/kg of the mixture) spaced 3 days apart (3 and 6 dpi). An additional animal was studied as a contemporaneous control. After lethal intramuscular challenge with target dose 1,000 PFU of EBOV (variant Kikwit), the inventors treated the animals with mAb mixture at 3 and 6 dpi. The control animals were left untreated. All six animals treated with mAb survived the infection and remained disease symptoms free except one animal with mild petechiae on 6 dpi that resolved by 7 dpi. Control untreated animal succumbed to the disease by 6 dpi (FIG. 15). These findings showed high efficacy of two-dose treatment of NHPs with mixture of two mAbs, EBOV-520 IgG1-LALA and EBOV-548 IgG1, to prevent the mortality and disease.

Example 3—Discussion

According to 2018 annual review of the WHO Blueprint list of priority diseases, there is an urgent need for accelerated research and development for EVD therapeutics (WHO, 2018). In this study, the inventors describe novel pan-ebolavirus reactive neutralizing mAbs isolated from the memory B cells of human survivors of the most recent EBOV outbreaks in West and Central Africa. The work demonstrates several new principles of protection. First, the studies identify unique binding poses for base region human antibodies that confer broad and potent activity against EBOV, BDBV and SUDV, including engagement of a quaternary epitope spanning GP1 and GP2 subunits. Second, the work identifies mAbs that mediate protection as monotherapy in vivo solely by neutralizing activity, including by a naturally-occurring IgG4 antibody. Third, the mAb EBOV-520 that binds to the GP base region reduces GP binding to the soluble NPC1-C, by an allosteric effect not previously described. Fourth, the inventors describe pan-ebolavirus glycan cap-specific antibodies that "prime" the GP to enhance accessibility of the deep base region site of vulnerability, establishing a new rational principal for development of mAb cocktails for ebolavirus prevention or therapy.

Three recent studies identified the IFL as a site of vulnerability on the ebolavirus GP for antibody recognition, and reported isolation of mouse 6D6 (Furuyama et al., 2016), macaque CA45 (Zhao et al., 2017), and two clonally related human antibodies ADI-15878 and ADI-15742 (Wec et al., 2017) that could neutralize many pathogenic human ebolaviruses. MAb 6D6 exhibited protective activity in murine models of EBOV and SUDV infection and neutralized the virus by inhibiting cellular entry. Similarly, mAbs CA45, ADI-15878, and ADI-15742 protected mice against EBOV, BDBV, and SUDV, and were suggested to act by targeting an EBOV $GP_{CL}$ intermediate in the endosome prior to the membrane fusion step, or they inhibit the GP cleavage. Here, the inventors identified the pan-ebolavirus neutralizing human mAbs EBOV-515 and EBOV-520. These clones competed for binding to GP with the EBOV species-specific base antibodies 2G4 and 4G7, and they targeted EBOV $GP_{CL}$, similarly to the pattern of CA45, ADI-15878 and ADI-15742. However, these new antibodies demonstrated unique structural and functional features. The EBOV-515 and EBOV-520 epitopes overlap in part with that of CA45, but the mAbs engage GP at different angles and with different contact residues. CA45 recognized Y517, G546, and N550 residues toward the C-terminus of the IFL, and R64 in the GP1 N-terminus (Zhao et al., 2017). In contrast, EBOV-515 recognized the P513 and N514 residues toward the N-terminus of the IFL, and EBOV-520 contacted N512 of the IFL in GP2 and E106 residues in GP1 with a binding pose shifted upward toward the GP head. EBOV-520 appeared to recognize a discontinuous epitope that span both GP subunits. The positions of bound EBOV-515 and EBOV-520 differ from those of ADI-15878 and ADI-15742, and they bind to a differing site near the IFL. EBOV-515 and EBOV-520, like CA45, inhibited GP cleavage. However, EBOV-520 also inhibited NPC1-C binding to $GP_{CL}$ and partially competed for binding with the RBS-specific mAb MR72, even though EBOV-520 does not contact the RBS. Therefore, EBOV-515 and EBOV-520 represent a distinct new class of broadly neutralizing human antibodies recognizing a distinct site of vulnerability. Recognition of diverse epitopes in the base region near the IFL with differing binding poses, breadth, potency and mechanism of action by EBOV-515, EBOV-520, CA45, ADI-15878, and ADI-15742 is reminiscent of findings for antibody recognition of HIV Env by diverse human antibodies (Wibmer et al., 2015). Study of the epitopes in this region of GP will inform rational vaccine design against ebolaviruses.

Here, the inventors show that neutralizing activity in a single antibody is sufficient to mediate a therapeutic effect for ebolavirus infection in vivo, using the IgG4 EBOV-520 mAb. Neutralizing Abs elicited by vaccination or infection are a correlate of protection for many infectious diseases (Plotkin, 2010). Recent studies also have emphasized an important role of Fc-mediated Ab function for protective human immunity against many viruses (Ackerman et al., 2016; Vanderven et al., 2017). The efficacy of the antibody cocktail ZMapp, which completely protected NHPs from lethal EBOV challenge, likely depends on both the moderate neutralizing activity of mAbs 2G4 and 4G7 and the Fc-mediated functional activity of the weakly neutralizing mAb c13C6 (Qiu et al., 2014). Previously, it was not clear whether neutralization alone is sufficient for protection against EVD with mAb monotherapy, or whether this activity also must be complemented by Fc-mediated function from the same mAb or another Ab in a therapeutic cocktail. The human EBOV neutralizing mAbs that have conferred protection to date in small animal models of EVD are of the IgG1 or IgG3 isotype, and hence likely also may function in vivo through the Fc region to protect (Overdijk et al., 2012). In this study, the inventors studied the role of isotype in protection using the antibody variable gene sequences of the potent neutralizing and protective human IgG4 mAb EBOV-520. Remarkably, this mAb possessed protective activity even though it was isolated in its naturally-occurring form as an IgG4 Ab. Naturally-occurring IgG4 molecules are not thought to be optimal for therapeutic use as they can undergo Fab-arm exchange in vivo, resulting in formation of functionally monovalent antibodies (van der Neut Kolfschoten et al., 2007). This effect can be prevented by isotype switch or stabilization of the IgG4 core-hinge (Labrijn et al., 2009). The IgG4 isotype also has reduced binding and activity for human FcγRIIIa on natural killer cells (Jefferis, 2012), and therefore, thought to be inert in the human immune system. However, human IgG4 can function through the Fc in mice (Overdijk et al., 2012). The inventors tested protective activity of EBOV-520 by switching the Ig subclass recombinantly to the more functionally capable IgG1, and the inventors generated a functionally impaired IgG1 LALA antibody variant lacking FcγR binding as a comparator. Testing these EBOV-520 Fc variant mAbs revealed a similar level of post-exposure efficacy of treatment for each in a murine EBOV challenge model. This finding suggests that some pan-ebolavirus human mAbs such as EBOV-520 can act principally or solely through neutralization to confer protection in vivo. Monotherapy with mAb EBOV-520 IgG4 conferred protection in mice, and partial protection in larger animal challenge models. In order to test for breadth of activity against BDBV and SUDV, the inventors used additional animal models including guinea pigs and ferrets. The inventors tested the mAb EBOV-520 only in the form of its naturally occurring IgG4 isotype in ferrets and showed partial protection. The IgG1 or IgG3 variants of this antibody likely would exhibit a higher level of protection, but the inventors were not able to test the isotype variant IgGs in the ferret model in a BSL4 environment, as this resource is currently limited.

Tuning Fc-mediated effector functions of ebolavirus neutralizing Abs is a promising strategy to enhance their activity. The mAbs EBOV-520 and EBOV-515 both showed a capacity to trigger multifunctional immune cell-associated responses by their naturally occurring isotypes (IgG4 and IgG1, respectively), but the function of EBOV-520 IgG4 in assays of Fc-mediated activity was low, as expected, and could be improved by switching of the isotype to IgG1. Notably, EBOV-520 IgG1-mediated human PBMC killing of target cells displaying a properly oriented native GP, suggesting that the IgG1 form of EBOV-520 also can function through the Fc in vivo. The capacity to provide protection through various mechanisms, such as direct virus neutralization and diverse Fc-mediated activities (designated here as multi-functionality), suggested that EBOV-515 and EBOV-520 are promising candidates for use as monotherapy for ebolavirus infection. Enhancing the Fc-mediated function of mAb EBOV-520 and related clones also may allow reduction of the mAb concentration required for effective treatment in vivo, thus prolonging the protective effect or reducing the dose needed.

Blocking attachment of viruses to receptors on host cells is an effective antiviral strategy, but the RBS on the intact ebolavirus GP is difficult to access prior to cleavage in the endosome. The inventors showed previously that the RBS on the MARV GP can be recognized directly by human neutralizing antibodies (Flyak et al., 2015; King et al., 2018), and such antibodies also can bind to cleaved or mucin-deleted forms of EBOV GP (Hashiguchi et al., 2015) in a manner that directly mimics NPC1 binding (Bornholdt et al., 2016a; Gong et al., 2016). However, prior to cleavage of the EBOV GP by cathepsins in the endosome, the glycan cap and mucin-like domain obscure the RBS and prevent direct recognition by antibodies (Hashiguchi et al., 2015). Here, the inventors identified a new alternate mechanism for inhibiting GP attachment to NPC1, mediated by the base region specific antibody EBOV-520. Although the antibody clearly binds to the GP base (as shown by EM studies of antigen-antibody complexes, alanine scanning mutagenesis of GP, and generation of antibody virus escape mutants), it also inhibits NPC1-C binding by an indirect mechanism. Presumably, binding of EBOV-520 alters the conformation of the RBS by an allosteric effect that precludes proper engagement by NPC1-C, although the resolution of the EM studies did not allow the inventors to determine if a structural alteration occurred in the RBS on binding. Atomic resolution crystallography studies in future will be required to determine the extent of this effect.

Combination therapy with a cocktail of several potent mAbs has been considered necessary for treatment of ebolavirus infections, because combining mAbs of moderate potency increases the efficacy of treatment and theoretically reduces the chance of emergence of antibody escape mutant viruses (Mire and Geisbert, 2017; Saphire and Aman, 2016; Yamayoshi and Kawaoka, 2017). A mix of the potent IFL-specific macaque mAb CA45 with FVM04, a second macaque mAb that recognized the RBS, conferred protection against pathogenic ebolaviruses in animal challenge models (Zhao et al., 2017). However, it has been challenging to achieve a strong protective effect in vivo with monotherapy. For example, treatment with the broadly neutralizing human mAbs ADI-15742 or ADI-15878 achieved only partial protection when one considers the results from infection models for each of the three clinically relevant species EBOV, BDBV, and SUDV (Wec et al., 2017). The optimal design principles for therapeutic cocktails for broad action against diverse ebolavirus species are still unclear. Ideally, one could identify a panel of antibodies that each broadly recognize all relevant ebolavirus species, but also contribute to the overall protective effect of the cocktail by complementary or synergistic activities.

Here, the inventors showed that single antibodies that recognize the base region near the IFL and GP1 head in unique binding poses provide the broadest recognition of diverse ebolaviruses, but this unique site of broad vulnerability on the GP is partially obscured by the mucin-like domain, glycan cap, and other glycans. It appears that optimal protection by such novel base region mAbs depends on partial cleavage of GP or perhaps by alteration of the position of the mucin-like domain and glycan cap. The shielding of the most protective epitopes in the base region is supported by this study and also previous studies by others that demonstrated more efficient recognition of proteolytically primed GP by some antibodies binding near this region (Wec et al., 2017; Zhao et al., 2017). GP cleavage can be mediated in vitro with enzymes, but this approach is not feasible to include in a therapeutic regimen. Here, the inventors identified an alternate strategy in which binding of mAbs to different antigenic sites on GP alter the GP conformation and increase the susceptibility of virus to neutralization by base antibodies. They identified two mAbs with this activity, EBOV-437 and EBOV-442, which are glycan cap-specific mAbs that recognize all three pathogenic ebolaviruses and do not compete for binding with the base region specific mAbs EBOV-515 or EBOV-520. MAb EBOV-442 appears to be an optimal partner for enhancing the activity of the base region antibodies. This mAb potently neutralized EBOV, BDBV and to a lesser extent SUDV, partially protected mice from lethal EBOV challenge, exhibited multiple effector functions in in vitro assays, efficiently inhibited GP cleavage in vitro, and cooperated in binding with both EBOV-515 and EBOV-520. The second partner antibody EBOV-437 poorly neutralized EBOV but cooperated with both EBOV-515 and EBOV-520 in GP binding. These multifunctional mAbs appear to be promising candidates for inclusion in a combination therapy with EBOV-515 or EBOV-520 as a next-generation therapeutic antibody cocktail for ebolavirus treatment.

In summary, the inventors report here the isolation of potent mAbs from human survivors that recognize a unique site of broad vulnerability on the ebolavirus GP and that can mediate protection against EBOV, BDBV, and SUDV using multiple functions including direct neutralization, inhibition of GP cleavage, binding near the fusion loop, and indirect inhibition of NPC1 receptor binding. The antibodies also could be tuned for enhanced activities mediated by Fc engineering. The work emphasizes important features of multifunctional response by which individual human mAbs can exploit diverse mechanisms for contributing to broad protective immunity. These mAbs and related clones are promising candidates for development as broadly protective pan-ebolavirus therapeutic molecules.

Example 4—Materials and Methods

Human samples. Human PBMCs were obtained from a survivor of the 2014 EVD epidemic in Nigeria. A male human survivor of the 2014 EVD outbreak in Nigeria was age 31 when infected and age 32 when PBMCs were collected. PBMCs were collected well after the illness had resolved, following written informed consent. At time of blood collection, plasma samples were tested by qRT-PCR and found to be negative for the presence of viral RNA. The studies were approved by the Institutional Review Board of Vanderbilt University Medical Center.

Cell lines. Vero-E6 (monkey, female origin), THP-1 (human, male origin), and Jurkat (human, male origin) cell lines were obtained from the American Type Culture Collection (ATCC). Vero-E6 cells were cultured in Minimal Essential Medium (MEM) (ThermoFisher Scientific Scientific) supplemented with 10% fetal bovine serum (FBS; HyClone) and 1% penicillin-streptomycin at 5% $CO_2$, 37° C. THP-1 and Jurkat cells were cultured in RPMI 1640 (Gibco) medium supplemented with 10% heat-inactivated FBS (Gibco), 1% GlutaMax (Gibco), and 1% penicillin-streptomycin (Gibco) at 37° C. in 5% $CO_2$. The MFP-2 line is a non-secreting mouse-human trioma cell line (sex information is not available) that was generated by fusing a murine myeloma cell line with a human myeloma cell line, yielding the intermediate heteromyeloma B6B11, followed by fusion with a human lymphocyte. This cell line was cultured as described previously (Yu et al., 2008). A 293F cell line (human, female origin) stably-transfected to express SNAP-tagged EBOV GP was described recently (Domi et al., 2018). ExpiCHO (hamster, female origin) and FreeStyle 293F (human, female origin) cell lines were purchased from ThermoFisher Scientific Scientific and cultured according to the manufacturer's protocol. The Jurkat-EBOV GP (variant Makona; Davis et al., 2019), Jurkat-BDBV GP (strain Uganda), Jurkat-SUDV GP (strain Gulu) cell lines stably transduced to display respective GP on the surface (Davis and Ahmed, unpublished) were a kind gift from Carl Davis (Emory University, Atlanta, GA). An NIH3T3 engineered fibroblast line (mouse, male origin) constitutively expressing cell-surface human CD154 (CD40 ligand), secreted human B-cell activating factor (BAFF) and human IL-21 was kindly provided by Dr. Deepta Bhattacharya (Washington University in St. Louis, MO). All cell lines were tested on a monthly basis for *Mycoplasma* and found to be negative in all cases.

Viruses. The authentic EBOV-eGFP, mouse-adapted EBOV Mayinga (EBOV-MA, GenBank: AF49101) and SUDV strain Gulu were described previously (Bray et al., 1998; Sanchez and Rollin, 2005; Towner et al., 2005). The chimeric infectious EBOV/BDBV-GP and EBOV/SUDV-GP viruses expressing eGFP were obtained by replacing the gene encoding EBOV GP with that of BDBV (GenBank: KU174137) or SUDV (GenBank: KU174142), respectively (Ilinykh et al., 2016).

Mouse models. Seven- to eight-week old female BALB/c mice were obtained from the Jackson Laboratory, and 7- to 8-week-old 12956/SvEv-Stat1tm1Rds mice (STAT1 KO) were obtained from Taconic Biosciences. Mice were housed in microisolator cages and provided food and water ad libitum. Challenge studies were conducted under maximum containment in an animal biosafety level 4 (ABSL-4) facility of the Galveston National Laboratory, UTMB.

NHP model. NHP research adhered to principles stated in the eighth edition of the Guide for the Care and Use of Laboratory Animals (National Research Council, 2011). The facility where this research was conducted [University of Texas Medical Branch (UTMB)] is fully accredited by the Association for Assessment and Accreditation of Laboratory Animal Care International and has an approved Office of Laboratory Animal Welfare Assurance (#A3314-01).

Generation of human B cell hybridomas producing mAbs. PBMCs from a leukopak were isolated with Ficoll-Histopaque by density gradient centrifugation. The cells were cryopreserved in the vapor phase of liquid nitrogen until use. The EBOV GP-reactive memory B cells were labeled with the recombinant EBOV GP protein that was produced in *Drosophila* Schneider 2 (S2) cells as described below and purified by fluorescence activated cell sorting (FACS) as described previously (Bornholdt et al., 2016). Human B cell hybridomas were generated as described previously (Yu et al., 2008) with some modifications. Briefly, FACS-isolated GP-reactive B cells were bulk-expanded on irradiated NIH3T3 cells that had been engineered to express human IL-21, CD40L (CD154), and BAFF in medium A (STEMCELL Technologies) supplemented with CpG, a Chk2 inhibitor (Sigma-Aldrich), and cyclosporine A (Sigma-Aldrich). After 8 days cells were bulk-fused with MFP-2 myeloma cells using an established electrofusion technique (Yu et al., 2008). After the fusion reaction, hybridoma lines were cultured in ClonaCell-HY Medium E (STEMCELL Technologies) supplemented with HAT Media Supplement (Sigma-Aldrich) in 384-well plates for 18 days before screening of supernatants for antibody production. Supernatants from each well of the 384-well culture plates were assessed by ELISA for reactivity against EBOV, BDBV, and SUDV GP, and also for neutralizing activity against live EBOV, BDBV, and SUDV as described below. Hybridoma cell lines producing cross-reactive and neutralizing mAbs were cloned biologically by single-cell fluorescence-activated cell sorting. Hybridomas were expanded in Medium E until 50% confluent in 75-$cm^2$ flasks (Corning).

MAb isotype and gene sequence analysis. The isotype and subclass of secreted antibodies were determined using murine anti-human IgG1, IgG2, IgG3 or IgG4 mouse antibodies conjugated with alkaline phosphatase (Southern Biotech). Antibody heavy- and light-chain variable region genes were sequenced from RNA obtained from hybridoma lines that had been cloned biologically by flow cytometric sorting. Total RNA was extracted using the RNeasy Mini kit (Qiagen). A modified 5'RACE (Rapid Amplification of cDNA Ends) approach was used (Turchaninova et al., 2016). Briefly, 5 μL total RNA was mixed with cDNA synthesis primer mix (10 μM each) and incubated for 2 min at 70° C. and then decrease the incubation temperature to 42° C. to anneal the synthesis primers (1-3 min). After incubation, a mixture containing 5× first-strand buffer (Clontech), DTT (20 mM), 5' template switch oligo (10 μM), dNTP solution (10 mM each) and 10× SMARTScribe Reverse Transcriptase (Clontech) was added to the primer-annealed total RNA reaction and incubated for 60 min at 42° C. The first-strand synthesis reaction was purified using the Ampure Size Select Magnetic Bead Kit at a ratio of 1.8× (Beckman Coulter). Following, a single PCR amplification reaction containing 5 μL first-strand cDNA, 2×Q5 High Fidelity Mastermix (NEB), dNTP (10 mM each), forward universal primer (10 μM) and reverse primer mix (0.2 μM each in heavy-chain mix, 0.2 μM each in light-chain mix) were subjected to thermal cycling with the following conditions: initial denaturation for 1 min 30 s followed by 30 cycles of denaturation at 98° C. for 10 s, annealing at 60° C. for 20 s, and extension at 72° C. for 40 s, followed by a final extension step at 72° C. for 4 min. All primer sequences used in this protocol were previously described (Turchaninova et al., 2016). The first PCR reaction was purified using the Ampure Size Select Magnetic Bead Kit at a ratio of 0.6× (Beckman Coulter). Amplicon libraries were then prepared according to the Pacific Biosciences Multiplex SMRT Sequencing protocol and sequenced on a Pacific Biosciences Sequel platform. Raw sequencing data was demultiplexed and circular consensus sequences (CCS) were determined using the Pacific Biosciences SMRT Analysis tool suite. The identities of gene segments, CDRs, and mutations from germlines were determined by alignment using the ImMunoGeneTics database (Giudicelli and Lefranc, 2011).

MAb production and purification. For recombinant mAb production, cDNA encoding the genes of heavy and light chains were cloned into DNA plasmid expression vectors encoding IgG1 or IgG1-LALA - or Fab-heavy chain (McLean et al., 2000) and transformed into E. coli cells. MAb proteins were produced after transient transfection of ExpiCHO cells following the manufacturer's protocol and were purified from filtered culture supernatants by fast protein liquid chromatography (FPLC) on an AKTA instrument using HiTrap MabSelect Sure column (GE Healthcare Life Sciences). Purified mAbs were buffer exchanged into PBS, filtered using sterile 0.45-μm pore size filter devices (Millipore), concentrated, and stored in aliquots at −80° C. until use.

GP expression and purification. The ectodomains of EBOV GP ATM (residues 1-636; strain Makona; GenBank: KM233070), BDBV GP ATM (residues 1-643; strain 200706291 Uganda; GenBank: NC_014373), SUDV GP ATM (residues 1-637; strain Gulu; GenBank: NC_006432), and MARV GP ATM (residues 1-648; strain Angola2005; GenBank: DQ447653) were expressed and purified as described before (Gilchuk et al., 2018).

ELISA binding assays. Wells of microtiter plates were coated with purified, recombinant EBOV, BDBV, SUDV, or MARV GP ATM and incubated at 4° C. overnight. Plates were blocked with 2% non-fat dry milk and 2% normal goat serum in DPBS containing 0.05% Tween-20 (DPBS-T) for 1 hr. For mAb screening assays, hybridoma culture supernatants were diluted in blocking buffer 1:5, added to the wells, and incubated for 1 hr at ambient temperature. The bound antibodies were detected using goat anti-human IgG conjugated with HRP (Southern Biotech) and TMB substrate (ThermoFisher Scientific). Color development was monitored, iN hydrochloric acid was added to stop the reaction, and the absorbance was measured at 450 nm using a spectrophotometer (Biotek). For dose-response and cross-reactivity assays, serial dilutions of purified mAbs were applied to the wells in triplicate or quadruplicate, and mAb binding was detected as detailed above.

Kinetics of mAb binding analysis by biolayer interferometry (BLI). The Octet Red™ 96e instrument (FortdBio, Pall) was used to assess binding kinetics of indicated mAbs to EBOV GP. Streptavidin sensors (Forte'Bio) were used to capture biotinylated EBOV GP 0.5 mg/mL in 1× kinetics buffer (PBS containing 0.002% Tween-20 and 0.1 or 2% bovine serum albumin (BSA; Sigma-Aldrich), as indicated. Binding was performed using serial two-fold dilutions of mAbs. The baseline and dissociation steps were carried out in the 1× kinetics buffer at 30 or 37° C. as per the vendor's recommendations. Kinetic binding data are adequately described by 1:1 binding model but accounting for trimeric nature of immobilized GP and bivalent IgG analyte the associating stoichiometry is likely reflected more complex avidity effects. Therefore, data represent an apparent $K_D$ values ($K_D^{app}$), as previously described (Davidson et al., 2015).

Cell surface displayed GP mAb binding. Binding to Jurkat cell surface displayed EBOV, BDBV, or SUDV GPs was assessed with mAbs that were directly fluorescently-labeled. Briefly, mAbs were labeled with AF647 NHS ester (ThermoFisher Scientific) by following the manufacturer's protocol. Labeled mAbs were buffer exchanged into PBS using desalting Zeba columns (ThermoFisher Scientific) and stored at 4° C. with 0.1% BSA (Sigma-Aldrich) and 0.01% sodium azide. Cells were washed with the incubation buffer containing DPBS, 2% of heat-inactivated FBS and 2 mM EDTA (pH 8.0) by centrifugation at 400×g for 5 min at room temperature.

For antibody staining, ~5×10$^4$ cells were added per each well of V-bottom 96-well plate (Corning) in 5 μL of the incubation buffer. Serial dilutions of antibody were added to the cells in triplicate or quadruplicate for total volume of 50 μL per well, followed by 1 hr incubation at room temperature, or 4° C. in some experiments. Unbound antibody was removed by washing with 200 μL of the incubation buffer. Staining of cells was measured by flow cytometric analysis using an IntelliCyt iQue Screener Plus high throughput cytometer (Intellicyt Corp.). Data for up to 20,000 events were acquired, and data were analyzed with ForeCyt (Intellicyt Corp.) software. Dead cells were excluded from the analysis on the basis of forward and side scatter gate for viable cell population. Binding to un-transduced Jurkat cells or binding of dengue antigen-specific mAb DENV 2D22 served as negative controls for most experiments. In some experiments, cells were fixed with 4% paraformaldehyde (PFA) in DPBS after staining and before flow cytometric analysis.

To assess binding of mAbs to cleaved GP, Jurkat-EBOV, -BDBV, or -SUDV GP cells were treated with 0.5 mg/mL of thermolysin (Promega) in PBS for 20 min at 37° C. Cells staining and flow cytometric analysis was performed as described above. The reaction was inhibited by washing cells with the incubation buffer containing DPBS, 2% of heat-inactivated FBS and 2 mM EDTA (pH 8.0). Binding to un-transduced Jurkat (mock) or uncleaved Jurkat-EBOV GP served as controls. $EC_{50}$ values for saturated binding of mAb to $GP_{CL}$ were determined using Prism 7.2 software (GraphPad) after log transformation of mAb concentration and median fluorescence intensity (MFI) values using sigmoidal dose-response nonlinear regression analysis. For non-saturating mAb binding, which observed with intact GP, $EC_{50}$ values were calculated by linear regression analysis using $EC_{50}$ and maximum response (Bmax) values that determined from saturating binding to $GP_{CL}$ as above.

Cooperative binding to cell surface displayed GP. The assay was performed as described previously (Gilchuk et al., 2018). Briefly, Jurkat-EBOV, BDBV, or SUDV GP cells were incubated in triplicates with AF647-labeled first mAb alone (typically the GP-base specific mAb) or the same labeled mAb that titrated into a fixed concentration (typically 10 to 20 μg/mL) of the unlabeled second mAb (typically the GP glycan cap specific mAb). Cells were washed, and antibody binding was analyzed by flow cytometry using IntelliCyt iQue Screener Plus flow cytometer. Background values were determined from binding of the fluorescently labeled mAb to un-transduced (mock) Jurkat cells. Maximal values for saturated binding of rEBOV-520 or rEBOV-548 were estimated from the dose-response binding curves of the GP-base specific mAb rEBOV-520 with respective cell surface displayed cleaved GPs (GP$_{CL}$), which was based on a similar level of AF647 conjugation to rEBOV-520 and rEBOV-548. Results are expressed as the percent of maximal binding minus background signal from mock control for each tested condition with labeled mAb.

Epitope mapping using an EBOV GP alanine-scan mutation library. Epitope mapping was carried out as described previously (Davidson et al., 2015). Comprehensive high-throughput alanine scanning ('shotgun mutagenesis') was carried out on an expression construct for EBOV GP lacking the mucin-like domain (residues 311-461) (based on the Yambuku-Mayinga variant GP sequence), mutagenizing GP residues 33-310 and 462-676 to create a library of clones, each representing an individual point mutant. Residues were changed to alanine (with alanine residues changed to serine). The resulting library, covering 492 of 493 (99.9%) of target residues, was arrayed into 384-well plates, one mutant per well, then transfected into HEK-293T cells and allowed to express for 22 hrs. Cells, unfixed or fixed in 4% PFA, were incubated with primary antibody and then with an AF488-conjugated secondary antibody (Jackson ImmunoResearch Laboratories). After washing, cellular fluorescence was detected using the Intellicyt flow cytometer. MAb reactivity against each mutant EBOV GP clone was calculated relative to wild-type EBOV GP reactivity by subtracting the signal from mock-transfected controls and normalizing to the signal from wild-type GP-transfected controls. Mutated residues within clones were identified as critical to the mAb epitope if they did not support reactivity of the test mAb but did support reactivity of other control EBOV mAbs. This counter-screen strategy facilitated the exclusion of GP mutants that were misfolded locally or that exhibited an expression defect (Davidson and Doranz, 2014).

Generation of virus neutralization escape mutants. To generate escape mutants, 100 PFU of EBOV-eGFP were combined with 2-fold dilutions of the respective mAb starting at 200 µg/mL in U-bottom 96-well plates and incubated for 1 hr at 37° C. Mixtures were applied on Vero-E6 cell monolayer cultures in 96-well plates and incubated for 1 hr. Supernatants were removed, freshly-diluted mAb was added at the same concentrations in 200 µL of MEM supplemented with 2% FBS, and plates were incubated for 7 days at 37° C. Viruses that replicated in the presence of the highest concentrations of mAb, as determined by monitoring eGFP fluorescence by microscopy, were collected. Twenty (20) µL aliquots were incubated with 2-fold dilutions of mAbs starting at 200 µg/mL, and viruses were propagated in the presence of mAbs as described above. The procedure was repeated once more with mAb dilutions starting at 400 µg/mL. Viruses that replicated at the highest mAb concentrations were amplified in Vero-E6 cell culture monolayers in 24-well plates in the presence of mAbs at 200 µg/mL for 7 days. Cellular RNA was extracted using TRIzol reagent, and cDNA copies of viral RNA encoding GP were amplified by RT-PCR and sequenced. To verify isolated escape mutants, 100 PFU of the viruses in MEM supplemented with 2% FBS in triplicate were combined in U-bottom 96-well plates with 8 to 12 two-fold dilutions of mAb, starting at 200 µg/mL and incubated for 1 hr at 37° C. The virus/antibody mixtures then were applied in triplicate to Vero-E6 cell culture monolayers in 96-well plates, incubated for 1 hr at 37° C., washed with MEM, overlaid with 200 µL of MEM containing 2% FBS and 0.8% methylcellulose, and incubated for 48 hrs at 37° C. Plates were fixed with 10% phosphate-buffered formalin (Fisher). Plaques were counted using fluorescence microscopy.

Neutralization assays. Virus neutralization assays were performed in a high-throughput format using the recombinant EBOV-eGFP or chimeric EBOV viruses in which GP was replaced with its counterpart from BDBV or SUDV, as described previously (Ilinykh et al., 2016). For assessing cooperative neutralization of SUDV by the cocktail of two mAbs, virus was incubated with increasing concentrations of rEBOV-520 or rEBOV-548 alone, or rEBOV-520 titrated into a fixed concentration (20 Vg/mL) of rEBOV-548 in triplicate.

Rapid fluorometric antibody-mediated cytotoxicity assay (RFADCC). Antibody-dependent cell-mediated cytotoxicity (ADCC) activity of EBOV GP-reactive IgG or Fab was quantified with an EBOV-adapted modification of the RFADCC assay (Domi et al., 2018; Orlandi et al., 2016). Briefly, a target cell line was made by transfecting 293F cells with a full-length DNA expressing GP from the EBOV-Kikwit isolate followed by transfecting with two separate DNA constructs expressing eGFP and the chimeric CCR5-SNAP tag protein. The new cell line, designated EBOV GPkik-293FS eGFP CCR5-SNAP, expresses EBOV-Kikwit GP on the plasma membrane, eGFP in the cytoplasm and the SNAP-tag CCR5, which can be specifically labeled with SNAP-Surface AF647 (NEB), on the cell surface (Domi et al., 2018). A recombinant form of a human anti-EBOV GP mAb KZ52 (a neutralizing antibody) (IBT Bioservices) was used as a positive control and the unrelated human mAb DENV 2D22 as a negative control. The ADCC activity was quantified by incubating three-fold serial dilutions of mAbs with EBOV GPkik-293FS eGFP CCR5-SNAP target cells for 15 min at ambient temperature and then adding human PBMC as effector cells for 2 hrs at 37° C., after which cells were washed once with PBS, fixed with 2% PFA, stained and analyzed with an LSRII Fortessa flow cytometer (BD Biosciences). Data analysis was performed with FlowJo software (Tree Star Inc.). The percentage cytotoxicity of the mAb was determined as the number of target cells losing eGFP signal (by virtue of ADCC) but retaining the surface expression of CCR5-SNAP.

Antibody-mediated cellular phagocytosis by human monocytes (ADCP). Recombinant EBOV GP ATM (IBT Bioservices) was biotinylated and coupled to AF488 Neutravidin beads (Life Technologies). Antibodies were diluted to 5 µg/mL in cell culture medium and incubated with beads for 2 hrs at 37° C. THP-1 monocytes (ATCC) were added at $2.5 \times 10^4$ cells per well and incubated for 18 hrs at 37° C. Cells were fixed with 4% PFA and analyzed on a BD LSRII flow cytometer, and a phagocytic score was determined using the percentage of AF488+ cells and the MFI of the AF488+ cells. The glycan cap-specific mAb c13C6 (IBT Bioservices) was used as a positive control, and the DENV-specific mAb 2D22 was used as a negative control.

Antibody-mediated neutrophil phagocytosis (ADNP). Recombinant EBOV GP ATM (IBT Bioservices) was biotinylated and coupled to AF488 Neutravidin beads (Life Technologies). Antibodies were diluted to 5 µg/mL in cell culture medium and incubated with beads for 2 hrs at 37° C. White blood cells were isolated from donor peripheral blood by lysis of red blood cells, followed by three washes with PBS. Cells were added at a concentration of $5.0 \times 10^4$ cells/well and incubated for 1 hr at 37° C. Cells were stained with CD66b (Pacific Blue, Clone G10F5; BioLegend), CD3 (AF00, Clone UCHT1; BD Biosciences), and CD14 (APC-Cy7, Clone MφpP9; BD Biosciences), and fixed with 4% paraformaldehyde, and analyzed by flow cytometry on a BD LSR II flow cytometer. Neutrophils were defined as SSC-$A^{high}$ CD66b+, CD3−, CD14−. A phagocytic score was determined using the percentage of AF488+ cells and the MFI of the AF488+ cells. The glycan cap-specific mAb c13C6 (IBT Bioservices) was used as a positive control, and the DENV-specific mAb 2D22 was used as a negative control.

Antibody-dependent NK cell activation. Recombinant EBOV GP ATM (IBT Bioservices) was coated onto a MaxiSorp 96 well plates (Nunc) at 300 ng/well at 4° C. for 18 hrs. Wells were washed three times with PBS and blocked with 5% BSA in PBS. Antibodies were diluted to 10 μg/mL in PBS, and added to the plates, and were incubated for an additional 2 hrs at 37° C. Unbound antibodies were removed by washing three times with PBS, and human NK cells freshly isolated from peripheral blood of human donors by negative selection (Stem Cell Technologies, Canada) were added at $5\times10^4$ cells/well in the presence of 4 μg/mL brefeldin A (Sigma-Aldrich Aldrich) and 5 μg/mL GolgiStop (Life Technologies) and anti-CD107a antibody (PE-Cy5, Clone H4A3, BD Biosciences). Plates were incubated for 5 hrs at 37° C. Cells were stained for NK cell markers (CD56 PE-Cy7, clone B159, BD Biosciences; CD16 APC-Cy7, clone 3G8, BD Biosciences; CD3 AF700, clone UCHT1, BD Biosciences), followed by fixation and permeabilization with Fix and Perm (Life Technologies) according to the manufacturer's instructions to stain for intracellular IFNγ (APC, Clone B27, BD Biosciences) and MIP-10 (PE, Clone D21-1351, BD Biosciences). Cells were analyzed on a BD LSRII flow cytometer. The glycan cap-specific mAb c13C6 (IBT Bioservices) was used as a positive control, and the DENV-specific mAb 2D22 was used as a negative control.

Mouse challenge. For EBOV challenge study, groups of 7-8-week-old female BALB/c mice (n=5 per group) were inoculated with 1,000 PFU of the EBOV-MA by the intraperitoneal (i.p.) route. Mice were treated i.p. with 100 μg (~5 mg/kg) of individual mAb per mouse on 1 dpi. Human mAb DENV 2D22 served as negative control. Mice were monitored twice daily from day 0 to 14 dpi for illness, survival, and weight loss, followed by once daily monitoring from 15 dpi to the end of the study at 28 dpi. The extent of disease was scored using the following parameters: dyspnea (possible scores 0-5), recumbence (0-5), unresponsiveness (0-5), and bleeding/hemorrhage (0-5). Moribund mice were euthanized as per the IACUC-approved protocol. All mice were euthanized on day 28 after EBOV challenge. For SUDV challenge study, groups of 7-8-week-old STAT1 KO mice (n=5 per group) were inoculated i.p. with 1,000 PFU wt SUDV (Gulu). Animals were treated i.p. with indicated doses of indicated individual mAbs or two-antibody cocktail on 1 dpi and were monitored as above. The animal protocols for testing of mAbs in mice were approved by the Institutional Animal Care and Use Committee of the University of Texas Medical Branch (UTMB) in compliance with the Animal Welfare Act and other applicable federal statutes and regulations relating to animals and experiments involving animals.

NHP challenge. Five healthy adult rhesus macaques (*Macaca* mulatta) of Chinese origin (4 to 6 kg body weight) were studied. All animals were inoculated by i.m. route with a target dose of ~1,000 PFU of EBOV isolate 199510621 (variant Kikwit) originated from a 65-year-old female patient who had died on 5 May 1995. The study challenge material was from the second Vero E6 passage of EBOV isolate 199510621. Briefly, the first passage at UTMB consisted of inoculating CDC 807223 (passage 1 of EBOV isolate 199510621) at a MOI of 0.001 onto Vero E6 cells. The cell culture fluids were subsequently harvested at day 10 post-infection and stored at −80° C. as ~1 ml aliquots. Deep sequencing indicated the EBOV was greater than 98% 7U (consecutive stretch of 7 uridines). No detectable *mycoplasma* or endotoxin levels were measured (<0.5 endotoxin units (EU)/ml). The back titer of the inoculum identified 1,025PFU as the actual inoculation dose. Animals were randomized by random number assignment (with Microsoft Excel) into a treatment group of six animals and a control animal. The five EBOV-inoculated macaques in the treatment group received 30 mg/kg rEBOV-520 LALA+rEBOV-548 IgG1 (1:1) mAb mixture on days 3 and 6 after virus challenge by intravenous injection. Antibody concentration was ~20 mg/mL resulting in an administered volume of 1.5 mL/kg. The control animal was not treated. Historical untreated controls included nine animals from three separate studies that were challenged with the same target dose of EBOV and by the same route. All animals were given physical exams, and blood was collected at the time of inoculation and at indicated times after EBOV inoculation. In addition, all animals were monitored daily and scored for disease progression with an internal filovirus scoring protocol approved by the UTMB Institutional Animal Care and Use Committee. The scoring measured from baseline and included posture/activity level, attitude/behavior, food and water intake, respiration, and disease manifestations such as visible rash, hemorrhage, ecchymosis, or flushed skin. A score of ≥9 indicated that an animal met criteria for euthanasia. These studies were not blinded.

Detection of virus load by plaque assay or quantitative reverse transcription PCR analysis. Titration of virus in plasma samples was performed by plaque assay in Vero E6 cell culture monolayers. Briefly, increasing 10-fold dilutions of the samples were applied to Vero E6 cell monolayers in duplicate wells (200 μL); the limit of detection was 25 PFU/mL. For qRT-PCR analysis, RNA was isolated from whole blood using the Viral RNA Mini-kit (Qiagen) using 100 μL of blood into 600 μL of buffer AVL. Primers/probe targeting the VP35 intergenic region of EBOV were used for qRT-PCR with the probe sequence of 6-carboxyfluorescein (6FAM)-5' CCGTCAATCAAGGAGCGCCTC 3'-6 carboxytetramethylrhodamine (TAMRA) (ThermoFisher Scientific). EBOV RNA was detected using the CFX96 detection system (BioRad Laboratories) in One-step probe qRT-PCR kits (Qiagen) with the following cycle conditions: 50° C. for 10 min, 95° C. for 10 s, and 40 cycles of 95° C. for 10 s and 57° C. for 30 s. Threshold cycle (CT) values representing EBOV genomes were analyzed with CFX Manager Software, and data are depicted as genome equivalents (GEq); the limit of detection was $3.7 \log_{10}$ GEq/mL.

Hematology and serum biochemistry. Total white blood cell counts, white blood cell differential counts, red blood cell counts, platelet counts, hematocrit values, total hemoglobin concentrations, mean cell volumes, mean corpuscular volumes, and mean corpuscular hemoglobin concentrations were analyzed from blood collected in tubes containing EDTA using a laser based hematologic analyzer (Beckman Coulter). Serum samples were tested for concentrations of albumin, amylase, alanine aminotransferase, aspartate aminotransferase, alkaline phosphatase, gamma-glutamyltransferase, glucose, cholesterol, total protein, blood urea nitrogen, creatinine, uric acid, and C-reactive protein by using a Piccolo point-of-care analyzer and Biochemistry Panel Plus analyzer discs (Abaxis).

Single particle negative stain electron microscopy. Antibody Fabs were obtained by digesting IgG with 4% papain (w/w) and affinity purified using a CaptureSelectIgG-CH1 affinity column (ThermoFisher Scientific). Fab was further purified by size exclusion chromatography (SEC) using an S200I column (GE Healthcare Life Sciences) equilibrated in 1×TBS (20 mM Tris, 150 mM NaCl, pH 7.4). rEBOV-520 and/or rEBOV-548 Fab were added to EBOV GP ATM trimer in molar excess and incubated for 4 hrs on ice. Complexes were then added directly to copper 400 mesh grids (Electron Microscopy Sciences) that had been thinly coated with carbon and stained with a solution of 2% (w/v) uranyl formate. Negative stain images were collected on a 120 KeV Tecnai Spirit equipped with a 4 k×4 k TemCam 4F16 CMOS camera. Micrographs were collected using Leginon (Potter et al., 1999) and processed on Appion (Lander et al., 2009). Particles were picked using DoGpicker (Voss et al., 2009), extracted and aligned using MSA/MRA (Zhao and Singer, 2014) reference-free 2D classification. Particles were further classified using Relion (Scheres, 2012) by 3D classification, and homogeneous classes were further refined.

Single particle cryogenic electron microscopy. EBOV GP ΔMucΔTM (Makona strain) was produced in 293F cells and purified as described previously (Murin et al., 2018). rEBOV-520 Fab and rEBOV-548 Fab were produced recombinantly as described above. rEBOV-548 was added to 300 µg GP in 5M excess the first and allowed to incubate overnight at 4° C. The complex was purified by SEC on an S200I column using 1×TBS. A 5M excess of rEBOV-520 Fab and ADI-16061 Fab were then added to the purified rEBOV-548/GP complex and allowed to incubate at 4° C. for 4 hrs. A recombinant form of ADI-16061 Fab used for cryo-EM was generated as previously described (Murin et al., 2018). The complex containing rEBOV-520, rEBOV-548 and ADI-16061 was then concentrated to 5 mg/mL using a 30 MWCO spin column (Millipore) that had been equilibrated in 1×TBS. The complex was diluted to 4 mg/mL using 1×TBS and mixed with 0.01% (w/v) Fluorinated Octyl Maltoside (Anatrace), after which 3 µL was applied to 1.2/1.3-4C 400 mesh Cu grids (Quantifoil) that had been plasma cleaned with a mixture of Ag/O$_2$ for 10 s (Gatan Solarus 950 Plasma System). Samples were vitrified using a Vitrobot (Thermo Fisher) equilibrated at 4° C. in an environment of 100% humidity. Grids with sample applied were equilibrated for 10 s, followed by 0-force blotting on both sides of the grid using Whatman No. 1 filter paper for a total of 4.5 s.

Cryo-EM data were collected as listed in Table S7. Raw micrographs were aligned and dose-weighted using Motion-Corr2 (Zheng et al., 2017) followed by whole micrograph CTF-collection using GCTF (Zhang, 2016). Template-based picking, particle extraction and reference-free 2D classification were all performed using Cryosparc2 (Punjani et al., 2017). Cleaned particle stacks were then re-extracted in Relion 3.0 (Zivanov et al., 2018), followed by 3D-classification using C1 symmetry. A tight mask was generated around the GP core and rEBOV-548 Fabs and an additional round of classification was performed with tighter angular sampling. This procedure revealed several sub-states of the complex, with portions of the glycan cap in different positions in each protomer position. A single class with 13,144 particles was selected based off of estimated resolution and due to the appearance of C3 symmetry, indicating that all three glycan cap protomers were in the same position in this class. Particles from this class were re-extracted and 3D-refinement was performed suing a tight mask that just contained the Fv domains of rEBOV-520 and rEBOV-548 as well as the GP core and C3 symmetry was applied. Local resolution estimation and angular sampling was also performed using Relion 3.0

A crystal structure of EBOV GP ΔMucΔTM (Makona) (PDB ID XX) was used as an initial model. For Fabs, initial models were generated using Swiss Modeler (Biasini et al., 2014). Glycans were added from the unliganded structure of EBOV ΔMucΔTM (PDB ID). These components were fit into the EM density using UCSF Chimera (Pettersen et al., 2004) and a single round of real-space refinement was performed in Phenix (Adams et al., 2010) using NCS and secondary structure constraints. The resulting model was then refined in Rosetta (DiMaio et al., 2015). For each round of refinement, 319 models were produced and evaluated using Molprobity (Williams et al., 2018) and EM-Ringer (Barad et al., 2015). The model with the best statistics was then manually adjusted in Coot (Emsley et al., 2010) followed by a final round of refinement in Rosetta. Glycans were validated using PDBcare (Lutteke and von der Lieth, 2004) and Privateer (Agirre et al., 2015). All model figures were generated using UCSF Chimera (Pettersen et al., 2004).

Epitope mapping using peptide fragmentation and hydrogen-deuterium exchange mass spectrometry (HDX-MS). To maximize peptide sequence coverage, the optimized digestion/quench conditions were determined prior to deuteration studies. Briefly, EBOV GP ATM or EBOV GP$_{CL}$ samples were diluted with DPBS buffer (150 mM NaCl, 1.9 mM KH$_2$PO$_4$, pH=7.4) at 0° C. and then quenched with 0.8% formic acid (v/v) containing various concentration of guanidine hydrochloride (GuHCl; 0.8-8 M) and Tris(2-carboxyethyl) phosphine (TCEP) (0.1 or 1.0 M). Eight (8) M GuHCl, 0.5 M TCEP in PBS pH=2.0 gave an optimal peptide coverage map.

Hydrogen-deuterium exchange reactions were initiated by diluting protein samples with D$_2$O in DPBS buffer at a 1:2 ratio (v/v) at 10 s, 100 s or 1,000 s prior to quenching and on-line pepsin digestion. Non-deuterated samples served as controls. Using a Waters nano-ACQUITY UPLC system with an HDX manager (Waters Corp.), samples were injected onto an immobilized pepsin column (Waters Enzymate™) where digestion was performed at 20° C. and 4,700 psi at a flow of 100 µL/min of 0.1% formic acid in H$_2$O. The resulting peptides were collected on a VanGuard™ BEH C18 1.7 m guard column (Waters Corp.) and separated over a Waters BEH C18 1.7 m, 1 mm×100 mm column using a gradient of 5-25% acetonitrile over 6 minutes. The column was coupled to a Waters Xevo G2-XS instrument, eluent was electrosprayed, and MS$^E$ scans were performed with lock-mass acquisition (Leucine enkephalin, m/z 556.2771). The capillary was set to 2.8 kV, source temperature to 80° C., desolvation temperature to 175° C., desolvation gas to 400 L/h and the instrument was scanned over a m/z range of 50-2,000. All experiments were carried out in triplicate. Waters ProteinLynx LGobal Server 3.0.3 software (Waters Corp.) was used to identify the peptide ions with an FDR of 4%, using non-specific protease cleavage, a minimum number of fragment ion matches per peptide of three, and oxidation of methionine as variable modification. DXMS Explorer (Sierra Analytics Inc., Modesto, CA) was used for the analysis of the mass spectra. Non-deuterated samples and equilibrium-deuterated back-exchange control samples served as controls. The centroids of the isotopic envelopes of non-deuterated, functionally deuterated, and fully deuterated peptides were measured using DXMS Explorer, and then converted to corresponding deuteration levels with corrections for back-exchange.

Crystallography and structure determination. EBOV GP for co-crystallization with EBOV-520 was expressed as mucin-like domain-deleted GP (GP AMLD) in *Drosophila*

S2 cells using a single pMT-puro plasmid encoding a C-terminally Strep-tagged construct lacking the transmembrane domain. The protein was purified using a StrepTrap HP affinity chromatography column (GE Healthcare Life Sciences Lifesciences) followed by cleavage of the Strep tag at an Enterokinase cleavage site using EKMax (ThermoFisher Scientific Scientific). To prepare $GP_{CL}$, purified GP AMLD was incubated with 1.5% thermolysin overnight at room temperature to mimic endosomal cathepsin cleavage followed by further purification using a Superdex 200 Increase 10/300 GL SEC column (GE Healthcare Life Sciences Lifesciences). EBOV-520 Fab for co-crystallization with EBOV $GP_{CL}$ was prepared by incubating EBOV-520 IgG with 2% papain for 4 hrs at 37° C.; the digestion was quenched using 50 mM iodoacetamide. The Fab was purified from the reaction mixture using a MonoQ 5/50 GL ion-exchange column (GE Healthcare Life Sciences Lifesciences) followed by further purification using a Superdex 75 Increase 10/300 GL SEC column (GE Healthcare Life Sciences Lifesciences).

The $GP_{CL}$-EBOV-520 Fab complex was obtained by incubating $GP_{CL}$ with a 3-fold molar excess of EBOV-520 Fab overnight at 4° C. followed by purification using a Superdex 200 Increase 10/300 GL SEC column (GE Healthcare Life Sciences Lifesciences). The complex was screened for crystallization using a Douglas Instruments Oryx8, and the protein crystallized in a solution of 0.1 M HEPES pH 7.0 and 1.4 M Ammonium sulfate. Diffraction data to 3.46 Å resolution were collected at beamline 23-IDD at the Advanced Photon Source. The diffraction images were processed using iMosfim (Battye et al., 2011) and scaled using Aimless (Evans and Murshudov, 2013). Molecular replacement, model building, and structure refinement were carried out using the PHENIX suite of programs (Adams et al., 2010). Chains G and H of the PDB entry 5HJ3 were used as molecular replacement search models for $GP_{CL}$, and chains Y and Z of the PDB entry 4YK4 were used as a search model for EBOV-520 Fab following model pruning using Sculptor (Bunkoczi and Read, 2011). A molecular graphics application Coot (Emsley et al., 2010) was used for model inspection and manual refinement. A single $GP_{CL}$ monomer and a single EBOV-520 Fab were contained within the asymmetric unit of the $P4_132$ crystals, and crystal symmetry was applied to generate the model of the biologically relevant trimer shown in all figures.

Quantification and Statistical Analysis. The descriptive statistics mean±SEM or mean±SD were determined for continuous variables as noted. Survival curves were estimated using the Kaplan Meier method and curves compared using the two-sided log rank test (Mantel-Cox) with subjects right censored, if they survived until the end of the study. $EC_{50}$ values for mAb binding were determined after log transformation of antibody concentration using sigmoidal dose-response nonlinear regression analysis. In neutralization assays, $IC_{50}$ values were calculated after log transformation of antibody concentrations using a 3-parameter nonlinear fit analysis. The effect of antibody composition on the GP binding (single mAb or two-antibody mixture) and p-values were estimated by overall test from untransformed MFI flow cytometric values using two-way ANOVA. In neutralization assays, mAb synergy by cocktails was quantified with CompuSyn software using approach that estimates the combination index (CI) to define the effect of drug combination (Chou, 2010). CI values were calculated for each tested concentration of mAb combination, and CI values <1 considered as evidence of synergy. Viral titers in plasma were compared using a Wilcoxon signed-rank test (two-tailed) where column medians compared to a value that equals to the limit of detection for the plaque assay (1.4 $\log_{10}$ PFU/mL). p<0.05 considered as significant. Technical and biological replicates are indicated in the figure legends. Statistical analyses were performed using Prism v7.2 (GraphPad).

Data and Software Availability. The EBOV GPCL+ EBOV-520 Fab crystal structure and the EBOV GP ΔMuc ΔTM (Makona)+rEBOV-520+rEBOV-548 cryo-EM structure has been deposited in the PDB with accession code 6OZ9 and 6PCI, respectively. The accession numbers for the negative stain and cryo-EM reconstructions reported in this paper have been deposited to the Electron Microscopy Data Bank under accession numbers EMDB: EMD-20293 and EMD-20301, respectively.

Example 5—Results

Binding and functional properties of candidate cocktail human mAbs. The inventors identified and analyzed the activity of >1,800 new human mAb secreting hybridomas that were isolated from GP-reactive B cells in human survivors of EVD and identified sites of vulnerability for multifunctional pan-ebolavirus neutralizing mAbs (Gilchuk et al., 2018; unpublished data). This work also revealed several pairs of non-competing, broadly reactive mAbs that cooperated in binding to cell-surface displayed EBOV GP when used in combination. The first partner of each pair is a member of the class of Abs including the three human mAbs EBOV-515 (IgG1), EBOV-520 (IgG4), and EBOV-542 (IgG3), each of which bind to a highly conserved epitope on the base of intact EBOV GP, neutralize all three ebolaviruses infectious for humans (EBOV, SUDV, and BDBV), and protect against lethal infection by EBOV in mice (Gilchuk et al., 2018). The second partner of each pair is a member of a class including the three human mAbs EBOV-437, EBOV-442, and EBOV-548 (all IgG1 originally), each of which binds to the glycan cap, neutralizes EBOV and BDBV only, but poorly protects against EBOV in mice (Gilchuk et al., 2018; FIGS. 23A-E; Table S5).

Because of the potential utility of these mAbs as components of a therapeutic cocktail for humans, the inventors sought to characterize in depth the cooperative effects mediated by combinations of two mAbs. As the first partner of the cocktail, they selected the most well-characterized therapeutic base-region specific mAb (EBOV-520 IgG4). They then expressed this antibody's variable gene sequence in Chinese hamster ovary (CHO) cells as a recombinant IgG1-LALA Fc mutant molecule (rEBOV-520 LALA, or rEBOV-520) to diminish Fc effector function. rEBOV-520 LALA possessed the highest level of protective efficacy with low-dose treatment against EBOV in mice (Kuzmina et al., 2018) and acted principally via neutralization to protect against EBOV (Gilchuk et al., 2018). The second cocktail partner, mAb EBOV-548, showed the highest activity of three identified cooperative glycan cap specific mAbs in a cooperative binding to GP with rEBOV-520 as a partner mAb. EBOV-548 was produced as a functionally competent IgG1 (designated here as rEBOV-548 IgG1 or rEBOV-548), because engagement of the Fc region may be important for protection by GP glycan cap specific mAbs (Gunn et al., 2018).

Figure 16A:
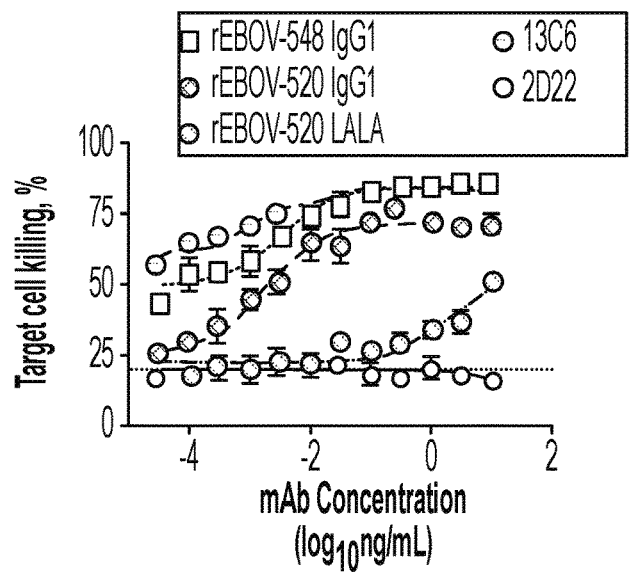
FIGS. 16A-C. Reactivity and function of candidate cocktail human mAbs rEBOV-520 and EBOV-548.
Figure 16B:
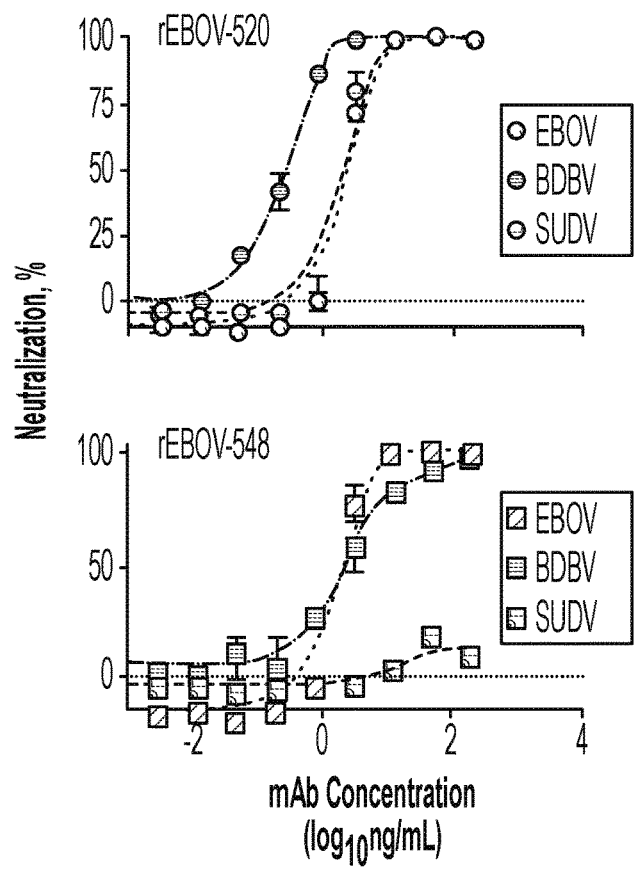
Figure 16C:
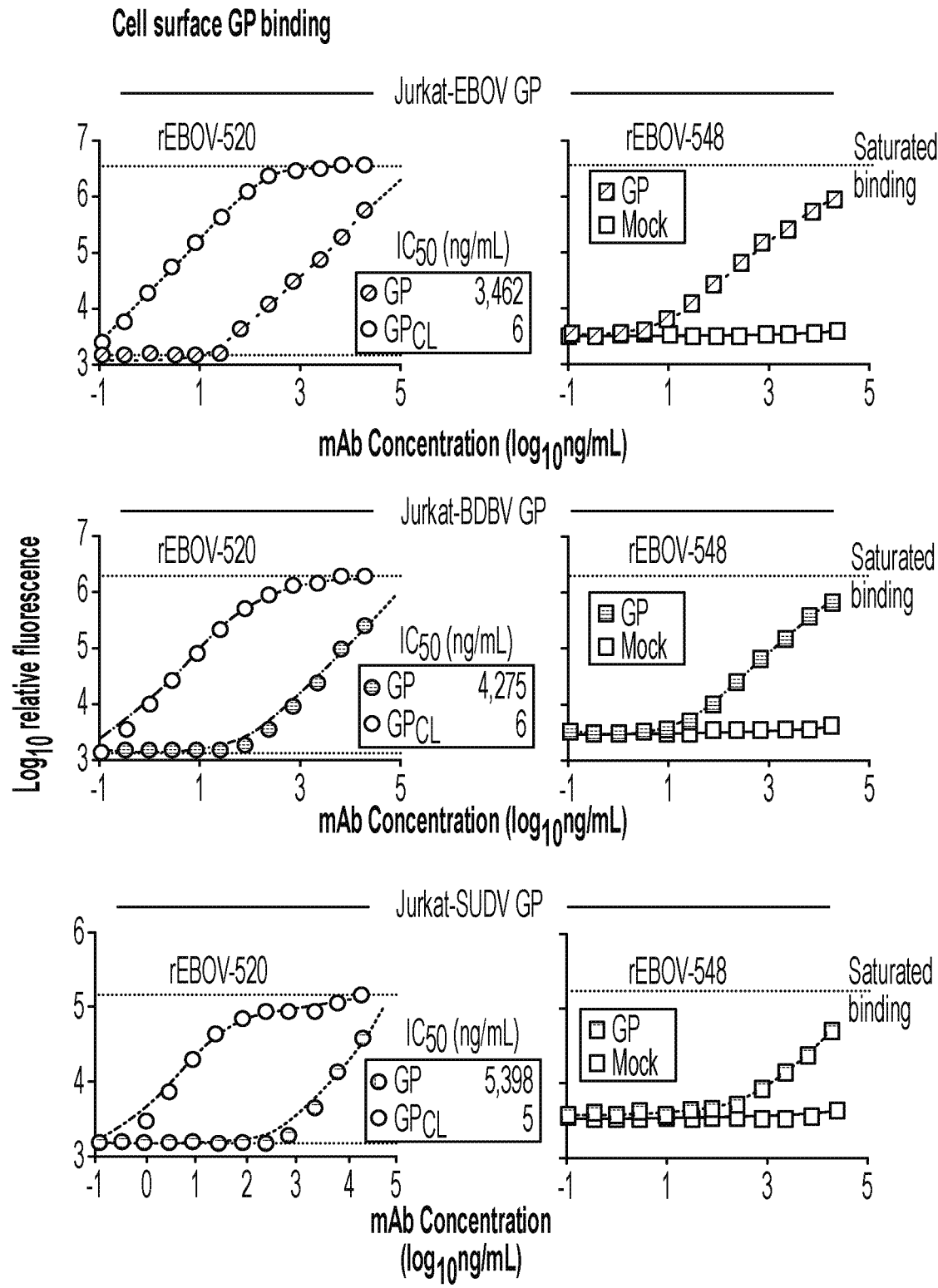
Figure 17B:
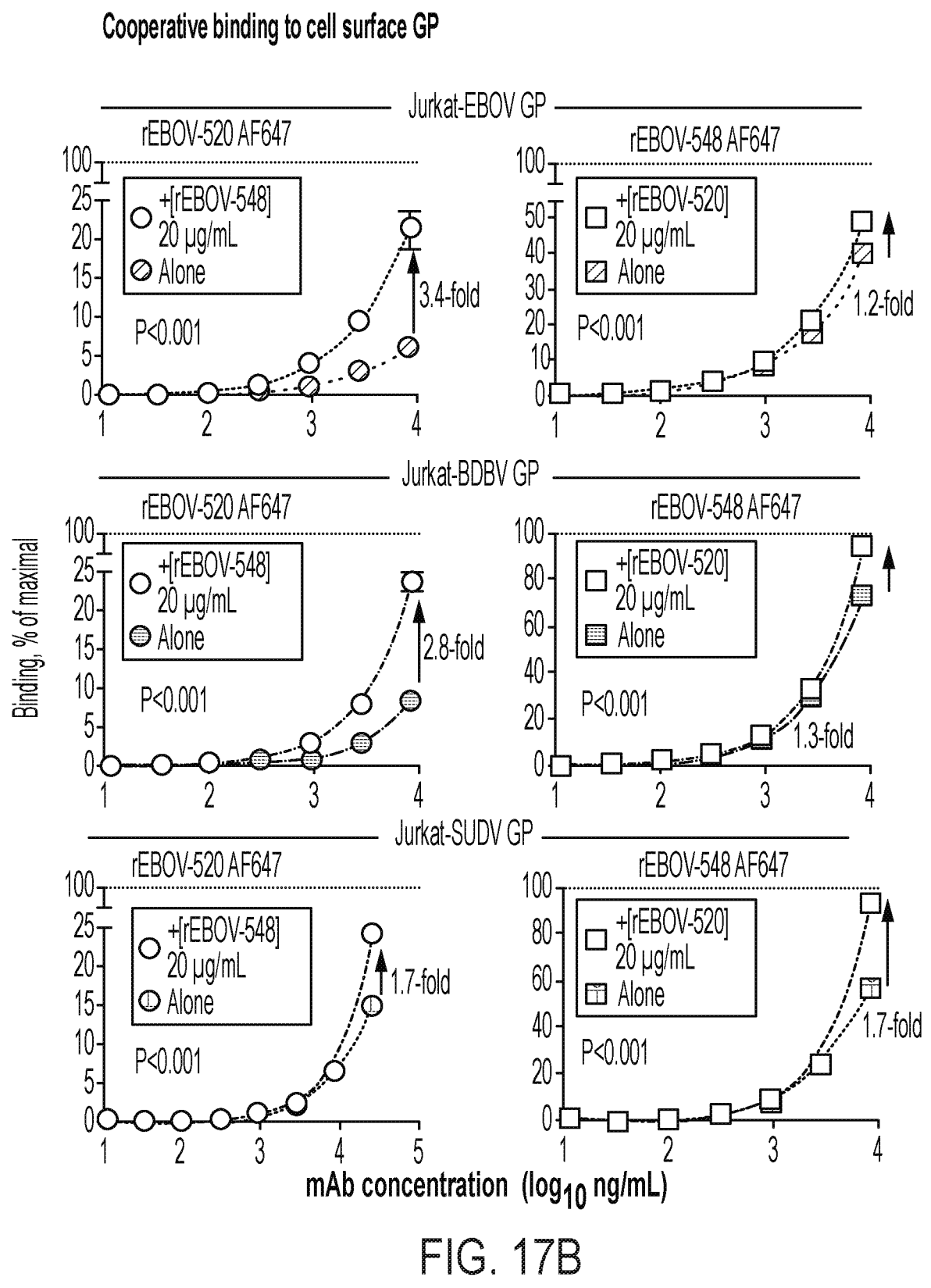
Figure 23B:
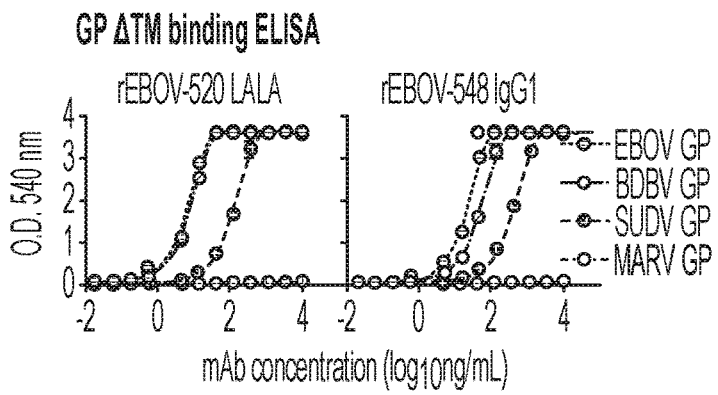
Figure 23C:
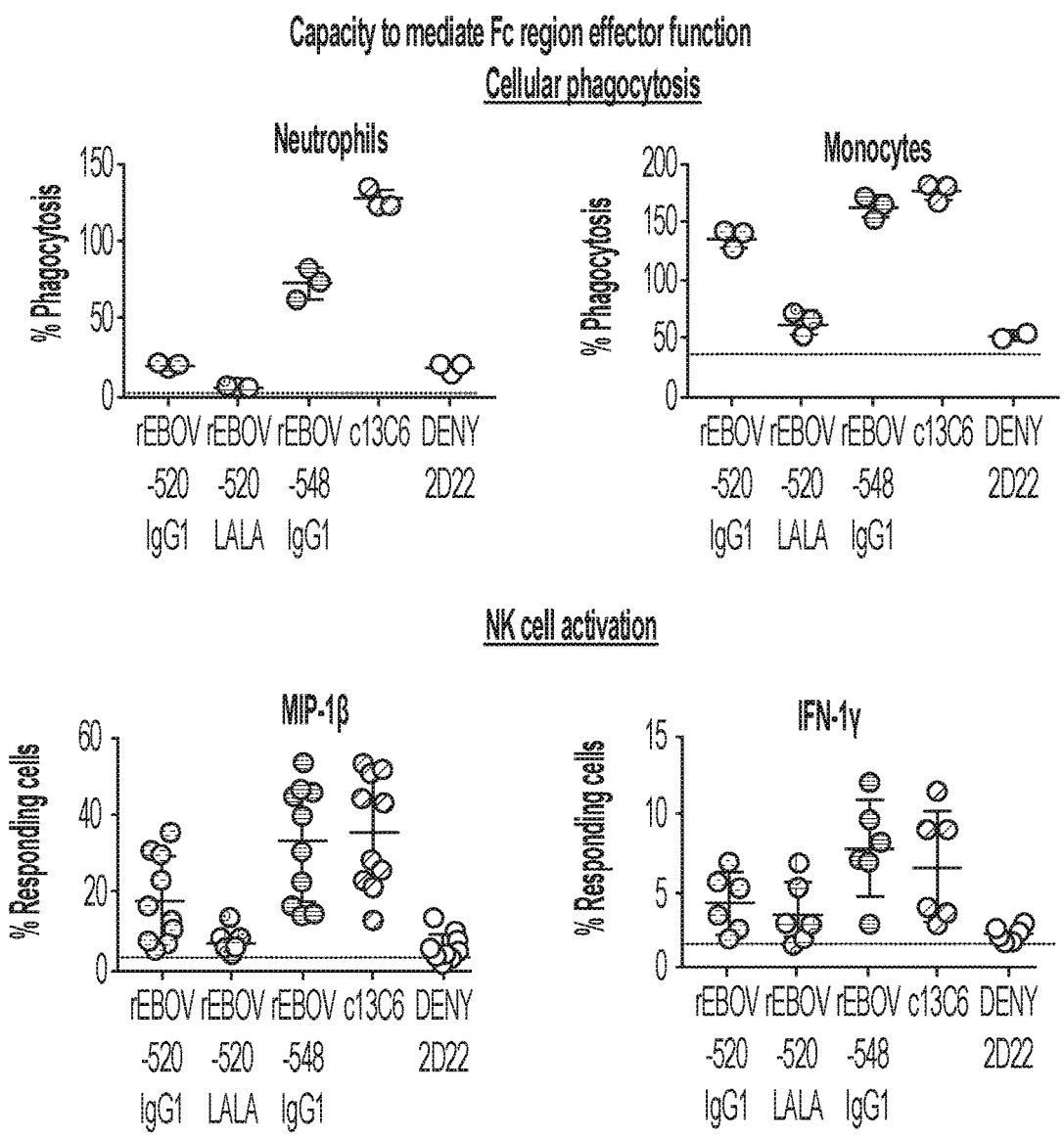
Figures 23D, 23E:
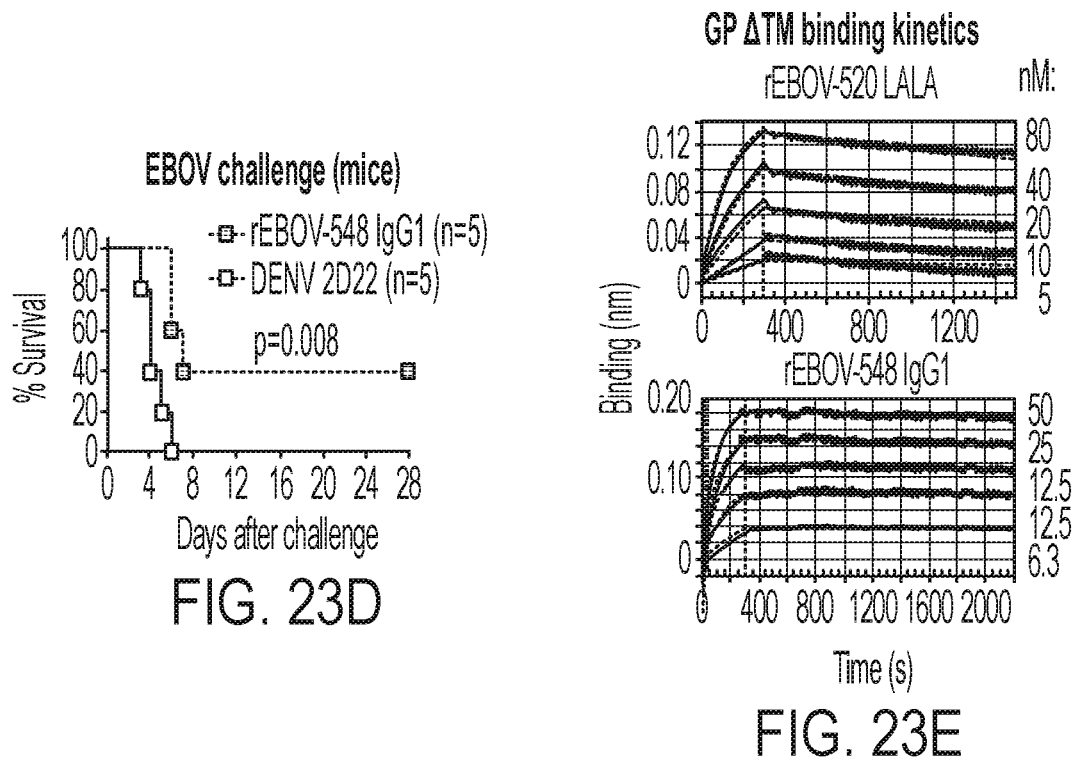

To assess the Fc-mediated effector function of these two engineered mAb variants to mediate cell killing of antigen-expressing cells, the inventors used a stably transfected EBOV GP-expressing SNAP-tagged 293F cell line as a target, with heterologous human PBMCs as source of effector cells. The SNAP-tag is a self-labeling protein tag that allows specific labeling of a target cell line with fluorescent dye, facilitating detection of effector cell-mediated killing activity by flow cytometry (Domi et al., 2081). rEBOV-520 LALA showed a low level of effector function activity when compared to that of the control rEBOV-520 wt IgG1. rEBOV-548 IgG1 exhibited a dose-responsive pattern of efficient cell killing that was comparable to that of a recombinant form of mAb c13C6, a glycan-cap directed mAb that is included in the ZMapp™ cocktail (FIG. 161A). Similar functional profiles of these two mAbs were obtained using bead- or solid phase-immobilized GP ectodomains and various human effector cells (FIGS. 23A, 23C). These findings confirmed the relatively high capacity of rEBOV-548 IgG1 to engage the innate immune system and diminished function of the LALA version of rEBOV-520 antibody. The inventors next assessed potency of virus neutralization by these two mAbs. rEBOV-520 potently neutralized all three ebolaviruses, while rEBOV-548 neutralized only EBOV and BDBV (FIGS. 17B and 23A). However, both mAbs reacted broadly with all three major filovirus species, as measured by binding to recombinant GP ectodomains in enzyme-linked immunosorbent assay (ELISA), or flow cytometric analysis of binding to full-length EBOV, BDBV, or SUDV GPs displayed on the surface of stably transduced Jurkat cell lines (FIGS. 16C, 23A-B). The inventors then tested mAb binding to each of the three Jurkat GP cell lines after treatment with thermolysin to mimic endosomal cathepsin cleavage to create membrane-displayed $GP_{CL}$. The neutralizing mAb rEBOV-520 bound weakly to intact GPs, but in contrast bound strongly to cleaved GPs ($GP_{CL}$), with a saturable dose-response curve and ~500- to ~1,000-fold increase in binding to cleaved over uncleaved GP (FIG. 16C). The observed increase in binding to cell surface displayed $GP_{CL}$ was concordant with the ~800-fold increase in neutralizing potency of EBOV-520 IgG4 against a replication-competent recombinant vesicular stomatitis virus (rVSV) displaying EBOV $GP_{CL}$, compared to rVSV with uncleaved EBOV GP that the inventors described in a previous study (Gilchuk et al., 2018). The glycan cap-specific rEBOV-548 bound moderately and less efficiently to intact, full-length, cell-surface displayed GPs when compared to its binding to recombinant GP ectodomains (FIGS. 16C, 23B). Together, these results defined key binding and functional features of the cocktail candidate mAbs and showed that the exposure of the site of vulnerability for recognition by the neutralizing mAb rEBOV-520 is limited on the intact GPs of all three ebolaviruses.

Enhancement of GP binding, virus neutralization and protection in vivo by the cocktail. The inventors considered the broadly reactive mAbs rEBOV-520 and rEBOV-548 to be suitable candidates for combining in an experimental cocktail, because they did not compete for binding, and both bound to GP simultaneously as shown by negative stain electron microscopy (EM) (FIGS. 17A, 24A-B). To characterize the cooperative effects of these two mAbs as a cocktail, the inventors first assessed the dose-response of GP binding for each mAb in the presence or absence of the partner mAb. Fluorescently labeled rEBOV-520 or rEBOV-548 was titrated into a constant, saturating concentration of unlabeled partner mAb, as previously described (Gilchuk et al., 2018), and relative fluorescence from binding of the labeled mAb to the intact cell-surface displayed EBOV, BDBV, or SUDV GP was determined. rEBOV-548 significantly enhanced binding of rEBOV-520 to the GP of all three ebolaviruses in a concentration-dependent manner and by 1.7- to 3.4-fold when compared to binding of rEBOV-520 alone. Similarly, rEBOV-520 enhanced binding of rEBOV-548 to GP, although to a lesser extent (FIG. 17B). The inventors also found that the monovalent Fab and bivalent IgG forms of rEBOV-548 mediated similar cooperative binding effects with EBOV GP (data not shown). Cooperative binding of rEBOV-520 to intact GP increased steadily with increased concentrations of rEBOV-548 and up to 4.6-fold higher than rEBOV-520 alone but did not fully match the strong saturating binding of rEBOV-520 by itself to the proteolytically primed $GP_{CL}$ (FIG. 25). This finding suggested that binding of rEBOV-548 only partially enhanced accessibility of the base epitope on intact GP for recognition by rEBOV-520, compared to the accessibility to the epitope on $GP_{CL}$.

Figure 17C:
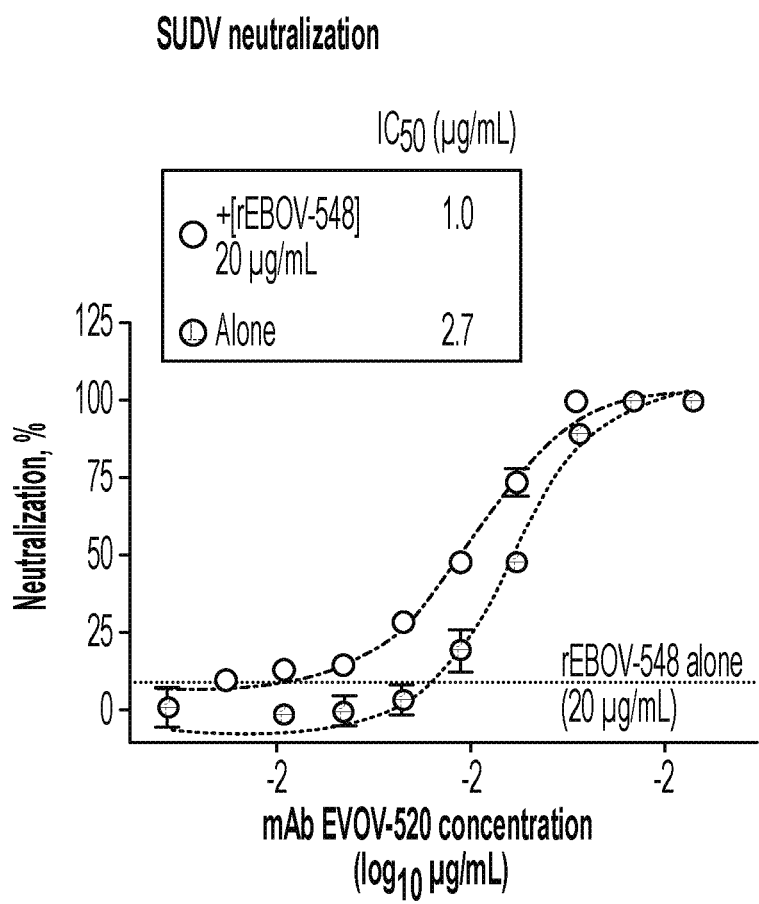

The inventors next assessed if cooperativity in binding conferred an enhanced neutralizing activity to the cocktail. As a proof of principle, they tested the effect of this cocktail with the most antigenically divergent virus, SUDV, because rEBOV-548 itself did not neutralize SUDV, and rEBOV-520 neutralized SUDV, but with modest potency (FIGS. 16B, 23A). Consistent with the observed increase in cooperative binding of SUDV GP (FIG. 17B), the non-neutralizing rEBOV-548 potentiated the neutralizing activity of rEBOV-520 against chimeric virus displaying SUDV GP by reducing the half-maximal inhibitory concentration ($IC_{50}$) value by ~3-fold (FIG. 17C). Neutralization by the cocktail was synergistic as determined by the Chou and Talalay method that estimates the combination index (CI) to define the effect of drug combination (Chou, 2010).

Figure 17D:
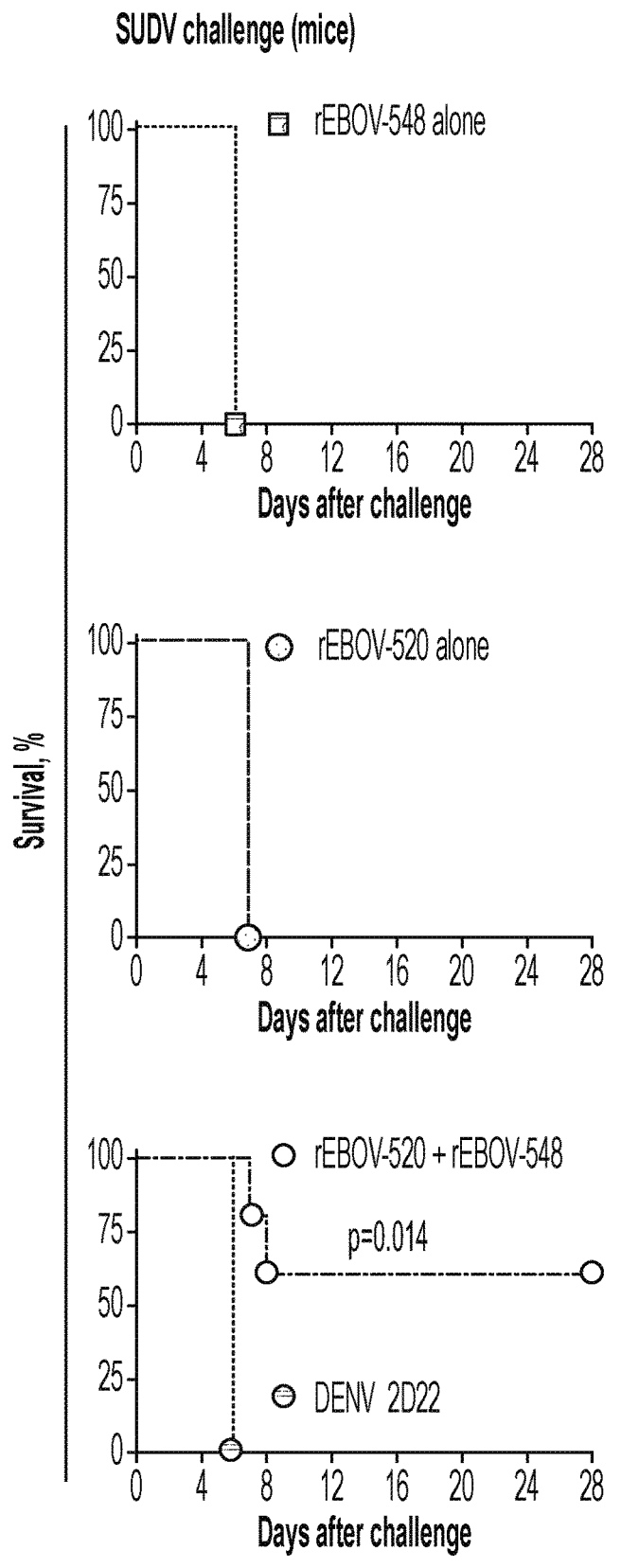

The inventors next tested if non-neutralizing rEBOV-548 (SUDV) potentiated protection by rEBOV-520 in the cocktail against SUDV in vivo using a stringent STAT1-deficient (STAT1 KO) mouse challenge model (Raymond et al., 2011). An irrelevant mAb DENV 2D22 (IgG1 isotype) specific to the dengue virus envelope (E) protein (Fibriansah et al., 2015) was used as a negative control. All SUDV-challenged mice that were treated with 10 mg/kg of the individual rEBOV-520 or rEBOV-548 mAbs on 1 dpi succumbed to the disease by 6-7 dpi, similarly to the animals in the control DENV 2D22-treated group. In contrast, treatment with the cocktail (a 1:1 mixture of rEBOV-520 and rEBOV-548) conferred protection with an associated p-value=0.014, as determined by a log rank (Mantel-Cox) test, with 60% of animals surviving (FIG. 17D). This finding showed that complementing the activity of the neutralizing but non-protective rEBOV-520 (SUDV) with the non-neutralizing, non-protective rEBOV-548 (SUDV) was beneficial for protection against SUDV. Together these data demonstrated that cooperativity in GP binding by the cocktail of rationally selected human mAbs extends activity to all three major ebolavirus species and could be translated to enhanced neutralization and enhanced in vivo protection against the most antigenically heterologous ebolavirus.

Figures 18A, 18B:
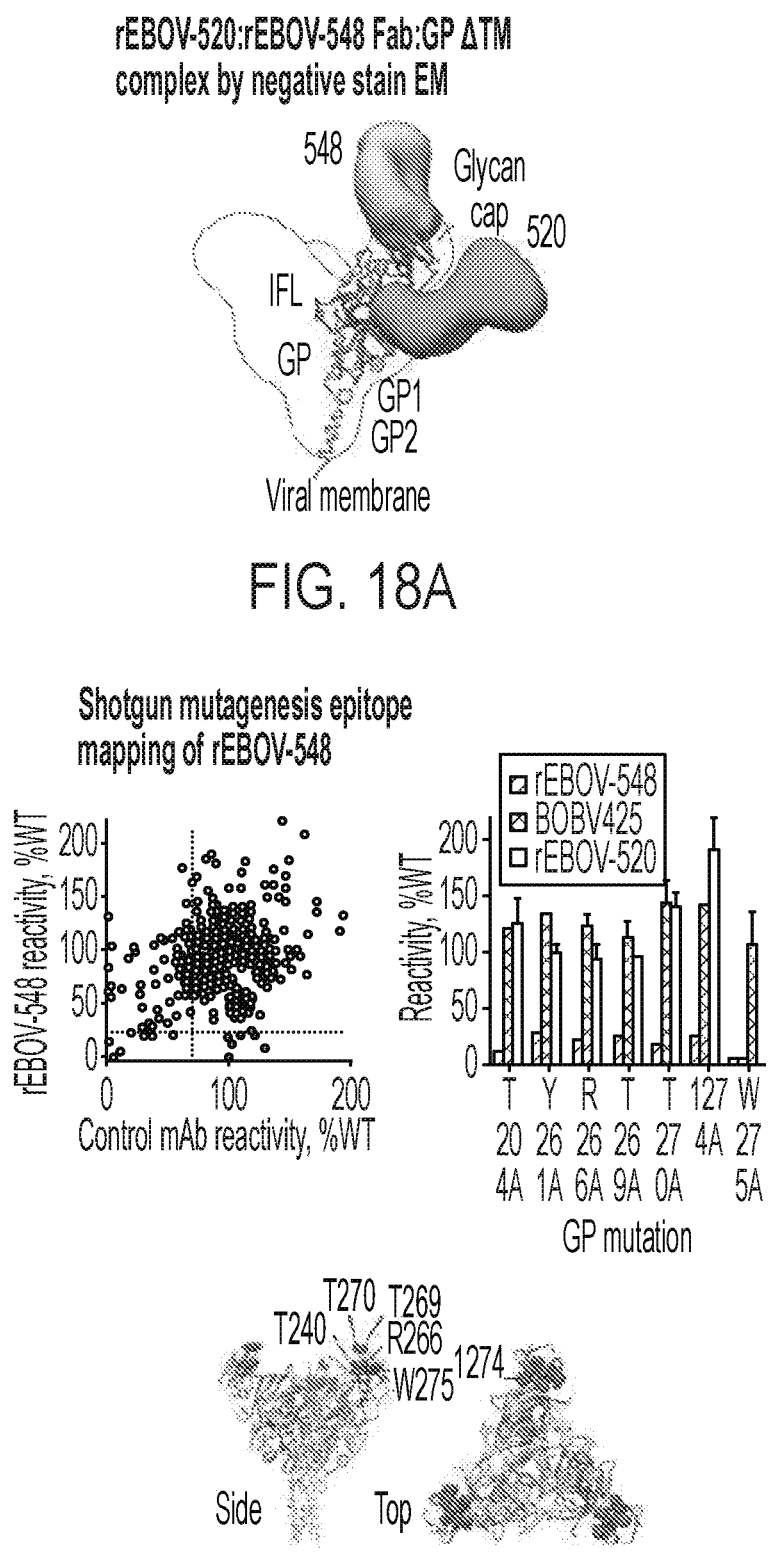

Epitopes for mAbs in the cocktail. The inventors recently reported negative stain EM reconstructions of EBOV-520 in complex with GP that suggested the mAb recognizes a conformational epitope spanning the GP1 and GP2 subunits of the trimer (Gilchuk et al., 2018). The epitope of EBOV-548 has not yet been characterized. They performed negative stain EM studies using complexes of rEBOV-548 Fab alone or a combination of both rEBOV-548 and -520 Fabs with recombinant trimeric EBOV GP ATM. The EM reconstructions confirmed that rEBOV-548 recognizes the glycan cap region of the GP trimer and that the cocktail mAbs target two distinct epitopes on the GP (FIGS. 18A, 24A-B). 2D class averages revealed that the majority of GP trimers were bound to one or two, and to a lesser extent by three, rEBOV-548 Fabs, in glycan cap. The 3D reconstruction indicated that rEBOV-548 binds nearly perpendicular to the surface of GP, similar to the binding pose of mAb c13C6, but also made interactions with the interior of the chalice within the outer domain of the glycan cap.

To define key contact residues of the epitope, the inventors used alanine scanning mutagenesis of GP and tested the binding of rEBOV-548 to individual GP members of a shotgun mutagenesis alanine mutation library of EBOV GP displayed in cells. They also generated antibody escape mutant viruses by passaging infectious EBOV in the presence of mAb and determined the GP sequence of antibody neutralization escape variants. Consistent with the EM data, T240A, Y261A, R266A, T269A, T270A, I274A, and W275A mutations reduced binding to GP (FIG. 18B), and escape mutation L273P reduced neutralizing potency. The key contact residues were positioned on the top of the glycan cap and within a region with relatively low sequence conservation. However, 5 of 7 contact residues were conserved among EBOV, BDBV, and SUDV GPs (EBOV GP residues Y261 and R266 are non-conserved), which explains the high level of cross-reactivity of rEBOV-548 and suggests a key role for the unusually long (twenty-four amino acids) heavy chain complementarity determining region 3 (CDRH3) in this interaction. Interestingly, two mAbs, EBOV-337 and EBOV-442, which are the other members of the same class as rEBOV-548 (but unique in sequence), had similar features that included a long CDRH3 (24 to 26 aa) and recognition of W275A as a key GP epitope residue with the most energetic contribution (Table S5 and data not shown). It is possible that these three mAbs use similar structural principles to bind GP and mediate broad and cooperative activities. Together, these studies identified a site of vulnerability for antibody recognition on the glycan cap that mediated cross-reactive and cooperative binding in the experimental pan-ebolavirus mAb cocktail.

Figure 18C:
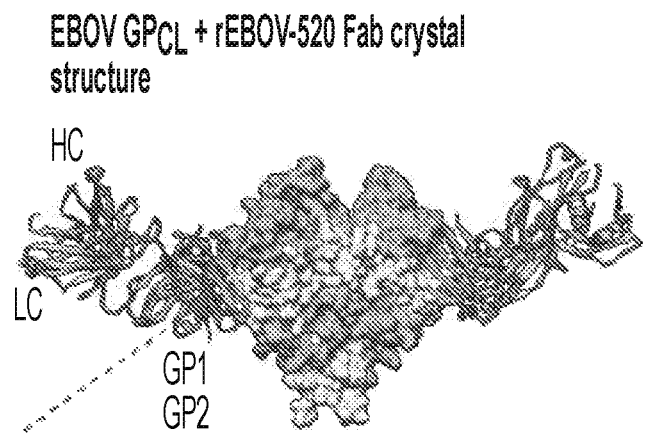
Figure 18D:
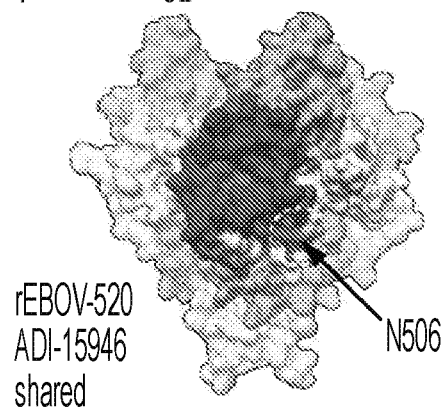

The inventors next defined the structural determinants of GP binding and reactivity breadth for rEBOV-520 by resolving the crystal structure of rEBOV-520 Fab in complex with EBOV $GP_{CL}$ to 3.46 Å resolution (Table S6). The rEBOV-520 Fab bound to the base of each protomer of $GP_{CL}$, with the constant domains oriented upward from the viral membrane (FIG. 18C). The rEBOV-520 footprint includes highly conserved ebolavirus GP regions including the internal fusion loop stem ($IFL_{stem}$) of the GP2 subunit and the hydrophobic pocket formed by five residues of the GP1 subunit and termed previously the '$3_{10}$' pocket (Zhao et al., 2016; West et al., 2019). The footprint of rEBOV-520 is distinct from that of the previously described human GP base mAb ADI-15878 (Murin et al., 2018; West et al., 2018) but is similar to the footprint of the potent human base-specific mAb ADI-15946 (FIG. 18D), which fully neutralizes EBOV and BDBV but not SUDV (Wec et al., 2017; West et al., 2019). Both ADI-15946 and EBOV-520 bind the '$3_{10}$' pocket and $IFL_{stem}$ regions of the fusion loop, unlike human mAb ADI-15878, which binds to the hydrophobic loop end of the structure and bridges to a neighboring GP protomer (King et al., 2019). However, EBOV-520 likely gains reactivity against SUDV by having a footprint slightly higher on the GP base than the ADI-15946, and/or a different angle of approach than that of ADI-15946, which was directed downward toward the viral membrane (FIG. 18C), in a contrast to ADI-15946 which is directed upward from the membrane (West et al., 2019). This footprint allows the mAb to avoid contact with the non-conserved EBOV GP residue N506 (R506 in SUDV GP) in the interface with EBOV-520 (FIG. 18D)—a key contact residue for binding with CDRH3 of ADI-15946 (West et al., 2019). Meanwhile, the footprint of EBOV-520 also differed from that of a previously described potent macaque mAb CA45, whose epitope extends to a site beneath the $IFL_{stem}$ termed the 'DFF" cavity (Janus et al., 2018). These findings highlight the variability in epitopes of lead therapeutic candidate mAbs and identify mAb EBOV-520 as a unique representative among the class of '$3_{10}$' pocket-targeting mAbs with an extended potency for binding and neutralization of SUDV.

Figure 26A:
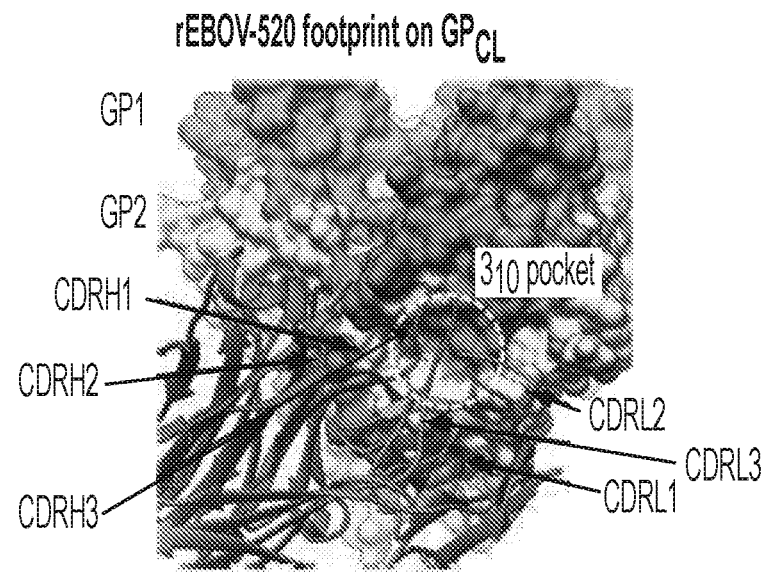
Figure 26B:
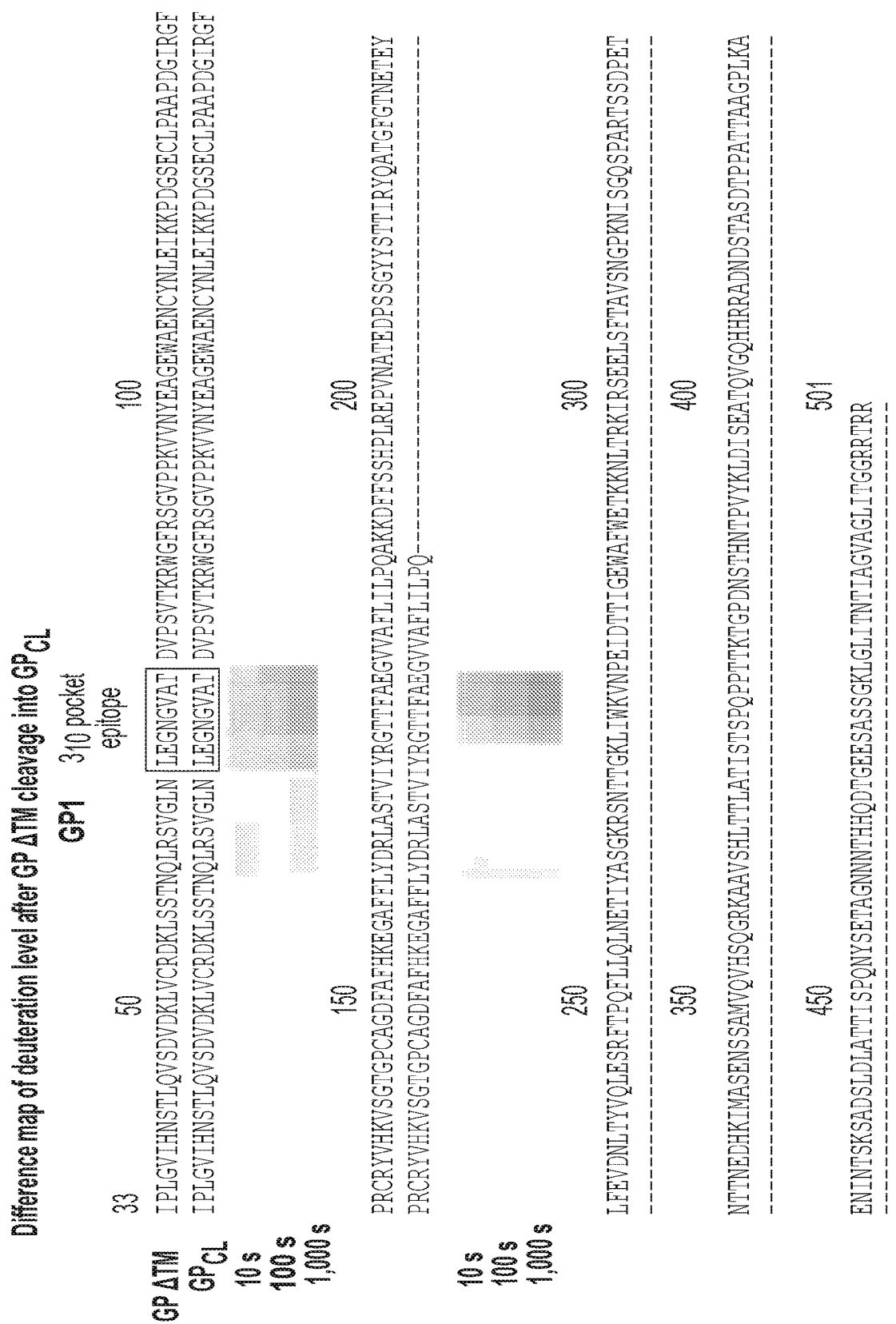
Figure 26B:
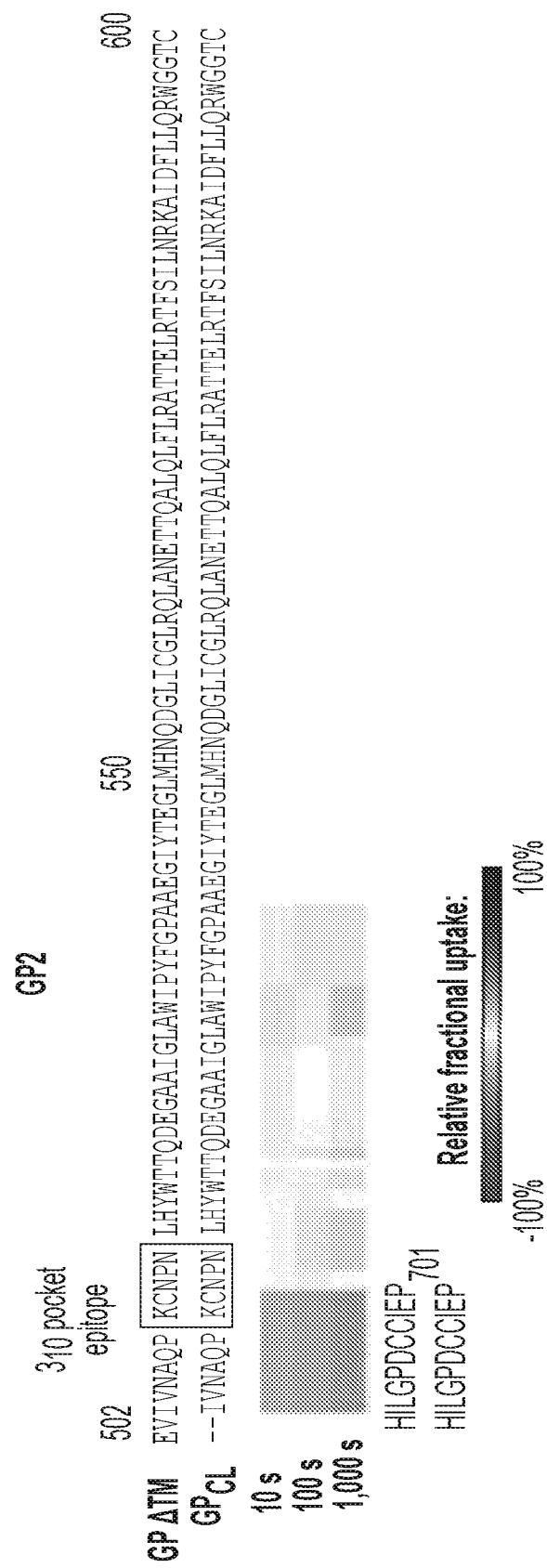

Structural basis for mAb cooperativity in the cocktail. Analysis of the rEBOV-520 Fab/$GP_{CL}$ crystal structure identified twenty-six $GP_{CL}$ residues in the interface with rEBOV-520 Fab, sixteen located in GP1 (aa 70-78, 104, 106, 107, 134, 136, 137, and 139) and ten located in GP2 (aa 510-514, 516, 545-547, and 549). The eighteen amino acid long CDR H3 interacts with a conformational epitope on the GP1/GP2 interface by making direct contacts with thirteen GP1 (aa 70-78, 106, 107, 127, and 139) and five GP2 (aa 510-514) residues that are highly conserved among EBOV, BDBV, and SUDV (FIG. 26A). rEBOV-520 binds to the hydrophobic '$3_{10}$' pocket of $GP_{CL}$ formed by GP1 residues 70-78 (all contacted with CDRH3), and GP2 residues 510-516 (four of seven contacted with CDRH3) that line the bottom part of the pocket (FIG. 19A). In the unbound, full-length GP, the $3_{10}$ pocket normally is occupied by the flexible descending β17-β18 loop of the glycan cap (GP1 residues 287-291) that impedes access to the pocket. Like ADI-15946 (West et al., 2019), EBOV-520 either binds a conformation of GP in which the β17-01 loop is displaced, or actively displaces it from the pocket upon binding. The loop is not present in $GP_{CL}$, being removed by cleavage. The inventors used hydrogen-deuterium exchange mass spectrometry (HDX-MS) to compare deuterium labeling of peptides generated after digestion of GP ATM and $GP_{CL}$ with pepsin. Decrease in labeling of GP ΔTM $3_{10}$ pocket residues involved in the interface with CDRH3 (located in GP1 and GP2), confirmed limited accessibility of rEBOV-520 epitope in a structure of intact GP trimer (FIGS. 19A, 26B). Cleavage removes the glycan cap with the β17-β18 loop and exposes the pocket, which explains enhanced binding of EBOV-520 to a proteolytically processed $GP_{CL}$ intermediate (FIG. 16C) and enhanced neutralization potency of this mAb against virions bearing cleaved GP compared to intact GP (Gilchuk et al., 2018).

Previous work showed that binding of the non-neutralizing macaque mAb FVM09 to the β17-β18 loop itself potentiated binding of mAbs 2G4 and ADI-15946 and suggested that binding of FVM09 displaces the loop causing unmasking of the neutralizing epitopes for mAbs 2G4 and ADI-15946 on the GP base (Howell et al., 2017; West et al., 2019). However, unlike with FVM09, whose binding was fully abolished by several alanine mutations in the β17-β18 loop (Howell et al., 2017), none of the alanine mutations within the β17-β18 loop reduced rEBOV-548 binding to the cell surface displayed GP. Interestingly, alanine substitutions in several residues of the β17-β18 loop, such as F290, W291, E292, N296, and E304 which are distal to the rEBOV-548 epitope in the upper portion of the glycan cap increased rEBOV-520 binding by ~1.6- to 3-fold compared to binding to wild-type GP (FIG. 19B). Similar enhancement of binding via mutations in the 117-318 loop have been reported for the murine mAb m8C4 (Howell et al., 2017). However, m8C4 neutralizes SUDV and weakly EBOV with the epitope mapped to the glycan cap, indicating that m8C4 and rEBOV-520 recognize distinct epitopes.

Figure 27:
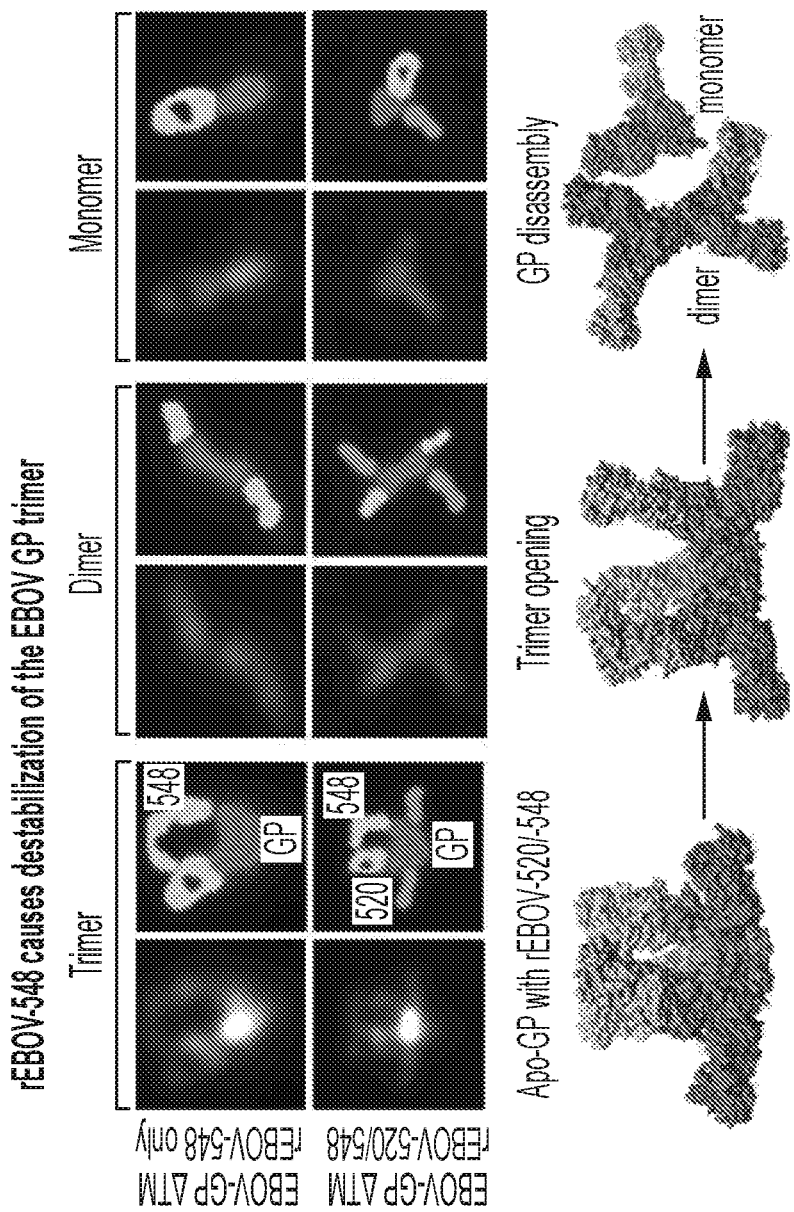
FIG. 27. rEBOV-548 causes destabilization of the EBOV GP trimer. Related to FIGS. 20A-H. Top panel: addition of rEBOV-548 Fab to EBOV GP ΔTM causes the trimer (left) to dissociate partially into dimers (middle) or monomers (right). Bottom panel: trimer dissociation was not seen with rEBOV-520 alone but did cause the complex (left) to dissociate partially into dimers (middle) or monomers (right) after first incubating the complex with rEBOV-548 and then adding rEBOV-520.

Given the significance of the contribution of the rEBOV-548 interaction to cooperative GP binding by rEBOV-520, the inventors hypothesized that binding of rEBOV-548 potentiates binding of rEBOV-520 by unmasking an otherwise cryptic epitope. To determine the structural determinants of cooperativity within the cocktail, they solved a cryogenic EM (cryo-EM) structure of rEBOV-520/rEBOV-548 Fab in complex with EBOV ΔMuc GP with the glycan cap intact at 4.1 Å resolution (FIG. 20A, Table S7). Unlike the previously described for mAb FVM09, the inventors' structure revealed that rEBOV-548 does not bind directly to the β17-β18 loop. Instead, the CDRH3 loop of rEBOV-548 directly interacts with the β17 strand (residues 272-275) of GP1, forming an extended beta sheet with the glycan cap, including highly conserved critical epitope residues 1274 and W275 that were defined by loss of binding with alanine substitution. Two non-conserved GP1 residues Y261 and R266, whose mutation to alanine decreased binding of rEBOV-548 (FIG. 18B), interact within the glycan cap and are likely important for stabilization of the rEBOV-548 epitope. In the rEBOV-548 bound state the β18-β18' region and the β17-β18 loop were displaced by the CDRH3 loop of rEBOV-548 (FIG. 20B). The rEBOV-548 LC contacts GP1 through hydrophobic interactions at the loop between al and β17 (residues 268-269) and through $Q27_{L1}$ contacting residue D117, making a possible salt bridge (FIG. 20C) that anchors the mAb to the inner chalice of GP (FIG. 20A). Interestingly the inventors observed partial rEBOV-548-mediated destabilization and dissociation of the GP trimer when rEBOV-520/rEBOV-548 Fab bound to full-length EBOV ATM GP (FIG. 27), although it is unclear if this disruption seen with soluble GP also occurs in membrane-anchored GP. Analysis of rEBOV-520 interactions in the structure of rEBOV-520/rEBOV-548 bound to GP showed that the rEBOV-520 CDRH3 loop makes additional contacts beyond the $3_{10}$ pocket when the glycan cap is intact. These contacts include $Y108_{H3}$ with K510 in GP2, $Y106_{H3}$ with T77 in GP1 and $T104_{H3}$ with P250 in the base of the al loop of GP1. The rEBOV-520 CDRH3 residue $W100_{H3}$ binds to N512 in GP2, displacing the β17-β18 loop and mimicking the N512 interaction with $W291_{GP1}$ of the β17-β18 loop in the unliganded structure (FIG. 20D). Of note, the inventors' previous study identified N512 as a key epitope residue for rEBOV-520, since N512A mutation reduced binding to the GP (Gilchuk et al., 2018). Therefore, for efficient binding rEBOV-520 must overcome interference of the β17-β18 loop (at $W291_{GP1}$) and al helix (at $P250_GP1$) contained in the glycan cap structure (FIG. 20E). When rEBOV-548 binds, the β18-β18' region is displaced and the glycan cap pulled back, along with the β17-β18 loop, to allow improved binding of rEBOV-520 (FIG. 20F). The inventors conclude that rEBOV-548 potentiates binding of rEBOV-520 through allosteric effects that reposition the β17-β18 loop and al helix structures of the GP, thereby facilitating binding to the cryptic rEBOV-520 epitope on the GP base (FIGS. 20G-H, 28A-C). These results strongly suggest that GP base epitope remodeling is the principal mechanism for the enhancement of broad ebolavirus neutralization and protection by combinations of naturally occurring human mAbs from EVD survivors. In addition, the details of the molecular interaction between rEBOV-520 and rEBOV-548 with GP illustrated that both antibodies use molecular mimicry whereby CDRH3 binds to the GP in a manner analogous to the interactions in unliganded GP. Thus, rEBOV-548 CDRH3 interfaces with the β17 sheet of the glycan cap and mimics the interaction of β18-β18' region with the β17 sheet (FIGS. 20B, 21A), and rEBOV-520 CDRH3 interfaces with the $3_{10}$ pocket residues mimicking the interaction by the β17-β18 loop in unliganded GP (FIGS. 20D, 21B). Together these experiments defined key molecular features that mediate binding and cooperativity by the cocktail of two human pan-ebolavirus mAbs.

Therapeutic potency of the cocktail in nonhuman primates. The inventors next used a nonhuman primate (NHP) rhesus macaque EBOV challenge model to determine the efficacy of treatment by the rationally designed mAb cocktail. This NHP model recapitulates many key features of EVD in humans and provides a uniform lethality (Geisbert et al., 2015; Bennett et al., 2017). In this study, rhesus macaques were assigned to one treatment group of five animals. After intramuscular challenge with a lethal target dose of 1,000 plaque-forming units (PFU) of the Kikwit variant of EBOV, all NHPs of the treatment group received intravenously two 30 mg/kg doses of the cocktail (1:1 mixture of rEBOV-520 and rEBOV-548) spaced 3 days apart (3 and 6 dpi). An additional animal was studied as a contemporaneous control and was left untreated, along with 10 historical untreated controls (7 dpi median survival, inoculated by the same route with the same stock of virus) (Table S8). The control untreated animal developed a high clinical score and succumbed to the disease on 6 dpi. Remarkably, the two-dose therapeutic cocktail treatment provided complete protection of NHPs from mortality and clinical signs of EVD (FIGS. 22A-B, 29A-E). One treated animal presented mild petechiae on 6 dpi that was fully resolved on 7 dpi, after the second treatment. Before the first treatment (3 dpi) most (3/5) NHPs from the treatment-designated group and also the control, untreated NHP, developed detectable viremia, with plasma titers that ranged from 6.7 $\log_{10}$ to 7.3 $\log_{10}$ genome equivalents (GEQ) per mL, as measured by qRT-PCR (limit of detection=3.7 $\log_{10}$ (GEQ/mL)) (FIG. 29C). The plasma titer of infectious virus that was assessed by plaque assay on 3 dpi was below the limit of detection (1.4 $\log_{10}$ PFU/mL) in all animals. However, by 6 dpi the viral load in all untreated animals was as high as >5 $\log_{10}$ PFU/mL, including in the one NHP control from this study and in the ten historical controls, or >11 $\log_{10}$ GEQ/mL (FIGS. 22C, 29A-E). Concordant with a high level of therapeutic protection, by 6 dpi all treated animals, including three registered as highly viremic on 3 dpi, no longer had detectable viremia in the plasma as confirmed by qRT-PCR and plaque assays. In various tissues harvested from treated animals on 28 dpi, qRT-PCR analysis, which detects both infectious and noninfectious neutralized particles that have not yet been cleared, revealed virus, confirming active EBOV infection in all NHPs in the treatment group before treatment (Table S9). The inventors next assessed changes in blood chemistries and hematologic parameters that are typically associated with EVD to further characterize the efficacy of the mAb cocktail treatment (Tables 59-10). The liver enzymes alanine aminotransferase (ALT), gamma glutamyl transferase (GGT), alkaline phosphatase (ALP), and the other blood chemistries, which are indicators of EVD, were elevated in untreated NHPs on 6 dpi—the peak of viremia and the disease (FIGS. 22B-C). Treated animals did not show signs of acute liver injury on 6 dpi or later time points, displaying low levels of ALT, GGT, ALP when compared to those of untreated NHP (FIGS. 22D, 29A-E). Thus, the cocktail of two cooperative broadly reactive mAbs provided a high level of therapeutic efficacy against EBOV live virus challenge in NHPs with a limited number and modest dose of IgG protein treatments.

Example 6—Discussion

Cocktails are preferred for prevention or treatment of viral infections to accomplish breadth of coverage against diverse virus species and to prevent emergence of antibody escape mutant viruses (Saphire and Aman, 2016). Here, the inventors report rare classes of broadly reactive human mAbs that leverage a cooperative binding effect to improve neutralization breadth and therapeutic potency in the cocktail. These studies define essential principles for construction of potent therapeutic cocktails by detailed mapping of mAbs structure and function. First, the inventors describe an allosteric effect through binding of a pan-ebolavirus glycan cap-specific mAb that potentiates neutralization by a pan-ebolavirus base-specific mAb as a mechanism of mAb cooperativity, establishing a rational principle for development of broad mAb cocktails for ebolavirus prevention or therapy. Second, the inventors identified molecular mimicry when specific mAb-antigen residue interactions recapitulated similar interactions found in native antigen as a mechanism of antigen recognition by potent cooperative human mAbs. Third, the work identifies Fc-effector function variants of the GP base- and glycan cap-specific mAbs that mediate a high level of therapeutic protection in a two-antibody cocktail in NHPs.

To date, two fully human mAb cocktails—REGN-EB3 and MBP134$^{AF}$ have been evaluated for clinical development (Bornholdt et al., 2019; Pascal et al., 2018). Only MBP134$^{AF}$ possesses pan-ebolavirus activity, and hence, could be considered as a best-in-class experimental cocktail. MBP134$^{AF}$ incorporates Fc-region glycan engineered (afucosylated) forms of two mAbs, ADI-15878 (recognizes IFL$_{loop}$ and N-terminal pocket) and ADI-23774 (recognizes IFL$_{stem}$ and $3_{10}$ pocket). ADI-23774 is a derivative of the ADI-15946 that was selected for improved SUDV GP binding via yeast-display (Wec et al., 2019). MBP134$^{AF}$ exhibited a high level of therapeutic efficacy against EBOV, BDBV, and SUDV in NHPs (Bornholdt et al., 2019), demonstrating the utility of antibody engineering techniques for the design of therapeutic cocktails against ebolaviruses.

The systematic analysis of two-antibody interactions performed in the studies here, using antibodies derived from the largest panel of human mAbs to ebolavirus GP isolated to date (Gilchuk et al., 2018; this study), allowed us to define essential but less explored molecular and structural principles of broad human antibody-mediated responses against ebolaviruses. The inventors report several naturally-occurring, broadly reactive mAbs from EVD survivors that enabled cooperative binding to the GP in a two-antibody cocktail and describe allosteric potentiation as a new principle for rational design of therapeutic mAb cocktail. The cocktail of rEBOV-520+rEBOV-548 was formulated using this principle (e.g. incorporation of a pair of broad and cooperative mAbs targeting a distinct epitopes of the GP), and it potently neutralized heterologous ebolaviruses and offered protection against divergent SUDV in a stringent murine challenge model. Moreover, the cocktail fully protected EBOV challenged NHPs and reverted EVD with only two treatments and a relatively low 30 mg/kg dose. These findings demonstrate that a highly desirable activity profile (e.g., broad reactivity and high potency) could be achieved with a cocktail of two cooperative antibody specificities isolated from human survivors of EVD. The key new structural aspect of this work is the finding that the broad mAb rEBOV-548 acts via an allosteric effect through binding to a conserved epitope on GP1, which repositioned the flexible β17-β18 loop and the β18-β18' region of the glycan cap. Remodeling of the glycan cap then unmasks the cryptic epitope of the $3_{10}$ pocket on GP2 that facilitates binding of the broadly-neutralizing mAb rEBOV-520. Hence, this work defines cooperative interactions between mAbs of the two major epitope specificities for GP recognition, and unveils cooperative binding of the GP as a principal mechanism for broad ebolavirus neutralization and protection. Key principles of molecular mAb/antigen interactions demonstrated here with ebolavirus—molecular mimicry, remodeling of binding site, and allosteric potentiation—could aid in the design of therapeutic cocktails against the other viral targets.

Cooperativity in the cocktail of rEBOV-520+rEBOV-548 is mediated by recognition of the glycan cap epitope and conformational epitope spanning GP1 and the IFL of GP2. Several studies identified the IFL as a site of broad vulnerability on the ebolavirus GP for mAbs that can act solely through neutralization to protect in vivo (Gilchuk et al., 2018; Wec et al., 2017). MAbs targeting glycan cap epitopes have been considered as inferior for therapeutic development due to possible cross-reactivity with soluble GP (sGP) (Mohan et al., 2012). Recent studies, however, suggested an indispensable role for Fc-mediated effector functions in the protection against EBOV by glycan cap specific mAbs (Gunn et al., 2018). It was unknown whether these functions (e.g., neutralizing activity and Fc engagement) in the cocktail of these two mAb specificities were essential and sufficient for efficacy in NHPs. This study suggested that both functions could be important for virus control and EVD prevention by showing that the cocktail of the Fc-function competent IgG1 form of glycan cap-specific rEBOV-548 and functionally impaired IgG1-LALA form of neutralizing IFL-specific rEBOV-520 mediated a high level of therapeutic protection in NHPs. Next studies should compare the potency of this cocktail to the others and determine the optimal pairs of cooperative mAbs for therapeutic development.

In summary, the inventors show here that comprehensive study of the epitopes and mechanism of action of human mAbs to a virus can facilitate the rational development of therapeutic mAb cocktails.

TABLE S1

Germline origin genes and variable region analysis of newly identified broadly reactive human mAbs. Related to FIG. 1

| | Heavy chain variable gene sequence | | | | | | Light chain variable sequence | | | | |
|---|---|---|---|---|---|---|---|---|---|---|---|
| mAb* | V-gene and allele | V-region nucleotide homology to V-gene, % | D-gene and allele | J-gene and allele | CDR3 amino acids (aa) | CDR3 length (aa) | V-gene and allele | V.region nucleotide homology to V gene, % | J-gene and allele | CDR3 amino acids (aa) | CDR3 length (aa) |
| EBOV-434 | 1-2*02 | 99 | 3-10*01 | 4*03 | ARDSGELLFVGSDV (SEQ ID NO: 87) | 14 | 1-12*01 or 1-12*02 or 1D-12*02 | 98 | 2*01 | QQANSFPQT (SEQ ID NO: 150) | 9 |
| EBOV-437 | 1-69*06 | 95 | 3-10*01 | J6*03 | ARGPPLRGERSWFGESEKYDYFYMDV (SEQ ID NO: 90) | 26 | N/A | N/A | N/A | N/A | N/A |
| EBOV-442 | 3-15*01 | 91 | 3-16*01 | 6*03 | ATGSGKGPSASFGESYYYYDFINV (SEQ ID NO: 93) | 24 | 3-20*01 | 96 | 1*01 | HQYESSPWT (SEQ ID NO: 156) | 9 |
| EBOV-446 | 1-2*02 or 1-2*04 | 95 | 4-17*01 | 4*02 | ARGRRHGAYVD (SEQ ID NO: 96) | 11 | 1-9*01 | 96 | 5*01 | QQLNFYLGGLT (SEQ ID NO: 159) | 11 |
| EBOV-451 | 3-20*01 | 92 | 2-21*01 | 4*02 | VSWGERYDAYFDY (SEQ ID NO: 99) | 13 | 3-20*01 | 96 | 2*01 | QQYGSSPYT (SEQ ID NO: 162) | 9 |
| EBOV-502 | 3-23*04 | 93 | 5-18*01 | 6*02 | AKDAQQETDIVYFYYYDGMDV (SEQ ID NO: 102) | 21 | N/A | N/A | N/A | N/A | N/A |
| EBOV-507 | 1-2*02 | 90 | 2-8*02 | 3*01 | WIWFRSETFDF (SEQ ID NO: 105) | 11 | 1-17*03 | 96 | 1*01 | LQHNTYLT (SEQ ID NO: 168) | 8 |
| EBOV-508 | 1-46*01 or 1-46*02 or 1-46*03 | 95 | 3-16*02 | 4*02 | VSFQFYFDY (SEQ ID NO: 108) | 9 | 1-17*03 | 99 | 1*01 | LQHNSYPWT (SEQ ID NO: 171) | 9 |
| EBOV-510 | 4-30-4*01 | 93 | 4-17*01 | 6*02 | ARESDGDPSRLYFYFAMDV (SEQ ID NO: 111) | 19 | 2-14*01 | 96 | 2*01 or 3*01 or 3*02 | SSYTSNTTLV (SEQ ID NO: 174) | 10 |
| EBOV-511 | 4-39*01 | 92 | 3-3*01 | 4*02 | ARHLAPISGVIFIPSFFDS (SEQ ID NO: 114) | 19 | 3-15*01 | 97 | 4*01 | QQYNDWPPRLT (SEQ ID NO: 177) | 11 |
| EBOV-514 | 4-30-4*01 | 91 | 2-2*01 | 6*03 | ARDKAQAYGLLYHYHTDV (SEQ ID NO: 117) | 19 | 3-15*01 | 96 | 2*01 | QYYNDWPPGYT (SEQ ID NO: 180) | 11 |
| EBOV-515 | 4-31*03 or 4-31*07 | 93 | 3-22*01 | 4*02 | ARESSWVSELGRDN (SEQ ID NO: 120) | 18 | 3-15*01 | 97 | 1*01 | QQYNNWPRT (SEQ ID NO: 183) | 9 |
| EBOV-517 | 3-7*01 | 96 | 2-2*01 | 6*03 | ARGASIEVEILYYYHMDV (SEQ ID NO: 123) | 18 | 3-15*01 | 94 | 4*01 | QQYHTWPPLT (SEQ ID NO: 186) | 10 |

TABLE S1-continued

Germline origin genes and variable region analysis of newly identified broadly reactive human mAbs. Related to FIG. 1

| | Heavy chain variable gene sequence | | | | | | Light chain variable sequence | | | | |
|---|---|---|---|---|---|---|---|---|---|---|---|
| mAb* | V-gene and allele | V-region nucleotide homology to V-gene, % | D-gene and allele | J-gene and allele | CDR3 amino acids (aa) | CDR3 length (aa) | V-gene and allele | V.region nucleotide homology to V gene, % | J-gene and allele | CDR3 amino acids (aa) | CDR3 length (aa) |
| EBOV-518 | 2-5*09 | 92 | 3-16*02 | 4*02 | AHSGGLVAGAFDY (SEQ ID NO: 126) | 13 | 4-1*01 | 94 | 1*01 | QQYYNSPRT (SEQ ID NO: 189) | 9 |
| EBOV-520 | 4-59*01 | 93 | 5-12*01 | 6*02 | ARGAWNVATVYYYYGMDV (SEQ ID NO: 129) | 18 | 3-20*01 | 97 | 2*01 | QQYGNSLYT (SEQ ID NO: 192) | 9 |
| EBOV-524 | 3-30*02 or 3-30-5*02 | 90 | 2-2*01 | 6*03 | AKDVLDCSRADCFIYYYYMDV (SEQ ID NO: 132) | 21 | 1-12*01 or 1-12*02 or 1D-12*02 | 83 | 4*01 | QQGNRIPLS (SEQ ID NO: 195) | 9 |

N/A—not available.

*MAbs EBOV-434 to EBOV-451 were isolated from a survivor of the West African 2013-2016 EVD epidemic; MAbs EBOV-502 to EBOV-24 were isolated from a survivor of the 2014 EVD outbreak in the DRC.

TABLE S2

Binding capacity of newly isolated broadly-reactive mAbs, or previously described mAbs, assessed by ELISA. Related to FIG. 2

| mAb origin | mAb ID | Isotype | Binding, $EC_{50}$ ng/mL (95% CI) | | | |
|---|---|---|---|---|---|---|
| | | | EBOV GP ΔTM | BDBV GP ΔTM | SUDV GP ΔTM | MARV GP ΔTM |
| Survivor of the West African 2013-2016 EVD epidemic | EBOV-434 | IgG1 | 304 (237 to 389) | 415 (354 to 486) | 1,114 (977 to 1,268) | > |
| | EBOV-437 | IgG1 | 3 (2 to 4) | 11 (8 to 14) | 4 (3 to 5) | > |
| | EBOV-442 | IgG1 | 1 (1 to 2) | 3 (2 to 3) | 6 (5 to 8) | > |
| | EBOV-446 | IgG1 | 9 (8 to 12) | 2 (2 to 3) | 722 (584 to 892) | > |
| | EBOV-451 | IgG1 | 1 (1 to 2) | 7 (5 to 9) | 3 (2 to 3) | > |
| Survivor of the 2014 EVD outbreak in the DRC | EBOV-502 | IgG1 | 50 (41 to 61) | 285 (241 to 338) | 73 (62 to 85) | > |
| | EBOV-507 | IgG1 | 1 (1 to 1) | 4 (3 to 5) | 2 (1 to 2) | > |
| | EBOV-508 | IgG1 | 2 (1 to 2) | 5 (43 to 6) | 3 (2 to 4) | > |
| | EBOV-510 | IgG1 | 143 (112 to 182) | 261 (216 to 314) | 3,091 (2,783 to 3,433) | > |
| | EBOV-511 | IgG4 | 94 (74 to 119) | 289 (232 to 359) | 387 (323 to 463) | > |
| | EBOV-514 | IgG1 | 7 (5 to 8) | 10 (8 to 12) | 15 (12 to 18) | > |
| | EBOV-515 | IgG1 | 9 (7 to 11) | 15 (11 to 19) | 14 (11 to 18) | > |
| | EBOV-517 | IgG1 | 42 (33 to 53) | 865 (760 to 984) | 1,694 (1,506 to 1,906) | > |
| | EBOV-518 | IgG3 | 283 (220 to 365) | 2,626 (2,138 to 3,225) | 352 (282 to 440) | 780 (668 to 958) |
| | EBOV-520 | IgG4 | 12 (10 to 15) | 72 (58 to 88) | 136 (118 to 156) | > |
| | EBOV-524 | IgG4 | 123 (100 to 151) | 146 (125 to 170) | 701 (636 to 774) | > |
| Reference mAb | BDBV-289 | IgG1 | 3 (2 to 4) | 2 (1 to 2) | 18 (14 to 22) | > |
| | BDBV-317 | IgG1 | <1 | <1 | 19 (15 to 25) | > |
| | BDBV-223 | IgG3 | 2 (2 to 3) | <1 | 3 (3 to 5) | > |
| | 4G7 | IgG1 | 18 (14 to 22) | > | > | > |
| | KZ52 | IgG1 | 14 (11 to 18) | > | > | > |

">" Indicates binding was not detected, even at the highest concentration tested of 10,000 ng/mL

TABLE S3

Neutralizing capacity of newly isolated broadly-reactive mAbs, or previously described mAbs. Related to FIG. 2

| mAb origin | mAb ID | Neutralization, $IC_{50}$ ng/mL (95% CI) | | |
|---|---|---|---|---|
| | | EBOV | BDBV | SUDV |
| Survivor of the West African 2013-2016 EVD epidemic | EBOV-434 | > | > | > |
| | EBOV-437 | 8,660* | > | 27,030* |
| | EBOV-442 | 467 (321 to 679) | 1,489 (861 to 2,577) | 38,330* |
| | EBOV-446 | > | > | > |
| | EBOV-451 | > | > | > |
| Survivor of the 2014 EVD outbreak in the DRC | EBOV-502 | > | > | > |
| | EBOV-507 | > | > | > |
| | EBOV-508 | > | > | > |
| | EBOV-510 | > | > | > |
| | EBOV-511 | > | > | > |
| | EBOV-514 | > | > | > |
| | EBOV-515 | 1,224 (769 to 1,950) | 1,458 (1,070 to 1987) | 891 (653 to 1,217) |
| | EBOV-517 | > | > | > |
| | EBOV-518 | > | > | > |
| | EBOV-520 | 5,738 (3,818 to 8,624) | 3,810 (2,701 to 5,375) | 6,318 (3,636 to 10,980) |
| | EBOV-524 | > | > | > |
| Reference mAb | BDBV-289** | 588 | 32 | > |
| | BDBV-317** | 4,400 | 100 | > |
| | BDBV-223** | 100 | 20 | > |
| | 4G7** | 135 | > | > |
| | KZ52** | 400 | > | > |

*Incomplete (<100%) virus neutralization at the highest mAb concentration tested (200 μg/mL).

">" Neutralization was not detected at the highest mAb concentration tested (200 μg/mL).

**Neutralization data from previous reports that are included here for comparative purposes.

TABLE S4

Fc-mediated functional capacity of isolated broadly-reactive mAbs* (related to FIG. 3)

| mAb | Functional assay, z-score* | | | | | |
|---|---|---|---|---|---|---|
| | ADCD | ADNP | ADCP | NK CD107 | NK IFN-γ | NK MIP-1β |
| EBOV-434 | −0.29 | −0.23 | −0.60 | −0.27 | −1.02 | 0.08 |
| EBOV-437 | 1.10 | 0.78 | 1.66 | −0.09 | −1.51 | −0.55 |
| EBOV-442 | 3.80 | 2.33 | 1.97 | 0.71 | −0.03 | 0.95 |
| EBOV-446 | −0.36 | −0.40 | 0.51 | −0.82 | −0.03 | −0.91 |
| EBOV-451 | −0.34 | −0.12 | 1.47 | 0.68 | 0.03 | 1.04 |
| EBOV-502 | −0.36 | −0.44 | −0.44 | 0.26 | −0.87 | 0.28 |
| EBOV-507 | −0.35 | −0.25 | 0.39 | −0.86 | −1.59 | −0.78 |
| EBOV-508 | −0.33 | −0.45 | 0.17 | −0.51 | 0.09 | −0.66 |
| EBOV-510 | −0.31 | −0.28 | −0.54 | −0.10 | −0.54 | −0.09 |
| EBOV-511 | −0.37 | −0.49 | −0.98 | −0.82 | −0.27 | −0.76 |
| EBOV-514 | −0.32 | −0.48 | 0.30 | 3.05 | 2.53 | 2.53 |
| EBOV-515 | −0.41 | −0.06 | 1.42 | 1.48 | 1.71 | 1.26 |
| EBOV-517 | −0.34 | −0.27 | −0.43 | 0.97 | 0.97 | 0.93 |
| EBOV-518 | −0.34 | −0.44 | −1.10 | −0.89 | 0.03 | −0.83 |
| EBOV-520 | −0.37 | −0.26 | 0.72 | −0.74 | −0.11 | −0.97 |
| EBOV-524 | −0.38 | −0.45 | −0.99 | −0.87 | −0.03 | −0.90 |
| Neg. control | −0.63 | −0.44 | −1.04 | −0.86 | −1.16 | −1.01 |
| Pos. control | 1.44 | 3.52 | 0.93 | 3.08 | 0.80 | 1.34 |

*Z-score (z) = (x−μ)/σ, where x is raw score (a phagocytic score, or MFI, or percent activated cells that determined as described in the Methods Details section), μ is the mean of the population, and σ is the standard deviation of the population.

TABLE S5

Inferred antibody germline genes and variable region analysis of broadly reactive human mAbs that cooperate for GP binding (related to FIGS. 1A-C)

| | Heavy chain variable gene sequence | | | | | |
|---|---|---|---|---|---|---|
| mAb* | V-gene and allele | V-region nucleotide homology to V-gene, % | D-gene and allele | J-gene and allele | CDR3 amino acids (aa) | CDR3 length (aa) |
| EBOV-437 | 1-69708 | 95 | 3-10701 | 6703 | ARGPPLRGERSWFGESEKYDYFYMDV | 26 |
| EBOV-442 | 3-15701 | 91 | 3-16701 | 6703 | ATGSGKGPSASFGESYYYYDFINV | 24 |
| EBOV-548 | 3-30702 | 94 | 6-19701 | 6702 | AKELLQVYTSAWGEGHSYYYALDV | 24 |
| EBOV-515 | 4-31703 or 4-31707 | 93 | 3-22701 | 4702 | ARESSWVSELGRDN | 14 |
| EBOV-520 | 4-59701 | 93 | 5-12701 | 6702 | ARGAWNVATVYYYYGMDV | 18 |
| EBOV-542 | 3-66701 | 97 | 1-7701 | 4702 | ARELGNWSYGVSY | 13 |

| | Light chain variable sequence | | | | |
|---|---|---|---|---|---|
| mAb* | V-gene and allele | V-region nucleotide homology to V gene, % | J-gene and allele | CDR3 amino acids (aa) | CDR3 length (aa) |
| EBOV-437 | 3-20*01 | 97 | 2*02 | QQYGTSPCT | 9 |
| EBOV-442 | 3-20*01 | 96 | 1*01 | HQYESSPWT | 9 |
| EBOV-548 | 1-12*01 | 97 | 2*01 | QQGKSFPYT | 9 |
| EBOV-515 | 3-15*01 | 97 | 1*01 | QQYNNWPRT | 9 |

TABLE S5-continued

Inferred antibody germline genes and variable region analysis of
broadly reactive human mAbs that cooperate for GP binding
(related to FIGS. 1A-C)

| EBOV-520 | 3-20*01 | 97 | 2*01 | QQYGNSLYT | 9 |
| EBOV-542 | 3-25*03 | 98 | 2*01 | QSADGSGTYPVV | 12 |

*MAbs EBOV-437, -442, -542, and -548 were isolated from a survivor of the West African 2013-2016 EVD epidemic infected in Lagos, Nigeria; MAbs EBOV-515 and EBOV-520 were isolated from a survivor of the 2014 EVD outbreak in the DRC. MAbs EBOV-437, -442, and -548 are glycan cap-specific, and mAbs EBOV-515, -520, and -542 are GP base-specific, as indicated in FIG. S1A. Sequences of mAbs EBOV-437, -442, -515, and -520 are from a previous report (Gilchuk et al., 2018) and are included here for comparative purposes.

TABLE S6

Crystallographic data collection and refinement statistics (related to FIGS. 3A-D)

| | EBOV GP$_{CL}$ + rEBOV-520 Fab |
|---|---|
| Resolution$^a$ (Å) | 72.66-3.462 (3.586-3.462) |
| Space group | P 4$_1$ 3 2 |
| Unit cell (Å) | 217.97 217.97 217.97 |
| (°) | 90 90 90 |
| Total Reflections$^a$ | 868614 (181970) |
| Unique Reflections$^a$ | 23638 (2296) |
| Multiplicity$^a$ | 36.7 (38.2) |
| Completeness$^a$ (%) | 99.19 (97.04) |
| I/σ(I)$^a$ | 18.9 (4.3) |
| R$_{merge}^{a,b}$ | 0.220 (1.314) |
| R$_{pim}^{a,c}$ | 0.037 (0.214) |
| CC 1/2$^d$ | 0.999 (0.898) |
| Wilson B (Å$^2$) | 103.3 |
| R$_{work}^{e}$ | 0.200 |
| R$_{free}^{f}$ | 0.234 |
| RMSD$^g$ (bonds) (Å) | 0.003 |
| RMSD$^g$ (angles) (°) | 0.600 |
| Ramachandran favored (%) | 95.56 |
| Ramachandran outliers (%) | 0 |
| Clashscore | 5.55 |
| Average B-factor (Å$^2$) | 108.78 |

$^a$Values in parentheses are for the highest-resolution shell.
$^b$R$_{merge}$ = Σ$_{hkl}$ Σ$_i$|I$_i$(hkl) − <I(hkl)>|/ Σ$_{hkl}$Σ$_i$I$_i$(hkl)
$^c$R$_{pim}$ = Σ$_{hkl}${1/[N(hkl) − 1]}$^{1/2}$ × Σ$_i$|I$_i$(hkl) − <I(hkl)>|/ Σ$_{hkl}$Σ$_i$I$_i$(hkl)
$^d$CC = Σ(x − <x>)(y − <x>)/[Σ(x − <x>)$^2$Σ(y − <y>)$^2$]$^{1/2}$
$^e$R$_{work}$ = (Σ$_{hkl}$ ||F$_{obs}$| − k |F$_{calc}$||)/(Σ$_{hkl}$ |F$_{obs}$|).
$^f$R$_{free}$ is the same as R$_{work}$ with 5% of reflections chosen at random and omitted from refinement.
$^g$RMSD, root mean square deviation.

TABLE S7

Cryo-EM data collection and statistics of EBOV GP ΔmucΔTM:rEBOV-520:rEBOV-548 Fab complex (related to FIGS. 5A-H)

| Map | EBOV GP ΔmucΔTM:rEBOV-520:rEBOV-548 |
|---|---|
| Data collection | |
| Microscope | Titan Krios |
| Voltage (kV) | 300 |
| Detector | Gatan K2 Summit |
| Recording mode | Counting |
| Magnification (incl. post-magnification) | 48,543 |
| Movie micrograph pixel size (Å) | 1.03 |
| Dose rate (e-/[(camera pixel)*s]) | 5.05 |
| Number of frames per movie micrograph | 38 |
| Frame exposure time (ms) | 250 |
| Movie micrograph exposure time (s) | 9.5 |
| Total dose (e-/Å$^2$) | 51.85 |
| Defocus range (μm) | −0.5 to −3.0 |
| EM data processing | |
| Number of movie micrographs | 2,832 |
| Number of molecular projections images in map | 13,114 |
| Symmetry | C3 |
| Map resolution (FSC 0.143; Å) | 4.12 |
| Map sharpening B-factor (Å2) | −129.473 |
| Structure building and validation | — |
| Number of atoms in deposited model | 18,822 |
| GP1 | 5,442 |
| GP2 | 2,490 |
| rEBOV-520 | 5,319 |
| rEBOV-548 | 5,571 |
| glycans | 351 |
| MolProbity score | 0.9 |
| Clashscore | 0.89 |
| EMRinger score | 2.07 |
| RMSD from ideal | — |
| Bond length (Å) | 0.02 |
| Bond angle (degrees) | 1.722 |
| Ramachandran plot | — |
| Favored (%) | 97.31 |
| Allowed (%) | 2.44 |
| Outliers (%) | 0.26 |
| Average B-factor | 105.3 |

TABLE S8

Identification of individual NHPs that were described in this study (related to FIGS. 7A-D)

| Treatment | Designated ID, this paper* |
|---|---|
| Yes | Subject 1 (M1) |
| | Subject 2 (M2) |
| | Subject 3 (M3) |
| | Subject 4 (M4) |
| | Subject 5 (M5) |
| No | Subject 5 (C1) |
| | Subject 7 (HC1) |
| | Subject 8 (HC2) |
| | Subject 9 (HC3) |
| | Subject 10 (HC4) |
| | Subject 11 (HC5) |
| | Subject 12 (HC6) |
| | Subject 13 (HC7) |
| | Subject 14 (HC8) |
| | Subject 15 (HC9) |
| | Subject 16 (HC10) |

*numbers indicate individual NHPs from the respective group: "M"—treated, this study; "C"—untreated, this study; "HC"—untreated, historical control.

TABLE S9

Viral load determined by qRT-PCR in various organs of individual NHPs that were treated with a two-mAb cocktail or untreated (related to FIGS. 7A-D)

Viral load determined by RT-qPCR for indicated treatment group, animal and organ [mean log$_{10}$ genome equivalents per gram tissue] ± SD

| | Two-antibody cocktail treated NHP | | | | | Untreated |
|---|---|---|---|---|---|---|
| | Animal ID: | | | | | |
| Organ | M1 | M2 | M3 | M4 | M5 | M6 |
| Axillary LN | 6.5 ± 0.1 | 6.0 ± 0.0 | 6.9 ± 0.1 | 6.4 ± 0.0 | 6.5 ± 0.3 | 4.8 ± 0.2 |
| Inguinal LN | 6.6 ± 0.1 | 6.4 ± 0.1 | 7.0 ± 0.1 | 6.4 ± 0.0 | 6.7 ± 0.2 | 8.8 ± 0.1 |
| Liver | 7.1 ± 0.1 | 6.2 ± 0.3 | 6.3 ± 0.1 | < | < | 6.2 ± 0.1 |
| Spleen | 6.7 ± 0.0 | 5.7 ± 0.0 | 7.6 ± 00 | 6.2 ± 0.0 | 7.3 ± 0.1 | 7.6 ± 0.1 |
| Kidney | 7.4 ± 0.0 | 6.2 ± 0.1 | 6.4 ± 0.1 | 5.9 ± 0.3 | 6.3 ± 0.0 | 6.0 ± 0.1 |
| Adrenal | 7.1 ± 0.1 | 6.2 ± 0.0 | 5.9 ± 0.2 | 5.8 ± 0.2 | 6.0 ± 0.1 | 8.2 ± 0.2 |
| Lung | 7.2 ± 0.0 | 6.4 ± 0.1 | 6.8 ± 0.1 | 6.9 ± 0.0 | 6.6 ± 0.0 | 8.3 ± 0.1 |
| Brain front | 7.2 ± 0.0 | 6.0 ± 0.0 | 6.3 ± 0.1 | < | < | ND |
| Brain stem | 7.4 ± 0.0 | 6.6 ± 0.1 | 6.8 ± 0.1 | 5.7 ± 0.2 | < | ND |
| Cervical spinal cord | 6.6 ± 0.2 | 7.6 ± 0.1 | 6.8 ± 0.1 | < | 6.2 ± 0.4 | ND |
| Pancreas | 7.9 ± 0.0 | 6.5 ± 0.9 | < | < | 6.1 ± 0.2 | < |
| Urinary bladder | 6.6 ± 0.1 | 6.6 ± 0.2 | 5.7 ± 0.1 | < | 6.6 ± 0.1 | 7.8 ± 0.0 |
| Gonad | 6.3 ± 0.1 | 6.6 ± 0.0 | 6.8 ± 0.0 | 7.0 ± 0.2 | 6.8 ± 0.1 | < |
| Uterus/prostate | 7.3 ± 0.1 | 7.1 ± 0.0 | 6.87 ± 0.4 | 6.2 ± 0.1 | < | 5.6 ± 0.2 |
| Conjunctiva | 6.8 ± 0.1 | 6.9 ± 0.0 | 6.9 ± 0.2 | 6.2 ± 0.2 | 6.6 ± 0.1 | 6.2 ± 0.0 |
| Eye | 7.0 ± 0.0 | 7.1 ± 0.2 | 6.0 ± 0.3 | 6.5 ± 0.3 | 5.7 ± 0.0 | 7.9 ± 0.0 |

Viral load was determined by qRT-PCR [mean log$_{10}$ genome equivalents per gram tissue] ± SD of technical duplicates) in various organs of individual NHPs from treatment group on 28 dpi or untreated NHP (this study) on 6 dpi. Animal identifications as in Table S3. The < symbol indicates virus genome was not detected for that sample. The limit of detection was 3.7 log$_{10}$ (GEq/g).

TABLE S10

Hematology measurements from two-mAb cocktail-treated or -untreated individual NHP (related to FIGS. 7A-D)

| Animal ID | Day after challenge | WBC per mm$^3$ (×10$^3$) | RBC per mm$^3$ (×10$^3$) | HgB (g/dL) | HCT (%) | PLT per mm$^3$ (×10$^3$) | Lymph per mm$^3$ (×10$^3$) | Lymph (%) | MCH (pg/cell) | MO per mm$^3$ (×10$^3$) | GR per mm$^3$ (×10$^3$) | MO (%) | GR (%) | MPV (fL per cell) |
|---|---|---|---|---|---|---|---|---|---|---|---|---|---|---|
| M1 | 0 | 7 | 5 | 10 | 32 | 304 | 3 | 39 | 21 | 0 | 4 | 6 | 55 | 9 |
| M2 | 0 | 6 | 4 | 10 | 32 | 296 | 4 | 66 | 23 | 0 | 2 | 4 | 30 | 9 |
| M3 | 0 | 6 | 5 | 13 | 41 | 305 | 3 | 50 | 23 | 1 | 2 | 10 | 40 | 7 |
| M4 | 0 | 6 | 5 | 12 | 38 | 297 | 3 | 58 | 23 | 1 | 2 | 14 | 29 | 8 |
| M5 | 0 | 6 | 4 | 9 | 30 | 221 | 4 | 65 | 21 | 1 | 2 | 10 | 26 | 10 |
| C1 | 0 | 7 | 5 | 11 | 36 | 441 | 3 | 37 | 24 | 0 | 4 | 6 | 57 | 7 |
| M1 | 3 | 10 | 5 | 10 | 33 | 323 | 2 | 17 | 21 | 1 | 8 | 5 | 78 | 9 |
| M2 | 3 | 6 | 4 | 9 | 32 | 344 | 3 | 44 | 22 | 1 | 3 | 9 | 47 | 8 |
| M3 | 3 | 11 | 5 | 12 | 39 | 263 | 2 | 15 | 22 | 1 | 9 | 5 | 81 | 8 |
| M4 | 3 | 8 | 5 | 10 | 34 | 260 | 2 | 27 | 21 | 2 | 4 | 21 | 52 | 8 |
| M5 | 3 | 7 | 4 | 9 | 31 | 223 | 2 | 24 | 21 | 1 | 5 | 7 | 69 | 9 |
| C1 | 3 | 6 | 5 | 10 | 34 | 458 | 2 | 28 | 22 | 0 | 4 | 3 | 69 | 7 |
| M1 | 6 | 8 | 4 | 9 | 32 | 300 | 2 | 30 | 21 | 0 | 5 | 5 | 65 | 9 |
| M2 | 6 | 6 | 4 | 9 | 31 | 302 | 4 | 59 | 22 | 1 | 2 | 9 | 32 | 9 |
| M3 | 6 | 5 | 5 | 11 | 37 | 229 | 3 | 53 | 22 | 1 | 2 | 10 | 37 | 8 |
| M4 | 6 | 5 | 5 | 10 | 35 | 295 | 2 | 47 | 22 | 1 | 2 | 10 | 43 | 8 |
| M5 | 6 | 4 | 4 | 7 | 25 | 212 | 3 | 69 | 20 | 0 | 1 | 9 | 22 | 10 |
| C1 | 6 | 11 | 4 | 10 | 33 | 217 | ND | ND | 23 | ND | ND | ND | ND | 6 |
| M1 | 9 | 9 | 4 | 10 | 32 | 344 | 4 | 44 | 23 | 0 | 5 | 5 | 51 | 9 |
| M2 | 9 | 8 | 4 | 9 | 29 | 308 | 6 | 75 | 25 | 1 | 1 | 7 | 18 | 8 |
| M3 | 9 | 12 | 5 | 11 | 34 | 324 | 8 | 65 | 24 | 1 | 3 | 8 | 27 | 7 |
| M4 | 9 | 7 | 4 | 10 | 31 | 312 | 4 | 59 | 24 | 1 | 2 | 8 | 33 | 7 |
| M5 | 9 | 8 | 4 | 10 | 31 | 290 | 6 | 74 | 22 | 1 | 2 | 7 | 20 | 9 |
| M1 | 14 | 8 | 5 | 11 | 33 | 335 | 4 | 46 | 23 | 1 | 4 | 9 | 46 | 9 |
| M2 | 14 | 9 | 4 | 11 | 33 | 333 | 7 | 72 | 26 | 1 | 2 | 6 | 23 | 9 |
| M3 | 14 | 10 | 5 | 12 | 36 | 372 | 5 | 51 | 25 | 1 | 4 | 8 | 41 | 7 |
| M4 | 14 | 7 | 4 | 11 | 32 | 366 | 4 | 64 | 24 | 0 | 2 | 6 | 31 | 7 |
| M5 | 14 | 7 | 4 | 10 | 30 | 270 | 4 | 58 | 23 | 1 | 2 | 8 | 34 | 9 |
| M1 | 21 | 9 | 5 | 11 | 33 | 307 | 4 | 39 | 24 | 1 | 5 | 10 | 51 | 9 |
| M2 | 21 | 7 | 4 | 11 | 32 | 314 | 6 | 77 | 26 | 0 | 1 | 5 | 18 | 9 |
| M3 | 21 | 8 | 5 | 14 | 41 | 301 | 5 | 63 | 25 | 1 | 2 | 11 | 27 | 8 |
| M4 | 21 | 6 | 4 | 10 | 30 | 255 | 4 | 66 | 24 | 0 | 2 | 7 | 27 | 8 |
| M5 | 21 | 7 | 5 | 11 | 32 | 207 | 5 | 64 | 23 | 1 | 2 | 7 | 29 | 10 |

TABLE S10-continued

Hematology measurements from two-mAb cocktail-treated or -untreated individual NHP (related to FIGS. 7A-D)

| Animal ID | Day after challenge | WBC per mm$^3$ (×10$^3$) | RBC per mm$^3$ (×10$^3$) | HgB (g/dL) | HCT (%) | PLT per mm$^3$ (×10$^3$) | Lymph per mm$^3$ (×10$^3$) | Lymph (%) | MCH (pg/cell) | MO per mm$^3$ (×10$^3$) | GR per mm$^3$ (×10$^3$) | MO (%) | GR (%) | MPV (fL per cell) |
|---|---|---|---|---|---|---|---|---|---|---|---|---|---|---|
| M1 | 28 | 5 | 5 | 10 | 31 | 349 | 3 | 57 | 23 | 1 | 2 | 11 | 31 | 9 |
| M2 | 28 | 6 | 4 | 11 | 33 | 335 | 4 | 74 | 25 | 0 | 1 | 7 | 19 | 9 |
| M3 | 28 | 7 | 5 | 11 | 36 | 262 | 3 | 51 | 24 | 1 | 3 | 11 | 38 | 8 |
| M4 | 28 | 5 | 5 | 12 | 36 | 259 | 3 | 62 | 24 | 0 | 2 | 5 | 33 | 7 |
| M5 | 28 | 4 | 4 | 10 | 31 | 208 | 3 | 75 | 22 | 0 | 1 | 4 | 21 | 10 |

WBC, white blood cells; RBC, red blood cells; HgB, hemoglobin; HCT, hematocrit level; PLT, platelets; Lymph, lymphocytes; MCH, mean corpuscular hemoglobin; MO, monocytes; GR, granulocytes; MPV, mean platelet volume. * Sample was assessed at 5-fold dilution, and value from the measurement was multiplied by five to represent the recorded value. ND, not determined. Animal identifications as in Table S3.

TABLE S11

Blood biochemistry measurements from two-mAb cocktail-treated or -untreated NHP (related to FIGS. 7A-D)

| Animal ID | Day after challenge | GLU (mg/dL) | BUN (mg/dL) | CRE (mg/dL) | ALB (g/dL) | TP (g/dL) | ALT (U/L) | AST (U/L) | ALP (U/L) | GGT (U/L) | AMY (U/L) | CRP (mg/dL) |
|---|---|---|---|---|---|---|---|---|---|---|---|---|
| M1 | 0 | 78 | 15 | 1 | 3 | 7 | 45 | 26 | 115 | 49 | 297 | <5 |
| M2 | 0 | 89 | 29 | 1 | 4 | 7 | 51 | 42 | 284 | 83 | 259 | <5 |
| M3 | 0 | 76 | 18 | 1 | 3 | 7 | 37 | 35 | 328 | 64 | 348 | <5 |
| M4 | 0 | 75 | 21 | 1 | 3 | 7 | 34 | 30 | 328 | 63 | 395 | <5 |
| M5 | 0 | 102 | 14 | 1 | 4 | 7 | 27 | 22 | 300 | 67 | 262 | <5 |
| C1 | 0 | 81 | 22 | 1 | 3 | 7 | 100 | 51 | 189 | 94 | 545 | <5 |
| M1 | 3 | 78 | 13 | 1 | 3 | 7 | 40 | 21 | 126 | 48 | 278 | <5 |
| M2 | 3 | 63 | 23 | 1 | 4 | 7 | 59 | 43 | 268 | 79 | 256 | <5 |
| M3 | 3 | 70 | 17 | 1 | 3 | 7 | 36 | 35 | 321 | 65 | 275 | 14 |
| M4 | 3 | 72 | 21 | 1 | 3 | 6 | 37 | 29 | 319 | 58 | 432 | 14 |
| M5 | 3 | 94 | 15 | 1 | 4 | 7 | 29 | 25 | 287 | 67 | 300 | <5 |
| C1 | 3 | 81 | 24 | 1 | 3 | 7 | 260 | 152 | 202 | 106 | 513 | <5 |
| M1 | 6 | 77 | 15 | 1 | 3 | 7 | 35 | 27 | 118 | 45 | 314 | 8 |
| M2 | 6 | 76 | 25 | 1 | 3 | 7 | 123 | 72 | 248 | 79 | 250 | <5 |
| M3 | 6 | 67 | 21 | 1 | 3 | 7 | 34 | 32 | 256 | 56 | 249 | 14 |
| M4 | 6 | 62 | 22 | 1 | 3 | 6 | 34 | 27 | 275 | 55 | 357 | 17 |
| M5 | 6 | 92 | 19 | 1 | 3 | 7 | 31 | 24 | 226 | 62 | 274 | 6 |
| C1 | 6 | 28 | 80 | 4 | 3 | 7 | 1,781 | 3,670* | 1,046 | 743 | 416 | 116 |
| M1 | 9 | 84 | 16 | 1 | 3 | 7 | 38 | 26 | 119 | 47 | 339 | <5 |
| M2 | 9 | 93 | 24 | 1 | 4 | 7 | 98 | 44 | 252 | 81 | 283 | <5 |
| M3 | 9 | 76 | 23 | 1 | 3 | 7 | 41 | 42 | 265 | 61 | 256 | 9 |
| M4 | 9 | 66 | 25 | 1 | 3 | 7 | 40 | 30 | 254 | 55 | 383 | 6 |
| M5 | 9 | 94 | 18 | 1 | 3 | 7 | 29 | 22 | 248 | 63 | 313 | <5 |
| M1 | 14 | 88 | 14 | 1 | 3 | 7 | 35 | 23 | 106 | 46 | 298 | <5 |
| M2 | 14 | 90 | 26 | 1 | 3 | 7 | 71 | 43 | 236 | 78 | 259 | <5 |
| M3 | 14 | 75 | 19 | 1 | 3 | 7 | 37 | 28 | 300 | 60 | 269 | 7 |
| M4 | 14 | 66 | 22 | 1 | 3 | 7 | 32 | 26 | 247 | 55 | 378 | <5 |
| M5 | 14 | 101 | 18 | 1 | 3 | 7 | 28 | 21 | 278 | 68 | 293 | <5 |
| M1 | 21 | 84 | 13 | 1 | 3 | 7 | 44 | 23 | 115 | 46 | 314 | <5 |
| M2 | 21 | 80 | 25 | 1 | 3 | 7 | 43 | 36 | 282 | 78 | 268 | <5 |
| M3 | 21 | 82 | 19 | 1 | 3 | 7 | 31 | 31 | 317 | 63 | 271 | 6 |
| M4 | 21 | 70 | 23 | 1 | 3 | 7 | 31 | 28 | 283 | 54 | 373 | <5 |
| M5 | 21 | 107 | 19 | 1 | 3 | 7 | 28 | 24 | 304 | 72 | 271 | <5 |
| M1 | 28 | 75 | 15 | 1 | 3 | 7 | 63 | 30 | 115 | 45 | 330 | 5 |
| M2 | 28 | 80 | 27 | 1 | 3 | 6 | 44 | 40 | 285 | 76 | 223 | <5 |
| M3 | 28 | 86 | 19 | 1 | 3 | 7 | 29 | 34 | 344 | 65 | 279 | 8 |
| M4 | 28 | 67 | 23 | 1 | 3 | 6 | 24 | 28 | 286 | 56 | 340 | <5 |
| M5 | 28 | 84 | 20 | 1 | 3 | 6 | 25 | 21 | 276 | 63 | 294 | <5 |

GLU, glucose; BUN, blood urea nitrogen; CRE, creatinine; ALB, albumin; TP, total protein; ALT, alanine aminotransferase; AST, aspartate aminotransferase; ALP, alkaline phosphatase; GGT, gamma-glutamyl transpeptidase; AMY, amylase; CRP, C-reactive protein. * Sample was assessed at 5-fold dilution, and value from the measurement was multiplied by five to represent the recorded value. ND, not determined. Animal identifications as in the Table S3.

TABLE 1

| NUCLEOTIDE SEQUENCES FOR ANTIBODY VARIABLE REGIONS | | |
|---|---|---|
| Clone | Variable Sequence Region | SEQ ID NO: |
| [EBOV-434] heavy | caggtgcagctggtgcagtctggggctgaggtgaagaagcctggggcctcagtgaaggtctcctgcaa ggcttctggatacaccttcaccggctactatatgttctgggtgcgacaggcccctggacaagggcttga gtggatgggatggatcaaccctaacagtggtggcacaaactatacacagaagtttcagggcagggtc accatgaccagggacacgtccatcagcacagcctacatggagctgagcaggctgaaatctgacgaca cggccgtgtattactgtgcgagagactccggggagttattattcgtgggctcggacgtctggggccaag ggaccctggtcaccgtctcctca | 1 |
| [EBOV-434] light | gacatccagatgacccagtctccatcttccgtgtctgcatctgtaggagacagagtcaccatcacttgtc gggcgagtctggatattagctactggttagcctggtatcagcagaaaccaggtaaagcccctaagctc ctgatctatgctgcatccaatttgcaaagtggggtcccatcaaggttcagcggcagtggatctgggaca gatttcactctcaccatcagcagcctgcagcctgaagattttgcaacttactattgtcaacaggctaaca gtttccctcagacttttggccaggggaccaggctggagctcaaa | 2 |
| [EBOV-437] heavy | caggtccagctggtgcaatctggggctgaggtgaagaagcctgggtcctcggtgaaggtctcctgcaa ggcttctggaggcaccttcagtagggatattttcagctgggtgcgacaggcccctggacaagggcttga gtggatgggagggatcatccctatctttggtacggcaaactacgcacagaagttccagggcagagtca cgattaccgcggacaaatccacgagtacagtcttcatggagttgagcggcctgagatctgaggacacg gccgtgtatttctgtgcgagaggcccccccctccgcggggagaggtcatggttcggggagtccgaaaa gtacgactacttctacatggacgtgtggggcaaagggaccacggtcaccgtctcctca | 3 |
| [EBOV-437] light | caaattgttttgacgcagtctccaggcaccctgtctttgtctccaggggagagagccaccctctcctgca gggccagtcagagtgttagcaacagctacttagcctggtaccagcagaaacctggccaggctcccag gctcctcatctatggtgcatccagcagggccactggcatcccagacaggttcagtggcagtgggtctgg gacagacttcactctctccatcagcagactggagcctgaagattttgcagtgtattactgtcagcagtat ggtacgtcaccttgtacttttggccaggggaccaagctggagatcaaa | 4 |
| [EBOV-442] heavy | gaggtgcagttggtggagtctgggggaggcctcgtaaagccggggggtcccttagactctcctgtac aggctctggaggcactggattcactttcaagtatgccgggatgagctgggtccgccaggctccaggga aggggccggagtggattggccgtattaaaagcaggattgatggtgggacaacagactacgctgcacc cgtgaaagacagattcattgtctcaagagatgattcaagaaatacactctatctgcaaatgaacagcc tgaagaccgaggacacagccgtctattattgtgccacaggatcgggaaaggggccctctgcgtcgttc ggggagtcatactactactacgacttcattaacgtctggggcaaagggaccacggtcaccgtctcctca | 5 |
| [EBOV-442] light | gaaagtgtgttgacgcagtctccaggcaccctgtctttgtctccaggggaaagagccaccctctcgtgc agggccagtcagagtattagcaggaagtacttagcctggtaccagcagaaacctggccaggctccca ggctcctcatctatggttcatccagcagggccactggcatcccagacagattcagtggcagtgggtctg ggacagacttcactctcaccatcagcagactggagcctgaagattttgcagtgtattactgtcatcagt atgaaagctcaccttggacgttcggccaagggactaaggtggaaatcaaa | 6 |
| [EBOV-446] heavy | caggtgcagctggtgcagtctggggctgaggtgaaaaagcctggggcctcagtgaaggtctcctgtaa ggcttctggatacaccttcaccgactactatatctactgggtgcgacaggcccctggacaagggcttga atggatgggatggctcaaccctaatagtggtggcacagactatgcccagaagtttcagggccgggtca ccatgaccagggacacgtccatcaggacagcctacatggacctgagcaggctgagatctgacgacac agccgtatattactgtgcgagaggcagaagacacggtgcctatgttgactggggccagggaaccctgg tcaccgtctcctca | 7 |
| [EBOV-446] light | gacatccagttgacccagtctccatccttcctgtctgcatctgttggagacagagtcaccatcacttgcc gggccagtcagggcattagtacttatttagcctggtatcagcaaaaaccagggaaagcccctaacctc ctgatctatgatacatccactttgcaaagtggggtcccatcaagattcagcggcagtgcatctgggaca gaattcactctcacaatcagcagcctgcagcctgaagattttgcaacttattactgtcaacagcttaatt tttacctgggggcctcaccttcggccaagggacacgactggagattaaa | 8 |
| [EBOV-451] heavy | gaggtgcagctggtggagtctgggggaagtgtggtacggccggggggtccctgagactctcctgtgc agcctctggatttaagtttgatgaatatggcatgagttgggtccgccaggctccagggaaggggctgg agtgggtctctggaattacttggaatggtggtgtccgaacttatgcagactctgtgaagggccgattca ccatctccagggacaacgccaagaactccgtgtatctgcaaatgaaaagtctgagaggcgaagacac ggccttgtattactgtgttagttggggtgaacgctacgatgcgtacttcgactattggggccagggaacc ctggtcaccgtctcctca | 9 |
| [EBOV-451] light | gaaattgtgttgacgcagtctccaggcagtctgtctttgtctccaggggaaagagccaccctctcctgca gggccagtcagagtgttaacagccgctacttcgcctggtaccagcagagacctggccaggctcccaga ctcctcatctatgccacatccaccagggccactggcatcccagacaggttcagcggtagtgggtctggg acagacttcactctcaccatcagtaggctggagcctgaagattttgcagtgtattcctgtcagcagtatg gtagctcgccctacacttttggccaggggaccaagctggagatcaaa | 10 |
| [EBOV-502] heavy | gaggtgcagctggtggagtctgggggaggcttggtgcagccggggggtccctaagactctcctgtgc agcctctggattcagctttagcaactatgccatgacctgggtccgccaggctcccgggaaggggttgga gtgggtctccagtattggtattagtggtggtagcacatactacgcagactccgtgaagggccgcttcac catctccagagacaactccaagaacacactgtatctgcaaatgaacagcctgagagccgcggacacg gcccgatattactgtgcgaaagatgcccagcaggaaacagatatcgtttatttctactactacgacgga atggacgtctggggccaagggaccctggtcaccgtctcctca | 11 |

TABLE 1-continued

NUCLEOTIDE SEQUENCES FOR ANTIBODY VARIABLE REGIONS

| Clone | Variable Sequence Region | SEQ ID NO: |
|---|---|---|
| [EBOV-502] light | Not available | 12 |
| [EBOV-507] heavy | caggtgcagctggtgcagtctggggctgaggtgaagaagcctggggcctcagtgaaggtctcctgcaa ggcttctggatacaccttcaataattaccttataaattgggtgcgacaggcccctggacaagggcttga atggatgggatggatcaaccctcacagtggtggcacagagtatgcacagcagtttcagggcagactca ccgtgaccagggacacgtcaatcagaacagcctacatggaactgagaggtctgacatttgacgactcg gccatgtattattgctggatatggttcaggtctgagacttttgatttctggggccaagggaccctggtca ccgtctcctca | 13 |
| [EBOV-507] light | gacatccagatgacccagtctccatctgccatgtctgcatctgtaggagacagagtcaccatcacttgt cgggcgagtcaggacattagcaattatttagcctggtttcagcagaaaccagggcaaggccctaagcg cctgatctttgaggcatccattttgcacagtggggtcccttcaaggttcagcggcagtggatctgggaca gaattcactctcacaatcagcagcctgcagcctgaagattttgcaacttattactgtctacaacataata cttacctgacgttcggccaagggaccaaggtggaaatcaaa | 14 |
| [EBOV-508] heavy | caggtgcagctggtgcagtctggggctgaggtgaagaagcctggggcctcagtgaaggtttcctgcaa ggcatctggatacaccttcatcaactactatatgcactgggtgcgacaggcccctggacaagggcttga gtggatgggaacaatcaaccctagtactggtcgcccaaactacgcacagaagttccagggcagagtc accttgaccagggacacgtccacgaccacagtcgacatggagctgagcagcctgacatcagaggaca cggccgtgtattactgtgttagttttcagttttactttgactactggggccagggaaccctggtcaccgtc tcctca | 15 |
| [EBOV-508] light | gacatccagatgacccagtctccatctgccatgtctccatctgtaggagacagagtcaccatcacttgtc gggcgagtcagggcattaacaattatttagcctggtttcagcagaaaccagggaaagtccctaagcgc ctgatctatgctgcatccaatttgcaaagtggggtcccatcaaggttcagcggcagtggatctgggaca gaattcactctcacaatcagcagcctgcagcctgaagattttgcaacttattactgtctacagcataata gttatccctggacgttcggccaagggaccaaggtggaaatcaat | 16 |
| [EBOV-510] heavy | caggtgcagctgcaggagtcgggcccaggactggtgaagccttcacagaccctgtccctcacctgcac tgtctccggtggctccattaccagtggtgattactacttaacgtgggtccgccagcccccagggaaggg cctggagtggattgggcacatctattacagtgggagcacctcctacaacccgtccctcaagagtcgact tctcatgtcggtggacacgtccaagaaccagttctccctgaggttgagctctgtgacggccgcagacac ggccgtttactactgtgccagagagtctgacggtgacccttctcgactttacttctacttcgctatggacg tctggggccaagggaccctggtcaccgtctcctca | 17 |
| [EBOV-510] light | cagtctgccctgactcagcctgcctccgtgtctgggtctcctggacagtcgatcaccatctcctgcactg ggaccagcagtgacgttggtggttcttatttgtctcctggtaccaacaccacccaggcaaagcccccca aactcatgatttctgaggtcagtaatcggccctcaggggtttctaatcgcttctctggctccaagtctggc aacacggcctccctgaccatctctggactccggactgaggacgaggctgattattactgcagctcatat acgagcaacaccactctcgttttcggcggagagaccaaggtgaccgtccta | 18 |
| [EBOV-511] heavy | cagctgcagctgcaggagtcgggcccaggactggtgaagccttcggagaccctgtccctctcctgcact gtttctggtgactccatcagcgctaataattacttctggggctggatccgccagcccccagggaaggag ctggagtggattgggagcatccataacagtgggagcacctattacaatccgtccctcaagagtcgagt caccacatccgtagacacgtccaggacccagttctccctgaagctgcactctgtgaccgccgcagacg cggctatatattactgtgcgagacaccttgctccgatttctggagtgatttt-<br>catcccgtcgttctttgact<br>cctggggccagggaaccctggtcaccgtctcctca | 19 |
| [EBOV-511] light | gaaatagtgatgacgcagtctccagccaccctgtctgtgtctccaggggaaagagccaccctctcctgc agggccagtcagagtgtgagcagcaacttagcctggtaccagcagagacctggccaggctcccaggc tcctcatctttgatgcatccaccagggccactggtgtcccagccaggttcagtggcagtgggtctggga cagagttcacgctcaccatcagcagcctgcagtctgaagactttgcactttattactgtcagcagtataa tgactggcctccaaggctcactttcggcggagggaccaaggtcgagatcaaa | 20 |
| [EBOV-514] heavy | caggtgcagctgcaggagtcgggcccaggactggtgaagccttcacagactctgtccctcacctgcac tgtctctggtgcctccatcactggtggtgatgacttctggagctggatccgccagcccctgggaaggg cctggagtggattgggttcatccatcacagtgggaacgcctactacaggtcgtccctcaagagtcgagt gcacttttcagtagacacgtccaaggaccagttctccctgactctaacctctgtgactgccgcagacac ggccgtgtattactgtgccagagataaggcccaagcctatgggttattgtaccactatcacacggacgt ctggggcaaagggaccctggtcaccgtctcctca | 21 |
| [EBOV-514] light | gaaatagtgatgacgcagtctccagccaccctgtctgtgtctccaggggaaagagccaccctctcttgc agggccagtcagagtgttagcagcaacttagcctggtaccagcagaagcctggcctggctccccgact cctcatctatggtgcattcaccagggccactgatatcccagacaggttcagtggcagtgggtctgggac agagttcactctcaccatcagcagcctgcagtctgaagattttgcaatttattactgtcagtactataat gactggcctccggggtacacttttggccaggggaccaagctggagatcaaa | 22 |

TABLE 1-continued

| NUCLEOTIDE SEQUENCES FOR ANTIBODY VARIABLE REGIONS | | |
|---|---|---|
| Clone | Variable Sequence Region | SEQ ID NO: |
| [EBOV-515] heavy | caggtgcagctgcacgagtcgggcccaggactggtgaagccttcacagaccctgtccctcacctgcac tgtctctggtgggtccatcaacagtgctggttactactggacctggatccgccagcacccggggaaggg cctggagtggattgggtacatcgattatactgggaggacctactacaacccgtcccttgagagccgagt gatcatttcaatagacacgtctaagaaccacttctccctgagactgacctctgtgtctgccgcggacac ggccgtgtattactgtgcgcgagaatcgtcgtgggtatccgagttagggcgtgacaactggggccagg gaaccctggtcaccgtctcttca | 23 |
| [EBOV-515] light | gaaatagtgatgacgcagtctccagccaccctgcctgtgtctccaggggaaggagccaccctctcctgc agggccagtcagagtgttttcaccaacttagcctggtaccagcaaaaacctggccaggctcccaggct cctcatctatgatgcatccaccagggccactggtatcccagccaggttcagtggcagtgggtctgggac agagttcactctcaccatcagcagcctgcagtctgaagactttgcagtttattattgtcagcagtataat aactggcctcggacgtacggccaagggaccagggtggaagtcaaa | 24 |
| [EBOV-517] heavy | gaggtgcagctggtggagtctgggggaggcttggtccagcctggggggtccctgagactctcctgtgg agcctccggattcacctttaataagtattggatgacctgggtccgccaggctccagggaaggggctgg agtgggtggccaacataaatcaagatggaagtgagaaatactttgcggagtctgtgaagggccgattc accgtctccagagacaacgccaagaactcactgtatctgcaaatgaacagcctgagagccgaggaca cggctgtctattactgtgcgagaggggcgagtattgaagtagaaatcttgtattactaccacatggacg tctggggcaaagggaccctggtcaccgtctcctca | 25 |
| [EBOV-517] light | gaaatagtgatgacgcagtctccagccaccctgtctgtgtctccaggggaaagagccaccctctcctgc agggccagtcagagtattaccacccacttggcctggtaccagcagaagcctggccaggctcccaggct cctcatctatgatacatccaccagggccactggtatcccagccaggttcagtggctctgggtctgggac agagttcactctcaccatcagtaacatgcagtctgaagattttgcagtttattactgtcagcaatatcat acctggcctccgctcactttcggcggagggaccaaggtggagatcaaa | 26 |
| [EBOV-518] heavy | caggtcaccttgaaggagtctggtcctacactggtgaaacccacacagaccctcacgctgacctgcac cttctccggattctcaatgaatagtagtggaatgagtgtgacctggatccgtcagcccccaggaaaggc cctggagtgccttgccctcatttattgggatgatgataagtggtatggcccatctctggagaccagagtc accatcaccaaggacgcctcgaaaaaccaggtggtccttacaatgaccaacatggaccctgtggaca cagccacctattactgtgcacacagtgggggactcgtcgcgggggcctttgactactggggccagggt accctggtcaccgtctcctca | 27 |
| [EBOV-518] light | gaaatcgtgatgacccagtctccagactccctgaccgtgtctctgggcgagagggccaccatcaactg caggtccagccagagtgttttatacagggtcaacagtaagaactacttggcttggtaccagcagaagg caggacagactcctaaattgatcattaactgggcatctacccgggaatccggggtccctgaccgattca gtggcagcgggtctgggacagatttcactctcaccatcagcagcctgcaggctgaagatgtggcagttt attactgtcagcaatattataattctcctcggactttcggccaagggaccaaggtggaaatcaaa | 28 |
| [EBOV-520] heavy | caggtgcagctgcaggagtcgggcccaggactggggaagccttcggagaccctgtccctcagttgcac tgtctctggtgcctccatcaggggttacttctggaactggatccggcagcccccagggaagggactgga gtggattggctatatccattccactgggagcaccaactacaatccctccctcaagagtcgagtcaccat atcagtagacacgtccaagaaccaggtctccctgaatgtaaactctgtgaccgctgcggacacggccg tgtatttctgtgcgagaggggcctggaatgtggctactgtctactactactacggtatggacgtctgggg ccaagggaccctggtcaccgtctcctca | 29 |
| [EBOV-520] light | gaaattgtgttgacgcagtctccaggcaccctgtctttgtctccaggggaaagagccaccctctcgtgc agggccagtcagagtgttagcagcagctacttcgcctggtaccagcagaagcctggccaggctcccag gctcctcatctctggtacatccaccagggcccctggcatcccagacaggttcagtggcagtgggtctgg gacagacttcactctcaccatcagcagactggagcctgaagattttgcagtgtatttctgtcagcagtat ggtaactcactgtacacttttggccaggggaccaagctggagatcaaa | 30 |
| [EBOV-524] heavy | caggtgcagctggtggagtctggaggaggcgtggtccagccggggggtccctgagactctcctgtgc agcgtctggattcaagttcagtacctatggcatgaactgggtccgccaggttccaggccaggggctgg agtgggtctcatttgtaaggcatgatggaagtaataagtattatagtgattccgtgaagggccgcttca ccatcttcagagacaactccaacaataagttgtatctgcaaatgaacaacctgagagctgaggacacg gctgtctattactgtgcgaaagatgtcctcgattgcagtagagccgactgtttcatctactactactacat ggacgtctggggcaaagggaccctggtcaccgtctcctca | 31 |
| [EBOV-524] light | gacatccagatgacccagtctccctcttccgtgtctgcatctccaggagacagagtcaccatcacttgtc gggcgagtcagactattagcggctggttagcctggtatcagcagaaaccagggaaagcccctaagct cctgatctatgatgtatccactttgcaaagtggggtcccatctaggttcagcggcggtggatctgggac agagttcactttcaccatcagcagtctgcagcctgaagattatgcaacttacttttgtcagcagggtaac aggatccctctctctttcggcggagggaccagggttgagatcaaa | 32 |
| [EBOV-542] heavy | gaggtgcagctggtggagtctgggggaggcttggtccagcctggggggtccctgagactctcctgtgc agcctctggattcaccgtcagtaacaactacatgagctgggtccgccaggctccagggaaggggctgg agtgggtctcacttatttacaccagtgttaccacatactacgcagactccgtgaagggcagattcacca tctccagagacaattccaagaacacgttgtatcttcaaatgaacagtctgagagccgaggacacggct gtgtattactgtgcgagagaattgggcaactggagctacggagtaagctactggggccggggaacgtt ggtcaccgtctcctca | 33 |

TABLE 1-continued

NUCLEOTIDE SEQUENCES FOR ANTIBODY VARIABLE REGIONS

| Clone | Variable Sequence Region | SEQ ID NO: |
|---|---|---|
| [EBOV-542] light | tcctatgagctgacacagccaccctcggtgtcagtgtcccaggacagacggccaggatcacctgctct<br>ggagatgcactgccaaagcaatatgcttattggtaccagcagaagccaggccaggcccctgtgttggt<br>gatatataaggacagtgagaggccctcagggatccctgagcgattctctggctccagctcagggacaa<br>cagtcacgttgaccatcagtggagtccaggcagaagacggggctgactattactgtcaatcagcagac<br>ggcagtggtacttatcctgtggtattcggcggagggaccaagctgaccgtccta | 34 |
| [EBOV-543] heavy | caggtgcagctacagcagtggggcgcaggactgttgaagccctcggagacactgtcctcacctgcgc<br>tgtctctggtgggtccctcaccggttactactggggctggatccgccagcccccagggaaggggctgga<br>gtggattgggaaatcaatcacggtgtcagcaccatgtacaacccgtccctcaagagtcgagtcaccc<br>tttcagttgacacgtccaagaaccagttctccctgaagctgagctctgtgaccgccgcggacacggctg<br>tctattactgtgcgagaagcagattacgctctggttcttaggagcttttgatatctggggccaagggac<br>aatggtcaccgtctcctca | 35 |
| [EBOV-543] light | gaaatagtgatgacgcagtctccagccaccctgtctgtgtctccaggggaaagagccaccctctcctgt<br>agggccagtcagagtatttacaccaacttagcctggtaccagcagaaacctggccagcctcccaggct<br>cctcatcgatgatgcatccaccagggccactggcatccccagccaggttcagtggcagtgggtctggga<br>ctgagttcactctcaccatcagcagcctgcagtctgaagattttgcagtttatttctgtcagcagtataac<br>agctggcgtacgttcggccaagggaccaaggtggagatcaag | 36 |
| [EBOV-544] heavy | gaggtgcagctggtgcagtctggagcagaggtgaaaaagccggggagagtctctgaagatctcctgta<br>agggtgctggatacagctttcccaattactggatcggctgggtgcgccagatgcccgggaaaggcctg<br>gagtggatgggggatcatctatcctggtgagtctaaaaccagatacagcccgtccttccaaggccaagt<br>caccatctcagccgacaagtccatcagcaccgcctacctgcagtggagcagcctgaaggcctcggaca<br>ccggcatgtattattgtgccctt ccccgaataggaccaactagtaactggggcagcagctggtacgag<br>ggtattttgacatctggggccaagggacaatggtcaccgtctcttca | 37 |
| [EBOV-544] light | caggctgtggtgactcaggaatctgcactcaccacatcacctggtgaaacagtcacactcacttgtcgc<br>tcaagtactggggctgttacaactagtaactatgccaactgggtccaagaaaaaccagatcatttattc<br>actggtctaataggtggtaccaacaaccgagctccaggtgttcctgccagattctcaggctccctgattg<br>gagacaaggctgccctcaccatcacaggggcacagactgaggatgaggcaatatatttctgtgctcta<br>tggtacagcaaccatttatctttt ggcagtggaaccaaggtcactgtccta | 38 |
| [EBOV-546] heavy | caggtgcagctgcaggagtcgggcccaggactggtgaagccttcggagaccctgtcctcacctgcac<br>tgtctctggtggctccatcagtagtcactactggagctggatccggcagcccccagggaagggactgg<br>agtggattgggtatatctcttacagtgggagtaccaactacaatccctccctcaagagtcgagtcacca<br>tatcagtggacacgtctaagaaccagttctccctggggctgaggtctgtgaccgctgcggacacggcc<br>gtgtattactgtgcgagaatgactcgtgtcacaatctttggagtacttactgacgattattacaagtggtt<br>cgacccctggggccagggaaccctggtcaccgtctcctca | 39 |
| [EBOV-546] light | cagtctgccctgactcagcctccctccgtgtccgggtctcctggacagtcagtcaccatctcctgcactg<br>gaaccagcactgacgttggtggttctaaccgtgtctcctggtaccagcagcccccaggcacagccccc<br>aaactcatgatttatgaggtcactaatcggccctcaggggtccctgatcgcttctctggctccaagtctg<br>gcaacacggcctccctgaccatctctgggctccggggctgaggacgaggctgattattactgcagcttat<br>atacaagcagcactttgtcttcggaactgggaccaaggtcaccgtccta | 40 |
| [EBOV-548] heavy | caggttcaggtggaggagtctggggggaggcgtggccagcctggggggtccctgagactctcctgcgc<br>agcgtctggattcatgttcagtaactatggcatgcactgggtccgtcaggctccagggaaggggactgga<br>gtggatggcatttatccggtatgatgacagtaagaaatctatgcagactccgtgaagggccgattcac<br>catctccagagacaattccaagaacaccctgtatctgcaaatgaacagcctgagagctgaggacacg<br>gctctatattactgtgcgaaagaacttctacaagtgtataccagtgcctggggggagggacactcctac<br>tactacgctttggacgtctggggcctagggaccgcggtcaccgtctcctca | 41 |
| [EBOV-548] light | gacatccagatgacccagtctccatcttccgtgtctgcatctgtaggagacagagtcaccatcacttgtc<br>gggcgagtcaggatataagcaactggttagcctggtatcagcagaaaccagggaaagcccctgaact<br>cctgatctatactgcatccattttgcaaagtggggtctcatcaaggttcagcggcagtggttctgggaca<br>gatttcactctcaccatcagcagcctgcagcctgaagattctgcaacttactattgtcaacagggtaag<br>agtttcccgtacacttttggccaggggaccaagctggagatcaaa | 42 |

TABLE 2

PROTEIN SEQUENCES FOR ANTIBODY VARIABLE REGIONS

| Clone | Variable Sequence | SEQ ID NO. |
|---|---|---|
| [EBOV-434] heavy | QVQLVQSGAEVKKPGASVKVSCKASGYTFTGYYMFWVRQAPGQGLEWMGWI<br>NPNSGGTNYTQKFQGRVTMTRDTSISTAYMELSRLKSDDTAVYYCARDSGELLFV<br>GSDVWGQGTLVTVSS | 43 |

TABLE 2-continued

PROTEIN SEQUENCES FOR ANTIBODY VARIABLE REGIONS

| Clone | Variable Sequence | SEQ ID NO. |
|---|---|---|
| [EBOV-434] light | DIQMTQSPSSVSASVGDRVTITCRASLDISYWLAWYQQKPGKAPKLLIYAASNLQ SGVPSRFSGSGSGTDFTLTISSLQPEDFATYYCQQANSFPQTFGQGTRLELK | 44 |
| [EBOV-437] heavy | QIVLTQSPGTLSLSPGERATLSCRASQSVSNSYLAWYQQKPGQAPRLLIYGASSRA TGIPDRFSGSGSGTDFTLSISRLEPEDFAVYYCQQYGTSPCTFGQGTKLEIK QIVLTQSPGTLSLSPGERATLSCRASQSVSNSYLAWYQQKPGQAPRLLIYGASSRA TGIPDRFSGSGSGTDFTLSISRLEPEDFAVYYCQQYGTSPCTFGQGTKLEIK | 45 |
| [EBOV-437] light | QIVLTQSPGTLSLSPGERATLSCRASQSVSNSYLAWYQQKPGQAPRLLIYGASSRA TGIPDRFSGSGSGTDFTLSISRLEPEDFAVYYCQQYGTSPCTFGQGTKLEIK | 46 |
| [EBOV-442] heavy | EVQLVESGGGLVKPGGSLRLSCTGSGGTGFTFKYAGMSWVRQAPGKGPEWIGR IKSRIDGGTTDYAAPVKDRFIVSRDDSRNTLYLQMNSLKTEDTAVYYCATGSGKGP SASFGESYYYYDFINVWGKGTTVTVSS | 47 |
| [EBOV-442] light | ESVLTQSPGTLSLSPGERATLSCRASQSISRKYLAWYQQKPGQAPRLLIYGSSSRAT GIPDRFSGSGSGTDFTLTISRLEPEDFAVYYCHQYESSPWTFGQGTKVEIK | 48 |
| [EBOV-446] heavy | QVQLVQSGAEVKKPGASVKVSCKASGYTFTDYYIYWVRQAPGQGLEWMGWLN PNSGGTDYAQKFQGRVTMTRDTSIRTAYMDLSRLRSDDTAVYYCARGRRHGAY VDWGQGTLVTVSS | 49 |
| [EBOV-446] light | DIQLTQSPSFLSASVGDRVTITCRASQGISTYLAWYQQKPGKAPNLLIYDTSTLQSG VPSRFSGSASGTEFTLTISSLQPEDFATYYCQQLNFYLGGLTFGQGTRLEIK | 50 |
| [EBOV-451] heavy | EVQLVESGGSVVRPGGSLRLSCAASGFKFDEYGMSWVRQAPGKGLEWVSGITW NGGVRTYADSVKGRFTISRDNAKNSVYLQMKSLRGEDTALYYCVSWGERYDAYF DYWGQGTLVTVSS | 51 |
| [EBOV-451] light | EIVLTQSPGSLSLSPGERATLSCRASQSVNSRYFAWYQQRPGQAPRLLIYATSTRA TGIPDRFSGSGSGTDFTLTISRLEPEDFAVYSCQQYGSSPYTFGQGTKLEIK | 52 |
| [EBOV-502] heavy | EVQLVESGGGLVQPGGSLRLSCAASGFSFSNYAMTWVRQAPGKGLEWVSSIGIS GGSTYYADSVKGRFTISRDNSKNTLYLQMNSLRAADTARYYCAKDAQQETDIVYF YYYDGMDVWGQGTLVTVSS | 53 |
| [EBOV-502] light | Not available | 54 |
| [EBOV-507] heavy | QVQLVQSGAEVKKPGASVKVSCKASGYTFNNYLINWVRQAPGQGLEWMGWI NPHSGGTEYAQQFQGRLTVTRDTSIRTAYMELRGLTFDDSAMYYCWIWFRSETF DFWGQGTLVTVSS | 55 |
| [EBOV-507] light | DIQMTQSPSAMSASVGDRVTITCRASQDISNYLAWFQQKPGQGPKRLIFEASILH SGVPSRFSGSGSGTEFTLTISSLQPEDFATYYCLQHNTYLTFGQGTKVEIK | 56 |
| [EBOV-508] heavy | QVQLVQSGAEVKKPGASVKVSCKASGYTFINYYMHWVRQAPGQGLEWMGTIN PSTGRPNYAQKFQGRVILTRDTSTTTVDMELSSLTSEDTAVYYCVSFQFYFDYWG QGTLVTVSS | 57 |
| [EBOV-508] light | DIQMTQSPSAMSPSVGDRVTITCRASQGINNYLAWFQQKPGKVPKRLIYAASNL QSGVPSRFSGSGSGTEFTLTISSLQPEDFATYYCLQHNSYPWTFGQGTKVEIN | 58 |
| [EBOV-510] heavy | QVQLQESGPGLVKPSQTLSLTCTVSGGSITSGDYYLTWVRQPPGKGLEWIGHIYY SGSTSYNPSLKSRLLMSVDTSKNQFSLRLSSVTAADTAVYYCARESDGDPSRLYFYF AMDVWGQGTLVTVSS | 59 |
| [EBOV-510] light | QSALTQPASVSGSPGQSITISCTGTSSDVGGSYFVSWYQHHPGKAPKLMISEVSN RPSGVSNRFSGSKSGNTASLTISGLRTEDEADYYCSSYTSNTTLVFGGETKVTVL] | 60 |
| [EBOV-511] heavy | QLQLQESGPGLVKPSETLSLSCTVSGDSISANNYFWGWIRQPPGKELEWIGSIHN SGSTYYNPSLKSRVTTSVDTSRTQFSLKLHSVTAADAAIYYCARHLAPISGVIFIPS FFDSWGQGTLVTVSS | 61 |

TABLE 2-continued

PROTEIN SEQUENCES FOR ANTIBODY VARIABLE REGIONS

| Clone | Variable Sequence | SEQ ID NO. |
|---|---|---|
| [EBOV-511] light | EIVMTQSPATLSVSPGERATLSCRASQSVSSNLAWYQQRPGQAPRLLIFDASTRA TGVPARFSGSGSGTEFTLTISSLQSEDFALYYCQQYNDWPPRLTFGGGTKVEIK | 62 |
| [EBOV-514] heavy | QVQLQESGPGLVKPSQTLSLTCTVSGASITGGDDFWSWIRQPPGKGLEWIGFIH HSGNAYYRSSLKSRVHFSVDTSKDQFSLTLTSVTAADTAVYYCARDKAQAYGLLY HYHTDVWGKGTLVTVSS | 63 |
| [EBOV-514] light | EIVMTQSPATLSVSPGERATLSCRASQSVSSNLAWYQQKPGLAPRLLIYGAFTRAT DIPDRFSGSGSGTEFTLTISSLQSEDFAIYYCQYYNDWPPGYTFGQGTKLEIK | 64 |
| [EBOV-515] heavy | QVQLHESGP.GLVKPSQTLSLTCTVSGGSIN..SAGYYWTWIRQHPGKGLEWIGYI DYTGRTYYNPSLE.SRVIISIDTSKNHFSLRLTSVSAADTAVYYCARESSWVSELGRD NWGQGTLVTVSS | 65 |
| [EBOV-515] light | EIVMTQSPATLPVSPGEGATLSCRASQSVFTNLAWYQQKPGQAPRLLIYDASTRA TGIPARFSGSGSGTEFTLTISSLQSEDFAVYYCQQYNNWPRTYGQGTRVEVK | 66 |
| [EBOV-517] heavy | EVQLVESGGGLVQPGGSLRLSCGASGFTFNKYWMTWVRQAPGKGLEWVANIN QDGSEKYFAESVKGRFTVSRDNAKNSLYLQMNSLRAEDTAVYYCARGASIEVEILY YYHMDVWGKGTLVTVSS | 67 |
| [EBOV-517] light | EIVMTQSPATLSVSPGERATLSCRASQSITTHLAWYQQKPGQAPRLLIYDTSTRAT GIPARFSGSGSGTEFTLTISNMQSEDFAVYYCQQYHTWPPLTFGGGTKVEIK | 68 |
| [EBOV-518] heavy | QVTLKESGPTLVKPTQTLTLTCTFSGFSMNSSGMSVTWIRQPPGKALECLALIYW DDDKWYGPSLETRVTITKDASKNQVVLTMTNMDPVDTATYYCAHSGGLVAGAF DYWGQGTLVTVSS | 69 |
| [EBOV-518] light | EIVMTQSPDSLTVSLGERATINCRSSQSVLYRVNSKNYLAWYQQKAGQTPKLIIN WASTRESGVPDRFSGSGSGTDFTLTISSLQAEDVAVYYCQQYYNSPRTFGQGTKV EIK | 70 |
| [EBOV-520] heavy | QVQLQESGPGLGKPSETLSLSCTVSGASIRGYFWNWIRQPPGKGLEWIGYIHSTG STNYNPSLKSRVTISVDTSKNQVSLNVNSVTAADTAVYFCARGAWNVATVYYYY GMDVWGQGTLVTVSS | 71 |
| [EBOV-520] light | EIVLTQSPGTLSLSPGERATLSCRASQSVSSSYFAWYQQKPGQAPRLLISGTSTRAP GIPDRFSGSGSGTDFTLTISRLEPEDFAVYFCQQYGNSLYTFGQGTKLEIK | 72 |
| [EBOV-524] heavy | QVQLVESGGGVVQPGGSLRLSCAASGFKFSTYGMNWVRQVPGQGLEWVSFVR HDGSNKYYSDSVKGRFTIFRDNSNNKLYLQMNNLRAEDTAVYYCAKDVLDCSRA DCFIYYYYMDVWGKGTLVTVSS | 73 |
| [EBOV-524] light | DIQMTQSPSSVSASPGDRVTITCRASQTISGWLAWYQQKPGKAPKLLIYDVSTLQ SGVPSRFSGGGSGTEFTFTISSLQPEDYATYFCQQGNRIPLSFGGGTRVEIK | 74 |
| [EBOV-542] heavy | EVQLVESGGGLVQPGGSLRLSCAASGFTVSNNYMSWVRQAPGKGLEWVSLIYTS VTTYYADSVKGRFTISRDNSKNTLYLQMNSLRAEDTAVYYCARELGNWSYGVSY WGRGTLVTVSS | 75 |
| [EBOV-542] light | SYELTQPPSVSVSPGQTARITCSGDALPKQYAYWYQQKPGQAPVLVIYKDSERPS GIPERFSGSSSGTTVTLTISGVQAEDGADYYCQSADGSGTYPVVFGGGTKLTVL | 76 |
| [EBOV-543] heavy | QVQLQQWGAGLLKPSETLSLTCAVSGGSLTGYYWGWIRQPPGKGLEWIGEINH GVSTMYNPSLKSRVTLSVDTSKNQFSLKLSSVTAADTAVYYCARSRLQLWFLGAF DIWGQGTMVTVSS | 77 |
| [EBOV-543] light | EIVMTQSPATLSVSPGERATLSCRASQSIYTNLAWYQQKPGQPPRLLIHDASTRAT GIPARFSGSGSGTEFTLTISSLQSEDFAVYFCQQYNSWRTFGQGTKVEIK | 78 |
| [EBOV-544] heavy | EVQLVQSGAEVKKPGESLKISCKGAGYSFPNYWIGWVRQMPGKGLEWMGIIYP GESKTRYSPSFQGQVTISADKSISTAYLQWSSLKASDTGMYYCALPRIGPTSNWG SSWYEGIFDIWGQGTMVTVSS | 79 |

TABLE 2-continued

PROTEIN SEQUENCES FOR ANTIBODY VARIABLE REGIONS

| Clone | Variable Sequence | SEQ ID NO. |
|---|---|---|
| [EBOV-544] light | QAVVTQESALTTSPGETVTLTCRSSTGAVTTSNYANWVQEKPDHLFTGLIGGTN NRAPGVPARFSGSLIGDKAALTITGAQTEDEAIYFCALWYSNHLSFGSGTKVTVL | 80 |
| [EBOV-546] heavy | QVQLQESGPGLVKPSETLSLTCTVSGGSISSHYWSWIRQPPGKGLEWIGYISYSGS TNYNPSLKSRVTISVDTSKNQFSLGLRSVTAADTAVYYCARMTRVTIFGVLTDDYY KWFDPWGQGTLVTVSS | 81 |
| [EBOV-546] light | QSALTQPPSVSGSPGQSVTISCTGTSTDVGGSNRVSWYQQPPGTAPKLMIYEVT NRPSGVPDRFSGSKSGNTASLTISGLRAEDEADYYCSLYTSSSTFVFGTGTKVTVL | 82 |
| [EBOV-548] heavy | QVQVEESGGGVVQPGGSLRLSCAASGFMFSNYGMHWVRQAPGKGLEWMAFI RYDDSKKFYADSVKGRFTISRDNSKNTLYLQMNSLRAEDTALYYCAKELLQVYTSA WGEGHSYYYALDVWGLGTAVTVSS | 83 |
| [EBOV-548] light | DIQMTQSPSSVSASVGDRVTITCRASQDISNWLAWYQQKPGKAPELLIYTASILQ SGVSSRFSGSGSGTDFTLTISSLQPEDSATYYCQQGKSFPYTFGQGTKLEIK | 84 |

TABLE 3

CDR HEAVY CHAIN SEQUENCES

| Antibody Clone | CDRH1 (SEQ ID NO:) | CDRH2 (SEQ ID NO:) | CDRH3 (SEQ ID NO:) |
|---|---|---|---|
| EBOV-434 | GYTFTGYY (85) | INPNSGGT (86) | ARDSGELLFVGSDV (87) |
| EBOV-437 | GGTFSRDI (88) | IIPIFGTA (89) | ARGPPLRGERSWFGESEKYDYFYMDV (90) |
| EBOV-442 | GFTFKYAG (91) | IKSRIDGGTT (92) | ATGSGKGPSASFGESYYYYDFINV (93) |
| EBOV-446 | GYTFTDYY (94) | LNPNSGGT (95) | ARGRRHGAYVD (96) |
| EBOV-451 | GFKFDEYG (97) | ITWNGGVR (98) | VSWGERYDAYFDY (99) |
| EBOV-502 | GFSFSNYA (100) | IGISGGST (101) | AKDAQQETDIVYFYYYDGMDV (102) |
| EBOV-507 | GYTFNNYL (103) | INPHSGGT (104) | WIWFRSETFDF (105) |
| EBOV-508 | GYTFINYY (106) | INP STGRP (107) | VSFQFYFDY (108) |
| EBOV-510 | GGSIT SGDYY (109) | IYYSGST (110) | ARESDGDPSRLYFYFAMDV (111) |
| EBOV-511 | GDSISANNYF (112) | IHNSGST (113) | ARHLAPISGVIFIPSFFDS (114) |
| EBOV-514 | GASITGGDDF (115) | IHHSGNA (116) | ARDKAQAYGLLYHYHTDV (117) |
| EBOV-515 | GGSINSAGYY (118) | IDYTGRT (119) | ARESSWVSELGRDN (120) |
| EBOV-517 | GFTFNKYW (121) | INQDGSEK (122) | ARGASIEVEILYYYHMDV (123) |
| EBOV-518 | GFSMNSSGMS (124) | IYWDDDK (125) | AHSGGLVAGAFDY (126) |

TABLE 3-continued

CDR HEAVY CHAIN SEQUENCES

| Antibody Clone | CDRH1 (SEQ ID NO:) | CDRH2 (SEQ ID NO:) | CDRH3 (SEQ ID NO:) |
|---|---|---|---|
| EBOV-520 | GASIRGYF (127) | IHSTGST (128) | ARGAWNVATVYYYYGMDV (129) |
| EBOV-524 | GFKFSTYG (130) | VRHDGSNK (131) | AKDVLDCSRADCFIYYYYMDV (132) |
| EBOV-542 | GFTVSNNY (133) | IYTSVTT (134) | ARELGNWSYGVSY (135) |
| EBOV-543 | GGSLTGYY (136) | INHGVST (137) | ARSRLQLWFLGAFDI (138) |
| EBOV-544 | GYSFPNYW (139) | IYPGESKT (140) | ALPRIGPTSNWGSSWYEGIFDI (141) |
| EBOV-546 | GGSISSHY (142) | ISYSGST (143) | ARMTRVTIFGVLTDDYYKWFDP (144) |
| EBOV-548 | GFMFSNYG (145) | IRYDDSKK (146) | AKELLQVYTSAWGEGHSYYYALDV (147) |

TABLE 4

CDR LIGHT CHAIN SEQUENCES

| Antibody Clone | CDRL1 (SEQ ID NO:) | CDRL2 (SEQ ID NO:) | CDRL3 (SEQ ID NO:) |
|---|---|---|---|
| EBOV-434 | LDISYW (148) | AAS (149) | QQANSFPQT (150) |
| EBOV-437 | QSVSNSY (151) | GAS (152) | QQYGTSPCT (153) |
| EBOV-442 | QSISRKY (154) | GSS (155) | HQYESSPWT (156) |
| EBOV-446 | QGISTY (157) | DTS (158) | QQLNFYLGGLT (159) |
| EBOV-451 | QSVNSRY (160) | ATS (161) | QQYGSSPYT (162) |
| EBOV-502 | Not available (163) | Not available (164) | Not available (165) |
| EBOV-507 | QDISNY (166) | EAS (167) | LQHNTYLT (168) |
| EBOV-508 | QGINNY (169) | AAS (170) | LQHNSYPWT (171) |
| EBOV-510 | SSDVGGSYF (172) | EVS (173) | SSYTSNTTLV (174) |
| EBOV-511 | QSVSSN (175) | DAS (176) | QQYNDWPPRLT (177) |
| EBOV-514 | QSVSSN (178) | GAF (179) | QYYNDWPPGYT (180) |
| EBOV-515 | QSVFTN (181) | DAS (182) | QQYNNWPRT (183) |
| EBOV-517 | QSITTH (184) | DTS (185) | QQYHTWPPLT (186) |
| EBOV-518 | QSVLYRVNSKNY (187) | WAS (188) | QQYNSPRT (189) |
| EBOV-520 | QSVSSSY (190) | GTS (191) | QQYGNSLYT (192) |
| EBOV-524 | QTISGW (193) | DVS (194) | QQGNRIPLS (195) |
| EBOV-542 | ALPKQY (196) | KDS (197) | QSADGSGTYPVV (198) |
| EBOV-543 | QSIYTN (199) | DAS (200) | QQYNSWRT (201) |
| EBOV-544 | TGAVTTSNY (202) | GTN (203) | ALWYSNHLS (204) |
| EBOV-546 | STDVGGSNR (205) | EVT (206) | SLYTSSSTFV (207) |
| EBOV-548 | QDISNW (208) | TAS (209) | QQGKSFPYT (210) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the dis

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N Y, 1988.
Abbondanzo et al., *Am. J. Pediatr. Hematol. Oncol.,* 12(4), 480-489, 1990.
Allred et al., *Arch. Surg.,* 125(1), 107-113, 1990.
Atherton et al., *Biol. of Reproduction,* 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.,* 12; 130(1), :111-121, 1990.
Campbell, In: *Monoclonal Antibody Technology, Laboratory Techniques in Biochemistry and Molecular Biology,* Vol. 13, Burden and Von Knippenberg, Eds. pp. 75-83, Amsterdam, Elsevier, 1984.
Capaldi et al., *Biochem. Biophys. Res. Comm.,* 74(2):425-433, 1977.
De Jager et al., *Semin. Nucl. Med.* 23(2), 165-179, 1993.
Dholakia et al., *J. Biol. Chem.,* 264, 20638-20642, 1989.
Diamond et al., *J Virol* 77, 2578-2586, 2003.
Doolittle and Ben-Zeev, *Methods Mol. Biol.,* 109, :215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.,* 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology,* 26, 210-219, 1989.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Kyte and Doolittle, *J. Mol. Biol.,* 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems,* Chapter 27, 1987.
O'Shannessy et al., *J. Immun. Meth.,* 99, 153-161, 1987.
Persic et al., *Gene* 187:1, 1997
Potter and Haley, *Meth. Enzymol.,* 91, 613-633, 1983.
Purpura et al., *Lancet Infect Dis.* 2016 October; 16(10): 1107-8. Epub 2016 Sep. 19. Remington's Pharmaceutical Sciences, 15th Ed., 3:624-652, 1990.
Tang et al., *J. Biol. Chem.,* 271:28324-28330, 1996.
Wawrzynczak & Thorpe, In: *Immunoconjugates, Antibody Conuugates In Radioimaging And Therapy Of Cancer,* Vogel (Ed.), NY, Oxford University Press, 28, 1987.
Yu et al., *J Immunol Methods* 336, 142-151, doi:10.1016/j.jim.2008.04.008, 2008.
Ackerman et al., (2016). *PLoS Pathog.* 12, e1005315.
Bender et al., (2016). *Biochemistry* 55, 4748-4763.
Beniac and Booth, (2017). *Sci. Rep.* 7, 1-8.
Bornholdt et al., (2016a). *mBio* 7, e02154-02115.
Bornholdt et al. (2016b). *Science* 351, 1078-1083.
Bray et al., (1998). *J. Infect. Dis.* 178, 651-661.
Brecher et al., (2012). *J. Virol.* 86, 364-372.
Brochet et al., (2008). *Nucleic Acids Res.* 36, W503-508.
Carette et al., (2011). *Nature* 477, 340-343.
CDC (2017). About Ebola virus disease, world-wide-web at cdc.gov/vhf/ebola/about.html (accessed 14 Jan. 2018).
Chandran et al., (2005). *Science* 308, 1643-1645.
Coltart et al., (2017). *Philos. Trans. R. Soc. Lond. B. Biol. Sci.* 372, 1-24.
Corti et al., (2016). *Science* 351, 1339-1342.
Cote et al., (2011). *Nature* 477, 344-U122.
Davidson et al., (2015). *J. Virol.* 89, 10982-10992.
Davidson and Doranz, (2014). *Immunology* 143, 13-20.
Domi et al. (2018). *Sci. Rep.* 8, 864.
Finn et al., (2016). *PloS one* 11, e0154811.
Flyak et al. (2015). *Cell* 160, 893-903.
Flyak al. (2016). *Cell* 164, 392-405.
Furuyama et al. (2016). *Sci. Rep.* 6, 20514.
Garbutt et al., (2004). *J. Virol.* 78, 5458-5465.
Giudicelli and Lefranc, (2011). *Cold Spring Harb. Protoc.* 2011, 716-725.
Gong et al. (2016). *Cell* 165, 1467-1478.
Group et al. (2016). *N. Eng. J. Med.* 375, 1448-1456.
Hashiguchi et al., (2015). *Cell* 160, 904-912.
Hessell et al. (2007). *Nature* 449, 101-U175.
Holmes et al., (2016). *Nature* 538, 193-200.
Howell et al. (2017). *Cell Rep* 19, 413-424.
Howell et al. (2016). *Cell Rep* 15, 1514-1526.
Huang et al. (2013). *Nat. Protoc.* 8, 1907-1915.
Ilinykh et al., (2016). *J. Virol.* 90, 3890-3901.
Jefferis, R. (2012). *Arch Biochem Biophys.* 526, 159-166.
Keck et al. (2016). *J. Virol.* 90, 279-291.
King et al. (2018). *Cell Host Microbe* 23, 101-109 e104.
Kozak et al. (2016). *J. Virol.* 90, 9209-9223.
Labrijn et al. (2009). *Nat. Biotechnol.* 27, 767-771.
Lander et al. (2009). *J Struct Biol* 166, 95-102.
Lee et al., (2008). *Nature* 454, 177-182.
Lee and Saphire, (2009). *Future Virology* 4, 621-635.
McLean et al., (2000). *Molecular immunology* 37, 837-845.
Miller et al. (2012). *EMBO J* 31, 1947-1960.
Mire and Geisbert, (2017). *Trends Mol Med* 23, 669-671.
Misasi et al. (2016). *Science* 351, 1343-1346.
Murin et al., (2014). *Proc. Natl. Acad. Sci. U.S. A.* 111, 17182-17187.
Ogura et al., (2003). *J. Struct. Biol.* 143, 185-200.
Orlandi et al., (2016). *J. Immunol. Methods* 433, 51-58.
Oswald et al., (2007). *PLoS Pathog.* 3, e9.
Overdijk et al., (2012). *Journal Immunol.* 189, 3430-3438.

Pallesen et al. (2016). *Nat. Microbiol.* 1, 16128.
Park et al. (2015). *Cell* 161, 1516-1526.
Plotkin, S. A. (2010). *Clin. Vaccine Immunol.* 17, 1055-1065.
Potter et al. (1999). *Ultramicroscopy* 77, 153-161.
Qiu et al. (2014). *Nature* 514, 47-53.
Raymond et al., (2011). *J. Infect. Dis.* 204 Suppl 3, S986-990.
Sanchez and Rollin, (2005). *Virus research* 113, 16-25.
Saphire and Aman, (2016). *Trends Microbiol.* 24, 684-686.
Scheres, S. H. (2012). *J. Struct. Biol.* 180, 519-530.
Schornberg et al., (2006). *J. Virol.* 80, 4174-4178.
Shedlock et al., (2010). *Virology* 401, 228-235.
Sivasubramanian et al., (2009). *Proteins* 74, 497-514.
Spence et al., (2016). *mBio* 7, e01857-01815.
Thornburg et al. (2013). *Journal Clinical Investigation* 123, 4405-4409.
Thornburg et al. (2016). *J. Clin. Invest.* 126, 1482-1494.
Tong et al. (2015). *Nature* 524, 93-96.
Towner et al., (2005). *Virology* 332, 20-27.
Towner et al. (2008). *PLoS Pathog.* 4, e1000212.
van der Neut Kolfschoten et al. (2007). *Science* 317, 1554-1557.
Vanderven et al. (2017). *J. Clin. Invest. Insight* 2, 1-15.
Voss et al., (2009). *J. Struct. Biol.* 166, 205-213.
Wang et al., (2016). *Cell* 164, 258-268.
Wee et al. (2017). *Cell* 169, 878-890 e815.
Wee et al., (2016). *Science* 354, 350-354.
WHO (2017). 2016 Ebola virus disease fact sheet. worldwide-web at who.int/mediacentre/factsheets/fs103/en/ (accessed 14 Jan. 2018).
Wibmer et al., (2015). *Curr. Opin. HIV AIDS* 10, 135-143.
Wong et al. (2015). *J. Virol.* 90, 392-399.
Yamayoshi and Kawaoka, (2017). *Cell* 169, 773-775.
Yu et al., (2008). *J. Immunol. Methods* 336, 142-151.
Zeitlin et al., (2016). *Curr. Opin. Virol.* 17, 45-49.
Zhao et al. (2017). *Cell* 169, 891-904 e815.
Zhao et al., (2016). *Nature* 535, 169-172.
Adams et al., Acta. Crystallogr. D. Biol. Crystallogr. 66, 213-221, 2010.
Agirre, et al., Nat. Struct. Mol. Biol. 22, 833-834, 2015.
Barad et al., Nat. Methods 12, 943-946, 2015.
Battye et al., Acta. Crystallogr. D. Biol. Crystallogr. 67, 271-281, 2011.
Bennett et al., Curr. Top. Microbiol. 411, 171-193, 2017.
Biasini et al., Nucleic Acids Res. 42, W252-W258, 2014.
Bornholdt et al., Cell Host Microbe 25, 49-58, 2019.
Bornholdt et al., Science 351, 1078-1083, 2016.
Bray et al., Journal Infect. Dis. 178, 651-661, 1998.
Bunkoczi, G., and Read, R. J. Acta. Crystallogr. D. Biol. Crystallogr. 67, 303-312, 2011
Carlsen et al., Hepatology 60, 1551-1562, 2014.
CDC. Ebola in Democratic Republic of the Congo. Worldwide-web at nc.cdc.gov/travel/notices/alert/ebola-democratic-republic-of-the-congo, 2019.
Chou, T. C., Cancer Res. 70, 440-446, 2010.
Coltart et al., Philos. Trans. R. Soc. Lond. B. Biol. Sci 372, 1-24, 2017.
Corti et al., Science 351, 1339-1342, 2016a.
Corti et al., J. Infect. Public Health 9, 231-235, 2016b.
Crowe, J. E., Jr., Cell Host Microbe 22, 193-206, 2017.
Davidson et al., J. Virol. 89, 10982-10992, 2015.
Davidson, E., and Doranz, B. J., Immunology 143, 13-20, 2014.
Davis et al., Cell 177, 1566-1582 e1517, 2019.
DiMaio et al., Nat. Methods 12, 361-365, 2015.
Domi et al., Sci. Rep. 8, 864, 2018.
Doria-Rose et al., J. Virol. 86, 3393-3397, 2012.
Emsley et al., Acta. Crystallogr. D. Biol. Crystallogr. 66, 486-501, 2010.
Evans, P. R., and Murshudov, G. N., Acta. Crystallogr. D. Biol. Crystallogr. 69, 1204-1214, 2013.
Fibriansah et al., Science 349, 88-91, 2015.
Flyak et al., Cell 160, 893-903, 2015.
Geisbert et al., Sci. Transl. Med. 6, 242ra282, 2014
Geisbert et al., Journal Infect. Dis. 212, S91-S97, 2015.
Gilchuk et al., Cell 167, 684-694 e689, 2016.
Gilchuk et al., Immunity 49, 363-374 e310, 2018.
Giudicelli, V., and Lefranc, M. P., Cold Spring Harb. Protoc. 2011, 716-725, 2011.
Gong et al., Cell 165, 1467-1478, 2016.
Gunn et al., Cell Host Microbe 24, 221-233 e225, 2018.
Howell et al., Cell. Rep. 19, 413-424, 2017.
Ilinykh et al., J. Virol. 90, 3890-3901, 2016.
Janus et al., Nat. Commun. 9, 3934, 2018.
Keeffe et al., Cell. Rep. 25, 1385-1394 e1387, 2018.
King et al., Curr. Opin. Virol. 34, 140-148, 2019.
Kuhn J. H., Guide to the Correct Use of Filoviral Nomenclature. In: Muhlberger E., Hensley L., Towner J. (eds) Marburg- and Ebolaviruses. Curr. Top. Microbiol. (Springer, Cham) 411, 447-460, 2017.
Kuzmina et al., Cell. Rep. 24, 1802-1815 e1805, 2018.
Lander et al., J. Struct. Biol. 166, 95-102, 2009.
Laursen, N. S., and Wilson, I. A., Antiviral. Res. 98, 476-483, 2013.
Lee, J. E., and Saphire, E. O., Future Virol. 4, 621-635, 2009.
Lu et al., Nat. Rev. Immunol. 18, 46-61, 2018.
Lutteke, T., and von der Lieth, C. W., BMC Bioinformatics 5, 69, 2004.
Mascola et al., J. Virol. 71, 7198-7206, 1997.
McLean et al., Mol. Immunol. 37, 837-845, 2000.
Mohan et al., PLoS Pathog. 8, e1003065, 2012.
Murin et al., Cell. Rep. 24, 2723-2732 e2724, 2018.
NIH. Investigational Therapeutics for the Treatment of People With Ebola Virus Disease. clinicaltrials.gov/ct2/show/NCT03719586?cond=ebola&rank=7, 2019
Orlandi, et al., J. Immunol. Methods 433, 51-58, 2016.
Park et al., Cell 161, 1516-1526, 2015.
Pascal et al., J. Infect. Dis. 218, S612-S626, 2018.
Pettersen et al., J. Comput. Chem. 25, 1605-1612, 2004.
Potter et al., Ultramicroscopy 77, 153-161, 1999.
Punjani et al., Nat. Methods 14, 290-296, 2017.
Raymond et al., J. Infect. Dis. 204 Suppl. 3, S986-990, 2011.
Robinson et al., Nat. Commun. 7, 11544, 2016.
Sanchez, A., and Rollin, P. E., Virus Res. 113, 16-25, 2005.
Saphire, E. O., and Aman, M. J., Trends Microbiol. 24, 684-686, 2016.
Sapparapu et al., Nature 540, 443-447, 2016.
Scheres, S. H., J. Struct. Biol. 180, 519-530, 2012.
Sok, D., and Burton, D. R., Nat. Immunol. 19, 1179-1188, 2018.
Stettler et al., Science 353, 823-826, 2016.
Towner et al., Virology 332, 20-27, 2005.
Turchaninova et al., Nat. Protoc. 11, 1599-1616, 2016.
Voss et al., J. Struct. Biol. 166, 205-213, 2009.
Walker, L. M., and Burton, D. R., Nat. Rev. Immunol. 18, 297-308, 2018.
Wang et al., Cell 164, 258-268, 2016a.
Wang et al., Sci. Transl. Med. 8, 369ra179, 2016b.
Wec et al., Cell Host Microbe 25, 39-48 e35, 2019.
Wec et al., Cell 169, 878-890 e815, 2017.
West et al., mBio 9, 2018.
West et al., Nat. Struct. Mol. Biol. 26, 204-212, 2019.
Williams et al., Protein Sci. 27, 293-315, 2018.
Urbanowicz et al., *Cell* 167, 1079-1087, 2016.

Yu et al., J. Immunol. Methods 336, 142-151, 2008.
Zhang, K., J. Struct. Biol. 193, 1-12, 2016.
Zhao et al., Nature 535, 169-172, 2016.
Zhao, Z., and Singer, A., J. Struct. Bio.1 186, 153-166, 2014.
Zheng et al., Nat. Methods 14, 331-332, 2017.
Zivanov et al., Elife 7, 2018.

What is claimed is:

1. A method of treating a subject infected with ebolavirus, or reducing the likelihood of infection of a subject at risk of contracting ebolavirus, comprising administering to said subject an antibody or antibody fragment having clone-paired heavy and light chain CDR sequences selected from heavy chain CDR1-3 of SEQ ID NOS: 91, 92 and 93, and light chain CDR1-3 of SEQ ID NOS: 154, 155, and 156; heavy chain CDR1-3 of SEQ ID NOS: 118, 119 and 120, and light chain CDR1-3 of SEQ ID NOS: 181, 182, and 183; or heavy chain CDR1-3 of SEQ ID NOS: 127, 128 and 129, and light chain CDR1-3 of SEQ ID NOS: 190, 191, and 192.

2. The method of claim 1, wherein the antibody or antibody fragment is encoded by clone-paired light and heavy chain variable sequences selected from SEQ ID NOS: 6 and 5, SEQ ID NOS: 24 and 23, or SEQ ID NOS: 30 and 29, respectively.

3. The method of claim 1, wherein the antibody or antibody fragment is encoded by clone-paired light and heavy chain variable sequences having 95% identity to SEQ ID NOS: 6 and 5, SEQ ID NOS: 24 and 23, or SEQ ID NOS: 30 and 29, respectively.

4. The method of claim 1, wherein said antibody or antibody fragment is encoded by light and heavy chain variable sequences having 70%, 80%, or 90% identity to SEQ ID NOS: 6 and 5, SEQ ID NOS: 24 and 23, or SEQ ID NOS: 30 and 29, respectively.

5. The method of claim 1, wherein said antibody or antibody fragment comprises light and heavy chain variable sequences SEQ ID NOS: 48 and 47, SEQ ID NOS: 66 and 65, or SEQ ID NOS: 72 and 71, respectively.

6. The method of claim 1, wherein said antibody or antibody fragment comprises light and heavy chain variable sequences having 70%, 80% or 90% identity to SEQ ID NOS: 48 and 47, SEQ ID NOS: 66 and 65, or SEQ ID NOS: 72 and 71, respectively.

7. The method of claim 1, wherein said antibody or antibody fragment comprises light and heavy chain variable sequences having 95% identity to SEQ ID NOS: 48 and 47, SEQ ID NOS: 66 and 65, or SEQ ID NOS: 72 and 71, respectively.

8. The method of claim 1, wherein the antibody fragment is a recombinant scFv (single chain fragment variable) antibody, Fab fragment, F(ab')2 fragment, or Fv fragment, and/or wherein said antibody fragment further comprises a cell penetrating peptide and/or is an intrabody.

9. The method of claim 1, wherein said antibody is an IgG, a recombinant IgG antibody, or an IgG antibody fragment comprising an Fc portion mutated to alter FcR interactions, to increase half-life or glycan modified to alter FcR interactions.

10. The method of claim 1, wherein said antibody is a chimeric antibody or a bispecific antibody, and/or wherein said antibody further comprises a cell penetrating peptide and/or is an intrabody.

11. The method of claim 1, wherein said subject is a pregnant female, a sexually active female, or a female undergoing fertility treatments.

12. The method of claim 1, wherein delivering comprises antibody or antibody fragment administration, or genetic delivery with an RNA or DNA sequence or vector encoding the antibody or antibody fragment.

13. A hybridoma or engineered cell encoding an antibody or antibody fragment wherein the antibody or antibody fragment is characterized by clone-paired heavy and light chain CDR sequences selected from heavy chain CDR1-3 of SEQ ID NOs: 91, 92 and 93, and light chain CDR1-3 of SEQ ID NOs: 154, 155, and 156; heavy chain CDR1-3 of SEQ ID NOs: 118, 119 and 120, and light chain CDR1-3 of SEO ID NOs: 181, 182, and 183; or heavy chain CDR1-3 of SEQ ID NOs: 127, 128 and 129, and light chain CDR1-3 of SEQ ID NOs: 190, 191, and 192.

14. A vaccine formulation comprising one or more antibodies or antibody fragments characterized by clone-paired heavy and light chain CDR sequences selected from heavy chain CDR1-3 of SEQ ID NOs: 91, 92 and 93, and light chain CDR1-3 of SEQ ID NOs: 154, 155, and 156;

heavy chain CDR1-3 of SEQ ID NOs: 118, 119 and 120, and light chain CDR1-3 of SEO ID NOs: 181, 182, and 183; or heavy chain CDR1-3 of SEQ ID NOs: 127, 128 and 129, and light chain CDR1-3 of SEQ ID NOs: 190, 191, and 192;

and a pharmaceutically acceptable carrier.

15. A method of detecting an ebolavirus infection in a subject comprising:

(a) contacting a sample from said subject with an antibody or antibody fragment having clone-paired heavy and light chain CDR sequences selected from heavy chain CDR1-3 of SEQ ID NOs: 91, 92 and 93, and light chain CDR1-3 of SEQ ID NOs: 154, 155, and 156; heavy chain CDR1-3 of SEQ ID NOs: 118, 119 and 120, and light chain CDR1-3 of SEO ID NOs: 181, 182, and 183; or heavy chain CDR1-3 of SEQ ID NOs: 127, 128 and 129, and light chain CDR1-3 of SEQ ID NOs: 190, 191, and 192; and (b) detecting ebolavirus in said sample by binding of said antibody or antibody fragment to an ebolavirus antigen in said sample.

* * * * *

```
                              SEQUENCE LISTING

<160> NUMBER OF SEQ ID NOS: 215

<210> SEQ ID NO 1
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtgcagtc tggggctgag gtgaagaagc ctggggcctc agtgaaggtc      60
tcctgcaagg cttctggata caccttcacc ggctactata tgttctgggt gcgacaggcc     120
cctggacaag ggcttgagtg gatgggatgg atcaaccctaa acagtggtgg cacaaactat    180
acacagaagt tcagggcag ggtcaccatg accagggaca cgtccatcag cacagcctac      240
atggagctga gcaggctgaa atctgacgac acggccgtgt attactgtgc gagagactcc     300
ggggagttat tattcgtggg ctcggacgtc tggggccaag ggaccctggt caccgtctcc     360
tca                                                                   363

<210> SEQ ID NO 2
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 2
gacatccaga tgacccagtc tccatcttcc gtgtctgcat ctgtaggaga cagagtcacc      60
atcacttgtc gggcgagtct ggatattagc tactggttag cctggtatca gcagaaacca    120
ggtaaagccc ctaagctcct gatctatgct gcatccaatt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tccctcagac ttttggccag    300
gggaccaggc tggagctcaa a                                              321

<210> SEQ ID NO 3
<211> LENGTH: 399
<212> TYPE: DNA
<213> ORGANISM: Artificial sequence
<220> FEATURE:
<223> OTHER INFORMATION: Synthetic oligonucleotide

<400> SEQUENCE: 3
caggtccagc tggtgcaatc tggggctgag gtgaagaagc ctgggtcctc ggtgaaggtc      60
tcctgcaagg cttctggagg caccttcagt agggatattt cagctgggt gcgacaggcc     120 cctggacaag ggcttgagtg gatgggaggg atcatcccta tctttggtac ggcaaactac    180
gcacagaagt tccagggcag agtcacgatt accgcggaca aatccacgag tacagtcttc    240
atggagttga gcggcctgag atctgaggac acggccgtgt atttctgtgc gagaggcccc    300
cccctccgcg gggagaggtc atggttcggg gagtccgaaa agtacgacta cttctacatg    360
gacgtgtggg gcaaagggac cacggtcacc gtctcctca                            399

<210> SEQ ID NO 4
```

<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 4

```
caaattgttt tgacgcagtc tccaggcacc ctgtctttgt ctccagggga gagagccacc      60
ctctcctgca gggccagtca gagtgttagc aacagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tctccatcag cagactggag     240
cctgaagatt ttgcagtgta ttactgtcag cagtatggta cgtcaccttg tactttggc     300
caggggacca agctggagat caaa                                             324
```

<210> SEQ ID NO 5
<211> LENGTH: 408
<212> TYPE: DNA
<213> ORGANISM: Artificial sequence
<220> FEATURE:
<223> OTHER INFORMATION: Synthetic oligonucleotide

<400> SEQUENCE: 5

```
gaggtgcagt tggtggagtc tgggggaggc ctcgtaaagc cggggggtc ccttagactc       60
tcctgtacag gctctggagg cactggattc actttcaagt atgccgggat gagctgggtc     120
cgccaggctc agggaaggg gccggagtgg attggccgta ttaaaagcag gattgatggt      180
gggacaacag actacgctgc acccgtgaaa gacagattca ttgtctcaag agatgattca     240
agaaatacac tctatctgca aatgaacagc ctgaagaccg aggacacagc cgtctattat     300
tgtgccacag gatcgggaaa ggggccctct gcgtcgttcg gggagtcata ctactactac     360
gacttcatta acgtctgggg caaagggacc acggtcaccg tctcctca                  408
```

<210> SEQ ID NO 6
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 6

```
gaaagtgtgt tgacgcagtc tccaggcacc ctgtctttgt ctccagggga aagagccacc      60
ctctcgtgca gggccagtca gagtattagc aggaagtact tagcctggta ccagcagaaa     120
cctggccagg ctcccaggct cctcatctat ggttcatcca gcagggccac tggcatccca     180
gacagattca gtggcagtgg gtctgggaca gacttcactc tcaccatcag cagactggag     240
cctgaagatt ttgcagtgta ttactgtcat cagtatgaaa gctcaccttg gacgttcggc     300
caagggacta aggtggaaat caaa                                             324
```

<210> SEQ ID NO 7
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 7

```
caggtgcagc tggtgcagtc tggggctgag gtgaaaaagc ctggggcctc agtgaaggtc       60
tcctgtaagg cttctggata caccttcacc gactactata tctactgggt gcgacaggcc     120
```

```
cctggacaag ggcttgaatg gatgggatgg ctcaaccta atagtggtgg cacagactat    180
gcccagaagt ttcagggccg ggtcaccatg accaggaca cgtccatcag acagcctac    240 atggacctga gcaggctgag atctgacgac acagccgtat attactgtgc gagaggcaga    300
agacacggtg cctatgttga ctggggccag ggaaccctgg tcaccgtctc ctca          354

<210> SEQ ID NO 8
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 8
gacatccagt tgacccagtc tccatccttc ctgtctgcat ctgttggaga cagagtcacc     60
atcacttgcc gggccagtca gggcattagt acttatttag cctggtatca gcaaaaacca    120
gggaaagccc ctaacctcct gatctatgat acatccactt tgcaaagtgg ggtcccatca    180
agattcagcg gcagtgcatc tgggacagaa ttcactctca caatcagcag cctgcagcct    240
gaagattttg caacttatta ctgtcaacag cttaattttt acctgggggg cctcaccttc    300
ggccaaggga cacgactgga gattaaa                                         327

<210> SEQ ID NO 9
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 9
gaggtgcagc tggtggagtc tgggggaagt gtggtacggc cggggggtc cctgagactc     60 tcctgtgcag cctctggatt taagtttgat gaatatggca tgagttgggt ccgccaggct    120
ccagggaagg ggctggagtg ggtctctgga attacttgga atggtggtgt ccgaacttat    180
gcagactctg tgaagggccg attcaccatc tccaggaca cgccaagaa ctccgtgtat    240 ctgcaaatga aaagtctgag aggcgaagac acggccttgt attactgtgt tagttggggt    300
gaacgctacg atgcgtactt cgactattgg ggccagggaa ccctggtcac cgtctcctca    360

<210> SEQ ID NO 10
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 10
gaaattgtgt tgacgcagtc tccaggcagt ctgtctttgt ctccagggga aagagccacc     60
ctctcctgca gggccagtca gagtgttaac agccgctact cgcctggta ccagcagaga    120 cctggccagg ctcccagact cctcatctat gccacatcca cagggccac tggcatccca    180 gacaggttca gcggtagtgg gtctgggaca gacttcactc tcaccatcag taggctggag    240
cctgaagatt ttgcagtgta ttcctgtcag cagtatggta gctcgcccta cacttttggc    300
caggggacca agctggagat caaa                                            324

<210> SEQ ID NO 11
<211> LENGTH: 384
<212> TYPE: DNA
```

<213> ORGANISM: Artificial sequence
<220> FEATURE:
<223> OTHER INFORMATION: Synthetic oligonucleotide

<400> SEQUENCE: 11

```
gaggtgcagc tggtggagtc tgggggaggc ttggtgcagc cggggggtc cctaagactc    60
tcctgtgcag cctctggatt cagctttagc aactatgcca tgacctgggt ccgccaggct   120
cccgggaagg ggttggagtg ggtctccagt attggtatta gtggtggtag cacatactac   180
gcagactccg tgaagggccg cttcaccatc tccagagaca actccaagaa cacactgtat   240
ctgcaaatga acagcctgag agccgcggac acggcccgat attactgtgc gaaagatgcc   300
cagcaggaaa cagatatcgt ttatttctac tactacgacg gaatggacgt ctggggccaa   360
gggaccctgg tcaccgtctc ctca                                          384
```

<210> SEQ ID NO 12

<400> SEQUENCE: 12

000

<210> SEQ ID NO 13
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 13

```
caggtgcagc tggtgcagtc tggggctgag gtgaagaagc ctggggcctc agtgaaggtc    60
tcctgcaagg cttctggata caccttcaat aattacctta taaattgggt gcgacaggcc   120
cctggacaag ggcttgaatg gatgggatgg atcaaccctc acagtggtgg cacagagtat   180
gcacagcagt tcagggcag actcaccgtg accaggaca cgtcaatcag aacagcctac    240
atggaactga gagtctgac atttgacgac tcggccatgt attattgctg gatatggttc   300
aggtctgaga cttttgattt ctggggccaa gggaccctgg tcaccgtctc ctca         354
```

<210> SEQ ID NO 14
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 14

```
gacatccaga tgacccagtc tccatctgcc atgtctgcat ctgtaggaga cagagtcacc    60
atcacttgtc gggcgagtca ggacattagc aattatttag cctggtttca gcagaaacca   120
gggcaaggcc ctaagcgcct gatctttgag gcatccattt tgcacagtgg ggtcccttca   180
aggttcagcg gcagtggatc tgggacagaa ttcactctca caatcagcag cctgcagcct   240
gaagattttg caacttatta ctgtctacaa cataatactt acctgacgtt cggccaaggg   300
accaaggtgg aaatcaaa                                                 318
```

<210> SEQ ID NO 15
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 15

| | |
|---|---|
| caggtgcagc tggtgcagtc tggggctgag gtgaagaagc ctggggcctc agtgaaggtt | 60 |
| tcctgcaagg catctggata caccttcatc aactactata tgcactgggt gcgacaggcc | 120 |
| cctggacaag gcttgagtg gatgggaaca atcaaccta gtactggtcg cccaaactac | 180 |
| gcacagaagt tccagggcag agtcaccttg accagggaca cgtccacgac cacagtcgac | 240 |
| atggagctga gcagcctgac atcagaggac acggccgtgt attactgtgt tagttttcag | 300 |
| ttttactttg actactgggg ccagggaacc ctggtcaccg tctcctca | 348 |

<210> SEQ ID NO 16
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 16

| | |
|---|---|
| gacatccaga tgacccagtc tccatctgcc atgtctccat ctgtaggaga cagagtcacc | 60 |
| atcacttgtc gggcgagtca gggcattaac aattatttag cctggtttca gcagaaacca | 120 |
| gggaaagtcc ctaagcgcct gatctatgct gcatccaatt tgcaaagtgg ggtcccatca | 180 |
| aggttcagcg gcagtggatc tgggacagaa ttcactctca caatcagcag cctgcagcct | 240 |
| gaagattttg caacttatta ctgtctacag cataatagtt atccctggac gttcggccaa | 300 |
| gggaccaagg tggaaatcaa t | 321 |

<210> SEQ ID NO 17
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 17

| | |
|---|---|
| caggtgcagc tgcaggagtc gggcccagga ctggtgaagc cttcacagac cctgtccctc | 60 |
| acctgcactg tctccggtgg ctccattacc agtggtgatt actacttaac gtgggtccgc | 120 |
| cagcccccag ggaagggcct ggagtggatt gggcacatct attacagtgg gagcacctcc | 180 |
| tacaacccgt ccctcaagag tcgacttctc atgtcggtgg acacgtccaa gaaccagttc | 240 |
| tccctgaggt tgagctctgt gacggccgca gacacggccg tttactactg tgccagagag | 300 |
| tctgacggtg acccttctcg actttacttc tacttcgcta tggacgtctg gggccaaggg | 360 |
| accctggtca ccgtctcctc a | 381 |

<210> SEQ ID NO 18
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 18

| | |
|---|---|
| cagtctgccc tgactcagcc tgcctccgtg tctgggtctc ctggacagtc gatcaccatc | 60 |
| tcctgcactg gaaccagcag tgacgttggt ggttcttatt ttgtctcctg gtaccaacac | 120 |
| cacccaggca agccccccaa actcatgatt tctgaggtca gtaatcggcc ctcagggggtt | 180 |
| tctaatcgct tctctggctc caagtctggc aacacggcct ccctgaccat ctctggactc | 240 |
| cggactgagg acgaggctga ttattactgc agctcatata cgagcaacac cactctcgtt | 300 |

```
ttcggcggag agaccaaggt gaccgtccta                                    330
```

<210> SEQ ID NO 19
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 19

```
cagctgcagc tgcaggagtc gggcccagga ctggtgaagc cttcggagac cctgtccctc    60
tcctgcactg tttctggtga ctccatcagc gctaataatt acttctgggg ctggatccgc   120
cagcccccag ggaaggagct ggagtggatt gggagcatcc ataacagtgg gagcacctat   180
tacaatccgt ccctcaagag tcgagtcacc acatccgtag acacgtccag gacccagttc   240
tccctgaagc tgcactctgt gaccgccgca gacgcggcta tatattactg tgcgagacac   300
cttgctccga tttctggagt gattttcatc ccgtcgttct tgactcctg gggccaggga   360
accctggtca ccgtctcctc a                                             381
```

<210> SEQ ID NO 20
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 20

```
gaaatagtga tgacgcagtc tccagccacc ctgtctgtgt ctccagggga aagagccacc    60
ctctcctgca gggccagtca gagtgtgagc agcaacttag cctggtacca gcagagacct   120
ggccaggctc ccaggctcct catctttgat gcatccacca gggccactgg tgtcccagcc   180
aggttcagtg gcagtgggtc tgggacagag ttcacgctca ccatcagcag cctgcagtct   240
gaagactttg cactttatta ctgtcagcag tataatgact ggcctccaag gctcactttc   300
ggcggaggga ccaaggtcga gatcaaa                                        327
```

<210> SEQ ID NO 21
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 21

```
caggtgcagc tgcaggagtc gggcccagga ctggtgaagc cttcacagac tctgtccctc    60
acctgcactg tctctggtgc ctccatcact ggtggtgatg acttctggag ctggatccgc   120
cagcccccctg ggaagggcct ggagtggatt gggttcatcc atcacagtgg gaacgcctac   180
tacaggtcgt ccctcaagag tcgagtgcac ttttcagtag acacgtccaa ggaccagttc   240
tccctgactc taacctctgt gactgccgca gacacggccg tgtattactg tgccagagat   300
aaggcccaag cctatgggtt attgtaccac tatcacacgg acgtctgggg caaagggacc   360
ctggtcaccg tctcctca                                                  378
```

<210> SEQ ID NO 22
<211> LENGTH: 327
<212> TYPE: DNA
<213> ORGANISM: Artificial sequence
<220> FEATURE:

<223> OTHER INFORMATION: Synthetic oligonucleotide

<400> SEQUENCE: 22

| | |
|---|---|
| gaaatagtga tgacgcagtc tccagccacc ctgtctgtgt ctccagggga aagagccacc | 60 |
| ctctcttgca gggccagtca gagtgttagc agcaacttag cctggtacca gcagaagcct | 120 |
| ggcctggctc cccgactcct catctatggt gcattcacca gggccactga tatcccagac | 180 |
| aggttcagtg gcagtgggtc tgggacagag ttcactctca ccatcagcag cctgcagtct | 240 |
| gaagattttg caatttatta ctgtcagtac tataatgact ggcctccggg gtacactttt | 300 |
| ggccagggga ccaagctgga gatcaaa | 327 |

<210> SEQ ID NO 23
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 23

| | |
|---|---|
| caggtgcagc tgcaggagtc gggcccagga ctggtgaagc cttcacagac cctgtccctc | 60 |
| acctgcactg tctctggtgg gtccatcaac agtgctggtt actactggac ctggatccgc | 120 |
| cagcacccgg ggaagggcct ggagtggatt gggtacatcg attatactgg gaggacctac | 180 |
| tacaacccgt cccttgagag ccgagtgatc atttcaatag acacgtctaa gaaccacttc | 240 |
| tccctgagac tgacctctgt gtctgccgcg gacacggccg tgtattactg cgcgagaaa | 300 |
| tcgtcgtggg tatccgagtt agggcgtgac aactggggcc agggaaccct ggtcaccgtc | 360 |
| tcttca | 366 |

<210> SEQ ID NO 24
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 24

| | |
|---|---|
| gaaatagtga tgacgcagtc tccagccacc ctgcctgtgt ctccagggga aggagccacc | 60 |
| ctctcctgca gggccagtca gagtgttttc accaacttag cctggtacca gcaaaaacct | 120 |
| ggccaggctc ccaggctcct catctatgat gcatccacca gggccactgg tatcccagcc | 180 |
| aggttcagtg gcagtgggtc tgggacagag ttcactctca ccatcagcag cctgcagtct | 240 |
| gaagactttg cagtttatta ttgtcagcag tataataact ggcctcggac gtacggccaa | 300 |
| gggaccaggg tggaagtcaa a | 321 |

<210> SEQ ID NO 25
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 25

| | |
|---|---|
| gaggtgcagc tggtggagtc tgggggaggc ttggtccagc ctgggggtc cctgagactc | 60 |
| tcctgtggag cctccggatt cacctttaat aagtattgga tgacctgggt ccgccaggct | 120 |
| ccagggaagg ggctgagtg ggtggccaac ataaatcaag atggaagtga gaaatacttt | 180 |
| gcggagtctg tgaagggccg attcaccgtc tccagagaca acgccaagaa ctcactgtat | 240 |

```
ctgcaaatga acagcctgag agccgaggac acggctgtct attactgtgc gagaggggcg    300
agtattgaag tagaaatctt gtattactac cacatggacg tctggggcaa agggaccctg    360
gtcaccgtct cctca                                                     375
```

<210> SEQ ID NO 26
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 26

```
gaaatagtga tgacgcagtc tccagccacc ctgtctgtgt ctccagggga aagagccacc     60
ctctcctgca gggccagtca gagtattacc acccacttgg cctggtacca gcagaagcct    120
ggccaggctc ccaggctcct catctatgat acatccacca gggccactgg tatcccagcc    180
aggttcagtg gctctgggtc tgggacagag ttcactctca ccatcagtaa catgcagtct    240
gaagattttg cagtttatta ctgtcagcaa tatcatacct ggcctccgct cactttcggc    300
ggagggacca aggtggagat caaa                                           324
```

<210> SEQ ID NO 27
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 27

```
caggtcacct tgaaggagtc tggtcctaca ctggtgaaac ccacacagac cctcacgctg     60
acctgcacct tctccggatt ctcaatgaat agtagtggaa tgagtgtgac ctggatccgt    120
cagcccccag gaaaggccct ggagtgcctt gccctcattt attgggatga tgataagtgg    180 tatgcccat ctctggagac cagagtcacc atcaccaagg acgcctcgaa aaaccaggtg     240
gtccttacaa tgaccaacat ggaccctgtg gacacagcca cctattactg tgcacacagt    300
gggggactcg tcgcggggc ctttgactac tggggccagg gtaccctggt caccgtctcc    360
tca                                                                  363
```

<210> SEQ ID NO 28
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 28

```
gaaatcgtga tgacccagtc tccagactcc ctgaccgtgt ctctgggcga gagggccacc     60
atcaactgca ggtccagcca gagtgtttta tacagggtca acagtaagaa ctacttggct    120
tggtaccagc agaaggcagg acagactcct aaattgatca ttaactgggc atctacccgg    180
gaatccgggg tccctgaccg attcagtggc agcgggtctg ggacagattt cactctcacc    240
atcagcagcc tgcaggctga agatgtggca gtttattact gtcagcaata ttataattct    300
cctcggactt tcggccaagg gaccaaggtg gaaatcaaa                            339
```

<210> SEQ ID NO 29
<211> LENGTH: 372
<212> TYPE: DNA

<213> ORGANISM: Artificial sequence
<220> FEATURE:
<223> OTHER INFORMATION: Synthetic oligonucleotide

<400> SEQUENCE: 29

| | | | | | |
|---|---|---|---|---|---|
| caggtgcagc | tgcaggagtc | gggcccagga | ctggggaagc | cttcggagac | cctgtccctc | 60 |
| agttgcactg | tctctggtgc | ctccatcagg | ggttacttct | ggaactggat | ccggcagccc | 120 |
| ccagggaagg | gactggagtg | gattggctat | atccattcca | ctgggagcac | caactacaat | 180 |
| ccctccctca | agagtcgagt | caccatatca | gtagacacgt | ccaagaacca | ggtctccctg | 240 |
| aatgtaaact | ctgtgaccgc | tgcggacacg | gccgtgtatt | tctgtgcgag | aggggcctgg | 300 |
| aatgtggcta | ctgtctacta | ctactacggt | atggacgtct | ggggccaagg | gaccctggtc | 360 |
| accgtctcct | ca | | | | | 372 |

<210> SEQ ID NO 30
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 30

| | | | | | |
|---|---|---|---|---|---|
| gaaattgtgt | tgacgcagtc | tccaggcacc | ctgtctttgt | ctccagggga | aagagccacc | 60 |
| ctctcgtgca | gggccagtca | gagtgttagc | agcagctact | tcgcctggta | ccagcagaag | 120 |
| cctggccagg | ctcccaggct | cctcatctct | ggtacatcca | ccagggcccc | tggcatccca | 180 |
| gacaggttca | gtggcagtgg | gtctgggaca | gacttcactc | tcaccatcag | cagactggag | 240 |
| cctgaagatt | ttgcagtgta | tttctgtcag | cagtatggta | actcactgta | cacttttggc | 300 |
| caggggacca | agctggagat | caaa | | | | 324 |

<210> SEQ ID NO 31
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 31

| | | | | | |
|---|---|---|---|---|---|
| caggtgcagc | tggtggagtc | tggaggaggc | gtggtccagc | cgggggggtc | cctgagactc | 60 |
| tcctgtgcag | cgtctggatt | caagttcagt | acctatggca | tgaactgggt | ccgccaggtt | 120 |
| ccaggccagg | ggctggagtg | ggtctcattt | gtaaggcatg | atggaagtaa | taagtattat | 180 |
| agtgattccg | tgaagggccg | cttcaccatc | ttcagagaca | actccaacaa | taagttgtat | 240 |
| ctgcaaatga | acaacctgag | agctgaggac | acggctgtct | attactgtgc | gaaagatgtc | 300 |
| ctcgattgca | gtagagccga | ctgtttcatc | tactactact | acatggacgt | ctggggcaaa | 360 |
| gggaccctgg | tcaccgtctc | ctca | | | | 384 |

<210> SEQ ID NO 32
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 32

| | | | | | |
|---|---|---|---|---|---|
| gacatccaga | tgacccagtc | tccctcttcc | gtgtctgcat | ctccaggaga | cagagtcacc | 60 |
| atcacttgtc | gggcgagtca | gactattagc | ggctggttag | cctggtatca | gcagaaacca | 120 |

```
gggaaagccc ctaagctcct gatctatgat gtatccactt tgcaaagtgg ggtcccatct    180
aggttcagcg gcggtggatc tgggacagag ttcactttca ccatcagcag tctgcagcct    240
gaagattatg caacttactt ttgtcagcag gtaacagga tccctctctc tttcggcgga    300
gggaccaggg ttgagatcaa a                                              321

<210> SEQ ID NO 33
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 33
gaggtgcagc tggtggagtc tgggggaggc ttggtccagc ctgggggtc cctgagactc     60 tcctgtgcag cctctggatt caccgtcagt aacaactaca tgagctgggt ccgccaggct    120
ccagggaagg ggctggagtg gtctcactt atttacacca gtgttaccac atactacgca    180
gactccgtga agggcagatt caccatctcc agagacaatt ccaagaacac gttgtatctt    240
caaatgaaca gtctgagagc cgaggacacg gctgtgtatt actgtgcgag agaattgggc    300
aactggagct acggagtaag ctactggggc cggggaacgt tggtcaccgt ctcctca      357

<210> SEQ ID NO 34
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 34
tcctatgagc tgacacagcc accctcggtg tcagtgtccc caggacagac ggccaggatc     60
acctgctctg gagatgcact gccaaagcaa tatgcttatt ggtaccagca gaagccaggc    120
caggcccctg tgttggtgat atataaggac agtgagaggc cctcagggat ccctgagcga    180
ttctctggct ccagctcagg gacaacagtc acgttgacca tcagtggagt ccaggcagaa    240
gacggggctg actattactg tcaatcagca gacggcagtg gtacttatcc tgtggtattc    300
ggcggaggga ccaagctgac cgtccta                                        327

<210> SEQ ID NO 35
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 35
caggtgcagc tacagcagtg gggcgcagga ctgttgaagc cctcggagac actgtccctc     60
acctgcgctg tctctggtgg gtccctcacc ggttactact ggggctggat ccgccagccc    120
ccagggaagg ggctggagtg gattggggaa atcaatcacg gtgtcagcac catgtacaac    180
ccgtccctca agagtcgagt caccctttca gttgacacgt ccaagaacca gttctccctg    240
aagctgagct ctgtgaccgc cgcggacacg gctgtctatt actgtgcgag aagcagatta    300
cagctctggt tcttaggagc ttttgatatc tggggccaag ggacaatggt caccgtctcc    360
tca                                                                  363

<210> SEQ ID NO 36
```

<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 36

| | | | | | |
|---|---|---|---|---|---|
| gaaatagtga | tgacgcagtc | tccagccacc | ctgtctgtgt | ctccagggga | aagagccacc | 60 |
| ctctcctgta | gggccagtca | gagtatttac | accaacttag | cctggtacca | gcagaaacct | 120 |
| ggccagcctc | ccaggctcct | catccatgat | gcatccacca | gggccactgg | catcccagcc | 180 |
| aggttcagtg | gcagtgggtc | tgggactgag | ttcactctca | ccatcagcag | cctgcagtct | 240 |
| gaagattttg | cagtttattt | ctgtcagcag | tataacagct | ggcgtacgtt | cggccaaggg | 300 |
| accaaggtgg | agatcaag | | | | | 318 |

<210> SEQ ID NO 37
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 37

| | | | | | |
|---|---|---|---|---|---|
| gaggtgcagc | tggtgcagtc | tggagcagag | gtgaaaaagc | cgggagagtc | tctgaagatc | 60 |
| tcctgtaagg | gtgctggata | cagctttccc | aattactgga | tcggctgggt | gcgccagatg | 120 |
| cccgggaaag | gcctggagtg | gatggggatc | atctatcctg | gtgagtctaa | aaccagatac | 180 |
| agcccgtcct | tccaaggcca | agtcaccatc | tcagccgaca | agtccatcag | caccgcctac | 240 |
| ctgcagtgga | gcagcctgaa | ggcctcggac | accgcatgt | attattgtgc | ccttccccga | 300 |
| ataggaccaa | ctagtaactg | gggcagcagc | tggtacgagg | gtattttga | catctggggc | 360 |
| caagggacaa | tggtcaccgt | ctcttca | | | | 387 |

<210> SEQ ID NO 38
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 38

| | | | | | |
|---|---|---|---|---|---|
| caggctgtgg | tgactcagga | atctgcactc | accacatcac | ctggtgaaac | agtcacactc | 60 |
| acttgtcgct | caagtactgg | ggctgttaca | actagtaact | atgccaactg | ggtccaagaa | 120 |
| aaaccagatc | atttattcac | tggtctaata | ggtggtacca | caaccgagc | tccaggtgtt | 180 |
| cctgccagat | tctcaggctc | cctgattgga | gacaaggctg | ccctcaccat | cacaggggca | 240 |
| cagactgagg | atgaggcaat | atatttctgt | gctctatggt | acagcaacca | tttatctttt | 300 |
| ggcagtggaa | ccaaggtcac | tgtccta | | | | 327 |

<210> SEQ ID NO 39
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 39

| | | | | | |
|---|---|---|---|---|---|
| caggtgcagc | tgcaggagtc | gggcccagga | ctggtgaagc | cttcggagac | cctgtccctc | 60 |
| acctgcactg | tctctggtgg | ctccatcagt | agtcactact | ggagctggat | ccggcagccc | 120 |

```
ccagggaagg gactggagtg gattgggtat atctcttaca gtgggagtac caactacaat    180
ccctccctca agagtcgagt caccatatca gtggacacgt ctaagaacca gttctccctg    240
gggctgaggt ctgtgaccgc tgcggacacg gccgtgtatt actgtgcgag aatgactcgt    300
gtcacaatct ttggagtact tactgacgat tattacaagt ggttcgaccc ctggggccag    360
ggaaccctgg tcaccgtctc ctca                                           384

<210> SEQ ID NO 40
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 40
cagtctgccc tgactcagcc tccctccgtg tccgggtctc ctggacagtc agtcaccatc     60
tcctgcactg gaaccagcac tgacgttggt ggttctaacc gtgtctcctg gtaccagcag    120
cccccaggca cagcccccaa actcatgatt tatgaggtca ctaatcggcc ctcaggggtc    180
cctgatcgct tctctgggtc caagtctggc aacacggcct ccctgaccat ctctgggctc    240
cgggctgagg acgaggctga ttattactgc agcttatata caagcagcag cacttttgtc    300
ttcggaactg ggaccaaggt caccgtccta                                     330

<210> SEQ ID NO 41
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 41
caggttcagg tggaggagtc tgggggaggc gtggtccagc ctgggggtc cctgagactc      60 tcctgcgcag cgtctggatt catgttcagt aactatggca tgcactgggt ccgtcaggct    120
ccaggcaagg gactggagtg gatggcattt atccggtatg atgacagtaa gaaattctat    180
gcagactccg tgaagggccg attcaccatc tccagagaca attccaagaa caccctgtat    240
ctgcaaatga acagcctgag agctgaggac acggctctat attactgtgc gaaagaactt    300
ctacaagtgt ataccagtgc ctgggggag gacactcct actactacgc tttgacgtc      360 tggggcctag gaccgcggt caccgtctcc tca                                  393

<210> SEQ ID NO 42
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 42
gacatccaga tgacccagtc tccatcttcc gtgtctgcat ctgtaggaga cagagtcacc     60
atcacttgtc gggcgagtca ggatataagc aactggttag cctggtatca gcagaaacca    120
gggaaagccc ctgaactcct gatctatact gcatccattt tgcaaagtgg ggtctcatca    180
aggttcagcg gcagtggttc tgggacagat ttcactctca ccatcagcag cctgcagcct    240
gaagattctg caacttacta ttgtcaacag ggtaagagtt tcccgtacac ttttggccag    300
gggaccaagc tggagatcaa a                                              321
```

<210> SEQ ID NO 43
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met Phe Trp Val Arg Gln Ala Pro Gly Gln Gly Leu Glu Trp Met
            35                  40                  45

Gly Trp Ile Asn Pro Asn Ser Gly Gly Thr Asn Tyr Thr Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Lys Ser Asp Asp Thr Ala Val Tyr Tyr Cys
                85                  90                  95

Ala Arg Asp Ser Gly Glu Leu Leu Phe Val Gly Ser Val Trp Gly
            100                 105                 110

Gln Gly Thr Leu Val Thr Val Ser Ser
        115                 120

<210> SEQ ID NO 44
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 44

Asp Ile Gln Met Thr Gln Ser Pro Ser Ser Val Ser Ala Ser Val Gly
1               5                   10                  15

Asp Arg Val Thr Ile Thr Cys Arg Ala Ser Leu Asp Ile Ser Tyr Trp
                20                  25                  30

Leu Ala Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Gln
                85                  90                  95

Thr Phe Gly Gln Gly Thr Arg Leu Glu Leu Lys
            100                 105

<210> SEQ ID NO 45
<211> LENGTH: 216
<212> TYPE: PRT
<213> ORGANISM: Artificial sequence
<220> FEATURE:
<223> OTHER INFORMATION: Synthetic polypeptide

<400> SEQUENCE: 45

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser

```
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Tyr Cys Gln Gln Tyr Gly Thr Ser Pro
                85                  90                  95

Cys Thr Phe Gly Gln Gly Thr Lys Leu Glu Ile Lys Gln Ile Val Leu
                100                 105                 110

Thr Gln Ser Pro Gly Thr Leu Ser Leu Ser Pro Gly Glu Arg Ala Thr
            115                 120                 125

Leu Ser Cys Arg Ala Ser Gln Ser Val Ser Asn Ser Tyr Leu Ala Trp
        130                 135                 140

Tyr Gln Gln Lys Pro Gly Gln Ala Pro Arg Leu Leu Ile Tyr Gly Ala
145                 150                 155                 160

Ser Ser Arg Ala Thr Gly Ile Pro Asp Arg Phe Ser Gly Ser Gly Ser
                165                 170                 175

Gly Thr Asp Phe Thr Leu Ser Ile Ser Arg Leu Glu Pro Glu Asp Phe
                180                 185                 190

Ala Val Tyr Tyr Cys Gln Gln Tyr Gly Thr Ser Pro Cys Thr Phe Gly
            195                 200                 205

Gln Gly Thr Lys Leu Glu Ile Lys
        210                 215

<210> SEQ ID NO 46
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 46

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Tyr Cys Gln Gln Tyr Gly Thr Ser Pro
                85                  90                  95

Cys Thr Phe Gly Gln Gly Thr Lys Leu Glu Ile Lys
            100                 105

<210> SEQ ID NO 47
<211> LENGTH: 136
<212> TYPE: PRT
<213> ORGANISM: Artificial sequence
<220> FEATURE:
<223> OTHER INFORMATION: Synthetic polypeptide

<400> SEQUENCE: 47
```

```
Glu Val Gln Leu Val Glu Ser Gly Gly Gly Leu Val Lys Pro Gly Gly
1               5                   10                  15

Ser Leu Arg Leu Ser Cys Thr Gly Ser Gly Thr Gly Phe Thr Phe
            20                  25                  30

Lys Tyr Ala Gly Met Ser Trp Val Arg Gln Ala Pro Gly Lys Gly Pro
        35                  40                  45

Glu Trp Ile Gly Arg Ile Lys Ser Arg Ile Asp Gly Thr Thr Asp
50                  55                  60

Tyr Ala Ala Pro Val Lys Asp Arg Phe Ile Val Ser Arg Asp Asp Ser
65                  70                  75                  80

Arg Asn Thr Leu Tyr Leu Gln Met Asn Ser Leu Lys Thr Glu Asp Thr
                85                  90                  95

Ala Val Tyr Tyr Cys Ala Thr Gly Ser Gly Lys Gly Pro Ser Ala Ser
            100                 105                 110

Phe Gly Glu Ser Tyr Tyr Tyr Asp Phe Ile Asn Val Trp Gly Lys
            115                 120                 125

Gly Thr Thr Val Thr Val Ser Ser
130                 135
```

<210> SEQ ID NO 48
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 48

```
Glu Ser Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Arg Lys
            20                  25                  30

Tyr Leu Ala Trp Tyr Gln Gln Lys Pro Gly Gln Ala Pro Arg Leu Leu
        35                  40                  45

Ile Tyr Gly Ser Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Glu Ser Ser Pro
                85                  90                  95

Trp Thr Phe Gly Gln Gly Thr Lys Val Glu Ile Lys
            100                 105
```

<210> SEQ ID NO 49
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Tyr Trp Val Arg Gln Ala Pro Gly Gln Gly Leu Glu Trp Met
        35                  40                  45

Gly Trp Leu Asn Pro Asn Ser Gly Gly Thr Asp Tyr Ala Gln Lys Phe
50                  55                  60
```

Gln Gly Arg Val Thr Met Thr Arg Asp Thr Ser Ile Arg Thr Ala Tyr
65                  70                  75                  80

Met Asp Leu Ser Arg Leu Arg Ser Asp Asp Thr Ala Val Tyr Tyr Cys
            85                  90                  95

Ala Arg Gly Arg Arg His Gly Ala Tyr Val Asp Trp Gly Gln Gly Thr
            100                 105                 110

Leu Val Thr Val Ser Ser
        115

<210> SEQ ID NO 50
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 50

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
            20                  25                  30

Leu Ala Trp Tyr Gln Gln Lys Pro Gly Lys Ala Pro Asn Leu Leu Ile
        35                  40                  45

Tyr Asp Thr Ser Thr Leu Gln Ser Gly Val Pro Ser Arg Phe Ser Gly
    50                  55                  60

Ser Ala Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Phe Tyr Leu Gly
                85                  90                  95

Gly Leu Thr Phe Gly Gln Gly Thr Arg Leu Glu Ile Lys
            100                 105

<210> SEQ ID NO 51
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 51

Glu Val Gln Leu Val Glu Ser Gly Gly Ser Val Val Arg Pro Gly Gly
1               5                   10                  15

Ser Leu Arg Leu Ser Cys Ala Ala Ser Gly Phe Lys Phe Asp Glu Tyr
            20                  25                  30

Gly Met Ser Trp Val Arg Gln Ala Pro Gly Lys Gly Leu Glu Trp Val
        35                  40                  45

Ser Gly Ile Thr Trp Asn Gly Val Arg Thr Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Lys Ser Leu Arg Gly Glu Asp Thr Ala Leu Tyr Tyr Cys
                85                  90                  95

Val Ser Trp Gly Glu Arg Tyr Asp Ala Tyr Phe Asp Tyr Trp Gly Gln
            100                 105                 110

Gly Thr Leu Val Thr Val Ser Ser
        115                 120

<210> SEQ ID NO 52
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 52

```
Glu Ile Val Leu Thr Gln Ser Pro Gly Ser Leu Ser Leu Ser Pro Gly
1               5                   10                  15

Glu Arg Ala Thr Leu Ser Cys Arg Ala Ser Gln Ser Val Asn Ser Arg
            20                  25                  30

Tyr Phe Ala Trp Tyr Gln Gln Arg Pro Gly Gln Ala Pro Arg Leu Leu
        35                  40                  45

Ile Tyr Ala Thr Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Ser Cys Gln Gln Tyr Gly Ser Ser Pro
                85                  90                  95

Tyr Thr Phe Gly Gln Gly Thr Lys Leu Glu Ile Lys
            100                 105
```

<210> SEQ ID NO 53
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asn Tyr
            20                  25                  30

Ala Met Thr Trp Val Arg Gln Ala Pro Gly Lys Gly Leu Glu Trp Val
        35                  40                  45

Ser Ser Ile Gly Ile Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Arg Tyr Tyr Cys
                85                  90                  95

Ala Lys Asp Ala Gln Gln Glu Thr Asp Ile Val Tyr Phe Tyr Tyr Tyr
            100                 105                 110

Asp Gly Met Asp Val Trp Gly Gln Gly Thr Leu Val Thr Val Ser Ser
        115                 120                 125
```

<210> SEQ ID NO 54

<400> SEQUENCE: 54

000

<210> SEQ ID NO 55
<211> LENGTH: 118
<212> TYPE: PRT
<213> ORGANISM: Artificial sequence
<220> FEATURE:
<223> OTHER INFORMATION: Synthetic polypeptide -continued

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asn Tyr
            20                  25                  30

Leu Ile Asn Trp Val Arg Gln Ala Pro Gly Gln Gly Leu Glu Trp Met
        35                  40                  45

Gly Trp Ile Asn Pro His Ser Gly Gly Thr Glu Tyr Ala Gln Gln Phe
    50                  55                  60

Gln Gly Arg Leu Thr Val Thr Arg Asp Thr Ser Ile Arg Thr Ala Tyr
65                  70                  75                  80

Met Glu Leu Arg Gly Leu Thr Phe Asp Asp Ser Ala Met Tyr Tyr Cys
                85                  90                  95

Trp Ile Trp Phe Arg Ser Glu Thr Phe Asp Phe Trp Gly Gln Gly Thr
            100                 105                 110

Leu Val Thr Val Ser Ser
            115

<210> SEQ ID NO 56
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 56

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Gln Gly Pro Lys Arg Leu Ile
        35                  40                  45

Phe Glu Ala Ser Ile Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Leu Thr
                85                  90                  95

Phe Gly Gln Gly Thr Lys Val Glu Ile Lys
            100                 105

<210> SEQ ID NO 57
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn Tyr
            20                  25                  30

Tyr Met His Trp Val Arg Gln Ala Pro Gly Gln Gly Leu Glu Trp Met
        35                  40                  45

Gly Thr Ile Asn Pro Ser Thr Gly Arg Pro Asn Tyr Ala Gln Lys Phe
    50                  55                  60

Gln Gly Arg Val Thr Leu Thr Arg Asp Thr Ser Thr Thr Val Asp
65                  70                  75                  80

Met Glu Leu Ser Ser Leu Thr Ser Glu Asp Thr Ala Val Tyr Tyr Cys
                85                  90                  95

Val Ser Phe Gln Phe Tyr Phe Asp Tyr Trp Gly Gln Gly Thr Leu Val
            100                 105                 110

Thr Val Ser Ser
            115

<210> SEQ ID NO 58
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 58

Asp Ile Gln Met Thr Gln Ser Pro Ser Ala Met Ser Pro Ser Val Gly
1               5                   10                  15

Asp Arg Val Thr Ile Thr Cys Arg Ala Ser Gln Gly Ile Asn Asn Tyr
            20                  25                  30

Leu Ala Trp Phe Gln Gln Lys Pro Gly Lys Val Pro Lys Arg Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Asn
            100                 105

<210> SEQ ID NO 59
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 59

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Asp Tyr Tyr Leu Thr Trp Val Arg Gln Pro Pro Gly Lys Gly Leu Glu
        35                  40                  45

Trp Ile Gly His Ile Tyr Tyr Ser Gly Ser Thr Tyr Asn Pro Ser
    50                  55                  60

Leu Lys Ser Arg Leu Leu Met Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Glu Ser Asp Gly Asp Pro Ser Arg Leu Tyr Phe Tyr Phe
            100                 105                 110

Ala Met Asp Val Trp Gly Gln Gly Thr Leu Val Thr Val Ser Ser
        115                 120                 125

<210> SEQ ID NO 60

<211> LENGTH: 110
<212> TYPE: PRT
<213> ORGANISM: Artificial sequence
<220> FEATURE:
<223> OTHER INFORMATION: Synthetic polypeptide

<400> SEQUENCE: 60

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Ser
            20                  25                  30

Tyr Phe Val Ser Trp Tyr Gln His Pro Gly Lys Ala Pro Lys Leu
        35                  40                  45

Met Ile Ser Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Arg Thr Glu Asp Glu Ala Asp Tyr Tyr Cys Ser Ser Tyr Thr Ser Asn
                85                  90                  95

Thr Thr Leu Val Phe Gly Gly Glu Thr Lys Val Thr Val Leu
            100                 105                 110

<210> SEQ ID NO 61
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 61

Gln Leu Gln Leu Gln Glu Ser Gly Pro Gly Leu Val Lys Pro Ser Glu
1               5                   10                  15

Thr Leu Ser Leu Ser Cys Thr Val Ser Gly Asp Ser Ile Ser Ala Asn
            20                  25                  30

Asn Tyr Phe Trp Gly Trp Ile Arg Gln Pro Pro Gly Lys Glu Leu Glu
        35                  40                  45

Trp Ile Gly Ser Ile His Asn Ser Gly Ser Thr Tyr Tyr Asn Pro Ser
    50                  55                  60

Leu Lys Ser Arg Val Thr Thr Ser Val Asp Thr Ser Arg Thr Gln Phe
65                  70                  75                  80

Ser Leu Lys Leu His Ser Val Thr Ala Ala Asp Ala Ala Ile Tyr Tyr
                85                  90                  95

Cys Ala Arg His Leu Ala Pro Ile Ser Gly Val Ile Phe Ile Pro Ser
            100                 105                 110

Phe Phe Asp Ser Trp Gly Gln Gly Thr Leu Val Thr Val Ser Ser
        115                 120                 125

<210> SEQ ID NO 62
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 62

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Tyr Gln Gln Arg Pro Gly Gln Ala Pro Arg Leu Leu Ile
            35                  40                  45

Phe Asp Ala Ser Thr Arg Ala Thr Gly Val Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Leu Tyr Tyr Cys Gln Gln Tyr Asn Asp Trp Pro Pro
                 85                  90                  95

Arg Leu Thr Phe Gly Gly Gly Thr Lys Val Glu Ile Lys
                100                 105
```

<210> SEQ ID NO 63
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 63

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Ala Ser Ile Thr Gly Gly
            20                  25                  30

Asp Asp Phe Trp Ser Trp Ile Arg Gln Pro Pro Gly Lys Gly Leu Glu
            35                  40                  45

Trp Ile Gly Phe Ile His His Ser Gly Asn Ala Tyr Tyr Arg Ser Ser
 50                  55                  60

Leu Lys Ser Arg Val His Phe Ser Val Asp Thr Ser Lys Asp Gln Phe
 65                  70                  75                  80

Ser Leu Thr Leu Thr Ser Val Thr Ala Ala Asp Thr Ala Val Tyr Tyr
                 85                  90                  95

Cys Ala Arg Asp Lys Ala Gln Ala Tyr Gly Leu Leu Tyr His Tyr His
                100                 105                 110

Thr Asp Val Trp Gly Lys Gly Thr Leu Val Thr Val Ser Ser
            115                 120                 125
```

<210> SEQ ID NO 64
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 64

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Leu Ala Pro Arg Leu Leu Ile
            35                  40                  45

Tyr Gly Ala Phe Thr Arg Ala Thr Asp Ile Pro Asp Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Ile Tyr Tyr Cys Gln Tyr Asn Asp Trp Pro Pro
                 85                  90                  95

Gly Tyr Thr Phe Gly Gln Gly Thr Lys Leu Glu Ile Lys
                100                 105
```

<210> SEQ ID NO 65
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 65

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Ala
            20                  25                  30

Gly Tyr Tyr Trp Thr Trp Ile Arg Gln His Pro Gly Lys Gly Leu Glu
        35                  40                  45

Trp Ile Gly Tyr Ile Asp Tyr Thr Gly Arg Thr Tyr Tyr Asn Pro Ser
    50                  55                  60

Leu Glu Ser Arg Val Ile Ile Ser Ile Asp Thr Ser Lys Asn His Phe
65                  70                  75                  80

Ser Leu Arg Leu Thr Ser Val Ser Ala Ala Asp Thr Ala Val Tyr Tyr
                85                  90                  95

Cys Ala Arg Glu Ser Ser Trp Val Ser Glu Leu Gly Arg Asp Asn Trp
            100                 105                 110

Gly Gln Gly Thr Leu Val Thr Val Ser Ser
        115                 120
```

<210> SEQ ID NO 66
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 66

```
Glu Ile Val Met Thr Gln Ser Pro Ala Thr Leu Pro Val Ser Pro Gly
1               5                   10                  15

Glu Gly Ala Thr Leu Ser Cys Arg Ala Ser Gln Ser Val Phe Thr Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Tyr Gly Gln Gly Thr Arg Val Glu Val Lys
            100                 105
```

<210> SEQ ID NO 67
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 67

```
Glu Val Gln Leu Val Glu Ser Gly Gly Gly Leu Val Gln Pro Gly Gly
1               5                   10                  15
```

Ser Leu Arg Leu Ser Cys Gly Ala Ser Gly Phe Thr Phe Asn Lys Tyr
            20                  25                  30

Trp Met Thr Trp Val Arg Gln Ala Pro Gly Lys Gly Leu Glu Trp Val
        35                  40                  45

Ala Asn Ile Asn Gln Asp Gly Ser Glu Lys Tyr Phe Ala Glu Ser Val
50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Ser Ile Glu Val Glu Ile Leu Tyr Tyr Tyr His Met
            100                 105                 110

Asp Val Trp Gly Lys Gly Thr Leu Val Thr Val Ser Ser
        115                 120                 125

<210> SEQ ID NO 68
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 68

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Thr Thr His
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Ile Pro Ala Arg Phe Ser Gly
    50                  55                  60

Ser Gly Ser Gly Thr Glu Phe Thr Leu Thr Ile Ser Asn Met Gln Ser
65                  70                  75                  80

Glu Asp Phe Ala Val Tyr Tyr Cys Gln Gln Tyr His Thr Trp Pro Pro
                85                  90                  95

Leu Thr Phe Gly Gly Gly Thr Lys Val Glu Ile Lys
            100                 105

<210> SEQ ID NO 69
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 69

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Met Asn Ser Ser
            20                  25                  30

Gly Met Ser Val Thr Trp Ile Arg Gln Pro Pro Gly Lys Ala Leu Glu
        35                  40                  45

Cys Leu Ala Leu Ile Tyr Trp Asp Asp Asp Lys Trp Tyr Gly Pro Ser
    50                  55                  60

Leu Glu Thr Arg Val Thr Ile Thr Lys Asp Ala Ser Lys Asn Gln Val
65                  70                  75                  80

Val Leu Thr Met Thr Asn Met Asp Pro Val Asp Thr Ala Thr Tyr Tyr
                85                  90                  95

```
Cys Ala His Ser Gly Gly Leu Val Ala Gly Ala Phe Asp Tyr Trp Gly
            100                 105                 110

Gln Gly Thr Leu Val Thr Val Ser Ser
        115                 120

<210> SEQ ID NO 70
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 70

Glu Ile Val Met Thr Gln Ser Pro Asp Ser Leu Thr Val Ser Leu Gly
1               5                   10                  15

Glu Arg Ala Thr Ile Asn Cys Arg Ser Ser Gln Ser Val Leu Tyr Arg
            20                  25                  30

Val Asn Ser Lys Asn Tyr Leu Ala Trp Tyr Gln Gln Lys Ala Gly Gln
        35                  40                  45

Thr Pro Lys Leu Ile Ile Asn Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Ser Pro Arg Thr Phe Gly Gln Gly Thr Lys Val Glu Ile
            100                 105                 110

Lys

<210> SEQ ID NO 71
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 71

Gln Val Gln Leu Gln Glu Ser Gly Pro Gly Leu Gly Lys Pro Ser Glu
1               5                   10                  15

Thr Leu Ser Leu Ser Cys Thr Val Ser Gly Ala Ser Ile Arg Gly Tyr
            20                  25                  30

Phe Trp Asn Trp Ile Arg Gln Pro Pro Gly Lys Gly Leu Glu Trp Ile
        35                  40                  45

Gly Tyr Ile His Ser Thr Gly Ser Thr Asn Tyr Asn Pro Ser Leu Lys
    50                  55                  60

Ser Arg Val Thr Ile Ser Val Asp Thr Ser Lys Asn Gln Val Ser Leu
65                  70                  75                  80

Asn Val Asn Ser Val Thr Ala Ala Asp Thr Ala Val Tyr Phe Cys Ala
                85                  90                  95

Arg Gly Ala Trp Asn Val Ala Thr Val Tyr Tyr Tyr Gly Met Asp
            100                 105                 110

Val Trp Gly Gln Gly Thr Leu Val Thr Val Ser Ser
        115                 120

<210> SEQ ID NO 72
<211> LENGTH: 108
<212> TYPE: PRT
<213> ORGANISM: Artificial sequence
```

```
<220> FEATURE:
<223> OTHER INFORMATION: Synthetic polypeptide

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
        35                  40                  45

Ile Ser Gly Thr Ser Thr Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Asn Ser Leu
                85                  90                  95

Tyr Thr Phe Gly Gln Gly Thr Lys Leu Glu Ile Lys
            100                 105

<210> SEQ ID NO 73
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 73

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Lys Phe Ser Thr Tyr
            20                  25                  30

Gly Met Asn Trp Val Arg Gln Val Pro Gly Gln Gly Leu Glu Trp Val
        35                  40                  45

Ser Phe Val Arg His Asp Gly Ser Asn Lys Tyr Tyr Ser Asp Ser Val
    50                  55                  60

Lys Gly Arg Phe Thr Ile Phe Arg Asp Asn Ser Asn Asn Lys Leu Tyr
65                  70                  75                  80

Leu Gln Met Asn Asn Leu Arg Ala Glu Asp Thr Ala Val Tyr Tyr Cys
                85                  90                  95

Ala Lys Asp Val Leu Asp Cys Ser Arg Ala Asp Cys Phe Ile Tyr Tyr
            100                 105                 110

Tyr Tyr Met Asp Val Trp Gly Lys Gly Thr Leu Val Thr Val Ser Ser
        115                 120                 125

<210> SEQ ID NO 74
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 74

Asp Ile Gln Met Thr Gln Ser Pro Ser Ser Val Ser Ala Ser Pro Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Gly Lys Ala Pro Lys Leu Leu Ile
        35                  40                  45
```

-continued

Tyr Asp Val Ser Thr Leu Gln Ser Gly Val Pro Ser Arg Phe Ser Gly
 50                  55                  60

Gly Gly Ser Gly Thr Glu Phe Thr Phe Thr Ile Ser Ser Leu Gln Pro
 65                  70                  75                  80

Glu Asp Tyr Ala Thr Tyr Phe Cys Gln Gln Gly Asn Arg Ile Pro Leu
                 85                  90                  95

Ser Phe Gly Gly Gly Thr Arg Val Glu Ile Lys
                100                 105

<210> SEQ ID NO 75
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 75

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Asn Asn
                20                  25                  30

Tyr Met Ser Trp Val Arg Gln Ala Pro Gly Lys Gly Leu Glu Trp Val
             35                  40                  45

Ser Leu Ile Tyr Thr Ser Val Thr Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Leu Gly Asn Trp Ser Tyr Gly Val Ser Tyr Trp Gly Arg Gly
                100                 105                 110

Thr Leu Val Thr Val Ser Ser
        115

<210> SEQ ID NO 76
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 76

Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
                20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Gly Ala Asp Tyr Tyr Cys Gln Ser Ala Asp Gly Ser Gly Thr Tyr
                 85                  90                  95

Pro Val Val Phe Gly Gly Gly Thr Lys Leu Thr Val Leu
                100                 105

<210> SEQ ID NO 77

<211> LENGTH: 121
<212> TYPE: PRT
<213> ORGANISM: Artificial sequence
<220> FEATURE:
<223> OTHER INFORMATION: Synthetic polypeptide

<400> SEQUENCE: 77

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Leu Thr Gly Tyr
            20                  25                  30

Tyr Trp Gly Trp Ile Arg Gln Pro Pro Gly Lys Gly Leu Glu Trp Ile
        35                  40                  45

Gly Glu Ile Asn His Gly Val Ser Thr Met Tyr Asn Pro Ser Leu Lys
    50                  55                  60

Ser Arg Val Thr Leu Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Arg Leu Gln Leu Trp Phe Leu Gly Ala Phe Asp Ile Trp Gly
            100                 105                 110

Gln Gly Thr Met Val Thr Val Ser Ser
        115                 120

<210> SEQ ID NO 78
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 78

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Tyr Thr Asn
            20                  25                  30

Leu Ala Trp Tyr Gln Gln Lys Pro Gly Gln Pro Pro Arg Leu Leu Ile
        35                  40                  45

His Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Ser Trp Arg Thr
                85                  90                  95

Phe Gly Gln Gly Thr Lys Val Glu Ile Lys
            100                 105

<210> SEQ ID NO 79
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 79

Glu Val Gln Leu Val Gln Ser Gly Ala Glu Val Lys Lys Pro Gly Glu
1               5                   10                  15

Ser Leu Lys Ile Ser Cys Lys Gly Ala Gly Tyr Ser Phe Pro Asn Tyr
            20                  25                  30

```
Trp Ile Gly Trp Val Arg Gln Met Pro Gly Lys Gly Leu Glu Trp Met
            35                  40                  45

Gly Ile Ile Tyr Pro Gly Glu Ser Lys Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Gly Met Tyr Tyr Cys
                 85                  90                  95

Ala Leu Pro Arg Ile Gly Pro Thr Ser Asn Trp Gly Ser Ser Trp Tyr
            100                 105                 110

Glu Gly Ile Phe Asp Ile Trp Gly Gln Gly Thr Met Val Thr Val Ser
            115                 120                 125

Ser
```

```
<210> SEQ ID NO 80
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 80

Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Leu Ser Phe Gly Ser Gly Thr Lys Val Thr Val Leu
            100                 105
```

```
<210> SEQ ID NO 81
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 81

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser His
            20                  25                  30

Tyr Trp Ser Trp Ile Arg Gln Pro Pro Gly Lys Gly Leu Glu Trp Ile
            35                  40                  45

Gly Tyr Ile Ser Tyr Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Gly Leu Arg Ser Val Thr Ala Ala Asp Thr Ala Val Tyr Tyr Cys Ala
                 85                  90                  95
```

Arg Met Thr Arg Val Thr Ile Phe Gly Val Leu Thr Asp Asp Tyr Tyr
            100                 105                 110

Lys Trp Phe Asp Pro Trp Gly Gln Gly Thr Leu Val Thr Val Ser Ser
        115                 120                 125

<210> SEQ ID NO 82
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 82

Gln Ser Ala Leu Thr Gln Pro Pro Ser Val Ser Gly Ser Pro Gly Gln
1               5                   10                  15

Ser Val Thr Ile Ser Cys Thr Gly Thr Ser Thr Asp Val Gly Gly Ser
            20                  25                  30

Asn Arg Val Ser Trp Tyr Gln Gln Pro Pro Gly Thr Ala Pro Lys Leu
        35                  40                  45

Met Ile Tyr Glu Val Thr Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Ser Leu Tyr Thr Ser Ser
                85                  90                  95

Ser Thr Phe Val Phe Gly Thr Gly Thr Lys Val Thr Val Leu
            100                 105                 110

<210> SEQ ID NO 83
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 83

Gln Val Gln Val Glu Glu Ser Gly Gly Gly Val Val Gln Pro Gly Gly
1               5                   10                  15

Ser Leu Arg Leu Ser Cys Ala Ala Ser Gly Phe Met Phe Ser Asn Tyr
            20                  25                  30

Gly Met His Trp Val Arg Gln Ala Pro Gly Lys Gly Leu Glu Trp Met
        35                  40                  45

Ala Phe Ile Arg Tyr Asp Asp Ser Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Glu Leu Leu Gln Val Tyr Thr Ser Ala Trp Gly Gly His
            100                 105                 110

Ser Tyr Tyr Tyr Ala Leu Asp Val Trp Gly Leu Gly Thr Ala Val Thr
        115                 120                 125

Val Ser Ser
    130

<210> SEQ ID NO 84
<211> LENGTH: 107
<212> TYPE: PRT
<213> ORGANISM: Artificial sequence

```
<220> FEATURE:
<223> OTHER INFORMATION: Synthetic polypeptide

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Glu Leu Leu Ile
        35                  40                  45

Tyr Thr Ala Ser Ile Leu Gln Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Gly Lys Ser Phe Pro Tyr
                85                  90                  95

Thr Phe Gly Gln Gly Thr Lys Leu Glu Ile Lys
            100                 105

<210> SEQ ID NO 85
<211> LENGTH: 8
<212> TYPE: PRT
<213> ORGANISM: Artificial sequence
<220> FEATURE:
<223> OTHER INFORMATION: Synthetic peptide

<400> SEQUENCE: 85

Gly Tyr Thr Phe Thr Gly Tyr Tyr
1               5

<210> SEQ ID NO 86
<211> LENGTH: 8
<212> TYPE: PRT
<213> ORGANISM: Artificial sequence
<220> FEATURE:
<223> OTHER INFORMATION: Synthetic peptide

<400> SEQUENCE: 86

Ile Asn Pro Asn Ser Gly Gly Thr
1               5

<210> SEQ ID NO 87
<211> LENGTH: 14
<212> TYPE: PRT
<213> ORGANISM: Artificial sequence
<220> FEATURE:
<223> OTHER INFORMATION: Synthetic peptide

<400> SEQUENCE: 87

Ala Arg Asp Ser Gly Glu Leu Leu Phe Val Gly Ser Asp Val
1               5                   10

<210> SEQ ID NO 88
<211> LENGTH: 8
<212> TYPE: PRT
<213> ORGANISM: Artificial sequence
<220> FEATURE:
<223> OTHER INFORMATION: Synthetic peptide

<400> SEQUENCE: 88

Gly Gly Thr Phe Ser Arg Asp Ile
1               5
```

```
<210> SEQ ID NO 89
<211> LENGTH: 8
<212> TYPE: PRT
<213> ORGANISM: Artificial sequence
<220> FEATURE:
<223> OTHER INFORMATION: Synthetic peptide

<400> SEQUENCE: 89

Ile Ile Pro Ile Phe Gly Thr Ala
1               5

<210> SEQ ID NO 90
<211> LENGTH: 26
<212> TYPE: PRT
<213> ORGANISM: Artificial sequence
<220> FEATURE:
<223> OTHER INFORMATION: Synthetic peptide

<400> SEQUENCE: 90

Ala Arg Gly Pro Pro Leu Arg Gly Glu Arg Ser Trp Phe Gly Glu Ser
1               5                   10                  15

Glu Lys Tyr Asp Tyr Phe Tyr Met Asp Val
            20                  25

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Gly Phe Thr Phe Lys Tyr Ala Gly
1               5

<210> SEQ ID NO 92
<211> LENGTH: 10
<212> TYPE: PRT
<213> ORGANISM: Artificial sequence
<220> FEATURE:
<223> OTHER INFORMATION: Synthetic peptide

<400> SEQUENCE: 92

Ile Lys Ser Arg Ile Asp Gly Gly Thr Thr
1               5                   10

<210> SEQ ID NO 93
<211> LENGTH: 24
<212> TYPE: PRT
<213> ORGANISM: Artificial sequence
<220> FEATURE:
<223> OTHER INFORMATION: Synthetic peptide

<400> SEQUENCE: 93

Ala Thr Gly Ser Gly Lys Gly Pro Ser Ala Ser Phe Gly Glu Ser Tyr
1               5                   10                  15

Tyr Tyr Tyr Asp Phe Ile Asn Val
            20

<210> SEQ ID NO 94
<211> LENGTH: 8
<212> TYPE: PRT
<213> ORGANISM: Artificial sequence
<220> FEATURE:
<223> OTHER INFORMATION: Synthetic peptide

<400> SEQUENCE: 94
```

Gly Tyr Thr Phe Thr Asp Tyr Tyr
1               5

<210> SEQ ID NO 95
<211> LENGTH: 8
<212> TYPE: PRT
<213> ORGANISM: Artificial sequence
<220> FEATURE:
<223> OTHER INFORMATION: Synthetic peptide

<400> SEQUENCE: 95

Leu Asn Pro Asn Ser Gly Gly Thr
1               5

<210> SEQ ID NO 96
<211> LENGTH: 11
<212> TYPE: PRT
<213> ORGANISM: Artificial sequence
<220> FEATURE:
<223> OTHER INFORMATION: Synthetic peptide

<400> SEQUENCE: 96

Ala Arg Gly Arg Arg His Gly Ala Tyr Val Asp
1               5                   10

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Gly Phe Lys Phe Asp Glu Tyr Gly
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Ile Thr Trp Asn Gly Gly Val Arg
1               5

<210> SEQ ID NO 99
<211> LENGTH: 13
<212> TYPE: PRT
<213> ORGANISM: Artificial sequence
<220> FEATURE:
<223> OTHER INFORMATION: Synthetic peptide

<400> SEQUENCE: 99

Val Ser Trp Gly Glu Arg Tyr Asp Ala Tyr Phe Asp Tyr
1               5                   10

<210> SEQ ID NO 100
<211> LENGTH: 8
<212> TYPE: PRT
<213> ORGANISM: Artificial sequence
<220> FEATURE:
<223> OTHER INFORMATION: Synthetic peptide

<400> SEQUENCE: 100

```
Gly Phe Ser Phe Ser Asn Tyr Ala
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic peptide

<400> SEQUENCE: 101

Ile Gly Ile Ser Gly Gly Ser Thr
1               5

<210> SEQ ID NO 102
<211> LENGTH: 21
<212> TYPE: PRT
<213> ORGANISM: Artificial sequence
<220> FEATURE:
<223> OTHER INFORMATION: Synthetic peptide

<400> SEQUENCE: 102

Ala Lys Asp Ala Gln Gln Glu Thr Asp Ile Val Tyr Phe Tyr Tyr
1               5                   10                  15

Asp Gly Met Asp Val
            20

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Gly Tyr Thr Phe Asn Asn Tyr Leu
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic peptide

<400> SEQUENCE: 104

Ile Asn Pro His Ser Gly Gly Thr
1               5

<210> SEQ ID NO 105
<211> LENGTH: 11
<212> TYPE: PRT
<213> ORGANISM: Artificial sequence
<220> FEATURE:
<223> OTHER INFORMATION: Synthetic peptide

<400> SEQUENCE: 105

Trp Ile Trp Phe Arg Ser Glu Thr Phe Asp Phe
1               5                   10

<210> SEQ ID NO 106
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 106

Gly Tyr Thr Phe Ile Asn Tyr Tyr
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Ile Asn Pro Ser Thr Gly Arg Pro
1               5

<210> SEQ ID NO 108
<211> LENGTH: 9
<212> TYPE: PRT
<213> ORGANISM: Artificial sequence
<220> FEATURE:
<223> OTHER INFORMATION: Synthetic peptide

<400> SEQUENCE: 108

Val Ser Phe Gln Phe Tyr Phe Asp Tyr
1               5

<210> SEQ ID NO 109
<211> LENGTH: 10
<212> TYPE: PRT
<213> ORGANISM: Artificial sequence
<220> FEATURE:
<223> OTHER INFORMATION: Synthetic peptide

<400> SEQUENCE: 109

Gly Gly Ser Ile Thr Ser Gly Asp Tyr Tyr
1               5                   10

<210> SEQ ID NO 110
<211> LENGTH: 7
<212> TYPE: PRT
<213> ORGANISM: Artificial sequence
<220> FEATURE:
<223> OTHER INFORMATION: Synthetic peptide

<400> SEQUENCE: 110

Ile Tyr Tyr Ser Gly Ser Thr
1               5

<210> SEQ ID NO 111
<211> LENGTH: 19
<212> TYPE: PRT
<213> ORGANISM: Artificial sequence
<220> FEATURE:
<223> OTHER INFORMATION: Synthetic peptide

<400> SEQUENCE: 111

Ala Arg Glu Ser Asp Gly Asp Pro Ser Arg Leu Tyr Phe Tyr Phe Ala
1               5                   10                  15

Met Asp Val

<210> SEQ ID NO 112
<211> LENGTH: 10
<212> TYPE: PRT
<213> ORGANISM: Artificial sequence
<220> FEATURE:
<223> OTHER INFORMATION: Synthetic peptide
```

-continued

<400> SEQUENCE: 112

Gly Asp Ser Ile Ser Ala Asn Asn Tyr Phe
1               5                   10

<210> SEQ ID NO 113
<211> LENGTH: 7
<212> TYPE: PRT
<213> ORGANISM: Artificial sequence
<220> FEATURE:
<223> OTHER INFORMATION: Synthetic peptide

<400> SEQUENCE: 113

Ile His Asn Ser Gly Ser Thr
1               5

<210> SEQ ID NO 114
<211> LENGTH: 19
<212> TYPE: PRT
<213> ORGANISM: Artificial sequence
<220> FEATURE:
<223> OTHER INFORMATION: Synthetic peptide

<400> SEQUENCE: 114

Ala Arg His Leu Ala Pro Ile Ser Gly Val Ile Phe Ile Pro Ser Phe
1               5                   10                  15

Phe Asp Ser

<210> SEQ ID NO 115
<211> LENGTH: 10
<212> TYPE: PRT
<213> ORGANISM: Artificial sequence
<220> FEATURE:
<223> OTHER INFORMATION: Synthetic peptide

<400> SEQUENCE: 115

Gly Ala Ser Ile Thr Gly Gly Asp Asp Phe
1               5                   10

<210> SEQ ID NO 116
<211> LENGTH: 7
<212> TYPE: PRT
<213> ORGANISM: Artificial sequence
<220> FEATURE:
<223> OTHER INFORMATION: Synthetic peptide

<400> SEQUENCE: 116

Ile His His Ser Gly Asn Ala
1               5

<210> SEQ ID NO 117
<211> LENGTH: 18
<212> TYPE: PRT
<213> ORGANISM: Artificial sequence
<220> FEATURE:
<223> OTHER INFORMATION: Synthetic peptide

<400> SEQUENCE: 117

Ala Arg Asp Lys Ala Gln Ala Tyr Gly Leu Leu Tyr His Tyr His Thr
1               5                   10                  15

Asp Val

<210> SEQ ID NO 118
<211> LENGTH: 10
<212> TYPE: PRT

```
<213> ORGANISM: Artificial sequence
<220> FEATURE:
<223> OTHER INFORMATION: Synthetic peptide

<400> SEQUENCE: 118

Gly Gly Ser Ile Asn Ser Ala Gly Tyr Tyr
1               5                   10

<210> SEQ ID NO 119
<211> LENGTH: 7
<212> TYPE: PRT
<213> ORGANISM: Artificial sequence
<220> FEATURE:
<223> OTHER INFORMATION: Synthetic peptide

<400> SEQUENCE: 119

Ile Asp Tyr Thr Gly Arg Thr
1               5

<210> SEQ ID NO 120
<211> LENGTH: 14
<212> TYPE: PRT
<213> ORGANISM: Artificial sequence
<220> FEATURE:
<223> OTHER INFORMATION: Synthetic peptide

<400> SEQUENCE: 120

Ala Arg Glu Ser Ser Trp Val Ser Glu Leu Gly Arg Asp Asn
1               5                   10

<210> SEQ ID NO 121
<211> LENGTH: 8
<212> TYPE: PRT
<213> ORGANISM: Artificial sequence
<220> FEATURE:
<223> OTHER INFORMATION: Synthetic peptide

<400> SEQUENCE: 121

Gly Phe Thr Phe Asn Lys Tyr Trp
1               5

<210> SEQ ID NO 122
<211> LENGTH: 8
<212> TYPE: PRT
<213> ORGANISM: Artificial sequence
<220> FEATURE:
<223> OTHER INFORMATION: Synthetic peptide

<400> SEQUENCE: 122

Ile Asn Gln Asp Gly Ser Glu Lys
1               5

<210> SEQ ID NO 123
<211> LENGTH: 18
<212> TYPE: PRT
<213> ORGANISM: Artificial sequence
<220> FEATURE:
<223> OTHER INFORMATION: Synthetic peptide

<400> SEQUENCE: 123

Ala Arg Gly Ala Ser Ile Glu Val Glu Ile Leu Tyr Tyr Tyr His Met
1               5                   10                  15

Asp Val

<210> SEQ ID NO 124
<211> LENGTH: 10
```

```
<212> TYPE: PRT
<213> ORGANISM: Artificial sequence
<220> FEATURE:
<223> OTHER INFORMATION: Synthetic peptide

<400> SEQUENCE: 124

Gly Phe Ser Met Asn Ser Ser Gly Met Ser
1               5                   10

<210> SEQ ID NO 125
<211> LENGTH: 7
<212> TYPE: PRT
<213> ORGANISM: Artificial sequence
<220> FEATURE:
<223> OTHER INFORMATION: Synthetic peptide

<400> SEQUENCE: 125

Ile Tyr Trp Asp Asp Asp Lys
1               5

<210> SEQ ID NO 126
<211> LENGTH: 13
<212> TYPE: PRT
<213> ORGANISM: Artificial sequence
<220> FEATURE:
<223> OTHER INFORMATION: Synthetic peptide

<400> SEQUENCE: 126

Ala His Ser Gly Gly Leu Val Ala Gly Ala Phe Asp Tyr
1               5                   10

<210> SEQ ID NO 127
<211> LENGTH: 8
<212> TYPE: PRT
<213> ORGANISM: Artificial sequence
<220> FEATURE:
<223> OTHER INFORMATION: Synthetic peptide

<400> SEQUENCE: 127

Gly Ala Ser Ile Arg Gly Tyr Phe
1               5

<210> SEQ ID NO 128
<211> LENGTH: 7
<212> TYPE: PRT
<213> ORGANISM: Artificial sequence
<220> FEATURE:
<223> OTHER INFORMATION: Synthetic peptide

<400> SEQUENCE: 128

Ile His Ser Thr Gly Ser Thr
1               5

<210> SEQ ID NO 129
<211> LENGTH: 18
<212> TYPE: PRT
<213> ORGANISM: Artificial sequence
<220> FEATURE:
<223> OTHER INFORMATION: Synthetic peptide

<400> SEQUENCE: 129

Ala Arg Gly Ala Trp Asn Val Ala Thr Val Tyr Tyr Tyr Gly Met
1               5                   10                  15

Asp Val

<210> SEQ ID NO 130
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 130

Gly Phe Lys Phe Ser Thr Tyr Gly
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic peptide

<400> SEQUENCE: 131

Val Arg His Asp Gly Ser Asn Lys
1               5

<210> SEQ ID NO 132
<211> LENGTH: 21
<212> TYPE: PRT
<213> ORGANISM: Artificial sequence
<220> FEATURE:
<223> OTHER INFORMATION: Synthetic peptide

<400> SEQUENCE: 132

Ala Lys Asp Val Leu Asp Cys Ser Arg Ala Asp Cys Phe Ile Tyr Tyr
1               5                   10                  15

Tyr Tyr Met Asp Val
            20

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133

Gly Phe Thr Val Ser Asn Asn Tyr
1               5

<210> SEQ ID NO 134
<211> LENGTH: 7
<212> TYPE: PRT
<213> ORGANISM: Artificial sequence
<220> FEATURE:
<223> OTHER INFORMATION: Synthetic peptide

<400> SEQUENCE: 134

Ile Tyr Thr Ser Val Thr Thr
1               5

<210> SEQ ID NO 135
<211> LENGTH: 13
<212> TYPE: PRT
<213> ORGANISM: Artificial sequence
<220> FEATURE:
<223> OTHER INFORMATION: Synthetic peptide

<400> SEQUENCE: 135

Ala Arg Glu Leu Gly Asn Trp Ser Tyr Gly Val Ser Tyr
1               5                   10
```

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Gly Gly Ser Leu Thr Gly Tyr Tyr
1               5

<210> SEQ ID NO 137
<211> LENGTH: 7
<212> TYPE: PRT
<213> ORGANISM: Artificial sequence
<220> FEATURE:
<223> OTHER INFORMATION: Synthetic peptide

<400> SEQUENCE: 137

Ile Asn His Gly Val Ser Thr
1               5

<210> SEQ ID NO 138
<211> LENGTH: 15
<212> TYPE: PRT
<213> ORGANISM: Artificial sequence
<220> FEATURE:
<223> OTHER INFORMATION: Synthetic peptide

<400> SEQUENCE: 138

Ala Arg Ser Arg Leu Gln Leu Trp Phe Leu Gly Ala Phe Asp Ile
1               5                   10                  15

<210> SEQ ID NO 139
<211> LENGTH: 8
<212> TYPE: PRT
<213> ORGANISM: Artificial sequence
<220> FEATURE:
<223> OTHER INFORMATION: Synthetic peptide

<400> SEQUENCE: 139

Gly Tyr Ser Phe Pro Asn Tyr Trp
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic peptide

<400> SEQUENCE: 140

Ile Tyr Pro Gly Glu Ser Lys Thr
1               5

<210> SEQ ID NO 141
<211> LENGTH: 22
<212> TYPE: PRT
<213> ORGANISM: Artificial sequence
<220> FEATURE:
<223> OTHER INFORMATION: Synthetic peptide

<400> SEQUENCE: 141

Ala Leu Pro Arg Ile Gly Pro Thr Ser Asn Trp Gly Ser Ser Trp Tyr
1               5                   10                  15

Glu Gly Ile Phe Asp Ile

<210> SEQ ID NO 142
<211> LENGTH: 8
<212> TYPE: PRT
<213> ORGANISM: Artificial sequence
<220> FEATURE:
<223> OTHER INFORMATION: Synthetic peptide

<400> SEQUENCE: 142

Gly Gly Ser Ile Ser Ser His Tyr
1               5

<210> SEQ ID NO 143
<211> LENGTH: 7
<212> TYPE: PRT
<213> ORGANISM: Artificial sequence
<220> FEATURE:
<223> OTHER INFORMATION: Synthetic peptide

<400> SEQUENCE: 143

Ile Ser Tyr Ser Gly Ser Thr
1               5

<210> SEQ ID NO 144
<211> LENGTH: 22
<212> TYPE: PRT
<213> ORGANISM: Artificial sequence
<220> FEATURE:
<223> OTHER INFORMATION: Synthetic peptide

<400> SEQUENCE: 144

Ala Arg Met Thr Arg Val Thr Ile Phe Gly Val Leu Thr Asp Asp Tyr
1               5                   10                  15

Tyr Lys Trp Phe Asp Pro
            20

<210> SEQ ID NO 145
<211> LENGTH: 8
<212> TYPE: PRT
<213> ORGANISM: Artificial sequence
<220> FEATURE:
<223> OTHER INFORMATION: Synthetic peptide

<400> SEQUENCE: 145

Gly Phe Met Phe Ser Asn Tyr Gly
1               5

<210> SEQ ID NO 146
<211> LENGTH: 8
<212> TYPE: PRT
<213> ORGANISM: Artificial sequence
<220> FEATURE:
<223> OTHER INFORMATION: Synthetic peptide

<400> SEQUENCE: 146

Ile Arg Tyr Asp Asp Ser Lys Lys
1               5

<210> SEQ ID NO 147
<211> LENGTH: 24
<212> TYPE: PRT
<213> ORGANISM: Artificial sequence
<220> FEATURE:
<223> OTHER INFORMATION: Synthetic peptide

<400> SEQUENCE: 147

Ala Lys Glu Leu Leu Gln Val Tyr Thr Ser Ala Trp Gly Glu Gly His
1               5                   10                  15

Ser Tyr Tyr Tyr Ala Leu Asp Val
            20

<210> SEQ ID NO 148
<211> LENGTH: 6
<212> TYPE: PRT
<213> ORGANISM: Artificial sequence
<220> FEATURE:
<223> OTHER INFORMATION: Synthetic peptide

<400> SEQUENCE: 148

Leu Asp Ile Ser Tyr Trp
1               5

<210> SEQ ID NO 149
<211> LENGTH: 3
<212> TYPE: PRT
<213> ORGANISM: Artificial sequence
<220> FEATURE:
<223> OTHER INFORMATION: Synthetic peptide

<400> SEQUENCE: 149

Ala Ala Ser
1

<210> SEQ ID NO 150
<211> LENGTH: 9
<212> TYPE: PRT
<213> ORGANISM: Artificial sequence
<220> FEATURE:
<223> OTHER INFORMATION: Synthetic peptide

<400> SEQUENCE: 150

Gln Gln Ala Asn Ser Phe Pro Gln Thr
1               5

<210> SEQ ID NO 151
<211> LENGTH: 7
<212> TYPE: PRT
<213> ORGANISM: Artificial sequence
<220> FEATURE:
<223> OTHER INFORMATION: Synthetic peptide

<400> SEQUENCE: 151

Gln Ser Val Ser Asn Ser Tyr
1               5

<210> SEQ ID NO 152
<211> LENGTH: 3
<212> TYPE: PRT
<213> ORGANISM: Artificial sequence
<220> FEATURE:
<223> OTHER INFORMATION: Synthetic peptide

<400> SEQUENCE: 152

Gly Ala Ser
1

<210> SEQ ID NO 153
<211> LENGTH: 9
<212> TYPE: PRT
<213> ORGANISM: Artificial sequence
<220> FEATURE:
<223> OTHER INFORMATION: Synthetic peptide

<400> SEQUENCE: 153

Gln Gln Tyr Gly Thr Ser Pro Cys Thr
1               5

<210> SEQ ID NO 154
<211> LENGTH: 7
<212> TYPE: PRT
<213> ORGANISM: Artificial sequence
<220> FEATURE:
<223> OTHER INFORMATION: Synthetic peptide

<400> SEQUENCE: 154

Gln Ser Ile Ser Arg Lys Tyr
1               5

<210> SEQ ID NO 155
<211> LENGTH: 3
<212> TYPE: PRT
<213> ORGANISM: Artificial sequence
<220> FEATURE:
<223> OTHER INFORMATION: Synthetic peptide

<400> SEQUENCE: 155

Gly Ser Ser
1

<210> SEQ ID NO 156
<211> LENGTH: 9
<212> TYPE: PRT
<213> ORGANISM: Artificial sequence
<220> FEATURE:
<223> OTHER INFORMATION: Synthetic peptide

<400> SEQUENCE: 156

His Gln Tyr Glu Ser Ser Pro Trp Thr
1               5

<210> SEQ ID NO 157
<211> LENGTH: 6
<212> TYPE: PRT
<213> ORGANISM: Artificial sequence
<220> FEATURE:
<223> OTHER INFORMATION: Synthetic peptide

<400> SEQUENCE: 157

Gln Gly Ile Ser Thr Tyr
1               5

<210> SEQ ID NO 158
<211> LENGTH: 3
<212> TYPE: PRT
<213> ORGANISM: Artificial sequence
<220> FEATURE:
<223> OTHER INFORMATION: Synthetic peptide

<400> SEQUENCE: 158

Asp Thr Ser
1

<210> SEQ ID NO 159
<211> LENGTH: 11
<212> TYPE: PRT
<213> ORGANISM: Artificial sequence
<220> FEATURE:
<223> OTHER INFORMATION: Synthetic peptide

```
<400> SEQUENCE: 159

Gln Gln Leu Asn Phe Tyr Leu Gly Gly Leu Thr
1               5                   10

<210> SEQ ID NO 160
<211> LENGTH: 7
<212> TYPE: PRT
<213> ORGANISM: Artificial sequence
<220> FEATURE:
<223> OTHER INFORMATION: Synthetic peptide

<400> SEQUENCE: 160

Gln Ser Val Asn Ser Arg Tyr
1               5

<210> SEQ ID NO 161
<211> LENGTH: 3
<212> TYPE: PRT
<213> ORGANISM: Artificial sequence
<220> FEATURE:
<223> OTHER INFORMATION: Synthetic peptide

<400> SEQUENCE: 161

Ala Thr Ser
1

<210> SEQ ID NO 162
<211> LENGTH: 9
<212> TYPE: PRT
<213> ORGANISM: Artificial sequence
<220> FEATURE:
<223> OTHER INFORMATION: Synthetic peptide

<400> SEQUENCE: 162

Gln Gln Tyr Gly Ser Ser Pro Tyr Thr
1               5

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166
<211> LENGTH: 6
<212> TYPE: PRT
<213> ORGANISM: Artificial sequence
<220> FEATURE:
<223> OTHER INFORMATION: Synthetic peptide

<400> SEQUENCE: 166

Gln Asp Ile Ser Asn Tyr
1               5
```

```
<210> SEQ ID NO 167
<211> LENGTH: 3
<212> TYPE: PRT
<213> ORGANISM: Artificial sequence
<220> FEATURE:
<223> OTHER INFORMATION: Synthetic peptide

<400> SEQUENCE: 167

Glu Ala Ser
1

<210> SEQ ID NO 168
<211> LENGTH: 8
<212> TYPE: PRT
<213> ORGANISM: Artificial sequence
<220> FEATURE:
<223> OTHER INFORMATION: Synthetic peptide

<400> SEQUENCE: 168

Leu Gln His Asn Thr Tyr Leu Thr
1               5

<210> SEQ ID NO 169
<211> LENGTH: 6
<212> TYPE: PRT
<213> ORGANISM: Artificial sequence
<220> FEATURE:
<223> OTHER INFORMATION: Synthetic peptide

<400> SEQUENCE: 169

Gln Gly Ile Asn Asn Tyr
1               5

<210> SEQ ID NO 170
<211> LENGTH: 3
<212> TYPE: PRT
<213> ORGANISM: Artificial sequence
<220> FEATURE:
<223> OTHER INFORMATION: Synthetic peptide

<400> SEQUENCE: 170

Ala Ala Ser
1

<210> SEQ ID NO 171
<211> LENGTH: 9
<212> TYPE: PRT
<213> ORGANISM: Artificial sequence
<220> FEATURE:
<223> OTHER INFORMATION: Synthetic peptide

<400> SEQUENCE: 171

Leu Gln His Asn Ser Tyr Pro Trp Thr
1               5

<210> SEQ ID NO 172
<211> LENGTH: 9
<212> TYPE: PRT
<213> ORGANISM: Artificial sequence
<220> FEATURE:
<223> OTHER INFORMATION: Synthetic peptide

<400> SEQUENCE: 172

Ser Ser Asp Val Gly Gly Ser Tyr Phe
1               5

<210> SEQ ID NO 173
```

```
<211> LENGTH: 3
<212> TYPE: PRT
<213> ORGANISM: Artificial sequence
<220> FEATURE:
<223> OTHER INFORMATION: Synthetic peptide

<400> SEQUENCE: 173

Glu Val Ser
1

<210> SEQ ID NO 174
<211> LENGTH: 10
<212> TYPE: PRT
<213> ORGANISM: Artificial sequence
<220> FEATURE:
<223> OTHER INFORMATION: Synthetic peptide

<400> SEQUENCE: 174

Ser Ser Tyr Thr Ser Asn Thr Thr Leu Val
1               5                   10

<210> SEQ ID NO 175
<211> LENGTH: 6
<212> TYPE: PRT
<213> ORGANISM: Artificial sequence
<220> FEATURE:
<223> OTHER INFORMATION: Synthetic peptide

<400> SEQUENCE: 175

Gln Ser Val Ser Ser Asn
1               5

<210> SEQ ID NO 176
<211> LENGTH: 3
<212> TYPE: PRT
<213> ORGANISM: Artificial sequence
<220> FEATURE:
<223> OTHER INFORMATION: Synthetic peptide

<400> SEQUENCE: 176

Asp Ala Ser
1

<210> SEQ ID NO 177
<211> LENGTH: 11
<212> TYPE: PRT
<213> ORGANISM: Artificial sequence
<220> FEATURE:
<223> OTHER INFORMATION: Synthetic peptide

<400> SEQUENCE: 177

Gln Gln Tyr Asn Asp Trp Pro Pro Arg Leu Thr
1               5                   10

<210> SEQ ID NO 178
<211> LENGTH: 6
<212> TYPE: PRT
<213> ORGANISM: Artificial sequence
<220> FEATURE:
<223> OTHER INFORMATION: Synthetic peptide

<400> SEQUENCE: 178

Gln Ser Val Ser Ser Asn
1               5

<210> SEQ ID NO 179
<211> LENGTH: 3
```

```
<212> TYPE: PRT
<213> ORGANISM: Artificial sequence
<220> FEATURE:
<223> OTHER INFORMATION: Synthetic peptide

<400> SEQUENCE: 179

Gly Ala Phe
1

<210> SEQ ID NO 180
<211> LENGTH: 11
<212> TYPE: PRT
<213> ORGANISM: Artificial sequence
<220> FEATURE:
<223> OTHER INFORMATION: Synthetic peptide

<400> SEQUENCE: 180

Gln Tyr Tyr Asn Asp Trp Pro Pro Gly Tyr Thr
1               5                   10

<210> SEQ ID NO 181
<211> LENGTH: 6
<212> TYPE: PRT
<213> ORGANISM: Artificial sequence
<220> FEATURE:
<223> OTHER INFORMATION: Synthetic peptide

<400> SEQUENCE: 181

Gln Ser Val Phe Thr Asn
1               5

<210> SEQ ID NO 182
<211> LENGTH: 3
<212> TYPE: PRT
<213> ORGANISM: Artificial sequence
<220> FEATURE:
<223> OTHER INFORMATION: Synthetic peptide

<400> SEQUENCE: 182

Asp Ala Ser
1

<210> SEQ ID NO 183
<211> LENGTH: 9
<212> TYPE: PRT
<213> ORGANISM: Artificial sequence
<220> FEATURE:
<223> OTHER INFORMATION: Synthetic peptide

<400> SEQUENCE: 183

Gln Gln Tyr Asn Asn Trp Pro Arg Thr
1               5

<210> SEQ ID NO 184
<211> LENGTH: 6
<212> TYPE: PRT
<213> ORGANISM: Artificial sequence
<220> FEATURE:
<223> OTHER INFORMATION: Synthetic peptide

<400> SEQUENCE: 184

Gln Ser Ile Thr Thr His
1               5

<210> SEQ ID NO 185
<211> LENGTH: 3
<212> TYPE: PRT
```

```
<213> ORGANISM: Artificial sequence
<220> FEATURE:
<223> OTHER INFORMATION: Synthetic peptide

<400> SEQUENCE: 185

Asp Thr Ser
1

<210> SEQ ID NO 186
<211> LENGTH: 10
<212> TYPE: PRT
<213> ORGANISM: Artificial sequence
<220> FEATURE:
<223> OTHER INFORMATION: Synthetic peptide

<400> SEQUENCE: 186

Gln Gln Tyr His Thr Trp Pro Pro Leu Thr
1               5                   10

<210> SEQ ID NO 187
<211> LENGTH: 12
<212> TYPE: PRT
<213> ORGANISM: Artificial sequence
<220> FEATURE:
<223> OTHER INFORMATION: Synthetic peptide

<400> SEQUENCE: 187

Gln Ser Val Leu Tyr Arg Val Asn Ser Lys Asn Tyr
1               5                   10

<210> SEQ ID NO 188
<211> LENGTH: 3
<212> TYPE: PRT
<213> ORGANISM: Artificial sequence
<220> FEATURE:
<223> OTHER INFORMATION: Synthetic peptide

<400> SEQUENCE: 188

Trp Ala Ser
1

<210> SEQ ID NO 189
<211> LENGTH: 9
<212> TYPE: PRT
<213> ORGANISM: Artificial sequence
<220> FEATURE:
<223> OTHER INFORMATION: Synthetic peptide

<400> SEQUENCE: 189

Gln Gln Tyr Tyr Asn Ser Pro Arg Thr
1               5

<210> SEQ ID NO 190
<211> LENGTH: 7
<212> TYPE: PRT
<213> ORGANISM: Artificial sequence
<220> FEATURE:
<223> OTHER INFORMATION: Synthetic peptide

<400> SEQUENCE: 190

Gln Ser Val Ser Ser Ser Tyr
1               5

<210> SEQ ID NO 191
<211> LENGTH: 3
<212> TYPE: PRT
<213> ORGANISM: Artificial sequence
```

<220> FEATURE:
<223> OTHER INFORMATION: Synthetic peptide

<400> SEQUENCE: 191

Gly Thr Ser
1

<210> SEQ ID NO 192
<211> LENGTH: 9
<212> TYPE: PRT
<213> ORGANISM: Artificial sequence
<220> FEATURE:
<223> OTHER INFORMATION: Synthetic peptide

<400> SEQUENCE: 192

Gln Gln Tyr Gly Asn Ser Leu Tyr Thr
1               5

<210> SEQ ID NO 193
<211> LENGTH: 6
<212> TYPE: PRT
<213> ORGANISM: Artificial sequence
<220> FEATURE:
<223> OTHER INFORMATION: Synthetic peptide

<400> SEQUENCE: 193

Gln Thr Ile Ser Gly Trp
1               5

<210> SEQ ID NO 194
<211> LENGTH: 3
<212> TYPE: PRT
<213> ORGANISM: Artificial sequence
<220> FEATURE:
<223> OTHER INFORMATION: Synthetic peptide

<400> SEQUENCE: 194

Asp Val Ser
1

<210> SEQ ID NO 195
<211> LENGTH: 9
<212> TYPE: PRT
<213> ORGANISM: Artificial sequence
<220> FEATURE:
<223> OTHER INFORMATION: Synthetic peptide

<400> SEQUENCE: 195

Gln Gln Gly Asn Arg Ile Pro Leu Ser
1               5

<210> SEQ ID NO 196
<211> LENGTH: 6
<212> TYPE: PRT
<213> ORGANISM: Artificial sequence
<220> FEATURE:
<223> OTHER INFORMATION: Synthetic peptide

<400> SEQUENCE: 196

Ala Leu Pro Lys Gln Tyr
1               5

<210> SEQ ID NO 197
<211> LENGTH: 3
<212> TYPE: PRT
<213> ORGANISM: Artificial sequence
<220> FEATURE:

<223> OTHER INFORMATION: Synthetic peptide

<400> SEQUENCE: 197

Lys Asp Ser
1

<210> SEQ ID NO 198
<211> LENGTH: 12
<212> TYPE: PRT
<213> ORGANISM: Artificial sequence
<220> FEATURE:
<223> OTHER INFORMATION: Synthetic peptide

<400> SEQUENCE: 198

Gln Ser Ala Asp Gly Ser Gly Thr Tyr Pro Val Val
1               5                   10

<210> SEQ ID NO 199
<211> LENGTH: 6
<212> TYPE: PRT
<213> ORGANISM: Artificial sequence
<220> FEATURE:
<223> OTHER INFORMATION: Synthetic peptide

<400> SEQUENCE: 199

Gln Ser Ile Tyr Thr Asn
1               5

<210> SEQ ID NO 200
<211> LENGTH: 3
<212> TYPE: PRT
<213> ORGANISM: Artificial sequence
<220> FEATURE:
<223> OTHER INFORMATION: Synthetic peptide

<400> SEQUENCE: 200

Asp Ala Ser
1

<210> SEQ ID NO 201
<211> LENGTH: 8
<212> TYPE: PRT
<213> ORGANISM: Artificial sequence
<220> FEATURE:
<223> OTHER INFORMATION: Synthetic peptide

<400> SEQUENCE: 201

Gln Gln Tyr Asn Ser Trp Arg Thr
1               5

<210> SEQ ID NO 202
<211> LENGTH: 9
<212> TYPE: PRT
<213> ORGANISM: Artificial sequence
<220> FEATURE:
<223> OTHER INFORMATION: Synthetic peptide

<400> SEQUENCE: 202

Thr Gly Ala Val Thr Thr Ser Asn Tyr
1               5

<210> SEQ ID NO 203
<211> LENGTH: 3
<212> TYPE: PRT
<213> ORGANISM: Artificial sequence
<220> FEATURE:
<223> OTHER INFORMATION: Synthetic peptide

```
<400> SEQUENCE: 203

Gly Thr Asn
1

<210> SEQ ID NO 204
<211> LENGTH: 9
<212> TYPE: PRT
<213> ORGANISM: Artificial sequence
<220> FEATURE:
<223> OTHER INFORMATION: Synthetic peptide

<400> SEQUENCE: 204

Ala Leu Trp Tyr Ser Asn His Leu Ser
1               5

<210> SEQ ID NO 205
<211> LENGTH: 9
<212> TYPE: PRT
<213> ORGANISM: Artificial sequence
<220> FEATURE:
<223> OTHER INFORMATION: Synthetic peptide

<400> SEQUENCE: 205

Ser Thr Asp Val Gly Gly Ser Asn Arg
1               5

<210> SEQ ID NO 206
<211> LENGTH: 3
<212> TYPE: PRT
<213> ORGANISM: Artificial sequence
<220> FEATURE:
<223> OTHER INFORMATION: Synthetic peptide

<400> SEQUENCE: 206

Glu Val Thr
1

<210> SEQ ID NO 207
<211> LENGTH: 10
<212> TYPE: PRT
<213> ORGANISM: Artificial sequence
<220> FEATURE:
<223> OTHER INFORMATION: Synthetic peptide

<400> SEQUENCE: 207

Ser Leu Tyr Thr Ser Ser Ser Thr Phe Val
1               5                   10

<210> SEQ ID NO 208
<211> LENGTH: 6
<212> TYPE: PRT
<213> ORGANISM: Artificial sequence
<220> FEATURE:
<223> OTHER INFORMATION: Synthetic peptide

<400> SEQUENCE: 208

Gln Asp Ile Ser Asn Trp
1               5

<210> SEQ ID NO 209
<211> LENGTH: 3
<212> TYPE: PRT
<213> ORGANISM: Artificial sequence
<220> FEATURE:
<223> OTHER INFORMATION: Synthetic peptide
```

```
<400> SEQUENCE: 209

Thr Ala Ser
1

<210> SEQ ID NO 210
<211> LENGTH: 9
<212> TYPE: PRT
<213> ORGANISM: Artificial sequence
<220> FEATURE:
<223> OTHER INFORMATION: Synthetic peptide

<400> SEQUENCE: 210

Gln Gln Gly Lys Ser Phe Pro Tyr Thr
1               5

<210> SEQ ID NO 211
<211> LENGTH: 13
<212> TYPE: PRT
<213> ORGANISM: Artificial sequence
<220> FEATURE:
<223> OTHER INFORMATION: Synthetic peptide

<400> SEQUENCE: 211

Tyr Glu Ala Gly Glu Trp Ala Glu Asn Cys Tyr Asn Leu
1               5                   10

<210> SEQ ID NO 212
<211> LENGTH: 10
<212> TYPE: PRT
<213> ORGANISM: Artificial sequence
<220> FEATURE:
<223> OTHER INFORMATION: Synthetic peptide

<400> SEQUENCE: 212

Lys Cys Asn Pro Asn Leu His Tyr Trp Thr
1               5                   10

<210> SEQ ID NO 213
<211> LENGTH: 10
<212> TYPE: PRT
<213> ORGANISM: Artificial sequence
<220> FEATURE:
<223> OTHER INFORMATION: Synthetic peptide

<400> SEQUENCE: 213

Lys Cys Asn Pro Asn Leu His Tyr Trp Thr
1               5                   10

<210> SEQ ID NO 214
<211> LENGTH: 569
<212> TYPE: PRT
<213> ORGANISM: Artificial sequence
<220> FEATURE:
<223> OTHER INFORMATION: Synthetic polypeptide

<400> SEQUENCE: 214

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60
```

```
Val Asn Tyr Glu Ala Gly Glu Trp Ala Glu Asn Cys Tyr Asn Leu Glu
 65                  70                  75                  80

Ile Lys Lys Pro Asp Gly Ser Glu Cys Leu Pro Ala Ala Pro Asp Gly
                 85                  90                  95

Ile Arg Gly Phe Pro Arg Cys Arg Tyr Val His Lys Val Ser Gly Thr
                100                 105                 110

Gly Pro Cys Ala Gly Asp Phe Ala Phe His Lys Glu Gly Ala Phe Phe
            115                 120                 125

Leu Tyr Asp Arg Leu Ala Ser Thr Val Ile Tyr Arg Gly Thr Thr Phe
130                 135                 140

Ala Glu Gly Val Val Ala Phe Leu Ile Leu Pro Gln Ala Lys Lys Asp
145                 150                 155                 160

Phe Phe Ser Ser His Pro Leu Arg Glu Pro Val Asn Ala Thr Glu Asp
                165                 170                 175

Pro Ser Ser Gly Tyr Tyr Ser Thr Thr Ile Arg Tyr Gln Ala Thr Gly
                180                 185                 190

Phe Gly Thr Asn Glu Thr Glu Tyr Leu Phe Glu Val Asp Asn Leu Thr
            195                 200                 205

Tyr Val Gln Leu Glu Ser Arg Phe Thr Pro Gln Phe Leu Leu Gln Leu
210                 215                 220

Asn Glu Thr Ile Tyr Ala Ser Gly Lys Arg Ser Asn Thr Thr Gly Lys
225                 230                 235                 240

Leu Ile Trp Lys Val Asn Pro Glu Ile Asp Thr Thr Ile Gly Glu Trp
                245                 250                 255

Ala Phe Trp Glu Thr Lys Lys Asn Leu Thr Arg Lys Ile Arg Ser Glu
                260                 265                 270

Glu Leu Ser Phe Thr Ala Val Ser Asn Gly Pro Lys Asn Ile Ser Gly
            275                 280                 285

Gln Ser Pro Ala Arg Thr Ser Ser Asp Pro Glu Thr Asn Thr Thr Asn
290                 295                 300

Glu Asp His Lys Ile Met Ala Ser Glu Asn Ser Ser Ala Met Val Gln
305                 310                 315                 320

Val His Ser Gln Gly Arg Lys Ala Ala Val Ser His Leu Thr Thr Leu
                325                 330                 335

Ala Thr Ile Ser Thr Ser Pro Gln Pro Pro Thr Thr Lys Thr Gly Pro
                340                 345                 350

Asp Asn Ser Thr His Asn Thr Pro Val Tyr Lys Leu Asp Ile Ser Glu
                355                 360                 365

Ala Thr Gln Val Gly His His Arg Arg Ala Asp Asn Asp Ser Thr
370                 375                 380

Ala Ser Asp Thr Pro Pro Ala Thr Thr Ala Ala Gly Pro Leu Lys Ala
385                 390                 395                 400

Glu Asn Ile Asn Thr Ser Lys Ser Ala Asp Ser Leu Asp Leu Ala Thr
                405                 410                 415

Thr Ile Ser Pro Gln Asn Tyr Ser Glu Thr Ala Gly Asn Asn Asn Thr
                420                 425                 430

His His Gln Asp Thr Gly Glu Glu Ser Ala Ser Ser Gly Lys Leu Gly
            435                 440                 445

Leu Ile Thr Asn Thr Ile Ala Gly Val Ala Gly Leu Ile Thr Gly Gly
            450                 455                 460

Arg Arg Thr Arg Arg Glu Val Ile Val Asn Ala Gln Pro Lys Cys Asn
465                 470                 475                 480

Pro Asn Leu His Tyr Trp Thr Thr Gln Asp Glu Gly Ala Ala Ile Gly
```

-continued

```
                    485                 490                 495
Leu Ala Trp Ile Pro Tyr Phe Gly Pro Ala Ala Glu Gly Ile Tyr Thr
                500                 505                 510

Glu Gly Leu Met His Asn Gln Asp Gly Leu Ile Cys Gly Leu Arg Gln
            515                 520                 525

Leu Ala Asn Glu Thr Thr Gln Ala Leu Gln Leu Phe Leu Arg Ala Thr
        530                 535                 540

Thr Glu Leu Arg Thr Phe Ser Ile Leu Asn Arg Lys Ala Ile Asp Phe
545                 550                 555                 560

Leu Leu Gln Arg Trp Gly Gly Thr Cys
                565

<210> SEQ ID NO 215
<211> LENGTH: 254
<212> TYPE: PRT
<213> ORGANISM: Artificial sequence
<220> FEATURE:
<223> OTHER INFORMATION: Synthetic polypeptide

<400> SEQUENCE: 215

Ile Pro Leu Gly Val Ile His Asn Ser Thr Leu Gln Val Ser Asp Val
1               5                   10                  15

Asp Lys Leu Val Cys Arg Asp Lys Leu Ser Ser Thr Asn Gln Leu Arg
            20                  25                  30

Ser Val Gly Leu Asn Leu Glu Gly Asn Gly Val Ala Thr Asp Val Pro
        35                  40                  45

Ser Val Thr Lys Arg Trp Gly Phe Arg Ser Gly Val Pro Pro Lys Val
    50                  55                  60

Val Asn Tyr Glu Ala Gly Glu Trp Ala Glu Asn Cys Tyr Asn Leu Glu
65                  70                  75                  80

Ile Lys Lys Pro Asp Gly Ser Glu Cys Leu Pro Ala Ala Pro Asp Gly
                85                  90                  95

Ile Arg Gly Phe Pro Arg Cys Arg Tyr Val His Lys Val Ser Gly Thr
            100                 105                 110

Gly Pro Cys Ala Gly Asp Phe Ala Phe His Lys Glu Gly Ala Phe Phe
        115                 120                 125

Leu Tyr Asp Arg Leu Ala Ser Thr Val Ile Tyr Arg Gly Thr Thr Phe
    130                 135                 140

Ala Glu Gly Val Val Ala Phe Leu Ile Leu Pro Gln Ile Val Asn Ala
145                 150                 155                 160

Gln Pro Lys Cys Asn Pro Asn Leu His Tyr Trp Thr Thr Gln Asp Glu
                165                 170                 175

Gly Ala Ala Ile Gly Leu Ala Trp Ile Pro Tyr Phe Gly Pro Ala Ala
            180                 185                 190

Glu Gly Ile Tyr Thr Glu Gly Leu Met His Asn Gln Asp Gly Leu Ile
        195                 200                 205

Cys Gly Leu Arg Gln Leu Ala Asn Glu Thr Thr Gln Ala Leu Gln Leu
    210                 215                 220

Phe Leu Arg Ala Thr Thr Glu Leu Arg Thr Phe Ser Ile Leu Asn Arg
225                 230                 235                 240

Lys Ala Ile Asp Phe Leu Leu Gln Arg Trp Gly Gly Thr Cys
                245                 250
```